United States Patent [19]

Tomalia et al.

[11] Patent Number: 5,714,166
[45] Date of Patent: Feb. 3, 1998

[54] BIOACTIVE AND/OR TARGETED DENDRIMER CONJUGATES

[75] Inventors: Donald A. Tomalia, Midland; James R. Baker, Ann Arbor; Roberta C. Cheng, Midland; Anna U. Bielinska, Ypsilanti; Michael J. Fazio; David M. Hedstrand, both of Midland; Jennifer A. Johnson, Livonia, all of Mich.; Donald A. Kaplan, deceased, late of Marina del Rey, Calif., by Margorie Kaplan, executor; Scott L. Klakamp, Russell, Pa.; William J. Kruper, Jr., Sanford, Mich.; Jolanta Kukowska-Latallo, Ann Arbor, Mich.; Bartley D. Maxon, St. Louis, Mich.; Lars T. Piehler; Ian A. Tomlinson, both of Midland, Mich.; Larry R. Wilson, Beaverton, Mich.; Rui Yin, Mt. Pleasant, Mich.; Herbert M. Brothers, II, Midland, Mich.

[73] Assignees: The Dow Chemical Company; Dendritech Incorporated, both of Midland; The Regents of the University of Michigan, Ann Arbor, all of Mich.

[21] Appl. No.: 400,203

[22] Filed: Mar. 7, 1995

Related U.S. Application Data

[63] Continuation-in-part of Ser. No. 316,536, Sep. 30, 1994, abandoned, which is a continuation-in-part of Ser. No. 207,494, Mar. 7, 1994, abandoned, which is a division of Ser. No. 43,198, Apr. 5, 1993, Pat. No. 5,527,524, and a continuation-in-part of Ser. No. 43,198, Apr. 5, 1993, Pat. No. 5,527,524, which is a continuation-in-part of Ser. No. 654,851, Feb. 13, 1991, Pat. No. 5,338,532, which is a continuation-in-part of Ser. No. 386,049, Jul. 26, 1989, abandoned, which is a continuation-in-part of Ser. No. 87,266, Aug. 18, 1987, abandoned, which is a continuation-in-part of Ser. No. 897,455, Aug. 18, 1986, abandoned.

[51] Int. Cl.$^6$ .......................... A61K 31/74; A61K 9/14; A61K 31/785

[52] U.S. Cl. .......................... 424/486; 424/1.29; 424/1.33; 424/1.37; 424/1.41; 424/1.49; 424/9.3; 424/9.322; 424/9.32; 424/9.36; 424/9.4; 424/9.42; 424/9.6; 424/78.08; 424/93.1; 424/178.1; 424/193.1; 424/204.1; 424/234.1; 424/280; 424/DIG. 16; 424/405; 424/417; 514/772; 523/105; 525/417; 935/52; 935/54

[58] Field of Search .......................... 424/1.29, 1.33, 424/1.37, 1.41, 1.49, 9.3, 9.322, 9.32, 9.36, 9.4, 9.42, 9.6, 78.08, 78.16, 78.18, 78.19, 78.22, 280, 93.1, 178.1, 193.1, 204.1, 234.1, DIG. 16, 405, 417, 486, 78.23, 78.26, 78.27, 78.34, 78.37; 514/772, 772.1, 772.3, 772.4–772.8; 523/105; 525/417; 935/52, 54

[56] References Cited

U.S. PATENT DOCUMENTS

| | | | |
|---|---|---|---|
| 3,200,106 | 8/1965 | Dickson et al. | 260/97.5 |
| 3,445,441 | 5/1969 | Rushton | 260/89.5 |
| 3,514,250 | 5/1970 | Rushton | 21/2.5 |
| 3,528,928 | 9/1970 | Rushton | 252/341 |
| 3,578,643 | 5/1971 | Wood et al. | 260/78.4 |
| 3,580,891 | 5/1971 | Rainer | 260/72 |
| 3,773,739 | 11/1973 | Bonvicini et al. | 260/78 A |
| 4,036,808 | 7/1977 | Rembaum et al. | 260/42.51 |
| 4,102,827 | 7/1978 | Rembaum et al. | 260/823 |
| 4,141,847 | 2/1979 | Kivosky | 252/51.5 A |
| 4,289,872 | 9/1981 | Denkewalter et al. | 528/328 |
| 4,315,087 | 2/1982 | Redmore et al. | 525/421 |
| 4,360,646 | 11/1982 | Denkewalter et al. | 525/420 |
| 4,410,688 | 10/1983 | Denkewalter et al. | 528/328 |
| 4,435,548 | 3/1984 | Tomalia et al. | 525/451 |
| 4,472,509 | 9/1984 | Goodwin et al. | 436/548 |
| 4,507,466 | 3/1985 | Tomalia et al. | 528/332 |
| 4,558,120 | 12/1985 | Tomalia et al. | 528/363 |
| 4,568,737 | 2/1986 | Tomalia et al. | 528/332 |
| 4,581,337 | 4/1986 | Frey et al. | 436/533 |
| 4,587,329 | 5/1986 | Tomalia et al. | 528/363 |
| 4,606,907 | 8/1986 | Simon et al. | 424/1.1 |
| 4,631,337 | 12/1986 | Tomalia et al. | 528/391 |
| 4,634,586 | 1/1987 | Goodwin et al. | 424/1.1 |
| 4,650,769 | 3/1987 | Kakini et al. | 436/533 |
| 4,675,173 | 6/1987 | Widdor | 424/9 |
| 4,694,064 | 9/1987 | Tomalia et al. | 528/332 |
| 4,703,018 | 10/1987 | Craig et al. | 436/533 |
| 4,713,975 | 12/1987 | Tomalia et al. | 73/865.8 |
| 4,737,550 | 4/1988 | Tomalia | 525/418 |

| | | | |
|---|---|---|---|
| 4,824,659 | 4/1989 | Hawthorne | 424/1.1 |
| 4,855,403 | 8/1989 | Meschke et al. | 528/419 |
| 4,857,218 | 8/1989 | Meschke et al. | 252/49.3 |
| 4,857,599 | 8/1989 | Tomalia et al. | 525/259 |
| 4,863,717 | 9/1989 | Keans | 424/9 |
| 4,871,779 | 10/1989 | Killat et al. | 521/28 |
| 4,916,246 | 4/1990 | Felder et al. | 556/1 |
| 4,931,553 | 6/1990 | Gill et al. | 536/121 |
| 4,938,885 | 7/1990 | Midgal | 252/51.5 A |
| 4,946,824 | 8/1990 | Meschke et al. | 503/216 |
| 4,980,148 | 12/1990 | Dean | 424/9 |
| 5,021,236 | 6/1991 | Gries et al. | 424/9 |
| 5,039,512 | 8/1991 | Kraft et al. | 424/9 |
| 5,041,516 | 8/1991 | Frechet et al. | 528/44 |
| 5,098,475 | 3/1992 | Winniket et al. | 106/22 |
| 5,120,361 | 6/1992 | Winniket et al. | 106/22 |
| 5,124,246 | 6/1992 | Urdea et al. | 435/6 |
| 5,154,853 | 10/1992 | Newkombe et al. | 252/311 |
| 5,175,270 | 12/1992 | Nilsen et al. | 536/27 |
| 5,338,532 | 8/1994 | Tomalia | 424/1.49 |
| 5,362,843 | 11/1994 | Vicari et al. | 424/78.26 |
| 5,527,524 | 6/1996 | Tomalia | 424/1.33 |

FOREIGN PATENT DOCUMENTS

| | | |
|---|---|---|
| 560604 | 7/1987 | Australia . |
| 3827589 | 5/1993 | Australia . |
| 0115771 | 8/1984 | European Pat. Off. . |
| 0430863 | 6/1991 | European Pat. Off. . |
| 0473088 | 8/1991 | European Pat. Off. . |
| 0469520 | 2/1992 | European Pat. Off. . |
| 0481526 | 4/1992 | European Pat. Off. . |
| 2168163 | 6/1990 | Japan ........... 426/533 |
| 206742 | 8/1987 | New Zealand . |
| 840128 | 8/1985 | South Africa . |
| 8402705 | 7/1984 | WIPO . |
| 9011778 | 10/1990 | WIPO . |
| 9012056 | 10/1990 | WIPO . |
| 9303406 | 2/1993 | WIPO . |

OTHER PUBLICATIONS

Wu, Biochemistry, vol. 27, pp. 887–892, 1988.
Paul Communications In Mass Spectrometry, vol. 5, 323–386 (1991).
Conjugate Chem., 1993, 372–379, Haensler et al.
Acc. Chem. Res., 1993, 26, 274–278, Behr.
Scientific American, Nov. 1990, 68–84 (Verma).
Chemistry in Britain, Jun. 1993, 484–488, Brown et al.
Science, vol. 260, May 14, 1993, 926–932, Mulligan.
The Journal of Biological Chemistry, Oct. 15, 1988, vol. 263, No. 29, 14621–14624, Wu et al.
Chem. & Eng. News, Aug. 16, 1993, pp. 20–23.
Cell, vol. 75 (1993), 207–216, Zabner et al.
Transfection–reagent, Klakamp, Cat. No. 1202 375.
Angewandte Chemie International Edition, vol. 29, Feb. 1990, 138–175.
Plant Physical, (1990) 93, 1492–1496, Horn et al.
Proc. Natl. Acad. Sci. USA, Nov. 1993, vol. 90, 10489–10493.
Biconjugate Chemistry, Sep./Oct. 1993, V4, No. 5, pp. 372–379.
J. Nucl. Med., 27, pp. 829–833 (1986), Anderson et al.
Proc. Nat'l Acad. Sci. (U.S.A.), 85, pp. 5409–5413 (1988), Tam.
Journal of Molecular Catalysis, 32, pp. 149–158 (1985), Savinova et al.
Journal of Molecular Catalysis, 32, pp. 159–175 (1985), Savinova et al.
Bioconjugate Chemistry, 1, pp. 305–308 (1990), Roberts et al.
Polymer Journal, 17(1), pp. 117–132 (Jan. 1985), Tomalia et al.
Macromolecules, 19(9), pp. 2466–2468, Tomalia et al. 1986.
Biochem. Biophys. Acta. 883, (1986), Manabe et al.
Byull, Eksp. Biol. Med. (BEBMAE), 102(7), pp. 63–65 (1986), Torchilin et al.
Nature, 225, pp. 487–488 (Jun. 5, 1975), Rowland et al.
Proceedings Nat'l Acad. Sc. (U.S.A.), 83, pp. 4277–4281 (1986), Curtet et al.
Polymer Journal, 24,(6), pp. 573–581 (1992).
J. Chem. Soc. Chem. Commun., 1992, pp. 608–610.
The Chemical Society of Japan, Chemistry Letters, pp. 959–962, (1992).
Angew. Chem. Int. Ed. Engl., 31,(12), (1992).
J. Org. Chem., 52, pp. 5305–5312, (1987).
J. Am. Chem. Soc., 109, pp. 1601–1603, (1987).
Macromolecules, 20, pp. 1164–1167, (1987).
Angew. Chem. Int. Ed. Engl., 31,(11), pp. 1493–1495, (1992).
J. Am. Chem. Soc., 111, pp. 2339–2341, (1989).
J. Am. Chem. Soc., 112, pp. 4592–4593, (1990).
J. Macromol. Sci. Chem., A17,(4), pp. 689–703, (1982).
J. Org. Chem., 50, pp. 2003–2004, (1985).
J. Am. Chem. Soc. 112, pp. 8458–8465, (1990).
Angew. Chem. Int. Ed. Engl., 30, pp. 1177–1180, (1991).
Acc. Chem. Res., 24, pp. 332–340, (1991).
J. Am. Chem. Soc., 113, pp. 7335–7342, 1991.
Macromolecules, 23, pp. 910–912, (1990).
Poly. Prep., 32, (31), pp. 602–603, (1991).
J. Org. Chem., 57, p. 435, (1992).
Progress in Neutron Capture Therapy for Cancer, Plenum Press, New York, 1992, pp. 265–268.
Genes IV, Benjamin Lewin, Oxford University Press, 1990, pp. 409–430.
Bioconjugate Chemistry, Kabanov et al., 1993, V 4, 448–454.
Polymer Science, Kabanov et al., V 36, No. 2, 1994, pp. 157–168.
J. Am. Chem. Soc., 1994, V 116, pp. 6975–6976.
Biopolymers, Kabanov et al., V 31, pp. 1437–1443 1991.
Kabanov's Lecture in MacroAkron Symposium (Jul. 11–15, 1994) "supramolecular devices for targeting DNA into cells".
Bioconjugate Chem., 1993, 4, 448–454, Kabanov et al.
Biopolymers, vol. 31, 1437–1443 (1991), Kabanov et al.
Polymer Science, vol. 16, No. 2 1994, pp. 157–168. Galligan. et al.
Chem. & Eng. News, Jul. 24, 1995 pp. 37–40 Borman.
Proceed. Intern. Symp. Sontrol. Rel. Bloact. Master. 22 (1985) 178–179, Mumper, R.J.
Communications. Sep. 1984. pp. 782–784.
Synthetic Communications. 23(22), 3191–3194 (1993), Cheng.
J. Chem. Phys., 11,45 (1943), pp. 2719–2723 Stockmayer.
Radio Communications in Mass Spect. vol. 5, pp. 383–386. (1991), Kallos.
Sci. Chem., A17(4), pp. 689–703 (1982), Macromol.
Nature., vol. 255, Jun. 5, 1975, pp. 487–488.
Science, vol. 267, Jan. 27, 1995, pp. 458–459.
Journal of Boiological Chemistry. vol. 269. No. 17 Apr. 29, 1994, pp. 12918–12924.
Proc. Natl. Acad. Sci. USA. vol. 34. pp. 7413–7417.
Bioconjugate Chem. 1994, vol. 5, pp. 382–389.

Proc. Natl. Acad. Sci. USA 87 (1990) pp. 3655–3659. Zenke et al.

"Complexes of DNA with Skynthetic . . . " Kabanov. Dept. of Polymer Science, Moscow State University, v–234, USSR and aboratory of Biopolymer Chemistry, Moscow 113149, USSR.

*Primary Examiner*—Gollamudi S. Kishore
*Attorney, Agent, or Firm*—Karen L. Kimble

[57] ABSTRACT

Dendritic polymer conjugates which are composed of at least one dendrimer in association with at least one unit of a carried material, where the carrier material can be a biological response modifier, have been prepared. The conjugate can also have a target director present, and when it is present then the carried material may be a bioactive agent. Preferred dendritic polymers are dense star polymers, which have been complexed with biological response modifiers. These conjugates and complexes have particularly advantageous properties due to their unique characteristics.

136 Claims, 68 Drawing Sheets

FIG. I

FIG. 2
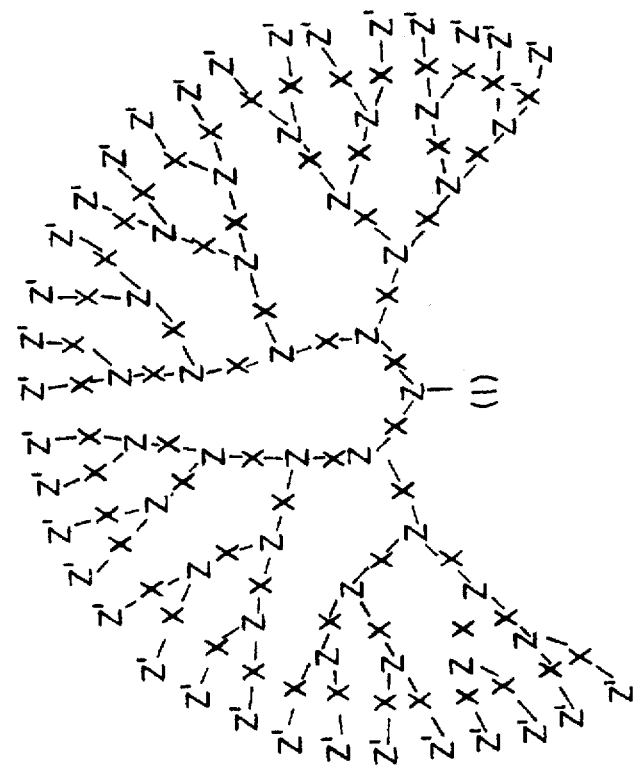
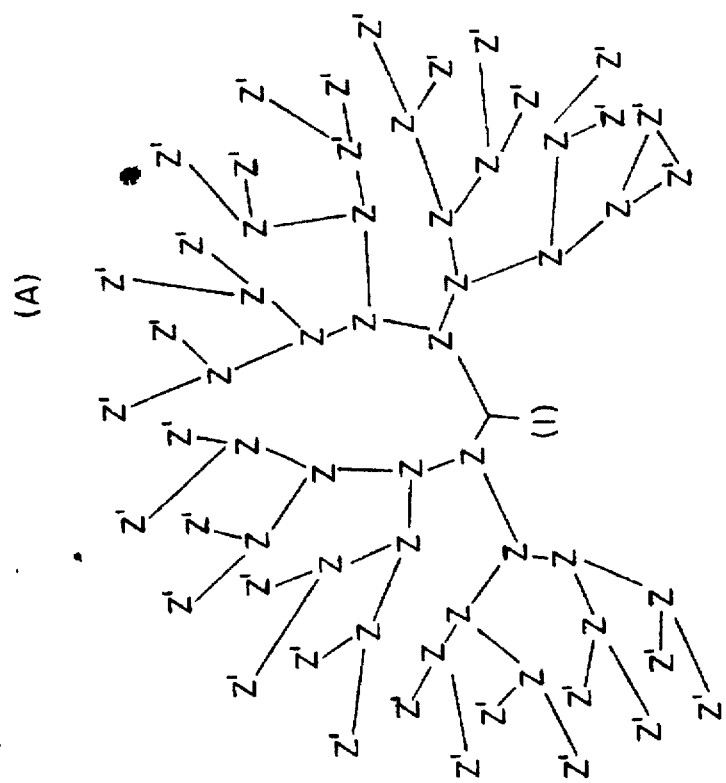

1 2 3 4 5 6 7 8 9 10 11 12

1 2 3 4 5 6 7 8 9 10 11 12

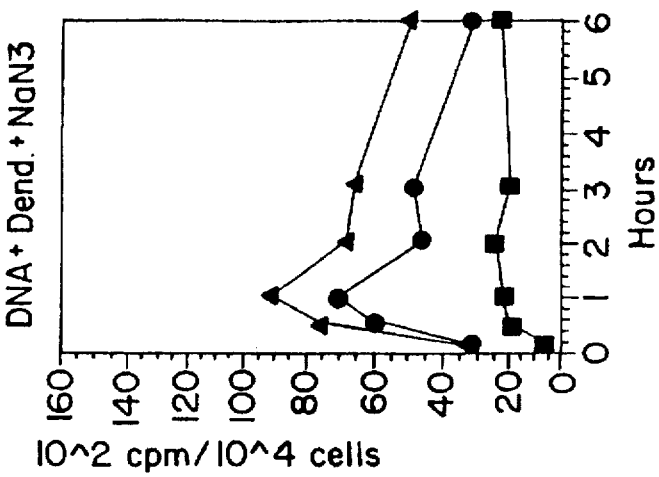
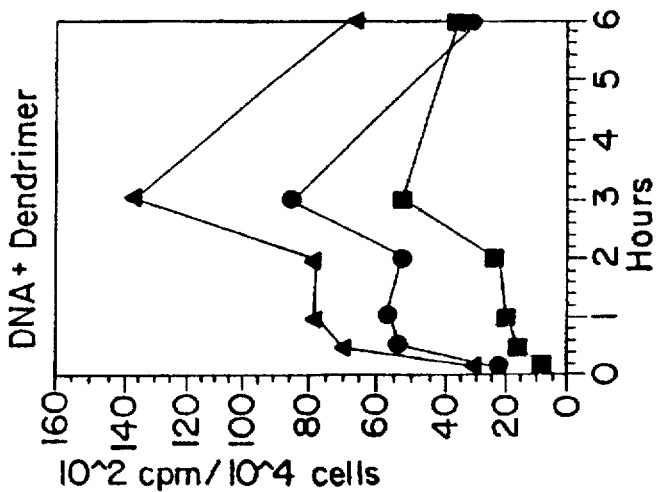
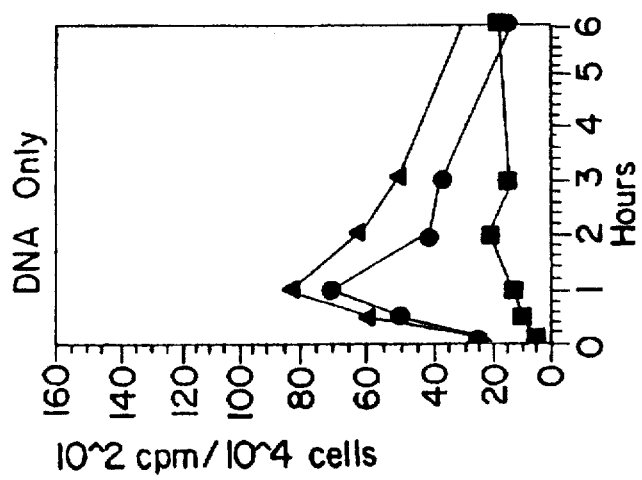

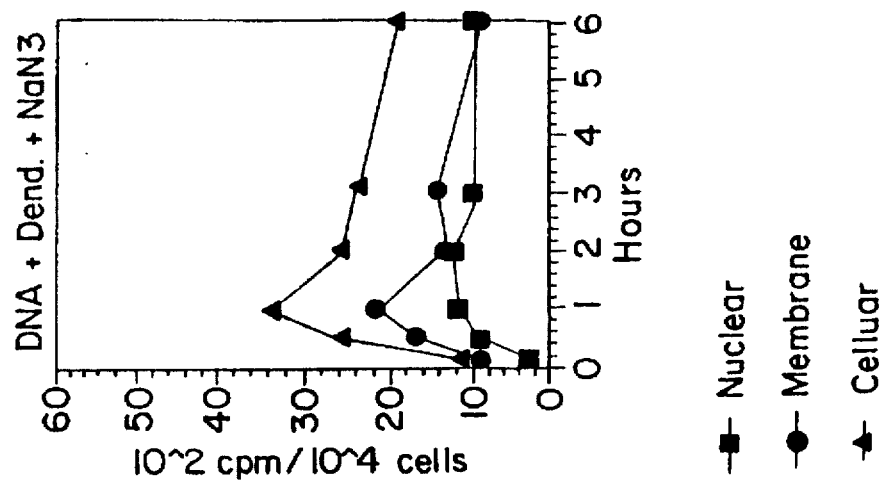
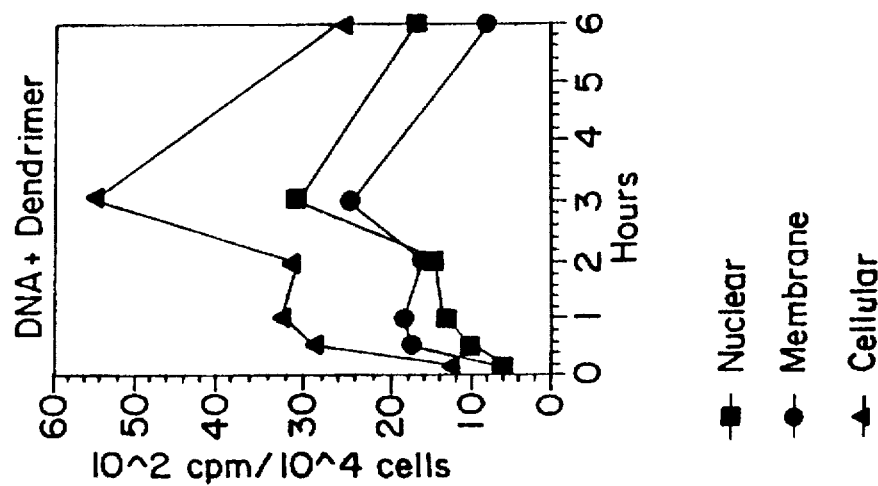
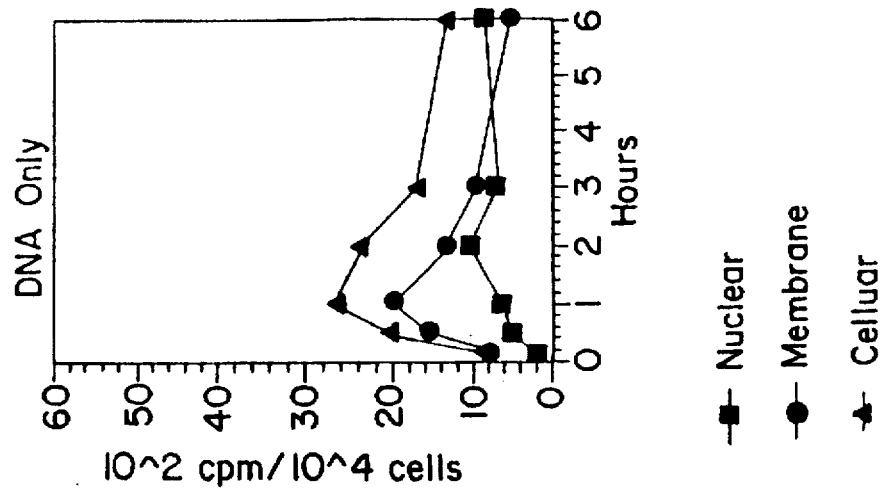

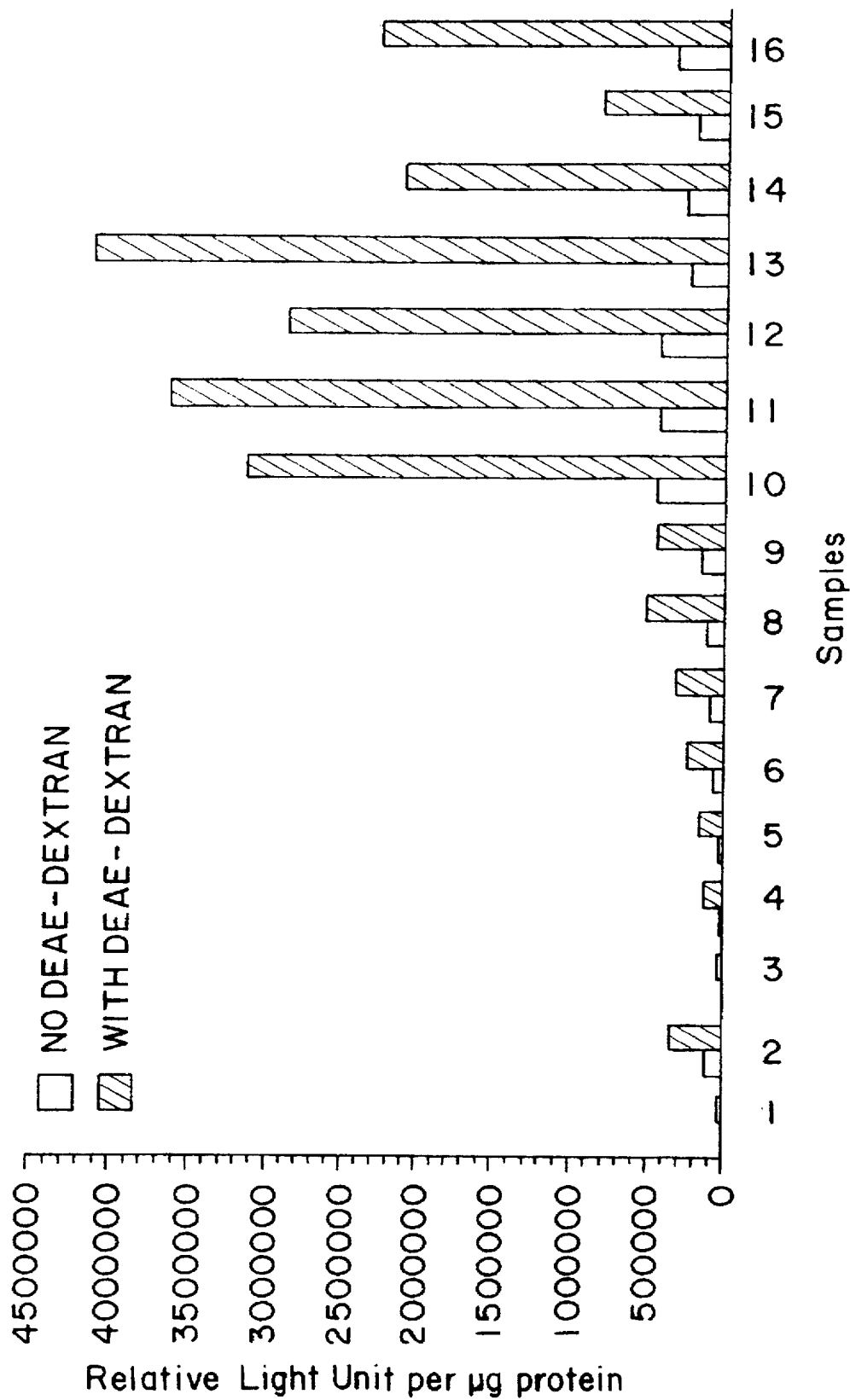

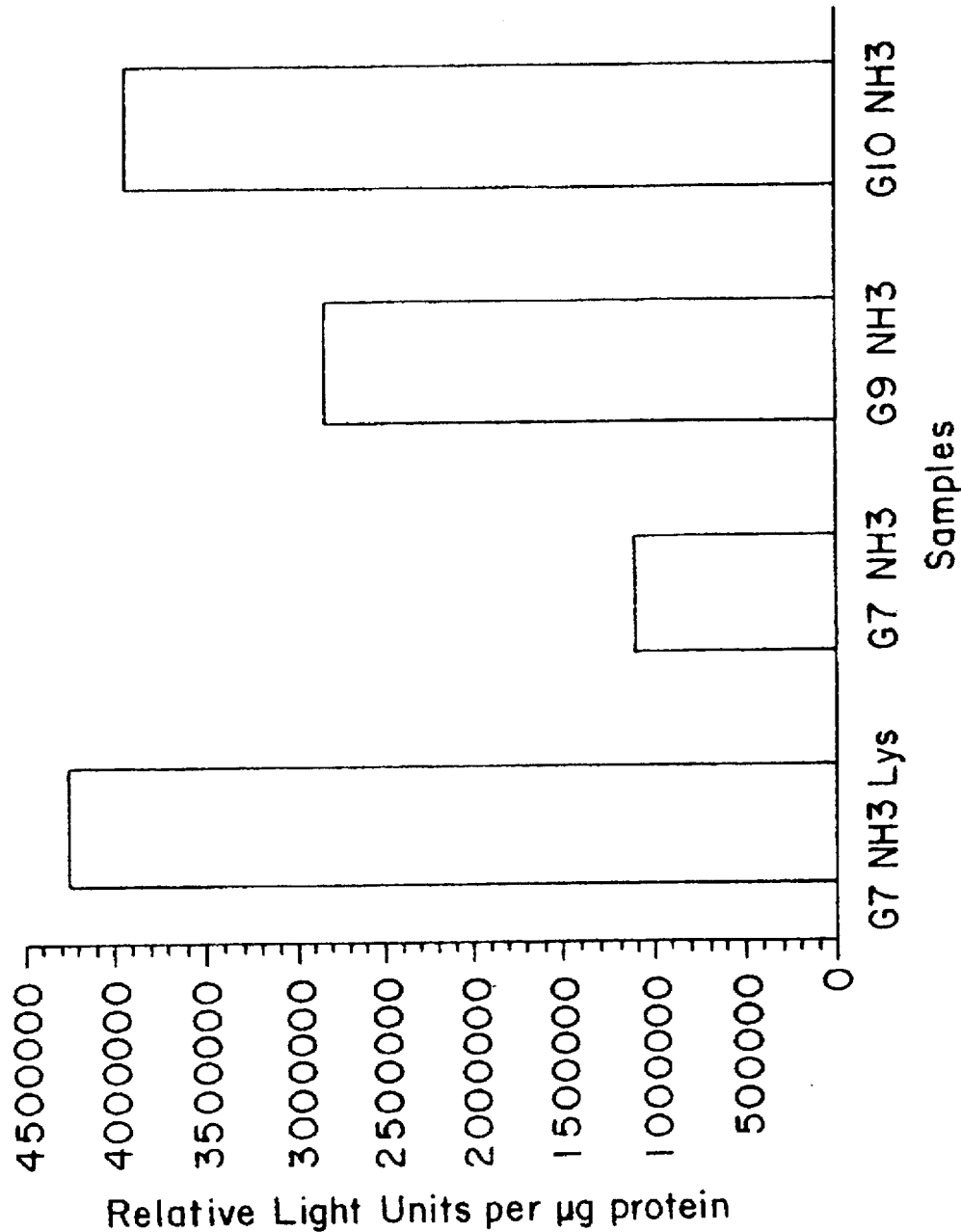

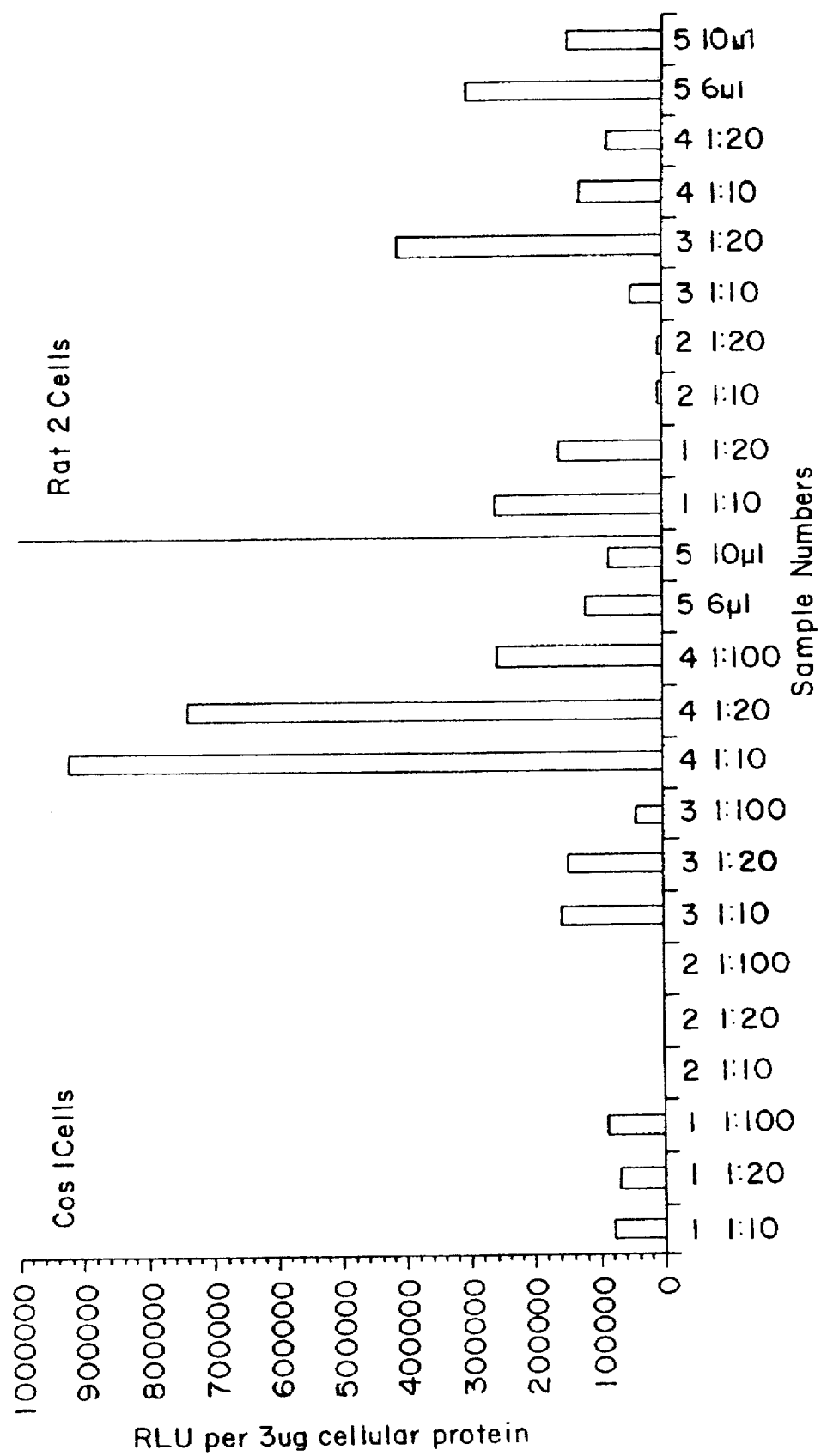

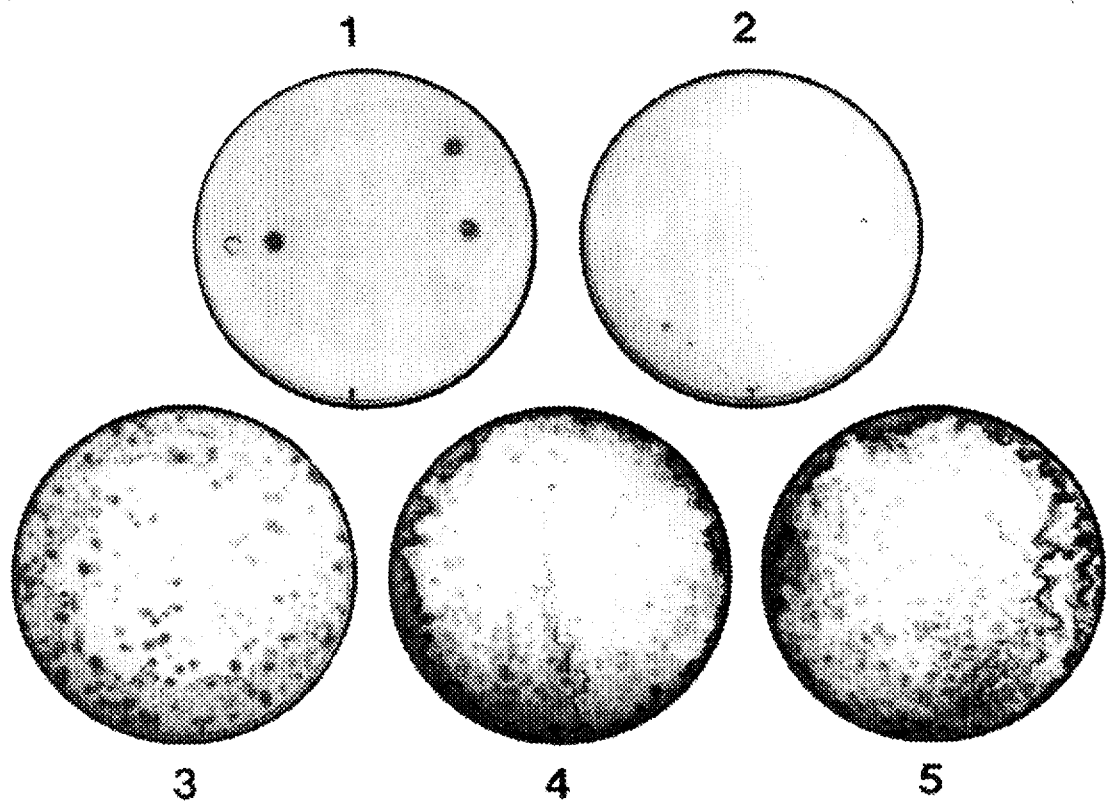

FIG. 60A
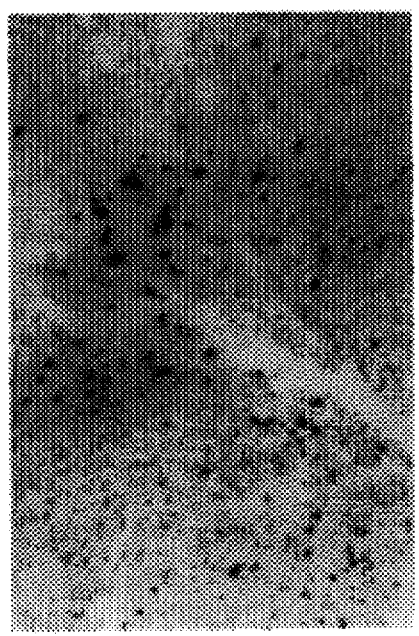
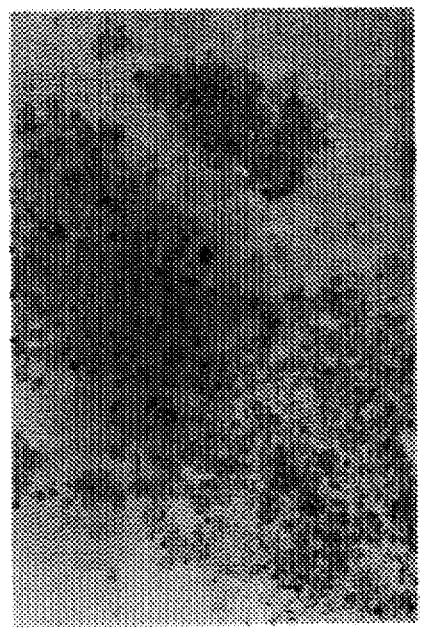
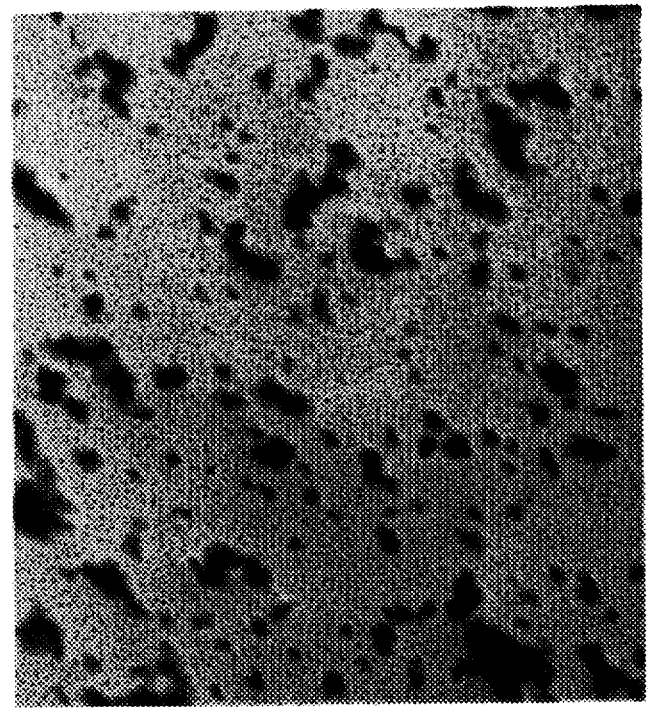

FIG. 60B
4
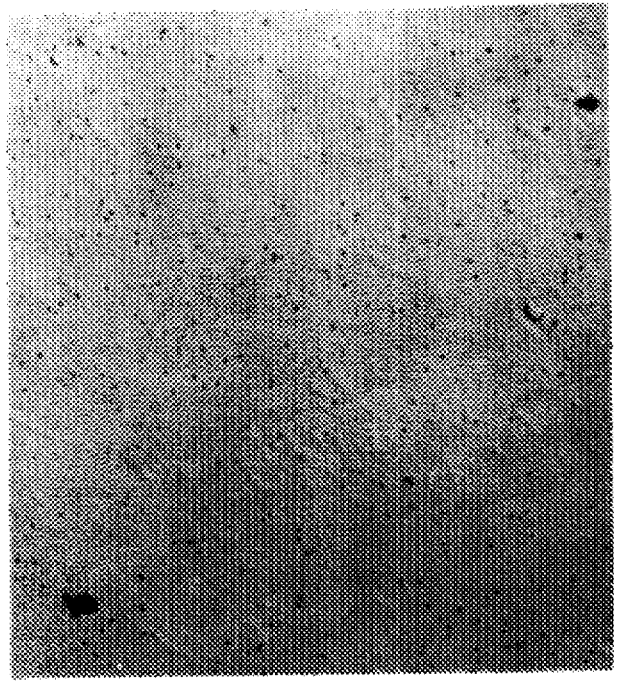
5
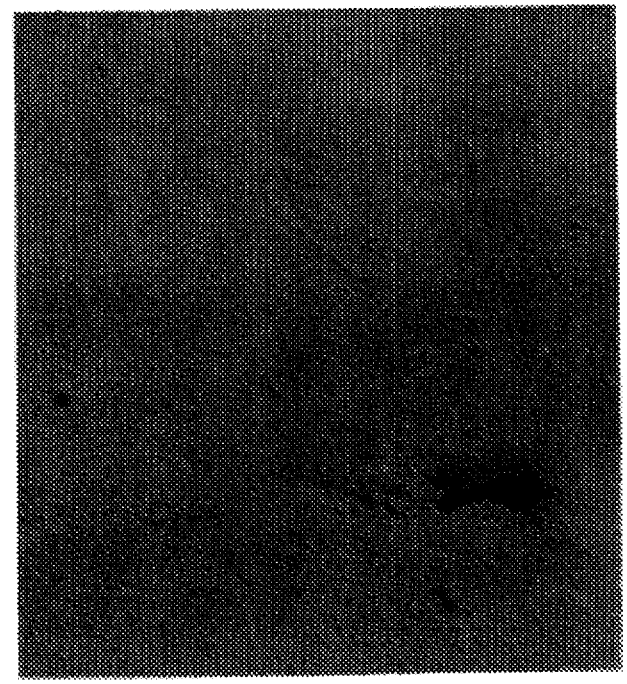

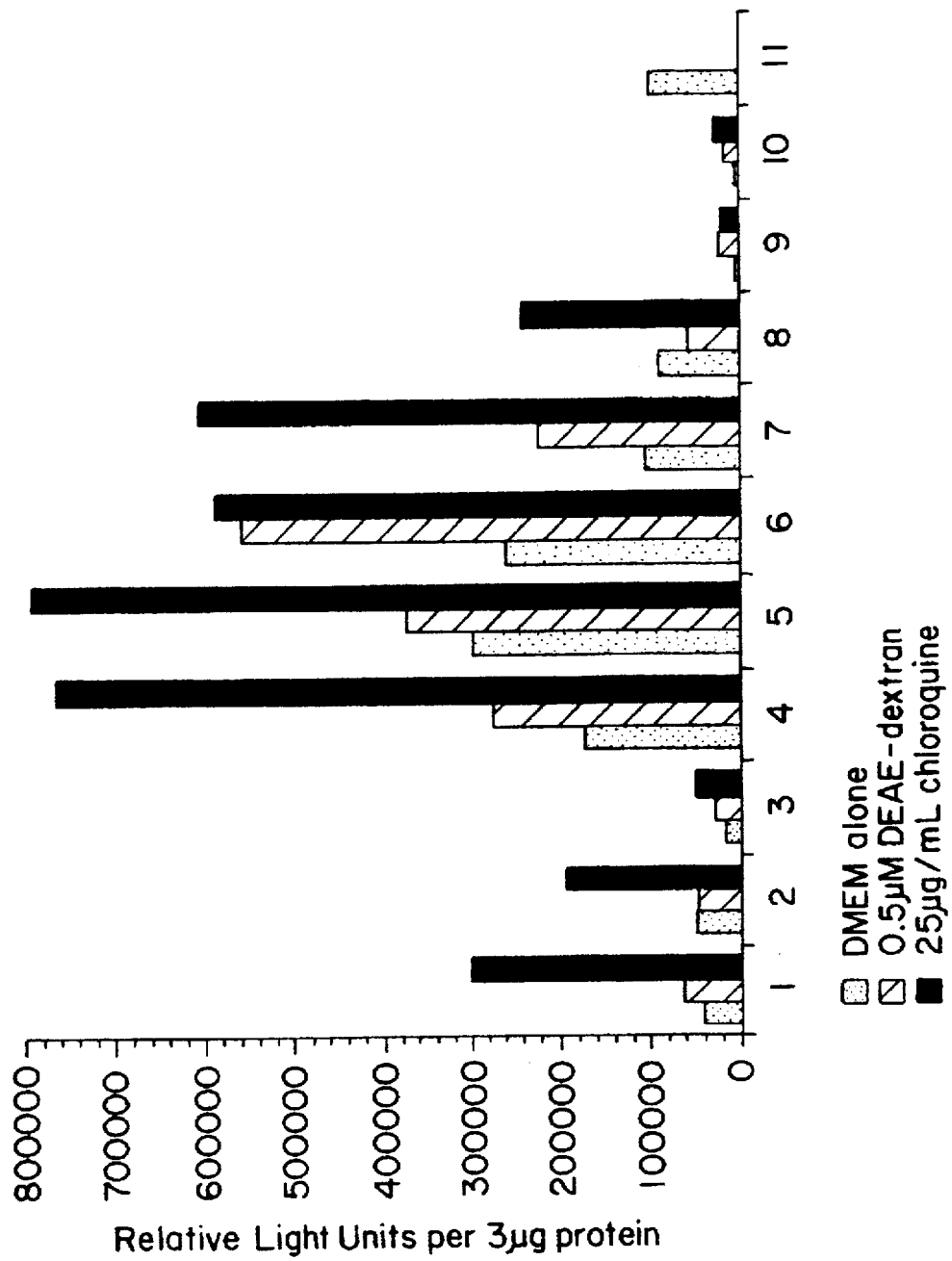

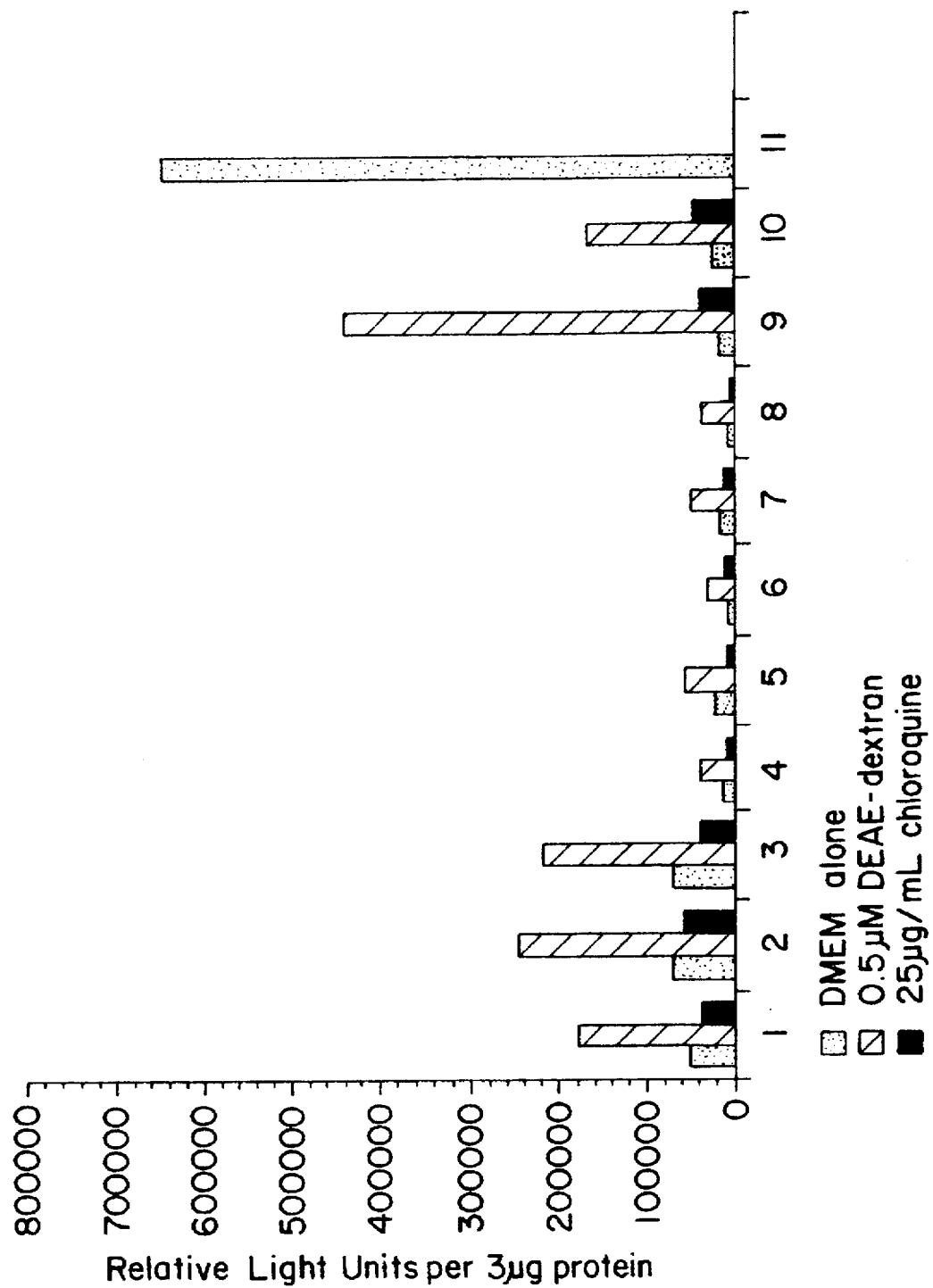

BIOACTIVE AND/OR TARGETED DENDRIMER CONJUGATES

CROSS REFERENCE TO RELATED APPLICATIONS

This application is a continuation-in-part of our applications Ser. No. 316,536, filed Sep. 30, 1994, now abandoned which is a continuation-in-part of our application Ser. No. 207,494, filed Mar. 7, 1994, now abandoned which is a divisional and continuation-in-part of application Ser. No. 043,198, filed Apr. 5, 1993, now U.S. Pat. No. 5,527,524, issued Jun. 18, 1996, which is a continuation-in-part of application Ser. No. 654,851, filed Feb. 13, 1991, now U.S. Pat. No. 5,338,532, issued Aug. 16, 1994, which is a continuation-in-part of application Ser. No. 386,049, filed Jul. 26, 1989, now abandoned, which is a continuation-in-part of application Ser. No. 087,266, filed Aug. 18, 1987, now abandoned, which is a continuation-in-part of application Ser. No. 897,455, filed Aug. 18, 1986, now abandoned. All of these prior application documents are hereby incorporated by reference in their entireties herein.

FIELD OF THE INVENTION

The present invention concerns the use of dense star polymers as carriers for agricultural, pharmaceutical, and other materials, especially those materials which are bioactive and/or targeted. Also included are dendritic polymers as carriers for biological response modifiers, which also may be targeted.

BACKGROUND OF THE INVENTION

In recent years polymers referred to as dense star polymers or STARBURST™ polymers (a trademark of Dendritech Inc.) have been developed. It has been found that the size, shape and properties of these dense star polymers or STARBURST™ polymers can be molecularly tailored to meet specialized end uses. STARBURST™ polymers have significant advantages which can provide a means for the delivery of high concentrations of carried material per unit of polymer, controlled delivery, targeted delivery and/or multiple species delivery or use.

SUMMARY OF THE INVENTION

In one aspect, the present invention is directed to polymer conjugate materials comprising dense star polymers or STARBURST™ polymers associated with desired materials (hereinafter these polymer conjugates will frequently be referred to as "STARBURST™ conjugates" or "dense star polymer conjugates" or "conjugates"), process for preparing these conjugates, compositions containing the conjugates, and methods of using the conjugates and compositions.

Also encompassed is a dense star polymer associated with at least one target director and at least one unit of a carried material. Such conjugates may be formulated with acceptable carriers, diluents or excipients for the use intended, e.g., pharmaceutical or agricultural.

The conjugates of the present invention are suitable for use in a variety of applications where specific delivery is desired, and are particularly suited for the delivery of biologically active agents. In a preferred embodiment of the present invention, the STARBURST™ conjugates are comprised of one or more STARBURST™ polymers associated with one or more bioactive agents.

In one aspect of the invention, a dense star polymer conjugate is used for delivery of a carried bioactive agent (e.g., a biological response modifier), having at least one dense star polymer associated with at least one unit of at least one carried bioactive agent, the polymer having (a) an initiator core, (b) at least two concentric dendritic layers ('generations') with symmetrical branch junctures, the layers extending radially in geometrically progressive fashion from a core branch, whereby the ratio of terminal groups to core branch(s) is at least 4:1, and (c) an exterior surface of terminal functionality.

Preferred conjugates of the present invention include those where a dense star polymer conjugate comprises at least one dense star polymer associated with at least one unit of at least one biological response modifier. Some examples of these biological response modifiers are interleukins, interferons, tumor necrosis factor, granulocyte colony stimulating factor, viruses, viral fragments and other genetic materials. The term "genetic material" as used herein refers to nucleotide based materials, including without limitation, viruses and viral fragments, plasmids, phages, cosmids, genes and gene fragments (i.e., exons, introns), deoxyribonucleic acid (DNA) both single and double stranded, ribonucleic acid (RNA), ribosomal RNA (rRNA), catalytic RNA (cRNA), small nuclear RNA (snRNA), messenger RNA (mRNA), transfer RNA (tRNA), DNA and RNA oligonucleotides (both single and double stranded) or oligomers and (anti-sense) oligonucleotides, protein nucleic acids (PNA), and substituted nucleic acid oligonucleotides. Genetic material, especially viruses and viral fragments, may be complexed or coupled with some protein. The term genetic material is also intended to include "modified nucleotides" as described more fully below.

The STARBURST™ conjugates offer significant benefits over other carriers known in the art due to the advantageous properties of the STARBURST™ polymers. STARBURST™ polymers are a particular type of dendritic polymer. However, in the broader aspects of the present invention, where a biological response modifier (especially genetic material) is the carried material, other types of dendritic polymers can be used.

A "dendritic polymer" is a polymer exhibiting regular dendritic branching, formed by the sequential or generational addition of branched layers to or from a core. The term dendritic polymer encompasses "dendrimers," which are characterized by a core, at least one interior branched layer, and a surface branched layer. (See Petar R. Dvornic and Donald A. Tomalia in *Chem. in Britain*, 641–645, August 1994.) A "dendron" is a species of dendrimer having branches emanating from a focal point which is or can be joined to a core, either directly or through a linking moiety to form a dendrimer. Many dendrimers comprise two or more dendrons joined to a common core. However, the term dendrimer is used broadly to encompass a single dendron.

Dendritic polymers include, but are not limited to, symmetrical and unsymmetrical branching dendrimers, cascade molecules, arborols, and the like, though the most preferred dendritic polymers are dense star polymers. The PAMAM dense star dendrimers disclosed herein are symmetric, in that the branch arms are of equal length. The branching occurs at the hydrogen atoms of a terminal —NH$_2$ group on a preceding generation branch. The lysine-based dendrimers are unsymmetric, in that the branch arms are of a different length. One branch occurs at the epsilon nitrogen of the lysine molecule, while another branch occurs at the alpha nitrogen, adjacent to the reactive carboxy group which attaches the branch to a previous generation branch.

Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

STARBURST™ polymers exhibit molecular architecture characterized by regular dendritic branching with radial symmetry, i.e., at the point of branching. These radially symmetrical molecules are referred to as possessing "STARBURST™ topology." These polymers are made in a manner which can provide concentric dendritic tiers around an initiator core. The STARBURST™ topology is achieved by the ordered assembly of organic repeating units in concentric, dendritic tiers around an initiator core; this is accomplished by introducing multiplicity and self-replication (within each tier) in a geometrically progressive fashion through a number of molecular generations. The resulting highly functionalized molecules have been termed "dendrimers" in deference to their branched (tree-like) structure as well as their oligomeric nature. Thus, the terms STARBURST™ oligomer and STARBURST™ dendrimer and dense star dendrimer are encompassed within the term STARBURST™ polymer or dense star polymer.

Topological polymers, with size and shape controlled domains, are dendrimers that are associated with each other (as an example covalently bridged or through other association as defined hereafter) through their reactive terminal groups, which are referred to as STARBURST™ "bridged dendrimers." The term bridged dendrimer is also encompassed within the term "STARBURST™ polymer" or dense star polymer. When more than two dense star dendrimers are associated together they are referred to as "STARBURST™ aggregates" or "dense star aggregates" and are also encompassed within the term "STARBURST™ polymer" or dense star polymer.

Therefore, dendritic polymers include bridged dendrimers and dendrimer aggregates. Dendritic polymers encompass both generationally monodisperse and generationally polydisperse solutions of dendrimers. The dendrimers in a monodisperse solution are substantially all of the same generation, and hence of uniform size and shape. The dendrimers in a polydisperse solution comprise a distribution of different generation dendrimers.

Dendritic polymers also encompass surface modified dendrimers. For example, the surface of a PAMAM dendrimer may be modified by the addition of an amino acid, e.g., lysine or arginine.

It should be understood that reference to any particular type of dendritic polymer as a "polymer," e.g., a "dense star polymer," an "unsymmetrical dendritic polymer," a "cascade polymer" is also intended to encompass bridged dendrimers of that type, dendrimer aggregates of that type, polydisperse dendrimers of that type, and surface modified dendrimers of that type.

Dendritic polymer conjugates of biological response modifiers are useful in a wide variety of therapeutic and diagnostic applications. For example, dendritic polymer conjugates of biological response modifiers comprising genetic materials have broad applicability in the fields of gene therapy, analysis, modification, activation, anti-sense applications and the like; and dendritic polymer conjugates of biological response modifiers comprising non-genetic materials such as proteins (e.g., interleukins, interferons, tumor necrosis factor, granulocyte colony stimulating factor, and other proteins) are useful as therapeutic agents (e.g., antiviral agents) and diagnostic agents.

Thus, encompassed are: a composition which comprises a complex of dendritic polymer with genetic material, optionally in solution with DEAE-dextran; and a composition which comprises a complex of a first dendritic polymer and genetic material, which has been placed in a solution containing a second dendritic polymer, said second dendritic polymer being larger than said first dendritic polymer.

Also encompassed within the present invention is a process to make these conjugates. For example, a process for preparing a conjugate of a dendritic polymer and biological response modifier comprises reacting the dendritic polymer with the biological response modifier in a suitable solvent at a temperature which facilitates the association of the biological response modifier and the dendritic polymer. When the biological response modifier is genetic material then a complex is prepared by: (1) reacting said dendritic polymer with said genetic material in a suitable solvent at a temperature which facilitates the complexing of said genetic material with said dendritic polymer, said process optionally including placing said complex in a solution with DEAE-dextran; or (2) complexing genetic material with a first dendritic polymer by reacting the polymer with the genetic material in a suitable solvent at a temperature which facilitates association of the genetic material with the polymer, then placing said complex in a solution containing a second dendritic polymer, said second dendritic polymer being larger than said first dendritic polymer. More specifically, with respect to process (1) above, 1 to 10 µg of genetic material per mL or per 20 µL, depending on the concentration desired, is reacted with sufficient dendritic polymer at a pH of about 5 to 10 and at a temperature of about 20° to 40° C. to yield genetic material:dendritic polymer complex in a charge ratio of about 3:1 to about 1:10,000. A more complete discussion of the processes are provided below.

Methods for the use of these conjugates include effecting cell transfection and bioavailability of genetic material comprising providing a complex of a dendritic polymer and genetic material, and making said complex available to cells to be transfected. The complexing stabilizes and contracts the genetic material, protects the genetic material from digestion during transit to and transfection into a cell, and facilitates transporting of genetic material through a cellular membrane and into a cell, including into a cellular nucleus.

Also included as methods of the present invention are: the transporting of genetic material through a cellular membrane and into a cellular nucleus comprising complexing genetic material with dendritic polymer, followed by making said complex available to cells to be transfected; and protecting genetic material from digestion during transit to and transfection into a cell comprising complexing said genetic material with dendritic polymer prior to exposing said genetic material to digestive enzymes; and stabilizing and contracting genetic material comprising complexing said genetic material with a dendritic polymer.

BRIEF DESCRIPTION OF THE DRAWINGS

The following description of the figures aid in understanding the present invention.

FIG. 2(A) depicts a dendrimer having unsymmetrical (unequal) branch junctures.

FIG. 2(B) depicts a dendrimer having symmetrical (equal) branch junctures.

Example 1. The vertical axis is the time (seconds), and the horizontal axis is the generation of added PAMAM STARBURST™ dendrimer.

Figure 5:
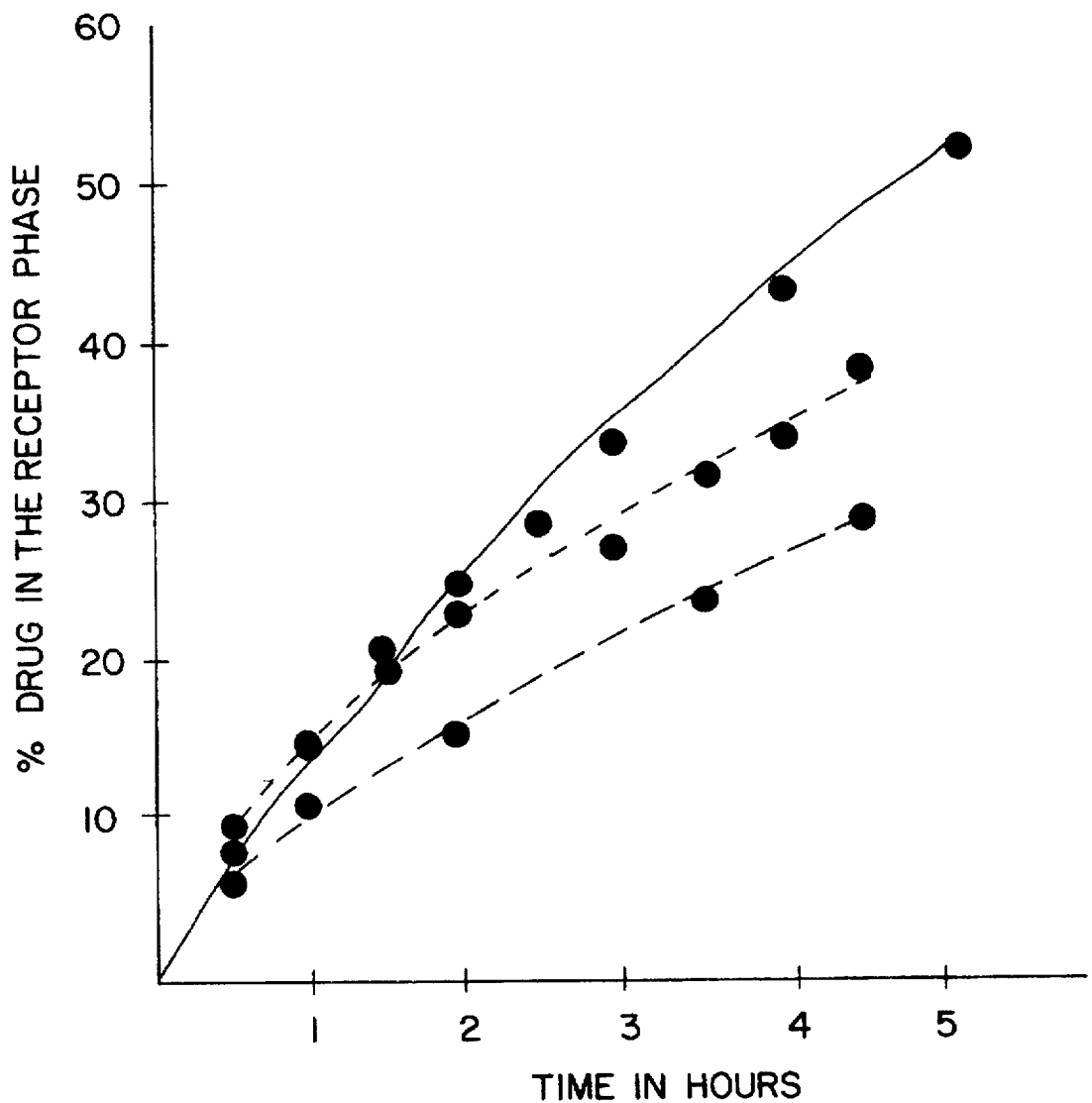

FIG. 5 shows the results of the dynamic analysis of Example 2. The vertical axis is the percent (%) drug in the receptor phase, and the horizontal axis is the time (hours).

Figure 6:
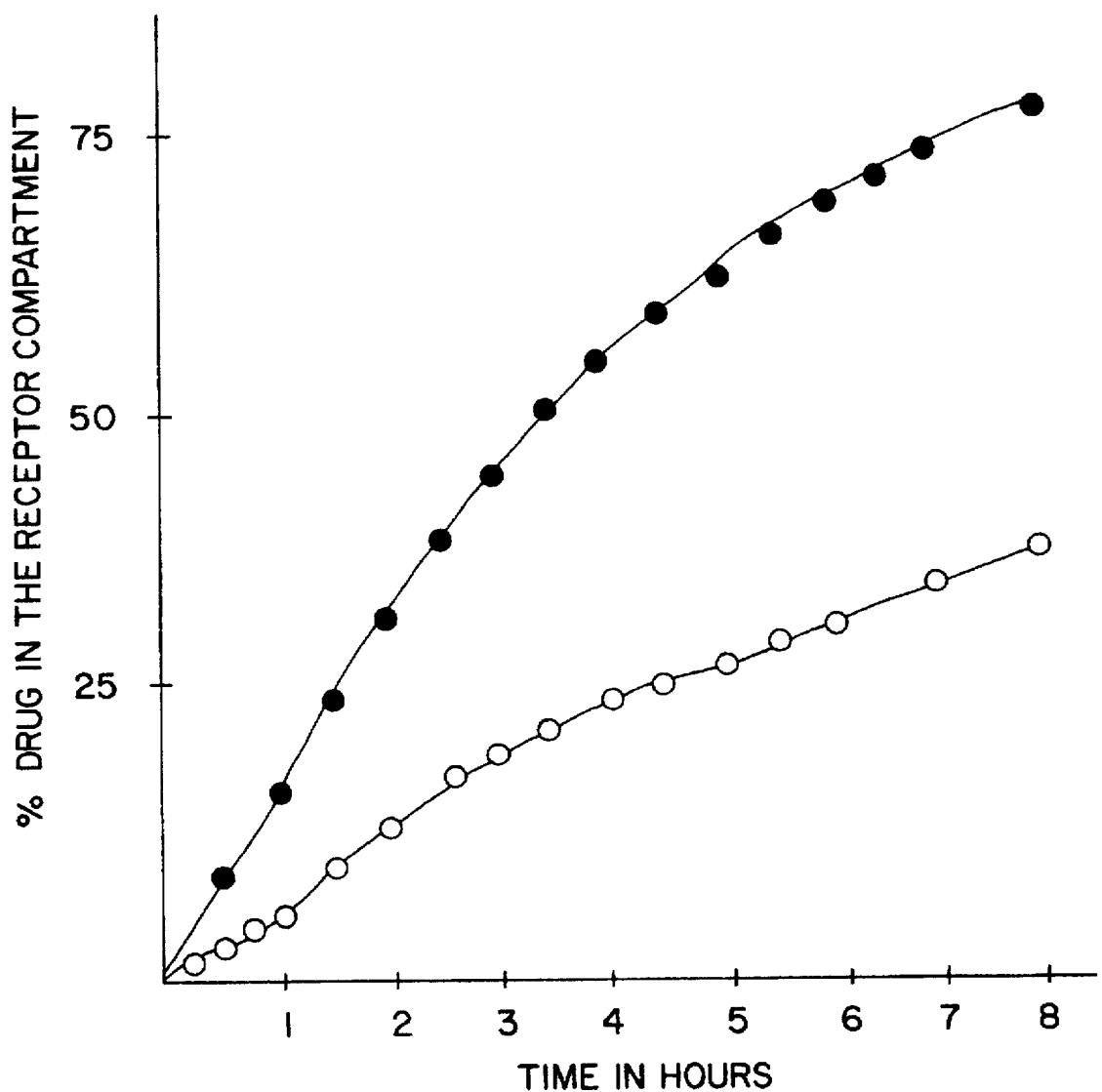

FIG. 6 shows the influence of generation 6.5 dendrimer on the dialysis rate of pseudoephedrine at pH 9.5 from Example 2. The vertical axis is the percent (%) drug in the receptor compartment, and the horizontal axis is the time (hours).

Figure 7:
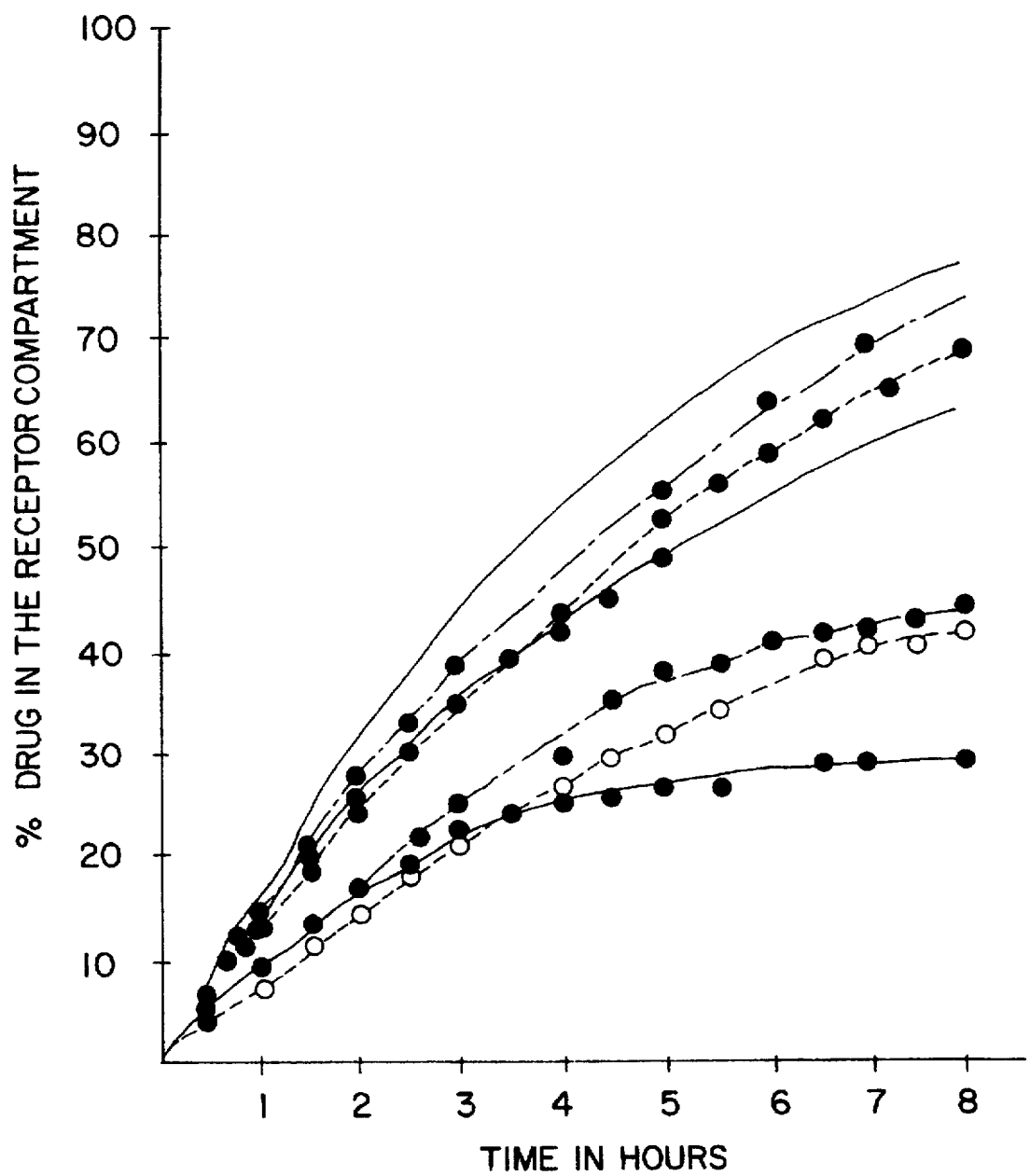

FIG. 7 shows the effect of dendrimer hydrolysis on the permeability of pseudoephedrine of Example 3. The vertical axis is the percent (%) drug in the receptor compartment, and the horizontal axis is the time (hours).

Figure 8:
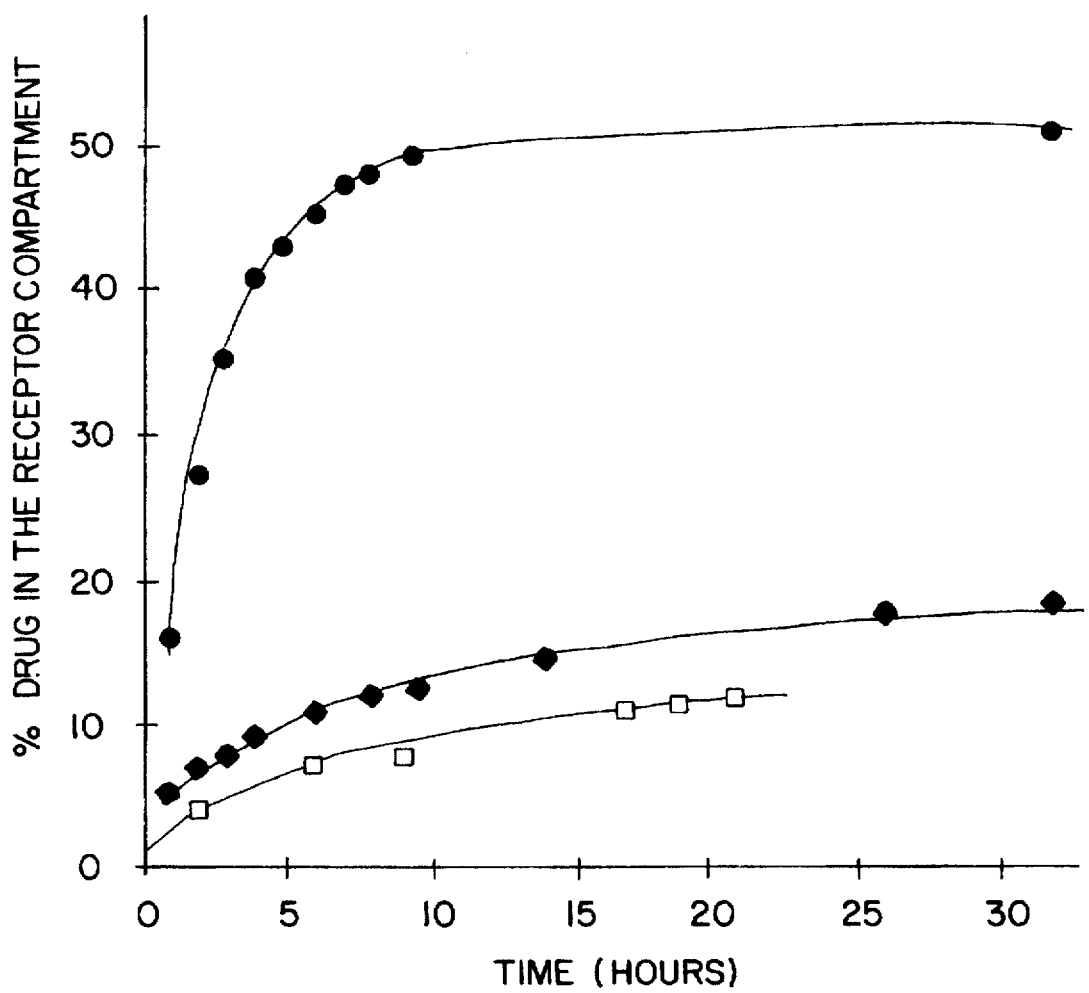

FIG. 8 shows the comparison of percent salicylic acid released into the receptor compartment in the presence of STARBURST™ polymer (Gen=4.0) at pH 5.0 and 6.65 with salicylic acid control, Example 4. The vertical axis is the percent (%) drug in the receptor compartment, and the horizontal axis is the time (hours).

Figure 9:
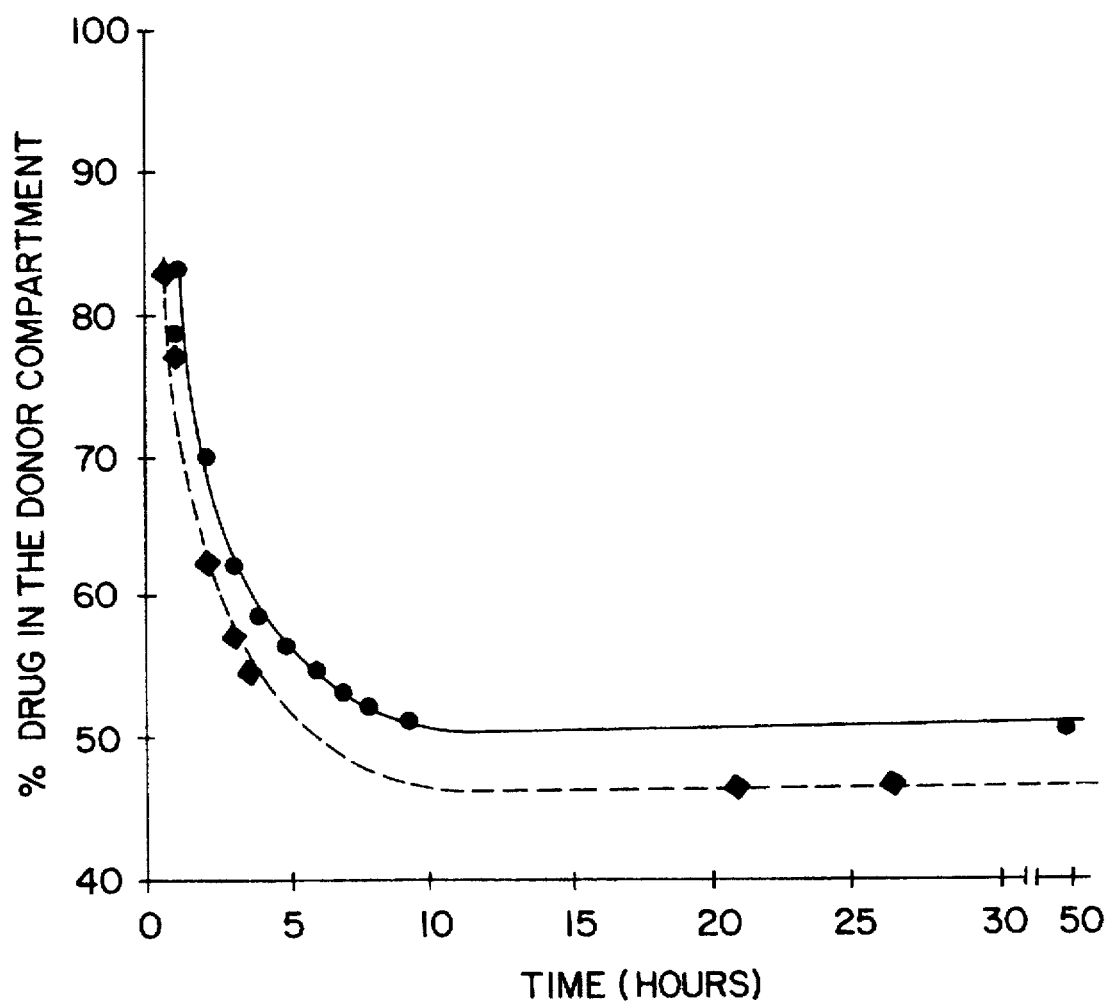

FIG. 9 shows the comparison of percent salicylic acid lost from donor compartment with STARBURST™ polymer (Gen=4.0) in receptor compartment at pH 8.0 to salicylic acid content, Example 4. The vertical axis is the percent (%) drug in the donor compartment, and the horizontal axis is the time (hours).

Figure 10:
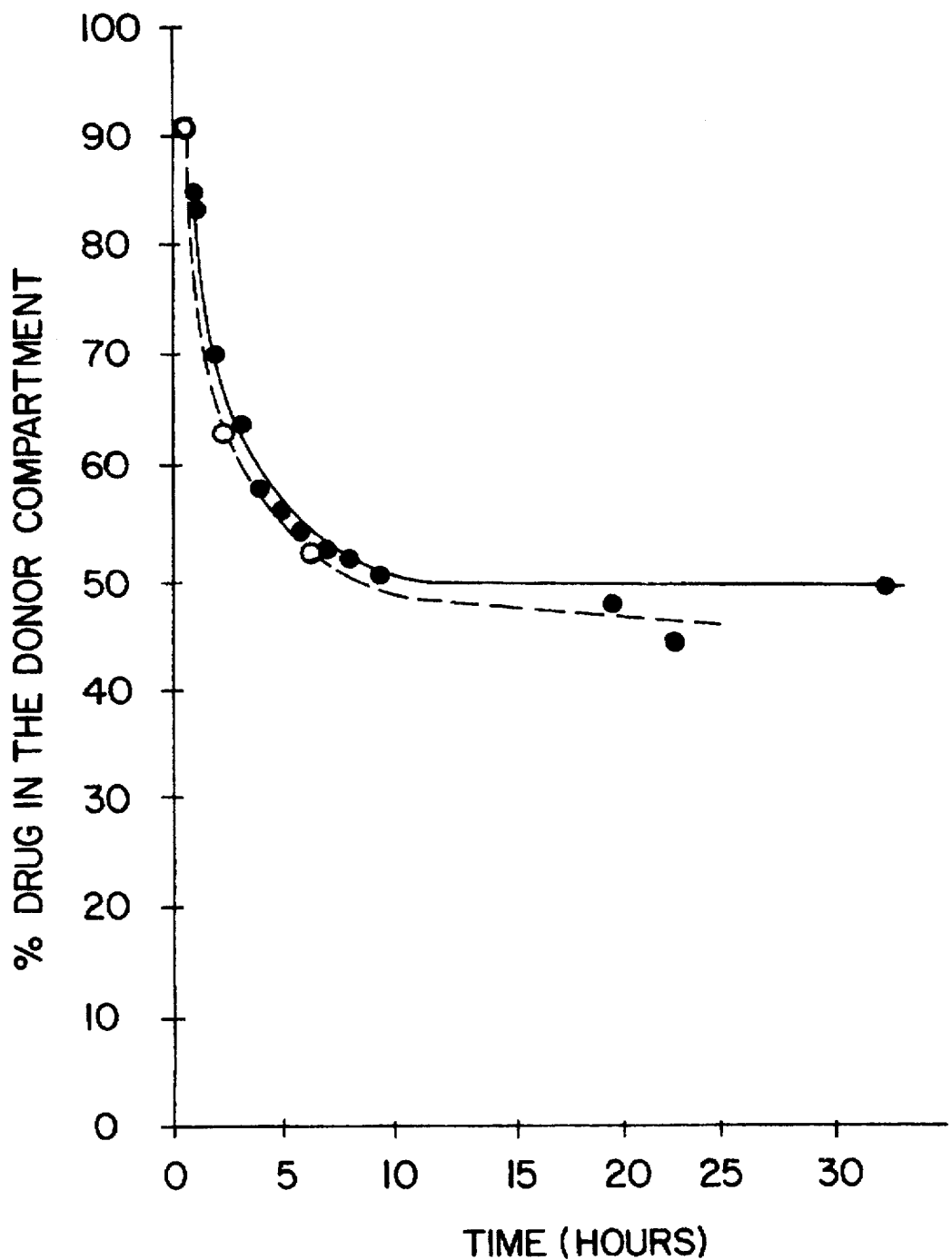

FIG. 10 shows the comparison of percent salicylic acid lost from donor compartment in presence of STARBURST™ polymer (Gen=4.5) to salicylic acid control, Example 4. The vertical axis is the percent (%) drug in the donor compartment, and the horizontal axis is the time (hours).

Figure 11:
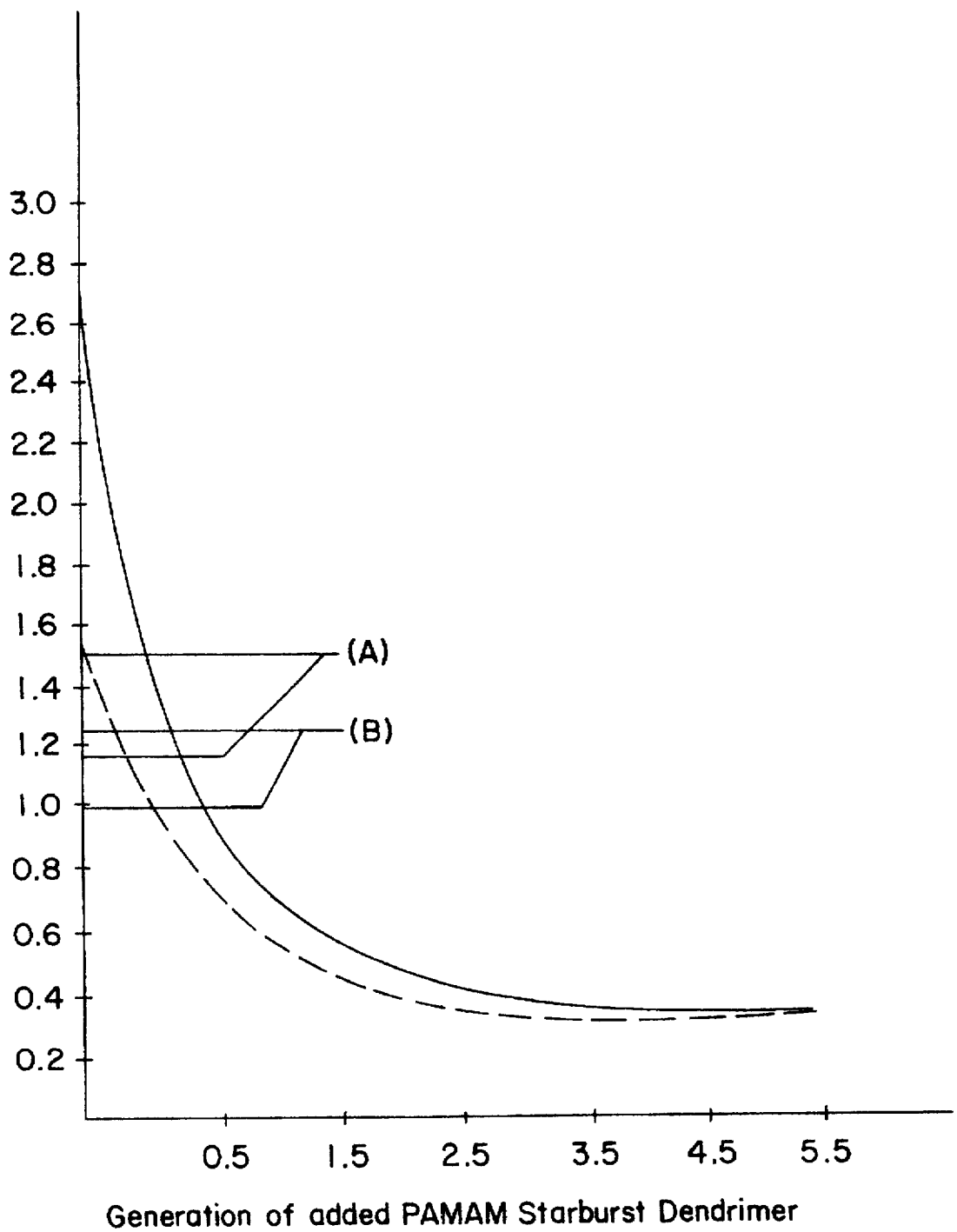

FIG. 11 shows carbon-13 spin lattice relaxation times ($T_1$) for 2,4-D incorporated into various dendrimer generations, Example 15. The vertical axis is the time (seconds), and the horizontal axis is the generation of added PAMAM STARBURST™ dendrimer.

Figure 12:
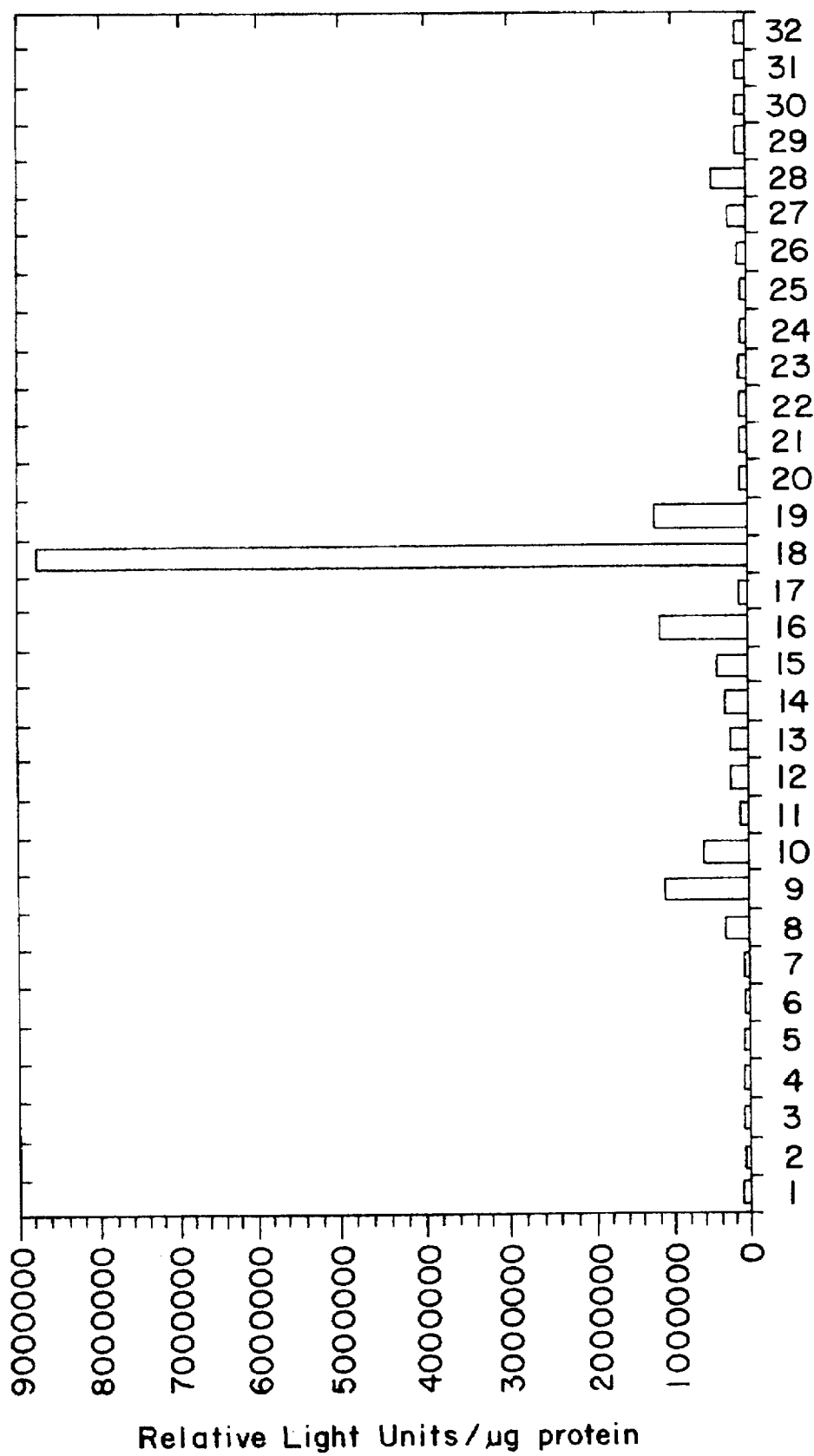

FIG. 12 is a bar graph comparing the DNA transfection ability of dendrimers at different DNA:dendrimer charge ratios, by examining luciferase activity after transfection, Example 44. The vertical axis is the relative light units/μg of protein and the numbers on the horizontal axis are the sample numbers (outlined in Example 44) for control and different dendrimer and DNA complexes at different DNA to dendrimer charge ratios, as listed in Table XV.

Figure 13:
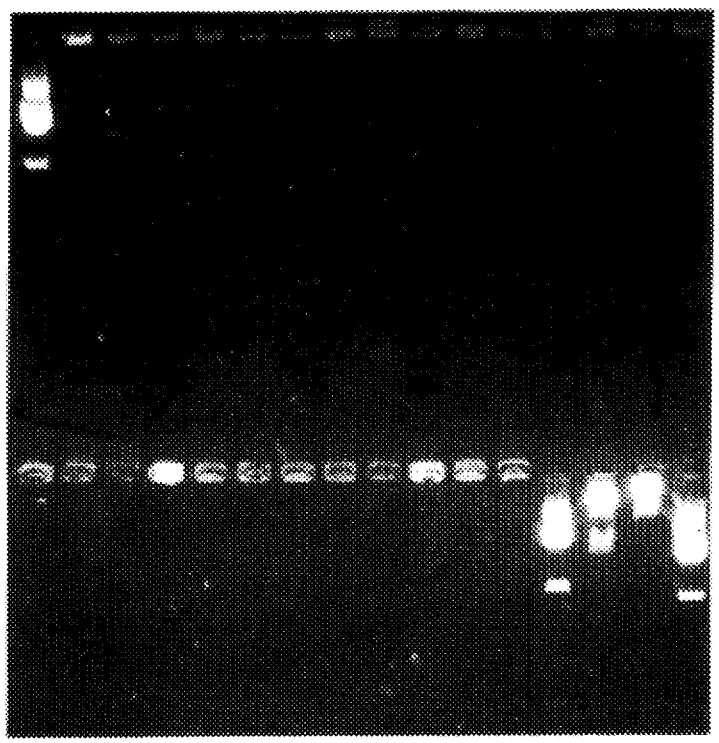

FIG. 13 is an electrophoretic gel comparing the DNA binding ability of dendrimers at different DNA:dendrimer charge ratios, using the same DNA:dendrimer complexes as were used in FIG. 12, Example 44.

Figure 14:
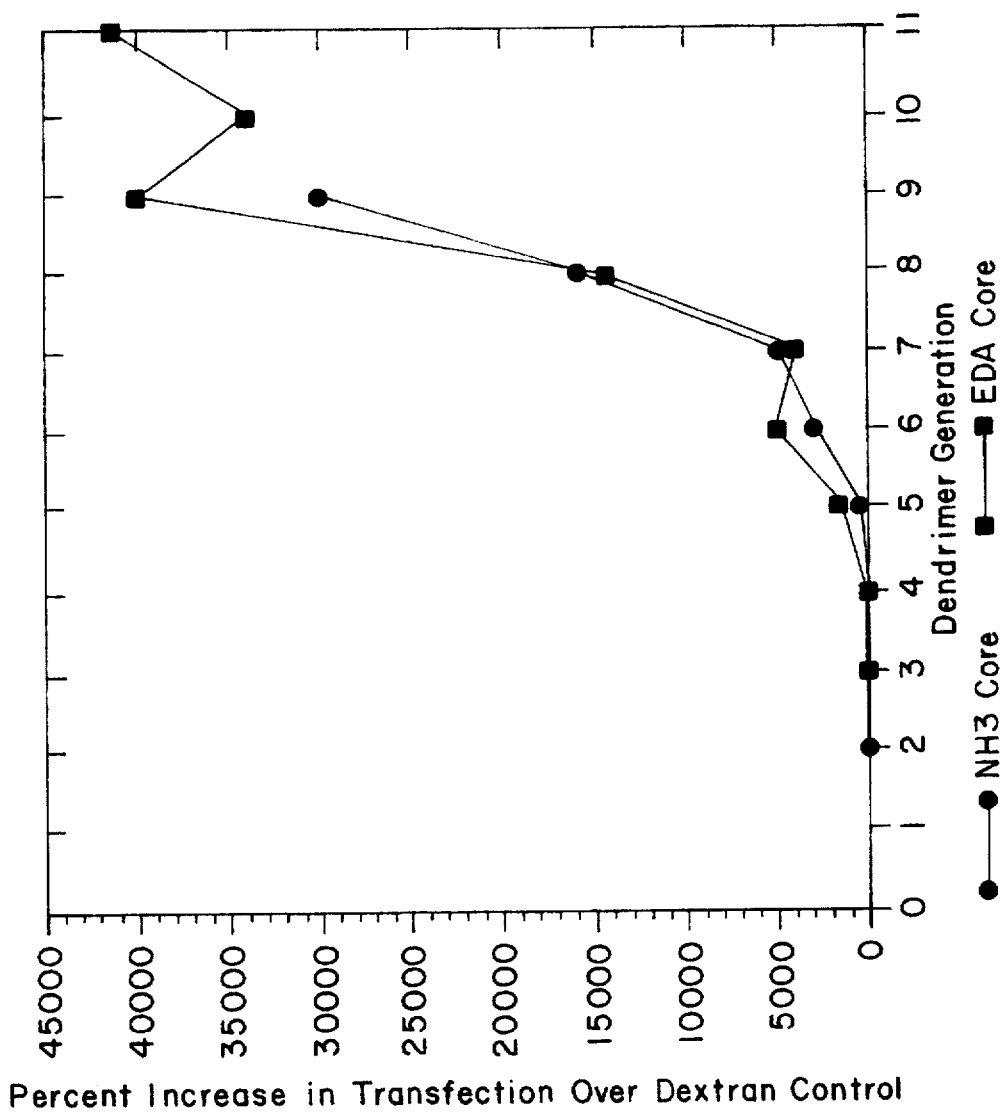

FIG. 14 is a graph charting the percent increase in transfection over a control against the generation of the dendrimer used in the DNA:dendrimer complex, Example 45. The vertical axis is the percent increase in transfection over dextran control, and the horizontal axis is the dendrimer generation. The solid circles are ammonia ($NH_3$) core dendrimers and the solid squares are ethylenediamine (EDA) core dendrimers.

Figure 15:
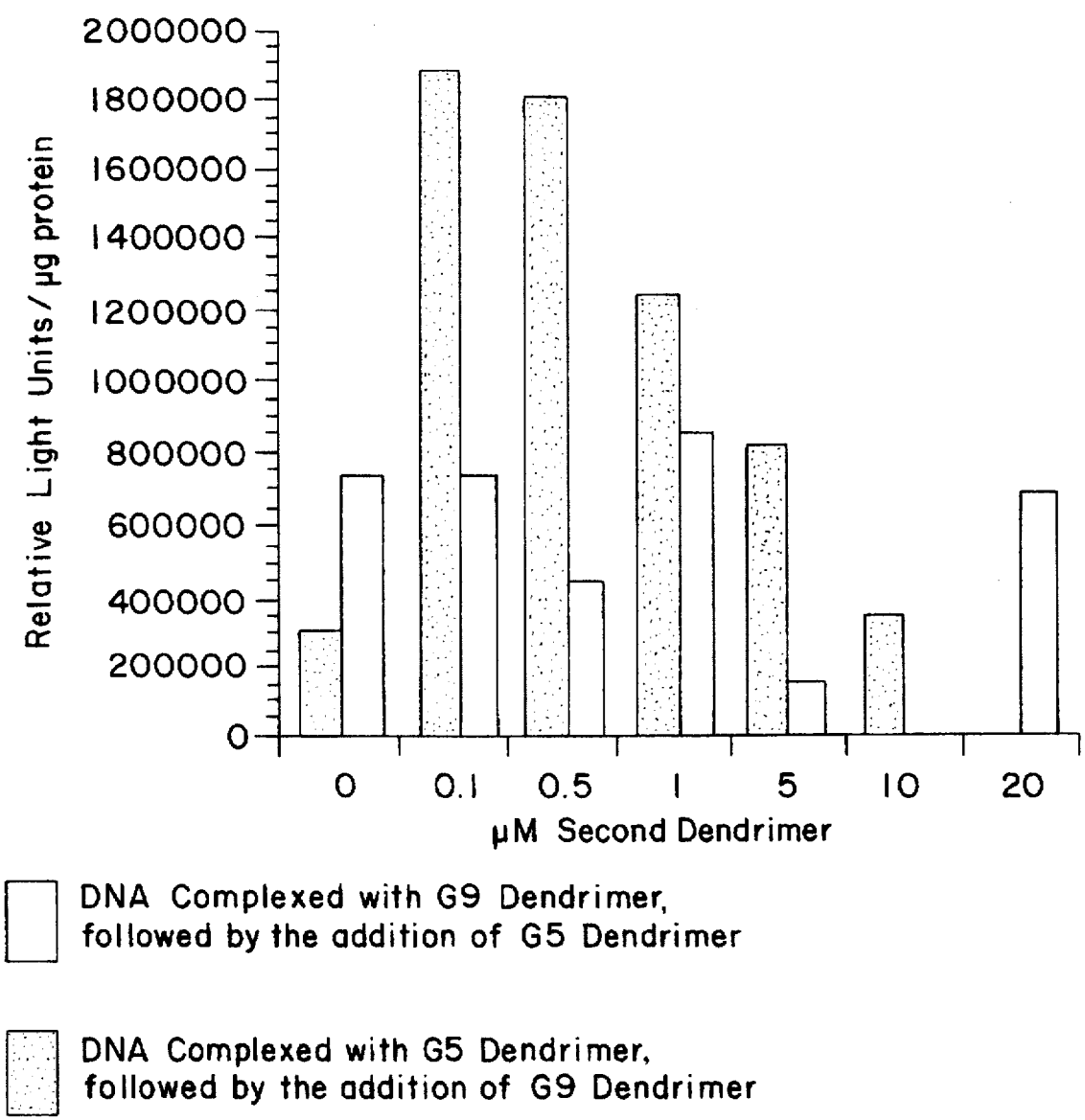

FIG. 15 is a bar graph comparing the impact of order of addition of diverse dendrimers to a DNA dendrimer complex on transfection efficiency in RAT2 cells for ethylenediamine (EDA) core dendrimers, Example 46. The vertical axis is the relative light units/μg of protein, and the horizontal axis is the concentration (μM) of the second dendrimer. The open bars are the results for DNA complexed with G9 dendrimer, followed by the addition of G5 dendrimer. The diagonally hatched bars are the results for DNA complexed with G5 dendrimer, followed by the addition of G9 dendrimer.

Figure 16:
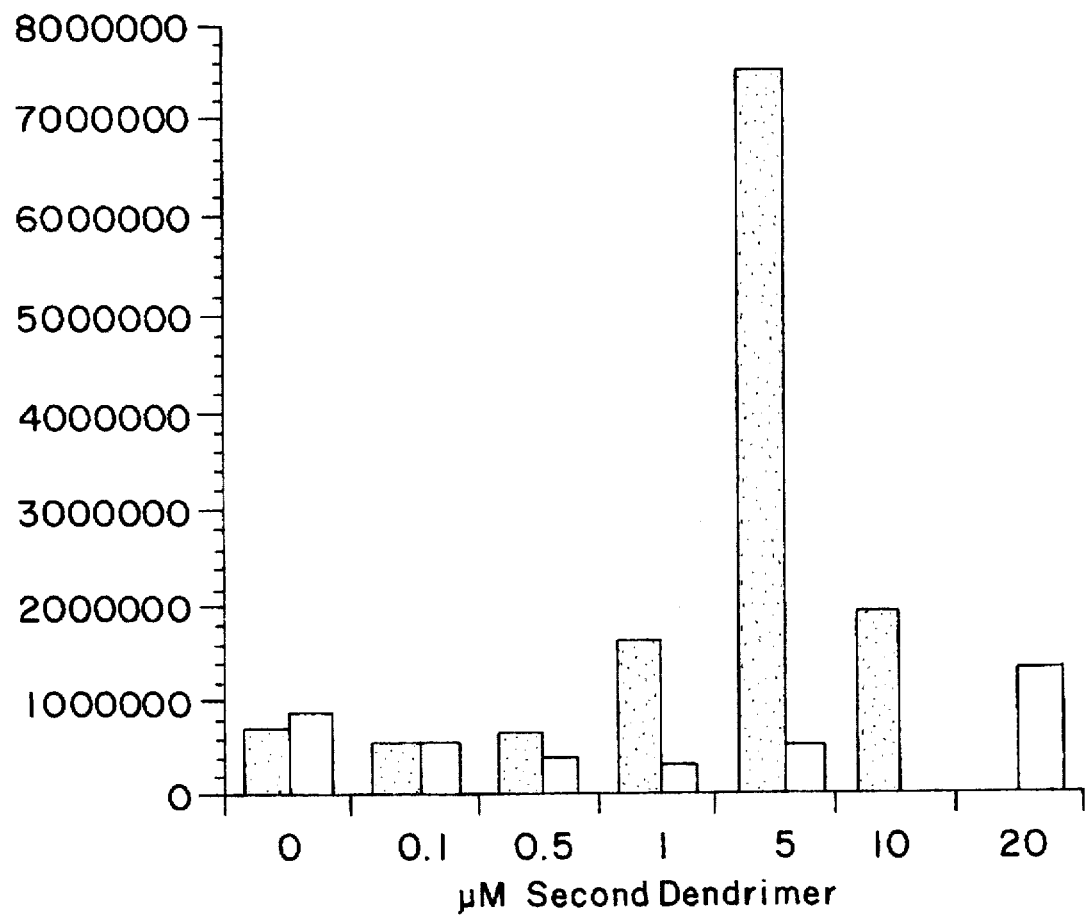

FIG. 16 graphs the same information as FIG. 15, but for ammonia ($NH_3$) core dendrimers, Example 46. The vertical axis is the relative light units/μg of protein, and the horizontal axis is the concentration (μM) of the second dendrimer. The open bars are the results for DNA complexed with G9 dendrimer, followed by the addition of G5 dendrimer. The diagonally hatched bars are the results for DNA complexed with G5 dendrimer, followed by the addition of G9 dendrimer.

Figure 17:
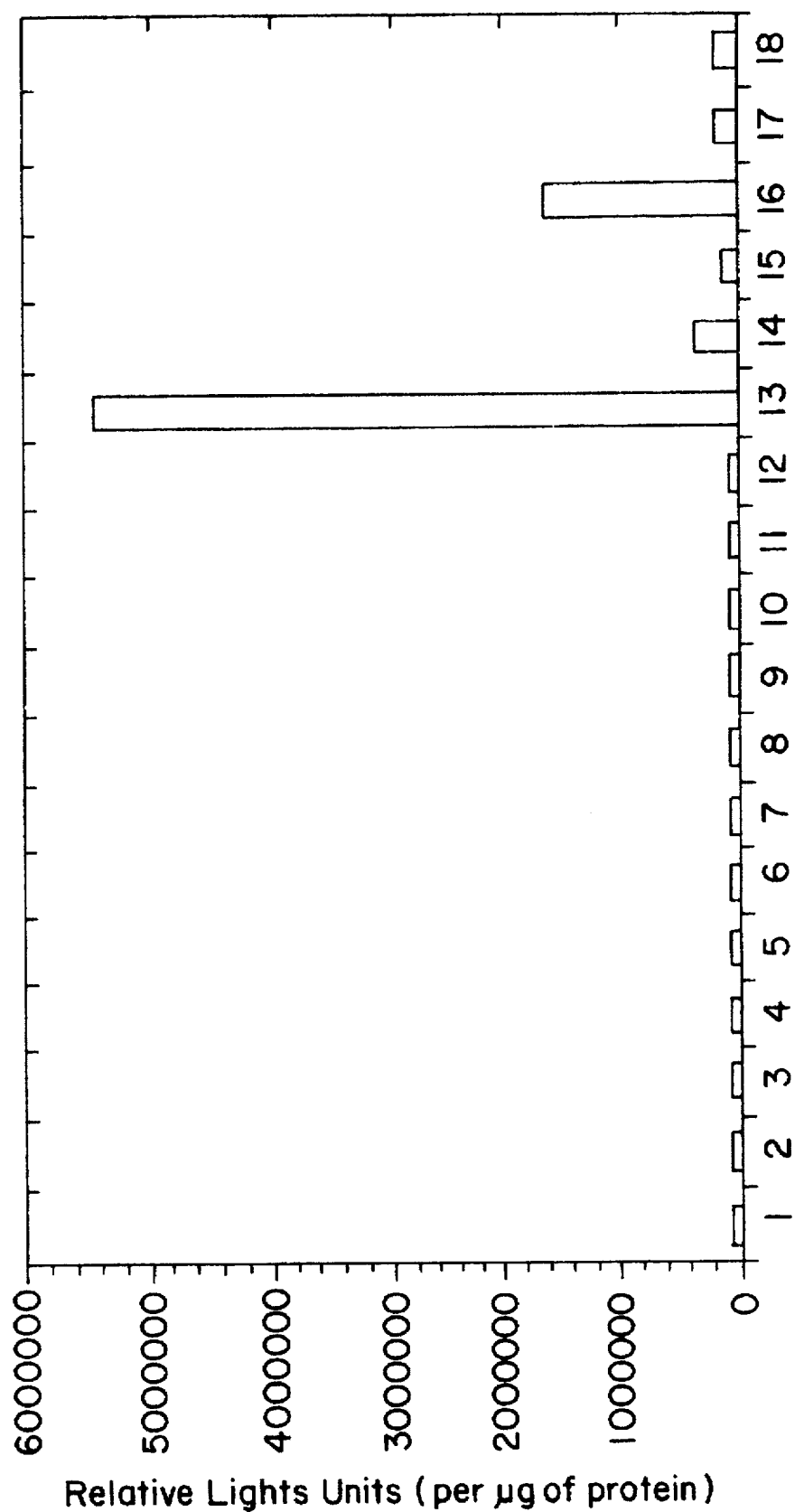

FIG. 17 graphs light units per μg of protein following transfections performed with various DNA-dendrimer conjugates and controls under different conditions, Example 42. The vertical axis is the relative light units/μg of protein and the numbers on the horizontal axis are the sample numbers for the controls and different DNA:dendrimer complexes at varying DNA to dendrimer ratios, as listed in Table XIII.

Figure 18:
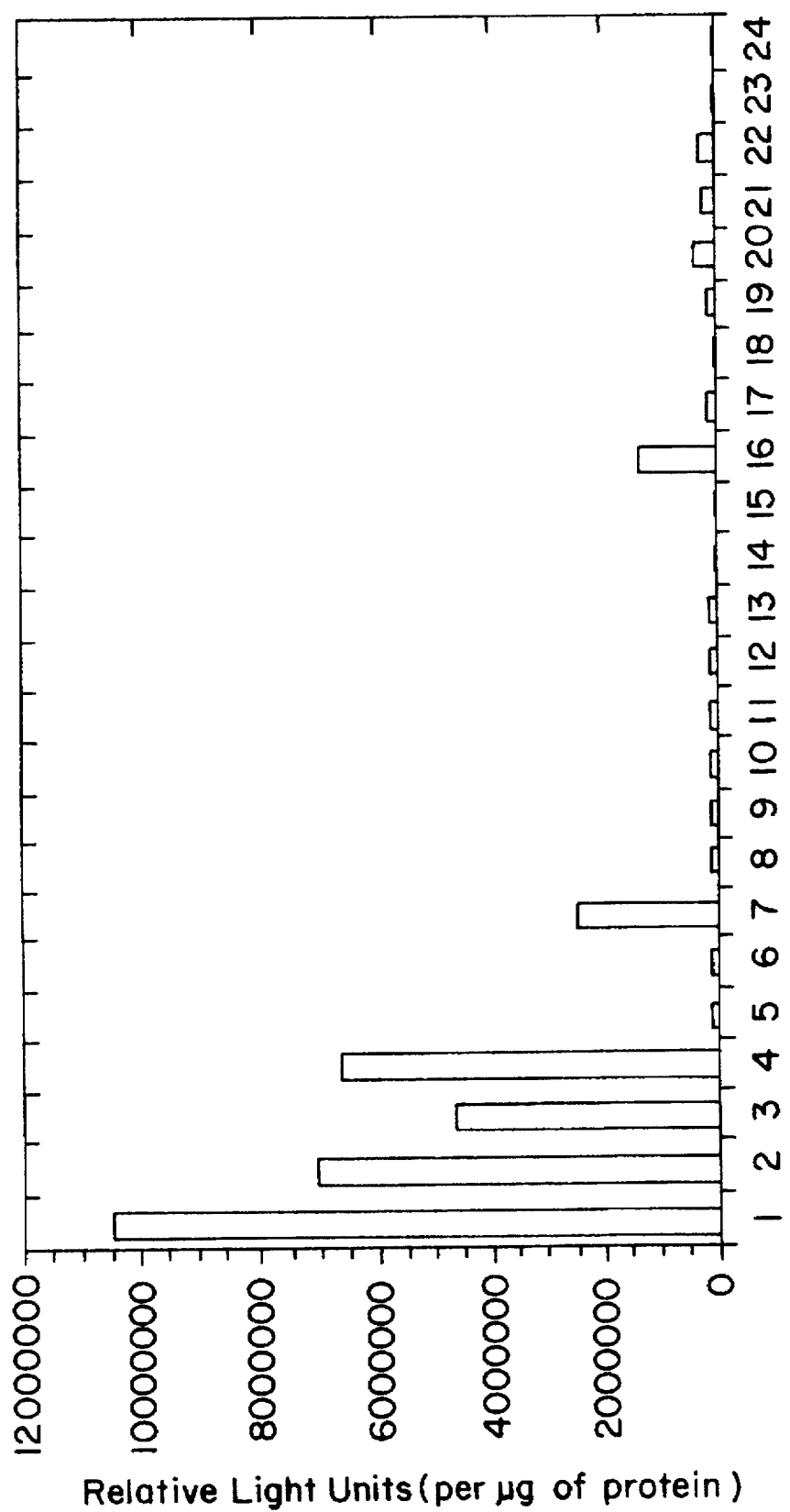

FIG. 18 is similar to FIG. 17, but graphs data for a wider variation in dendrimer:DNA ratios, Example 42. The vertical axis is the relative light units/μg of protein and the numbers on the horizontal axis are the sample numbers for the controls and different DNA:dendrimer complexes at varying DNA to dendrimer ratios, as listed in Table XIV.

Figure 19:
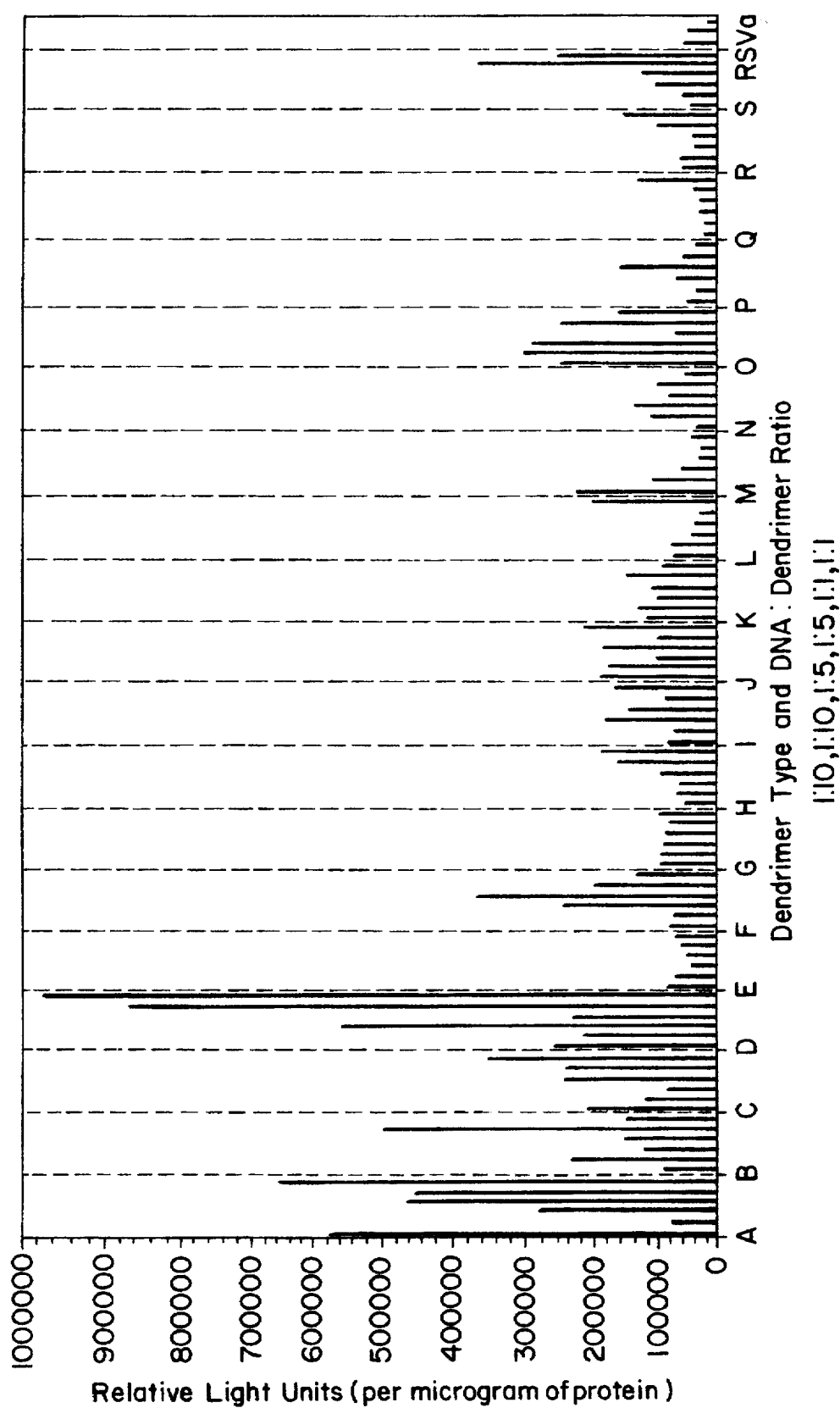

FIG. 19 is a bar graph of relative light units per μg of protein for transfection of dendrimer:DNA conjugate for dendrimers A–S, Example 42. The vertical axis is the relative light units/μg of protein and the horizontal axis is dendrimer used and DNA:dendrimer ratio within each segment of the axis of 1:2, 1:2, 1:10, 1:10, 1:20 and 1:20.

Figure 20:
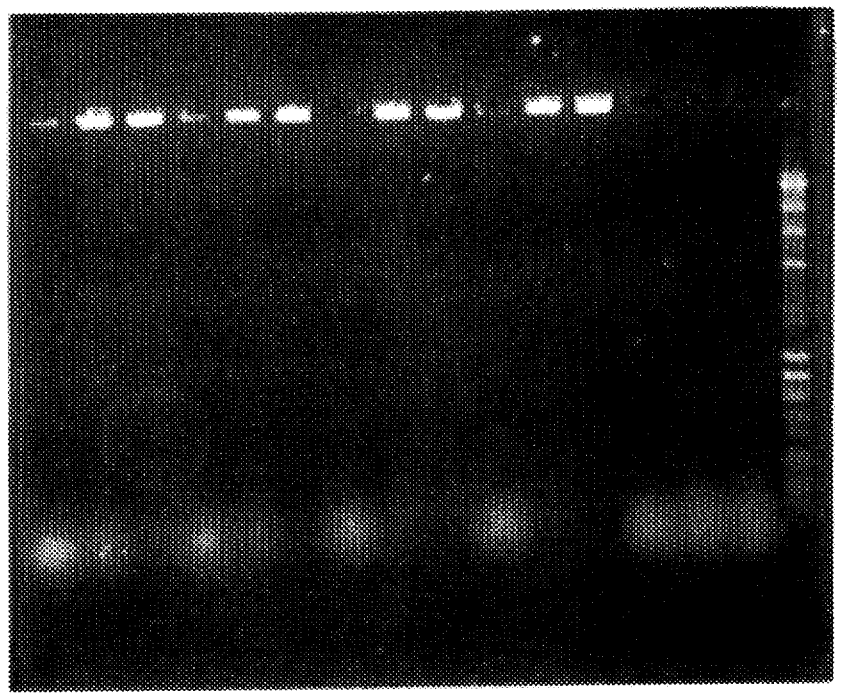

FIG. 20 is an electrophoretic gel comparing the complexing properties of several ammonia ($NH_3$) core dendrimers with 15 nucleotide long, synthetic single-stranded DNA, Example 47.

Figure 21:
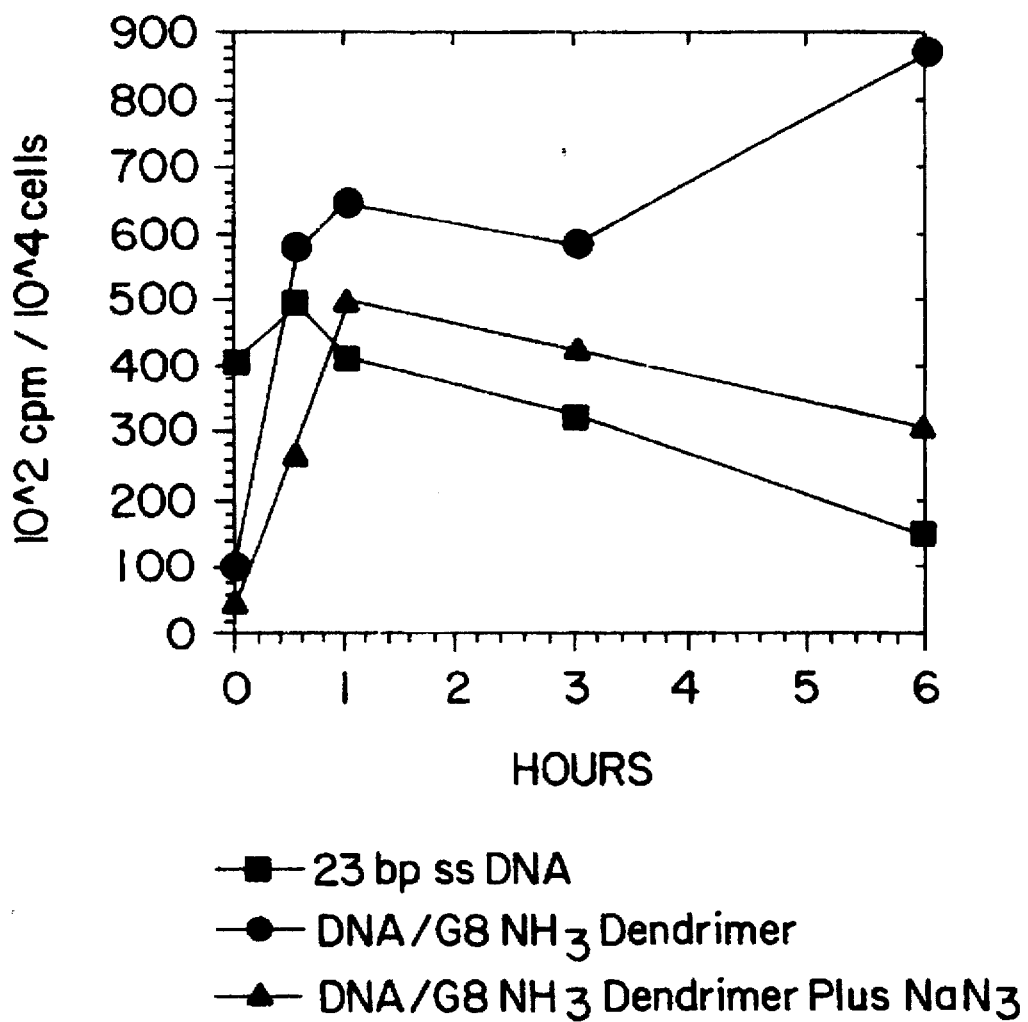

FIG. 21 charts the uptake of a radiolabeled 23 nucleotide long synthetic double stranded oligomer into a monocytic cell line over time, comparing transfection of the DNA alone, transfection of the DNA complexed with a generation 8 (G8) ammonia ($NH_3$) core dendrimer [i.e., G8 ($NH_3$) dendrimer] and transfection of the DNA-dendrimer complexes in the presence of sodium azide, Example 47. The vertical axis is the uptake in $10^2$ cpm/$10^4$ cells and the horizontal axis is time (hours). The solid squares represent the 23 nucleotide long synthetic single stranded oligomer; the solid circles represent DNA/G8 ($NH_3$) dendrimer; and the solid triangles represent DNA/G8 ($NH_3$) dendrimer plus sodium azide.

Figure 22:
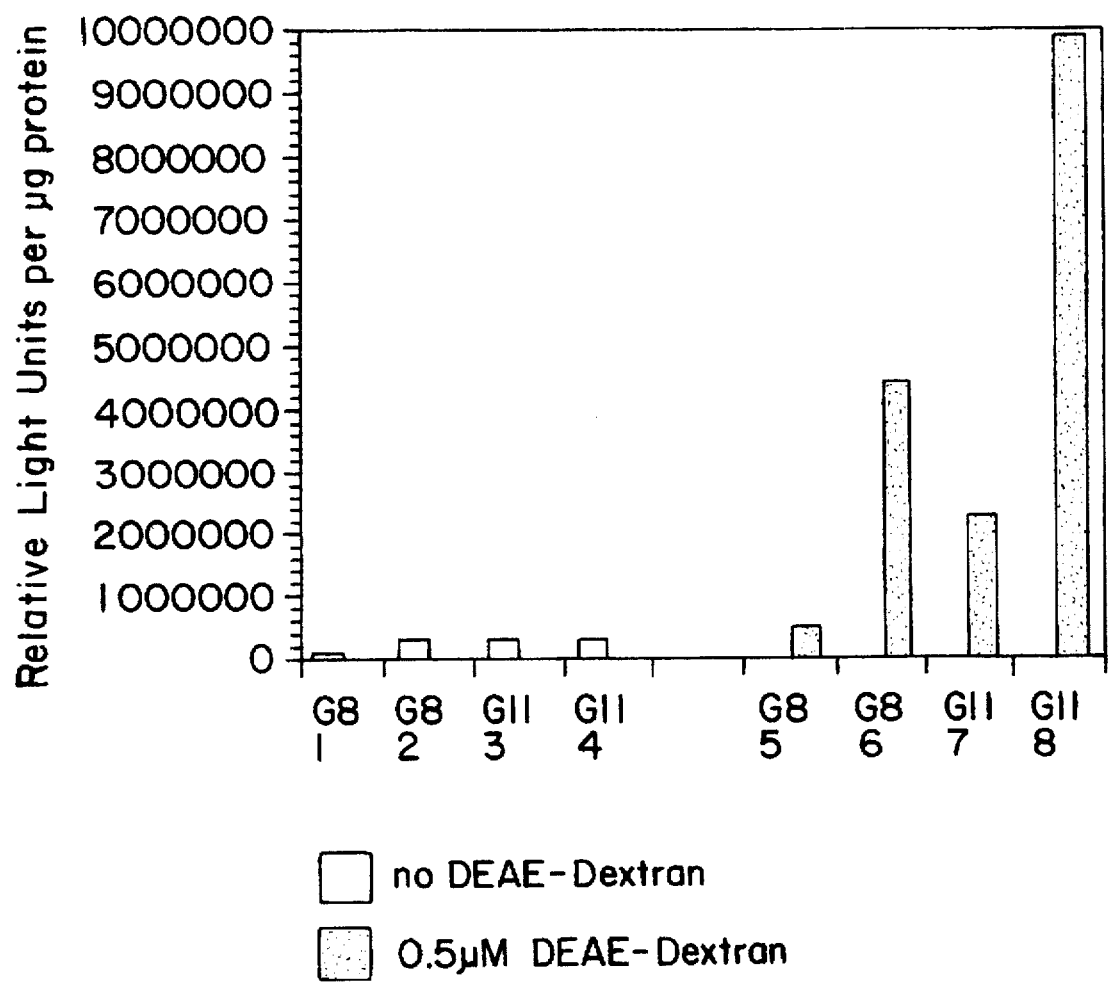
Figure 23A:
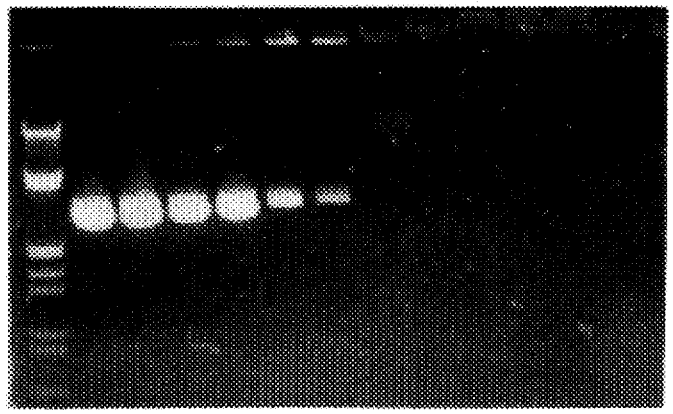
Figure 23B:
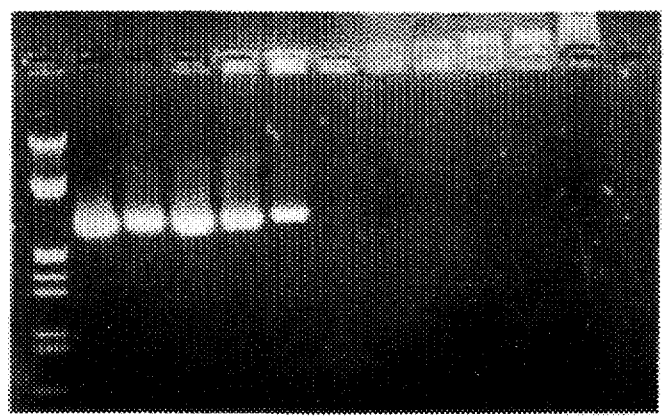
Figure 23C:
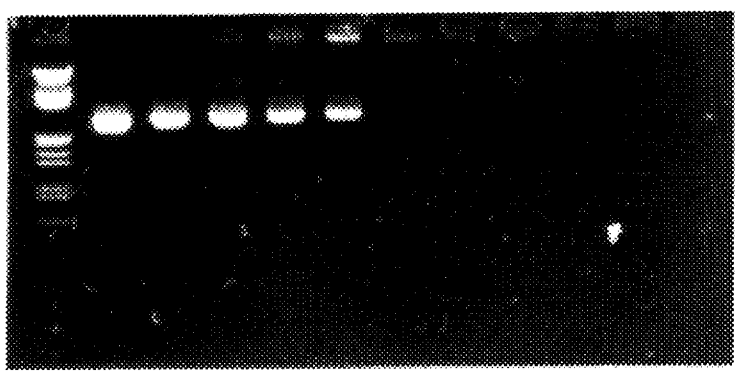
Figure 23D:
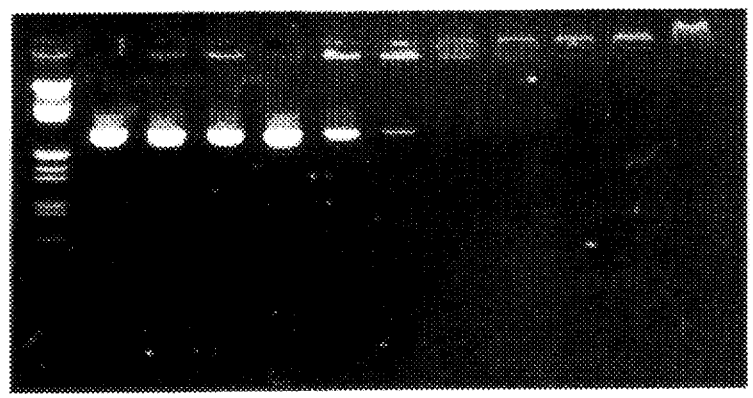

FIG. 22 is a bar graph of transfection charted against dendrimer-DNA complex, wherein some of the DNA is linear and some is circular or supercoiled, Example 48. The vertical axis is the relative light units/μg of protein and the horizontal axis is the dendrimer-DNA complex. The open bars are the results for no DEAE-dextran present. The solid bars are the results for 0.5 μM DEAE-dextran.

FIGS. 23(A)–(D) comprises four electrophoretic gels indicating the DNA complexing ability of a G8 ($NH_3$) dendrimer and a G8 (EDA) dendrimer under various charge ratios and various conditions, Example 49.

Figure 24:
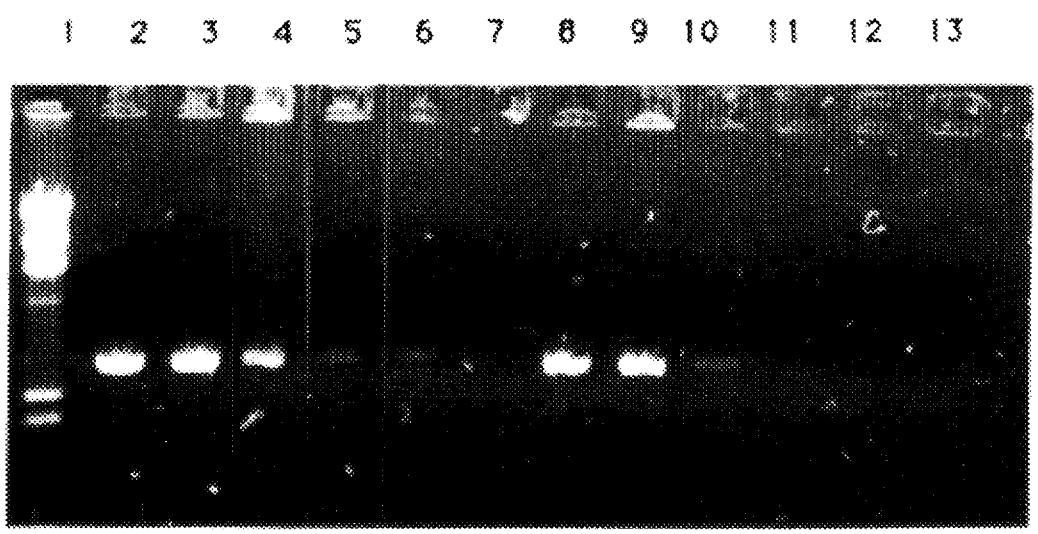

FIG. 24 is an electrophoretic gel comparing the DNA binding properties of G8 ($NH_3$) dendrimers and G11 (EDA) dendrimers in various molar ratios, Example 50.

Figure 25:
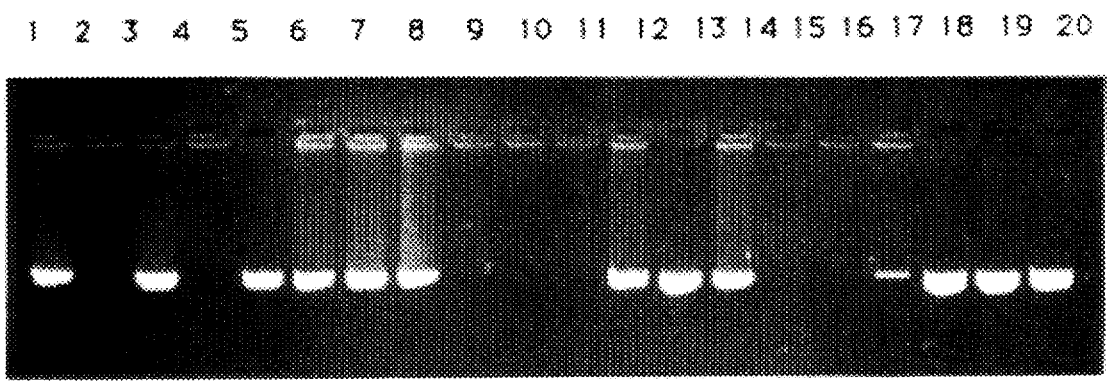

FIG. 25 is an electrophoretic gel indicating the DNA binding properties of G8 ($NH_3$) dendrimers and G8 (EDA) dendrimers over a broad range of pH, Example 51.

Figure 26A:
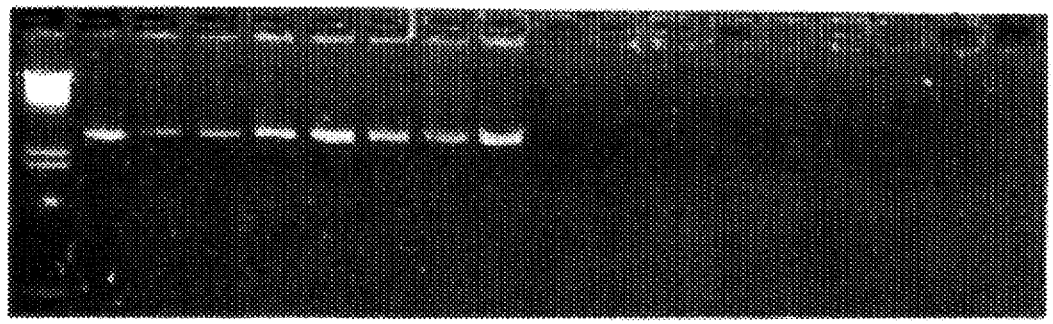

FIGS. 26(A) and (B) are electrophoretic gels indicating the DNA-dendrimer binding stability in salt solutions of increasing sodium chloride concentration, Example 52.

Figure 27:
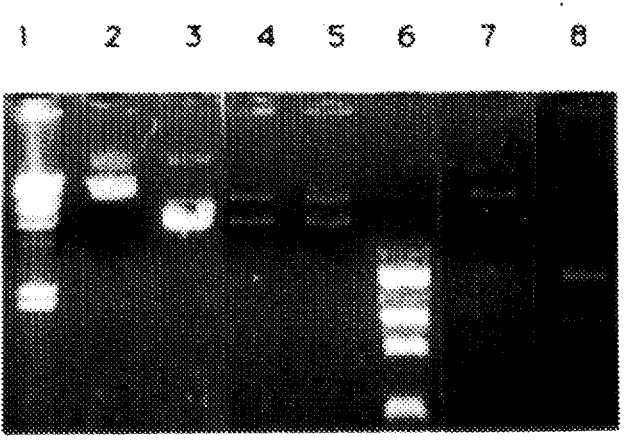

FIG. 27 is an electrophoretic gel illustrating the stability and protection of DNA complexed with G8 (NH$_3$) dendrimers and G11 (EDA) dendrimers in the presence of various restriction enzymes. Example 53.

Figure 28:
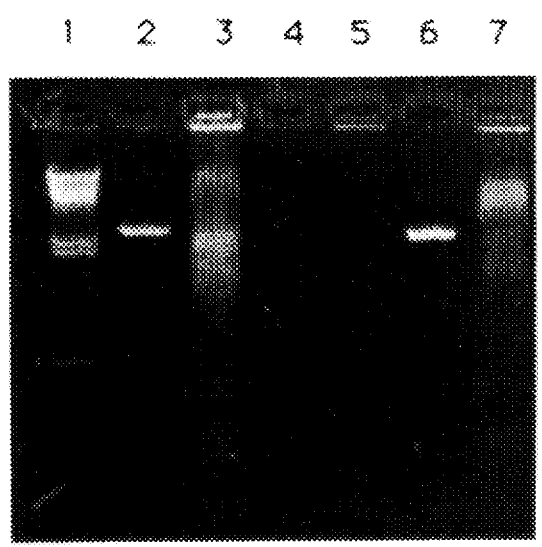

FIG. 28 is an electrophoretic gel illustrating the stability and protection of DNA complexed with G8 (EDA) dendrimers in the presence of cellular nucleases. Example 54.

Figure 29:
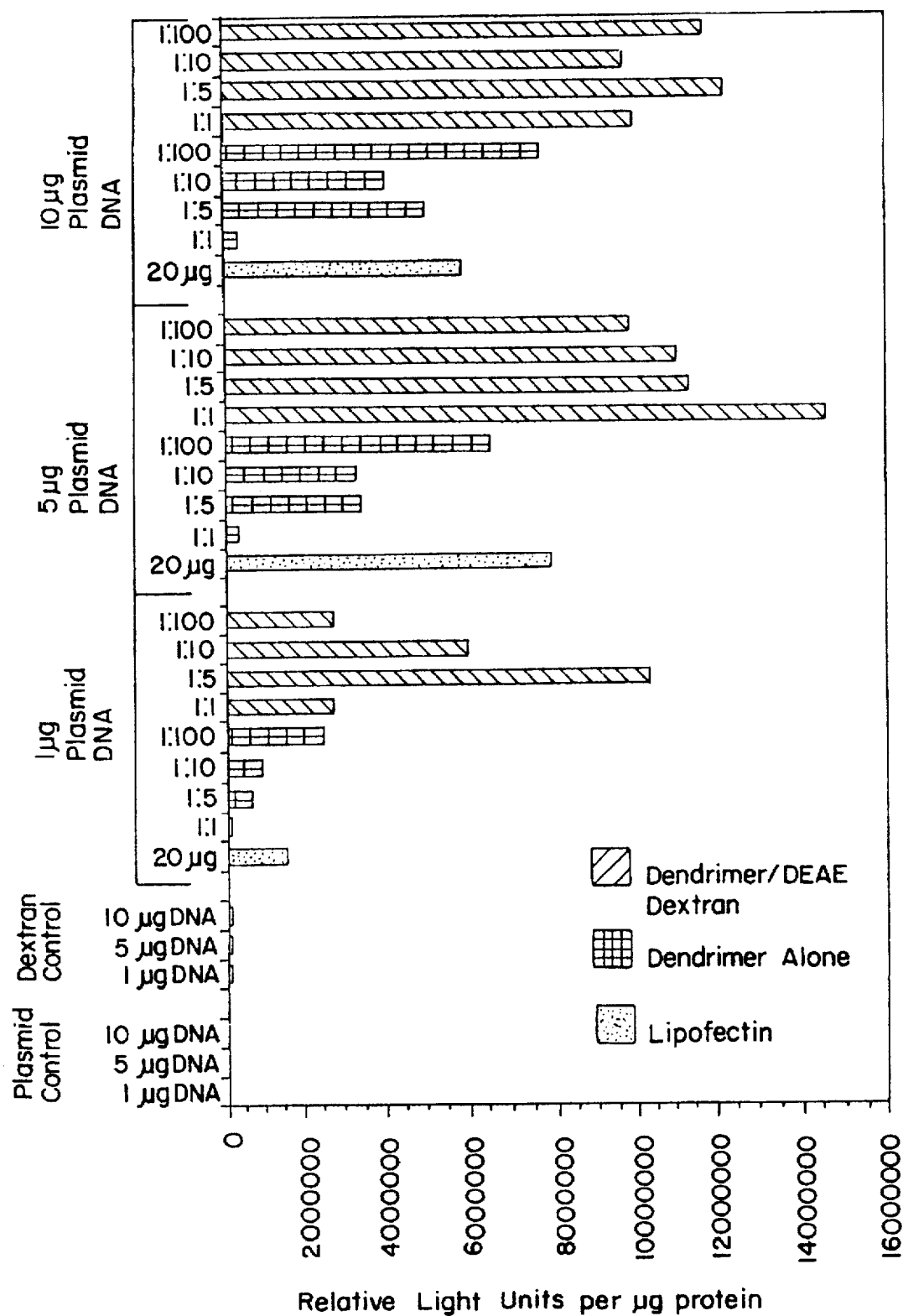

FIG. 29 compares the extent of transfection of DNA complexed with dendrimers at various DNA:dendrimer charge ratios and various DNA concentrations, versus the same combinations in the presence of a diethylaminoethyl ether of dextran (DEAE-dextran). There are examples of transfections with lipids, i.e., substituting LIPOFECTIN™ used instead of the dendrimer and in the absence of DEAE-dextran. Example 55. The vertical axis is the plasmid control, the dextran control, and the various plasmid DNA complexes of 1 µg, 5 µg, and 10 µg, and the horizontal axis is the relative light units/µg of protein. The diagonally hatched bars are the results for dendrimer/DEAE-dextran. The crosshatched bars are the results for the dendrimer alone. The speckled bars are the results for LIPOFECTIN™.

Figure 30:
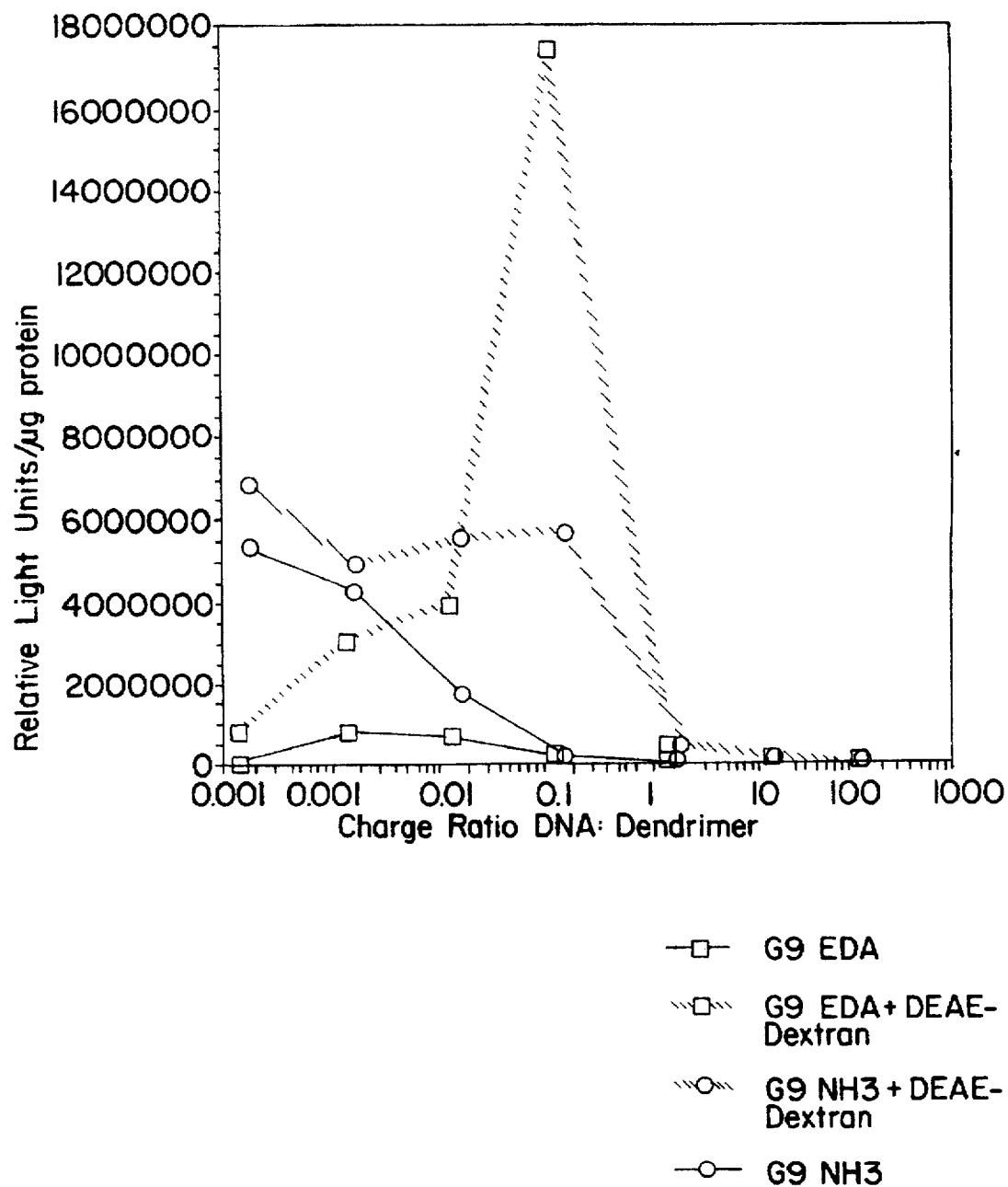

FIG. 30 graphs the degree of transfection for (NH$_3$) dendrimers and (EDA) dendrimers at variable DNA:dendrimer charge ratios, in the presence of DEAE-dextran in some cases and without DEAE-dextran in others, Example 56. The vertical axis is the relative light units/µg of protein, and the horizontal axis is the charge ratio of DNA:dendrimer. The solid squares with solid lines represent G9 (EDA) dendrimer; squares with hatched lines represent G9 (EDA) dendrimer plus DEAE-dextran; the solid circles with solid lines represent G9 (NH$_3$) dendrimer; and the open circles with hatched lines represent G9 (NH$_3$) dendrimer plus DEAE-dextran.

Figure 31:
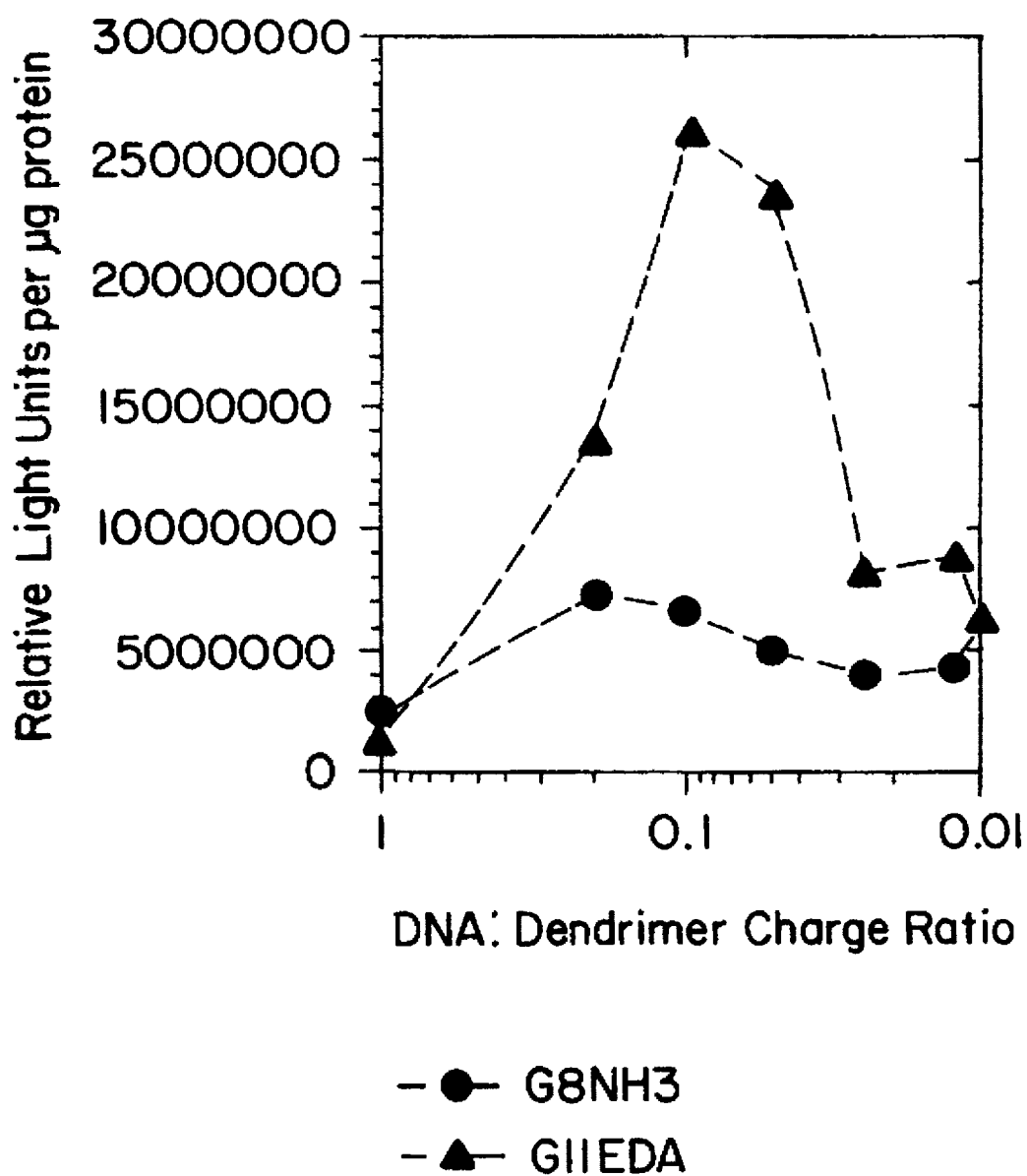

FIG. 31 is like FIG. 30, but for G8 (NH$_3$) dendrimers and G11 (EDA) dendrimers, and always in the presence of DEAE-dextran, Example 56. The vertical axis is the relative light units/µg of protein, and the horizontal axis is the charge ratio of DNA:dendrimer. The solid circles represent G8 (NH$_3$) dendrimer; and the solid triangles represent G11 (EDA) dendrimer.

Figure 32:
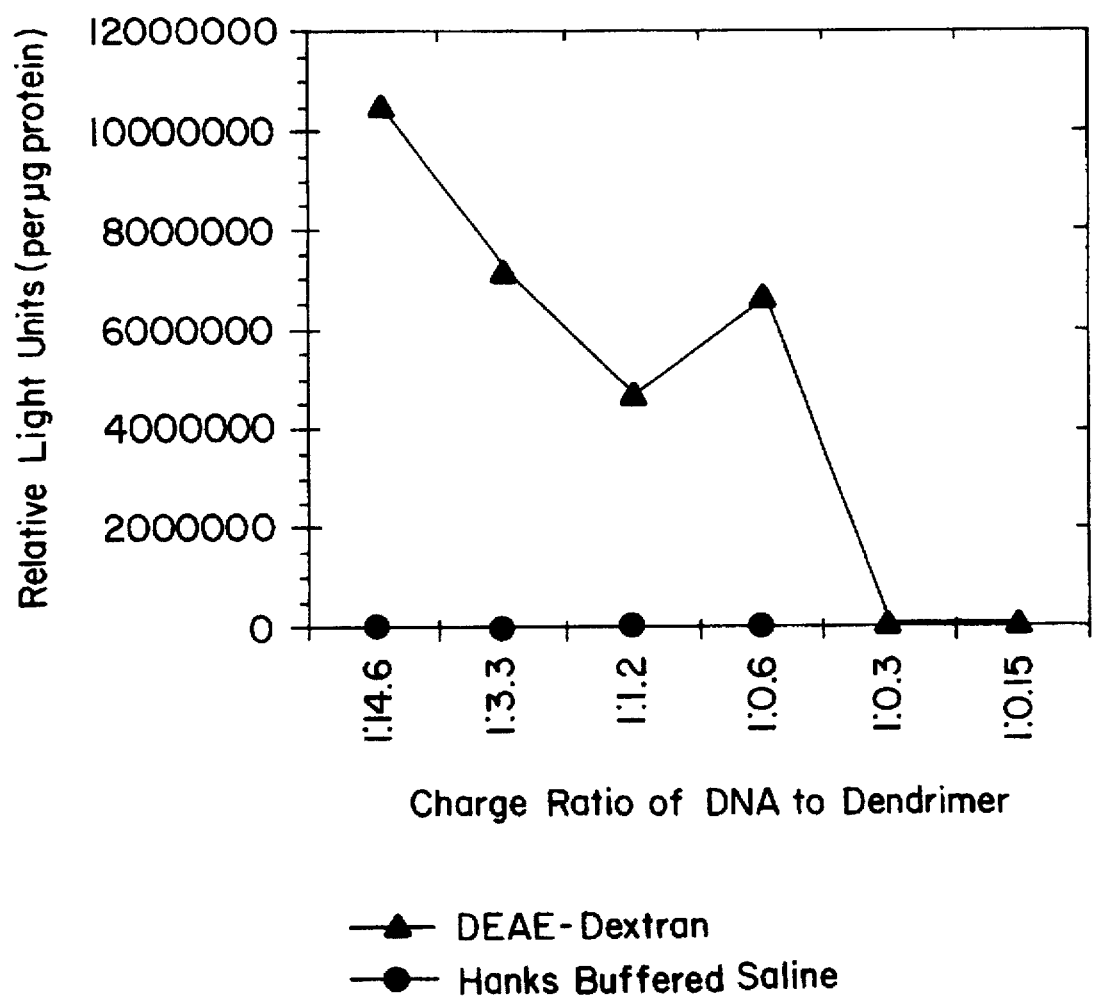

FIG. 32 is a graph of transfection effectiveness of DNA:G7 (NH$_3$) dendrimer complexes in the presence of either DEAE-dextran or Hanks buffered saline (HBS), Example 57. The vertical axis is the relative light units/pg of protein; and the horizontal axis is the charge ratio of DNA:dendrimer. The solid circles represent Hanks buffered saline; and the solid triangles represent DEAE-dextran.

Figure 33:
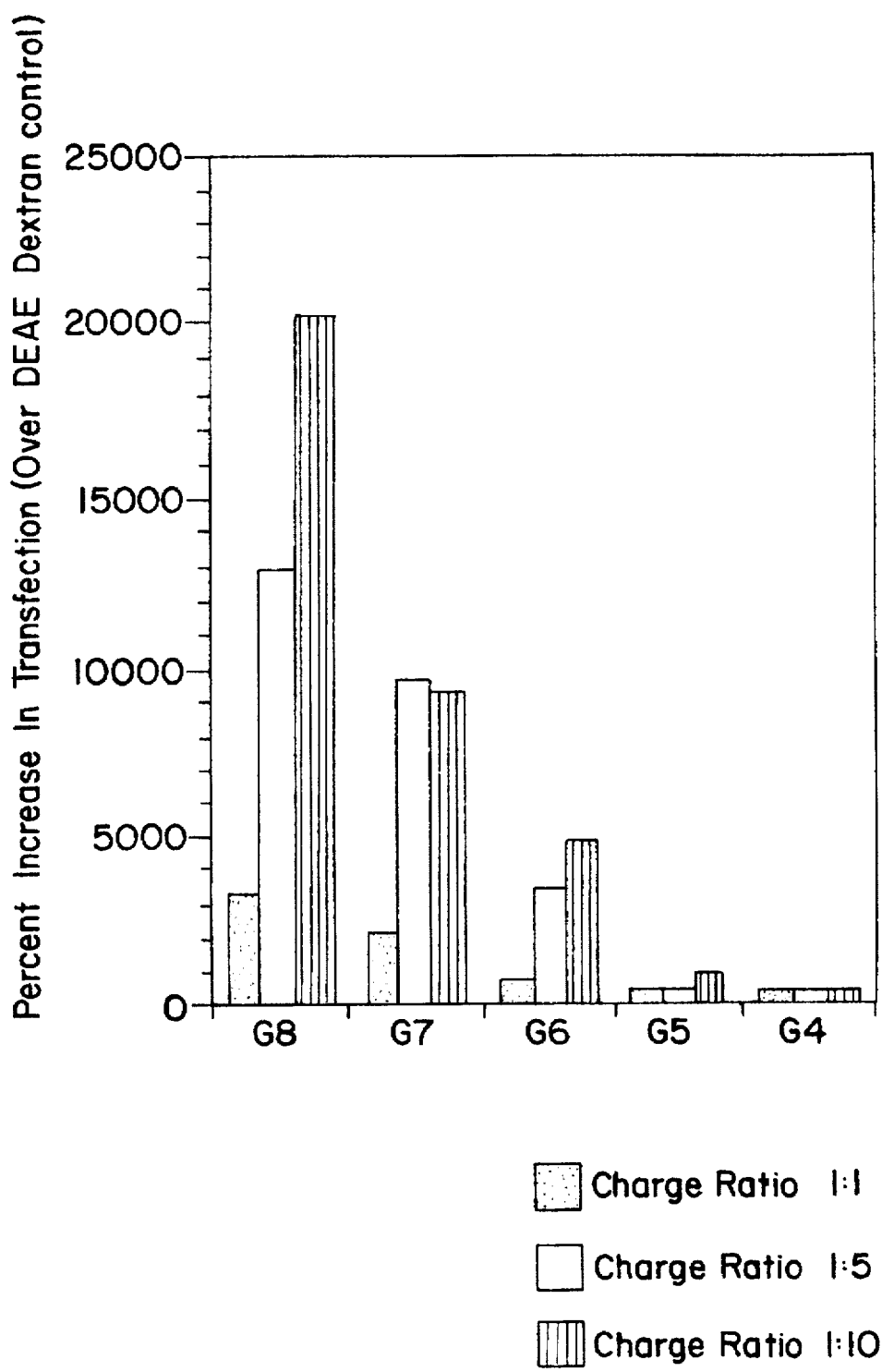

FIG. 33 is a graph of percent increase in transfection for (NH$_3$) dendrimer-DNA complexes in DEAE-dextran at various charge ratios of DNA to dendrimer, Example 58. The vertical axis is the percent increase in transfection (over DEAE-dextran control), and the horizontal axis is the dendrimer generation. The diagonally hatched bars represent a charge ratio of 1:1; the open bars represent a charge ratio of 1:5 and the cross hatched bars represent a charge ratio of 1:10.

Figure 34:
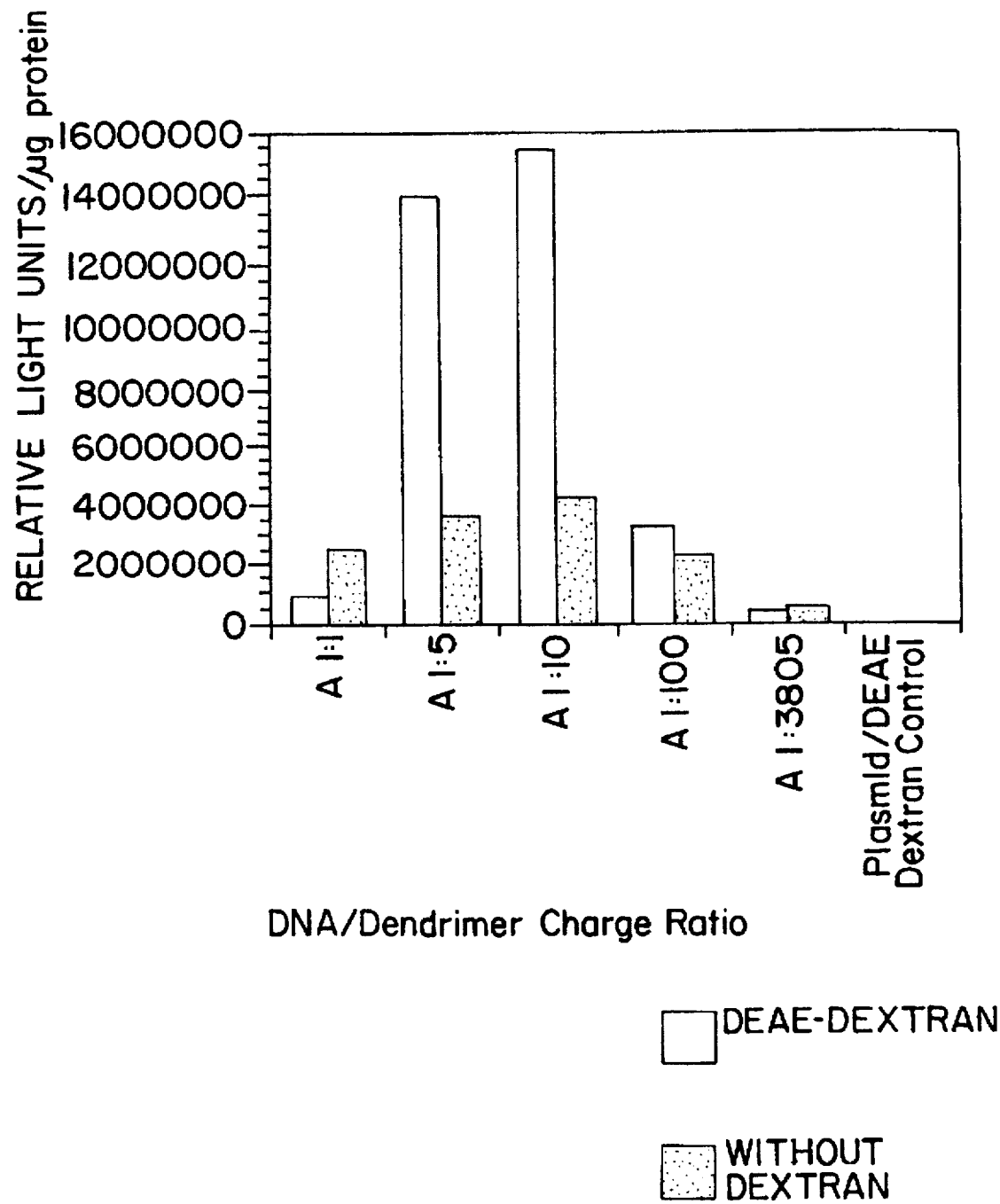

FIG. 34 is a graph of transfection effectiveness for DNA-dendrimer complexes at various charge ratios, in the presence of DEAE-dextran and without DEAE-dextran, Example 59. The vertical axis is the relative light units/µg of protein, and the horizontal axis is the charge ratio of DNA:dendrimer (the far right entry is having the plasmid/DEAE-dextran control). The open bars represent DEAE-dextran; and the solid bars represent without DEAE-dextran.

Figure 35:
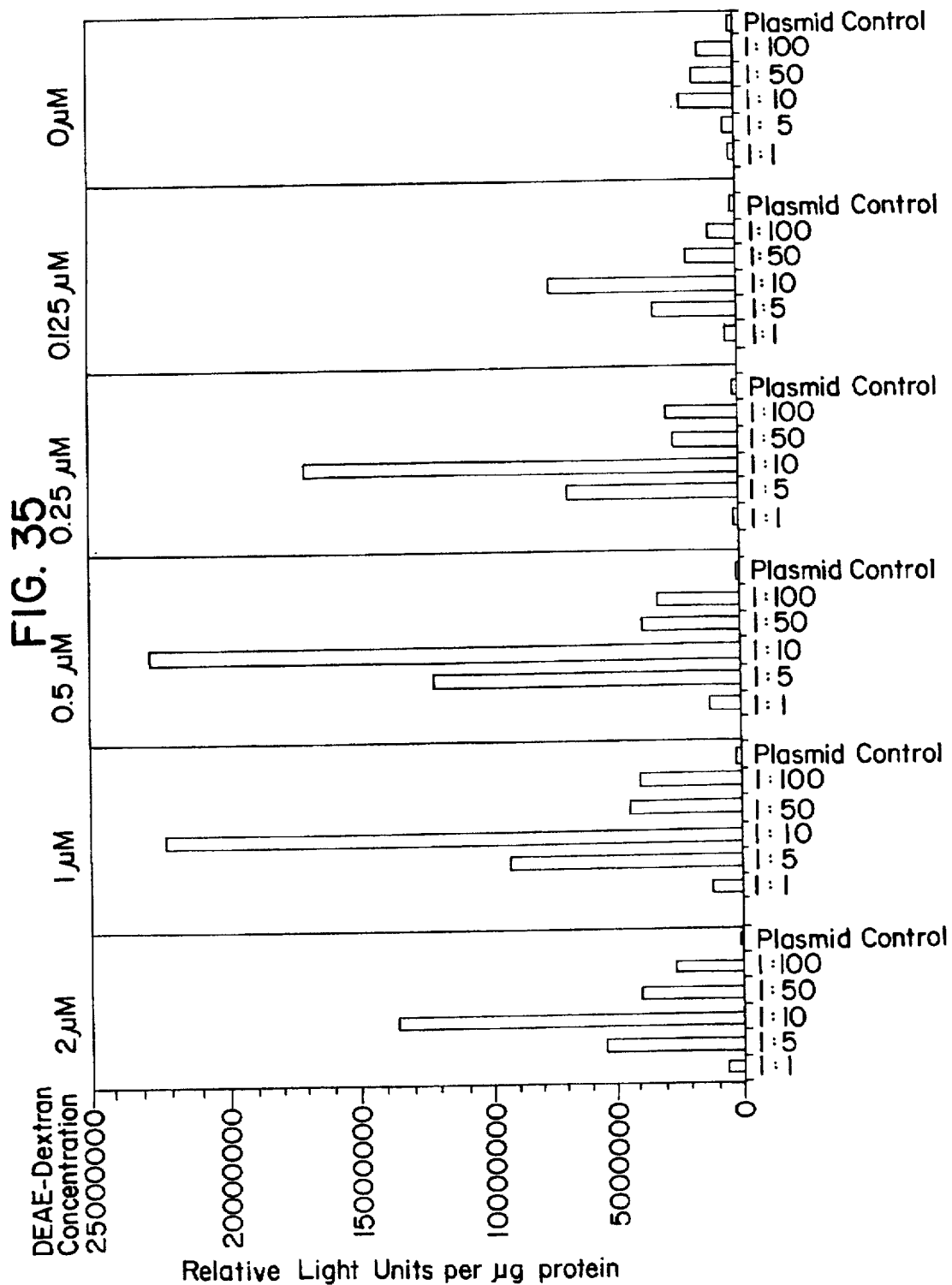

FIG. 35 is a bar graph of transfection effectiveness for DNA:dendrimer complexes at various charge ratios and at various concentrations of DEAE-dextran, Example 60. The vertical axis is the relative light units/µg of protein; and the top horizontal axis is the DEAE-dextran concentration in µM; and the bottom horizontal axis is various charge ratios of DNA:dendrimer for each segment, including a plasmid control.

Figure 36:
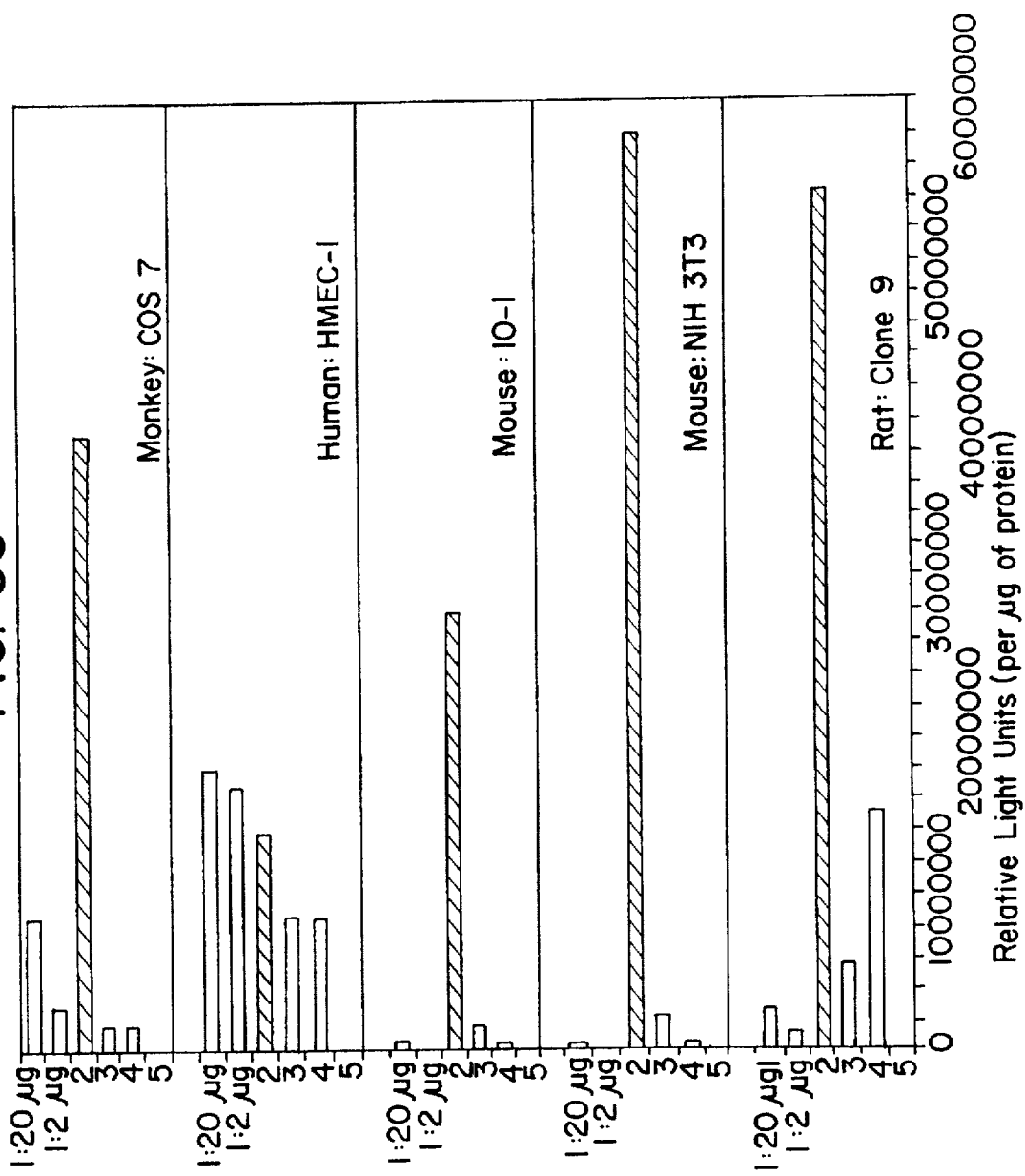

FIG. 36 is a bar graph of transfection effectiveness for DNA:dendrimer complexes at a 1:5 charge ratio, as compared to LIPOFECTIN™ mediated transfections, in different cell lines, Example 61. The numbers on the vertical axis are the sample numbers identifying the transfection agents used (as documented in Example 61); and the horizontal axis is the relative light units/µg of protein. The various segments (reading down the graph) for the cell lines tested are monkey:COS 7; human:HMEC-1; mouse:10-1; mouse:NIH 3T3; and rat:Clone9.

Figure 37:
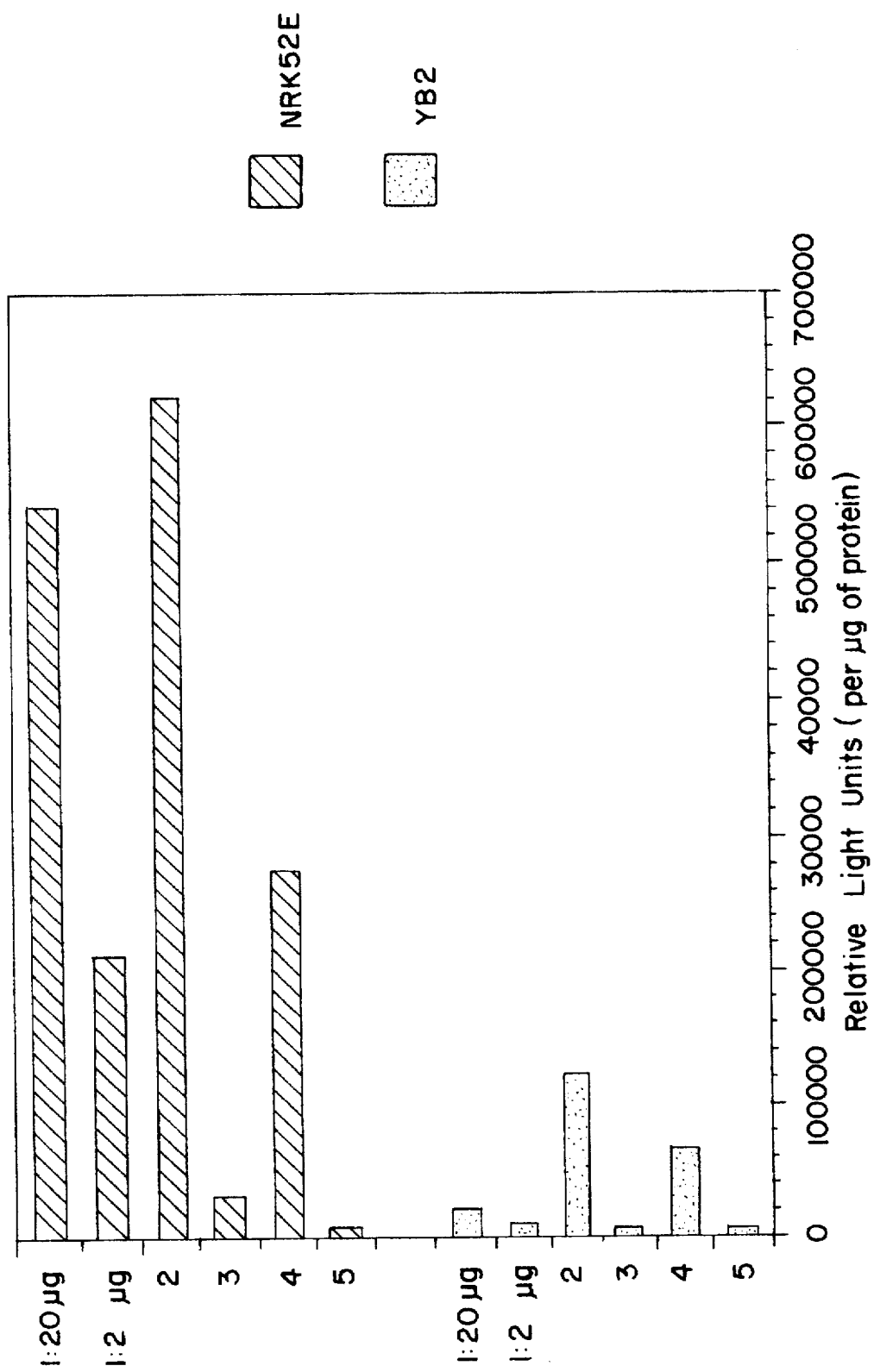

FIG. 37 is a graph of transfection effectiveness for DNA-dendrimer complexes at a 1:5 charge ratio in two difficult to transfect cell lines, as compared with LIPOFECTIN™ mediated transfections in those cell lines, Example 62. The vertical axis is sample numbers; and the horizontal axis is the relative light units/µg of protein. The cell lines used are represented by the slanted hatched bars for NRK52E, and the solid bars for YB2.

Figure 38:
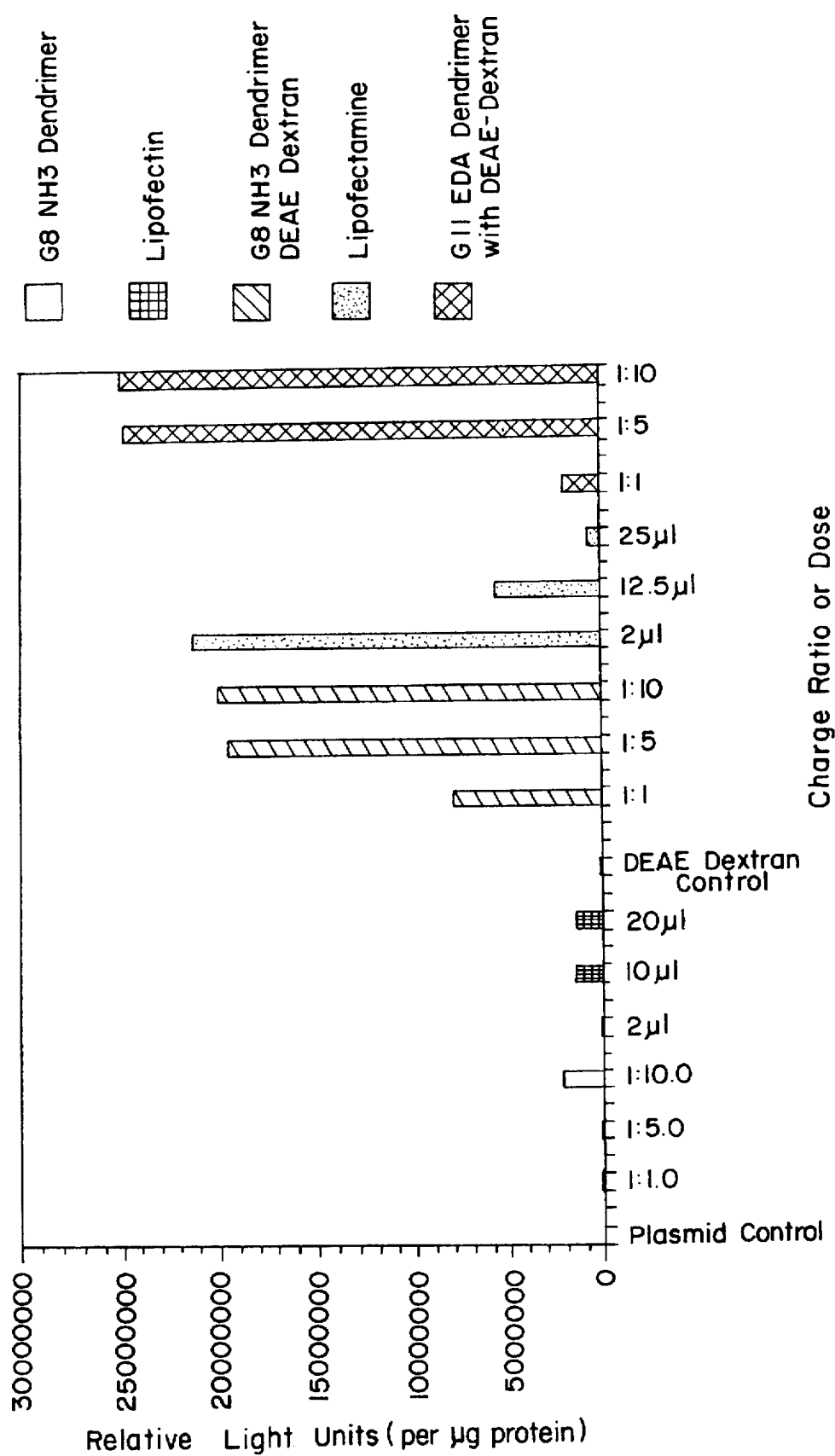

FIG. 38 is a graph of transfection effectiveness of various DNA-dendrimer complexes with and without DEAE-dextran, as compared to LIPOFECTIN™ and LIPOFECTAMINE™ mediated transfections, Example 63. The vertical axis is the relative light units/µg of protein; and the horizontal axis is the charge ratio or dose, including controls. The open bars represent G8 (NH$_3$) dendrimer; the vertical crosshatched bars represent LIPOFECTIN™; the diagonal hatched bars represent G8 (NH$_3$) dendrimer with DEAE-dextran; the speckled bars represent LIPOFECTAMINE™ and the slanted cross hatched bars represent G11 (EDA) dendrimer with DEAE-dextran.

Figure 39:
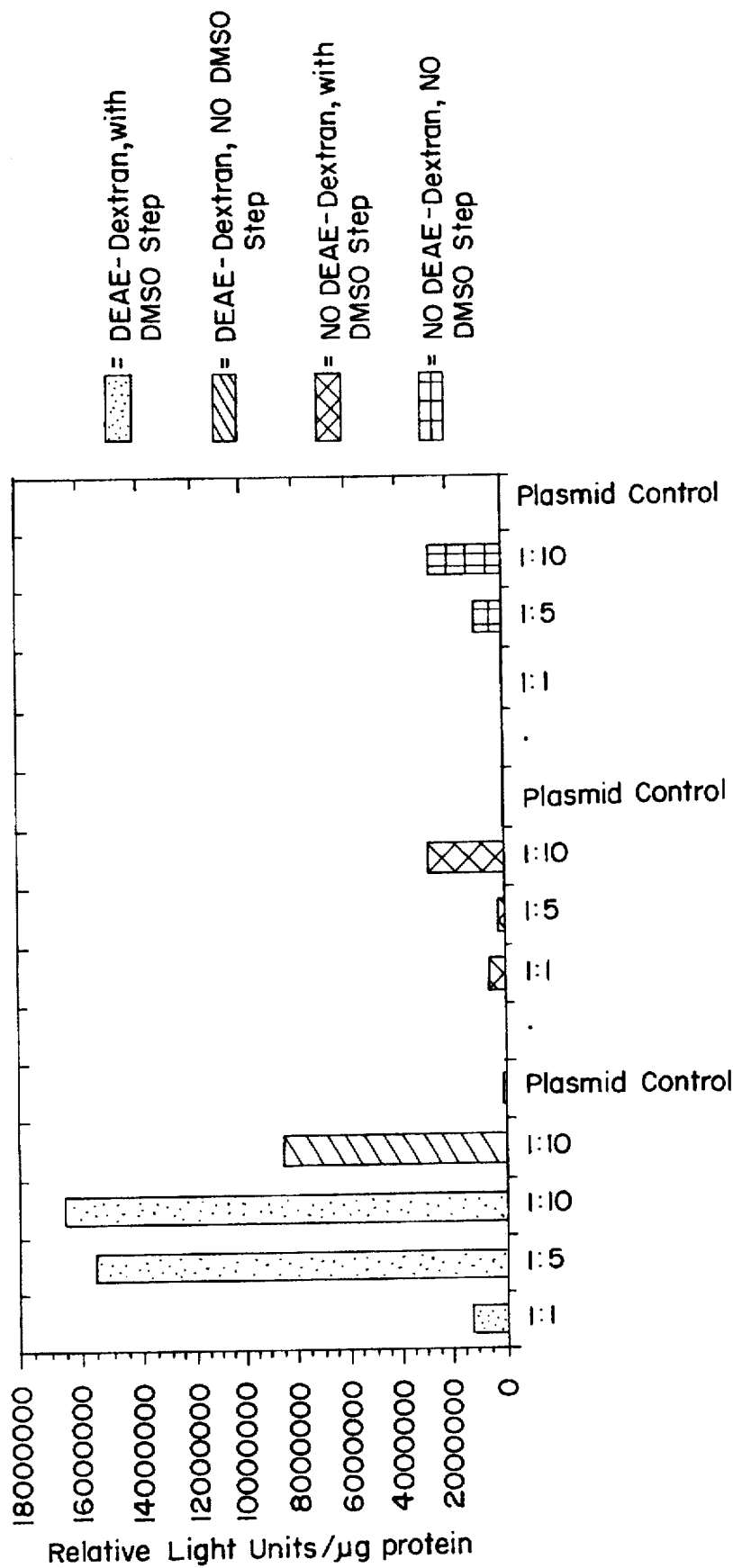

FIG. 39 is a graph of transfection effectiveness for DNA:dendrimer complexes at various charge ratios and in the presence of either DEAE-dextran, dimethylsulfoxide (DMSO), mixtures of the foregoing or none of the foregoing, Example 64. The vertical axis is the relative light units/µg of protein; and the horizontal axis is the charge ratio, including plasmid controls. The speckled bars represent DEAE-dextran with DMSO step; the diagonal hatched bars represent DEAE-dextran with no DMSO step; the slanted cross hatched bars represent no DEAE-dextran with DMSO step; and the vertical crosshatched bars represent no DEAE-dextran with no DMSO step.

Figure 40:
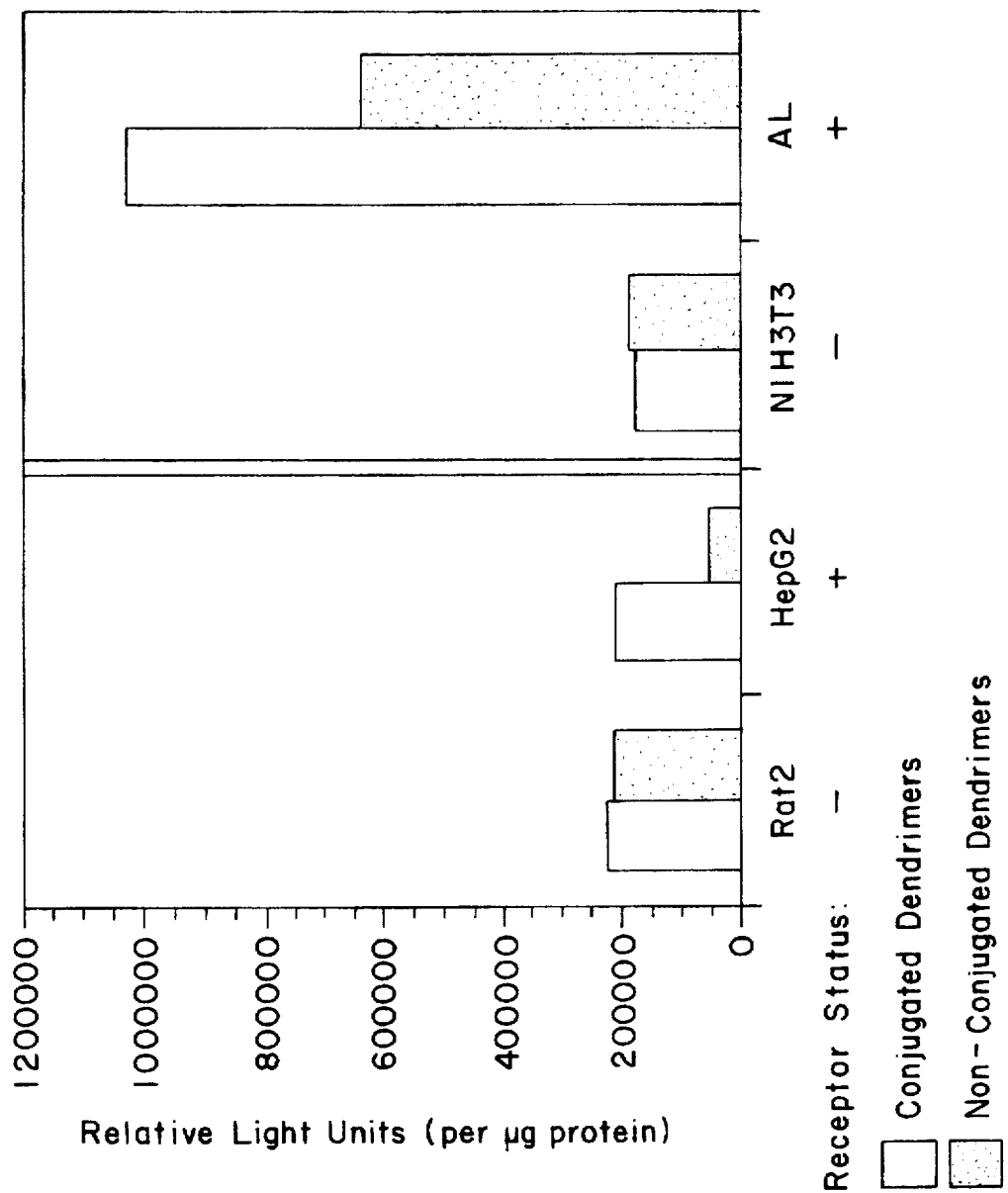

FIG. 40 is a graph of the transfection effectiveness of ASGPR targeted DNA complexed with galactose trisaccharide conjugated dendrimer, Example 65. The vertical axis is the relative light units/µg of protein; and the horizontal axis is the cell lines and receptor status. The open bars represent conjugated dendrimers; and the diagonally hatched bars represent non-conjugated dendrimers.

Figure 41:

FIG. 41 is an electrophoretic gel illustrating the DNA binding ability of a G11 (EDA) with and without galactose trisaccharide conjugated therewith, Example 65.

Figure 42:
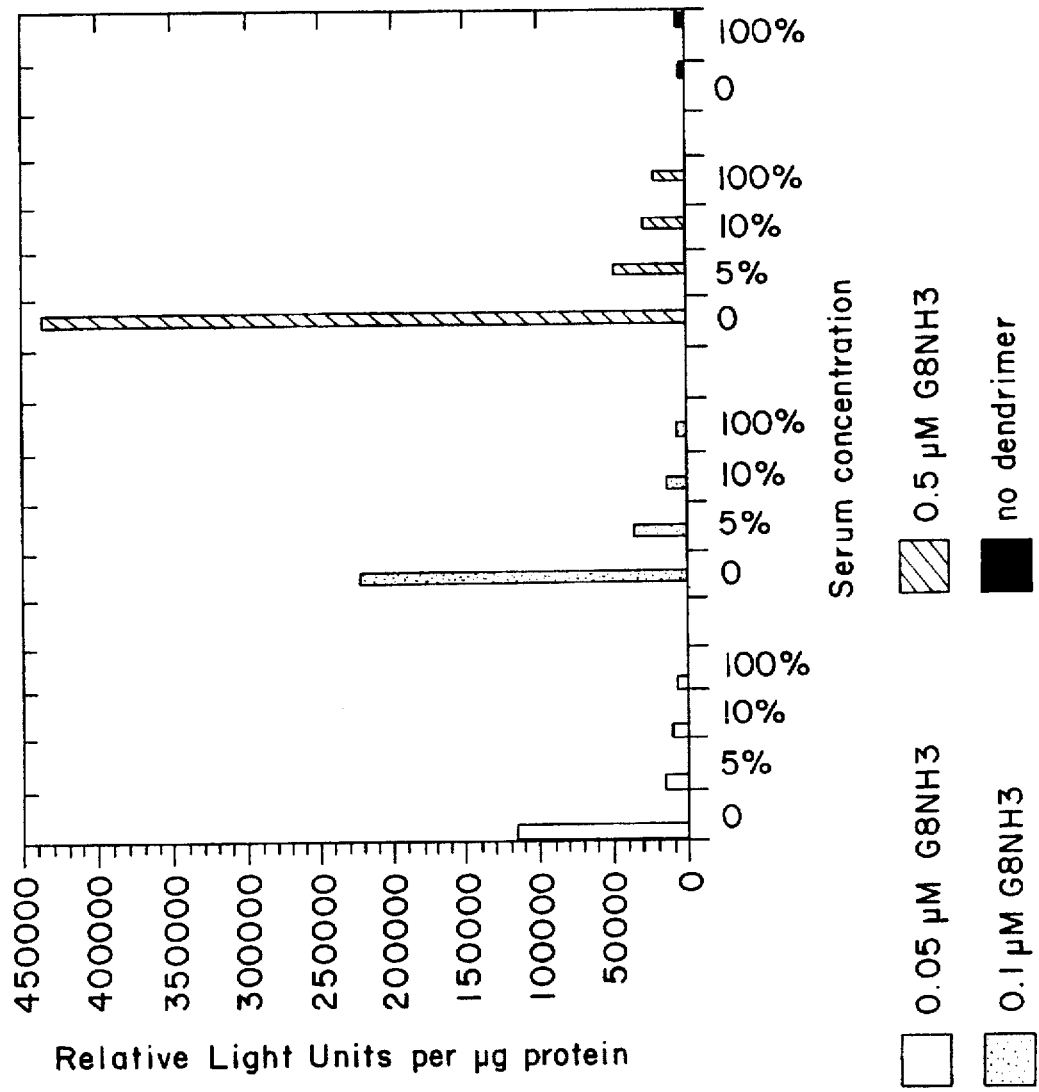

FIG. 42 is a graph of transfection effectiveness for DNA complexed with a G8 (NH$_3$) dendrimer, at various dendrimer concentrations and in various serum concentrations, Example 66. The vertical axis is the relative light units/µg of protein; and the horizontal axis is the serum concentration. The open bars represent 0.05 µM G8 (NH$_3$) dendrimers; the speckled bars represent 0.1 µM G8 (NH$_3$) dendrimers; the diagonal hatched bars represent 0.5 µM G8 (NH$_3$) dendrimers; and the solid bars represent no dendrimer.

Figure 43:
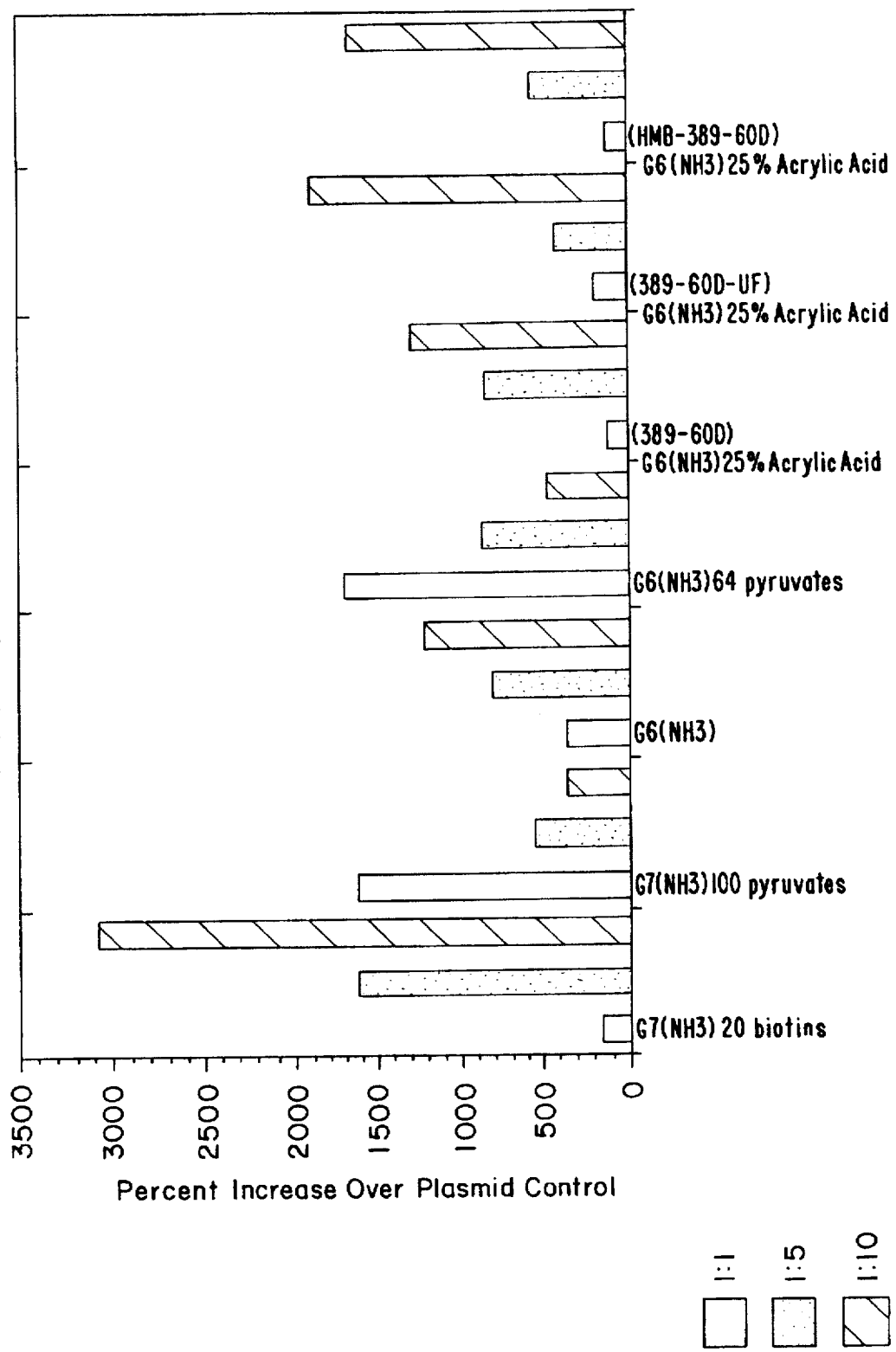

FIG. 43 is a graph of transfection effectiveness for DNA complexed with various targeted, nontargeted and surface modified dendrimers, Example 67. The vertical axis is the percent increase over plasmid control; and the horizontal axis is the various DNA-dendrimer complexes. The open bars are a DNA:dendrimer charge ratio of 1:1; the solid bars are a DNA:dendrimer charge ratio of 1:5; and the diagonally hatched bars are a DNA:dendrimer charge ratio of 1:10.

Figure 44:
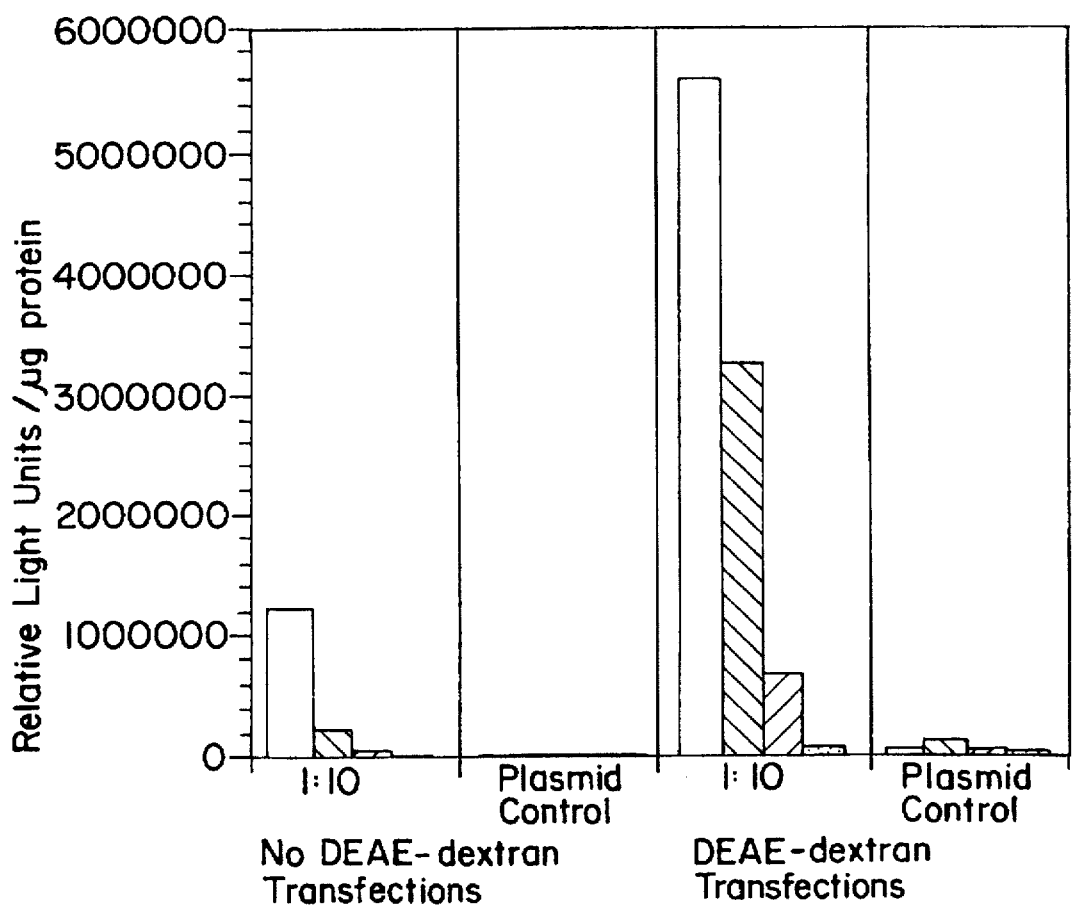

FIG. 44 is a graph of transfection effectiveness for DNA complexed with dendrimers, wherein expression of the transfected DNA is measured, Example 68. The vertical axis is the relative light units/µg of protein; and the horizontal axis is the various DNA-dendrimer complexes. The bars represent the time (hours) between transfection and harvest. The open bars represent 21 hours; the upper left to lower right diagonal hatched bars represent 45 hours; the upper right to lower left hatched bars represent 69 hours; and the solid bars represent 141 hours.

Figure 45:
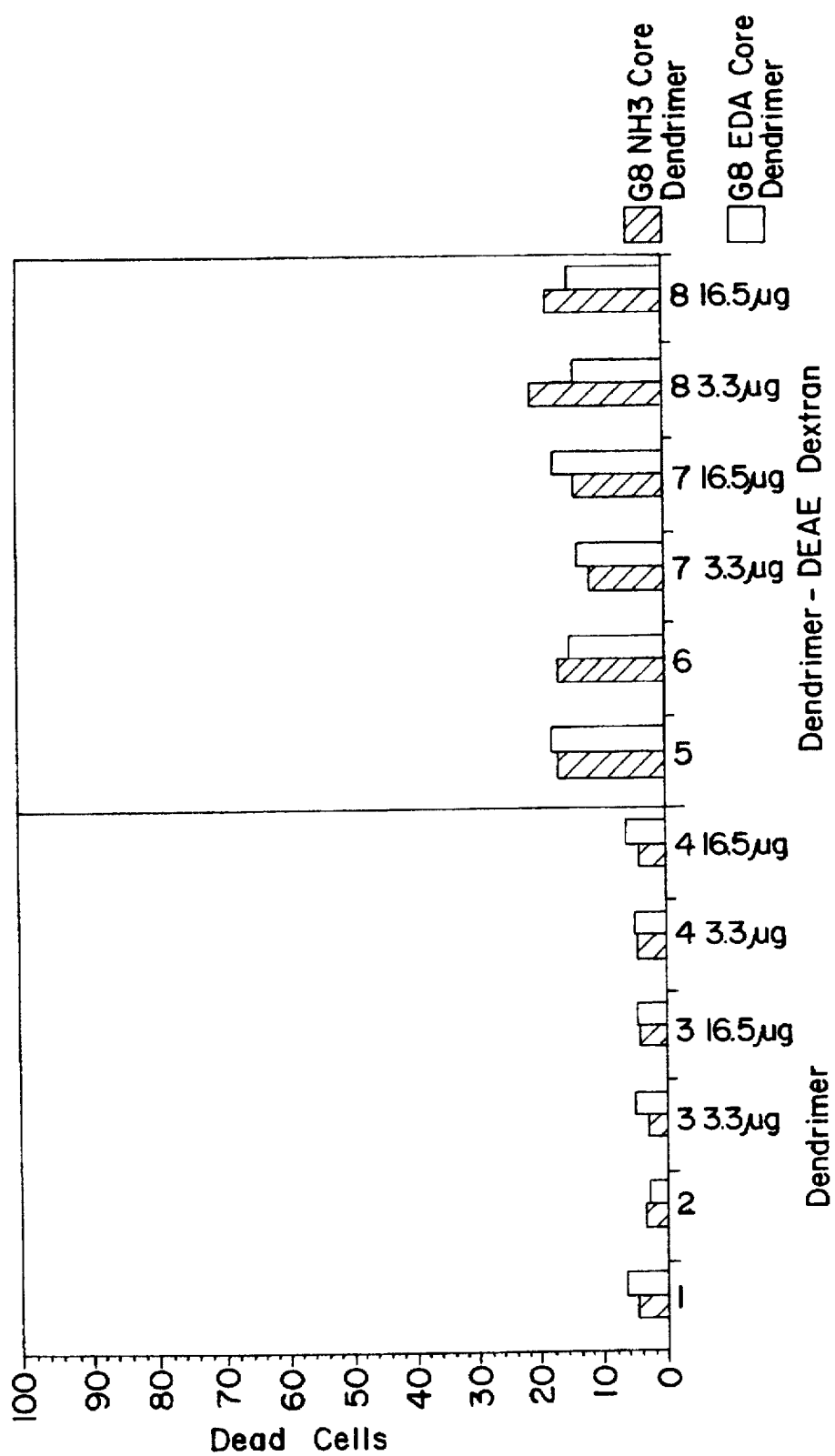

FIG. 45 is a graph of cytotoxicity in RAT2 cell line of G8 ($NH_3$) dendrimers and G8 (EDA) dendrimers with and without DNA and with and without DEAE-dextran present, Example 69. The vertical axis is the percentage of dead cells; and the horizontal axis is the concentration of the dendrimer on the left segment and the concentration of the dendrimer-DEAE-dextran on the right segment. The open bars represent G8 (EDA) dendrimer; and the diagonal hatched bars represent G8 ($NH_3$) dendrimer.

Figure 46:
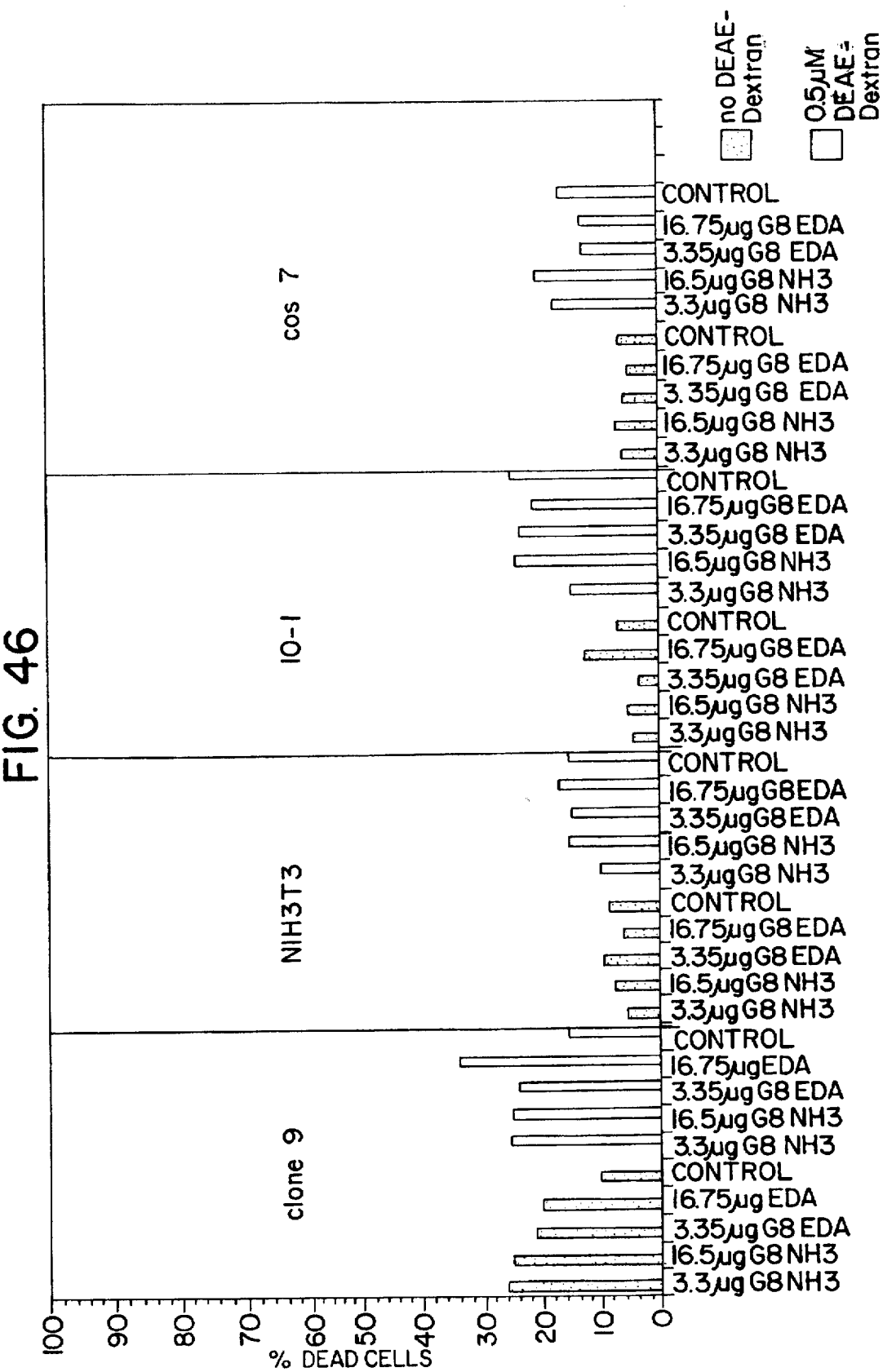

FIG. 46 is a similar graph of cytotoxicity of G8 ($NH_3$) dendrimers and G8 (EDA) dendrimers in various cell lines, Example 69. The vertical axis is the percentage of dead cells; and the horizontal axis is the concentration of the various dendrimers tested. The open bars represent no DEAE-dextran; and the solid bars represent 0.5 µM DEAE-dextran. The cell lines used (reading the segments from left to right) were Clone9, NIH 3T3, 10-1 and COS7.

FIGS. 47(a)–(f) graphs cellular uptake and localization of DNA in two different cell lines, some of which was transfected without dendrimer, some with dendrimer and some with dendrimer in the presence of sodium azide, Example 70. The vertical axis for all figures is the cellular uptake in $10^2$ cpm/$10^4$ cells; and the lower horizontal axis is the time (hours). FIGS. (A)–(C) used U937 cells; and FIGS. (D)–(F) used Rat 2 cells. The upper horizontal axis for FIGS. (A) and (D) is DNA only, for FIGS. (B) and (E) is DNA plus dendrimer, and for FIGS. (C) and (F) is DNA plus dendrimer plus sodium azide. In all figures the solid squares represent nuclear, the solid circles represent membrane, and the solid triangles represent cellular fractions.

Figure 48A:
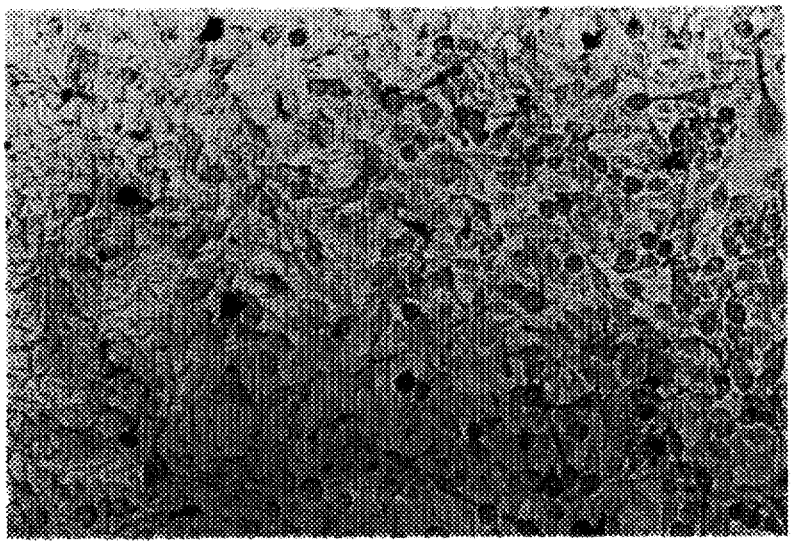

FIGS. 48(a) and (b) are photographs of cells, some of which have been successfully transfected with RSV-lacZ DNA, which expresses β-galactosidase enzyme, Example 71.

Figure 48B:
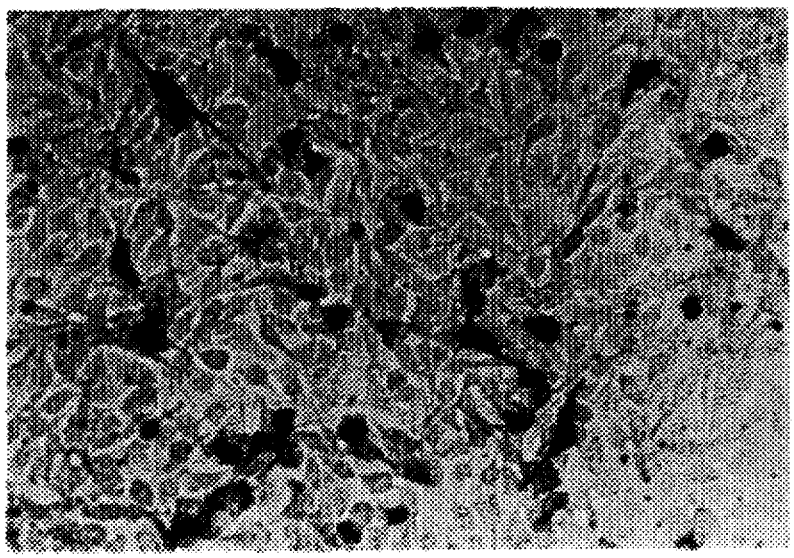
Figure 49:
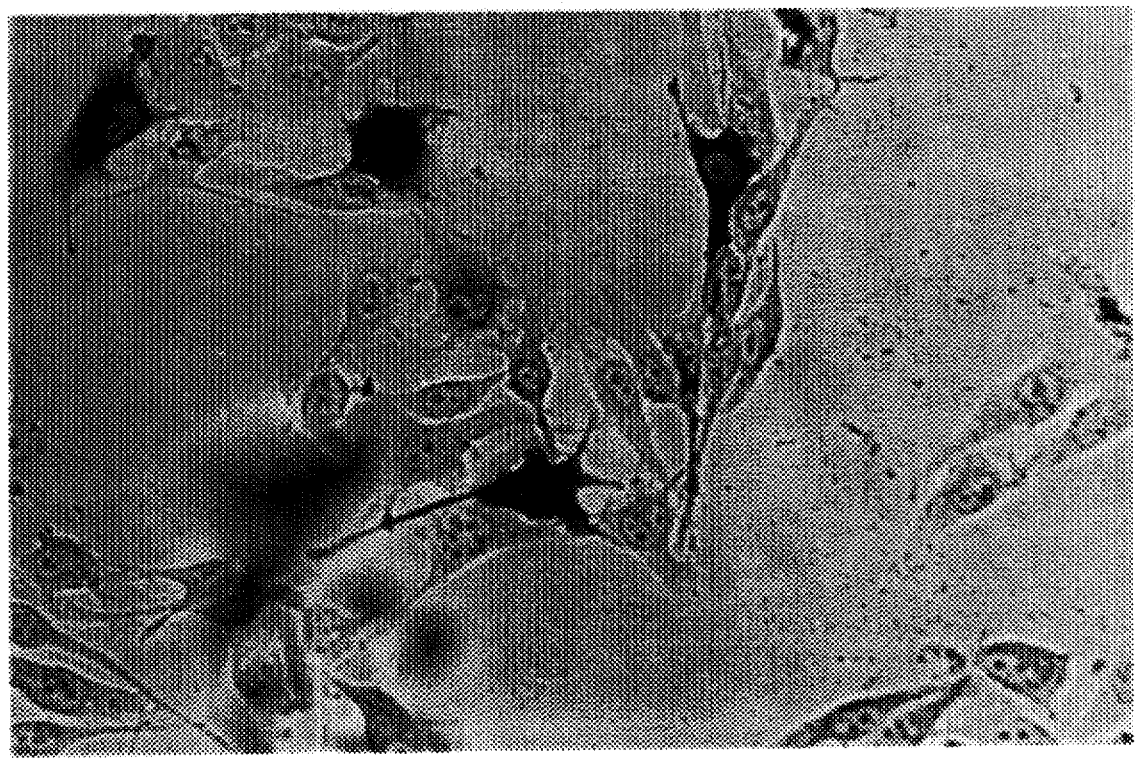

FIG. 49 is like FIG. 48, except that it is an enlarged photograph and the RSV-lacZ plasmid was used at three micrograms per test well, Example 71.

Figure 50A:
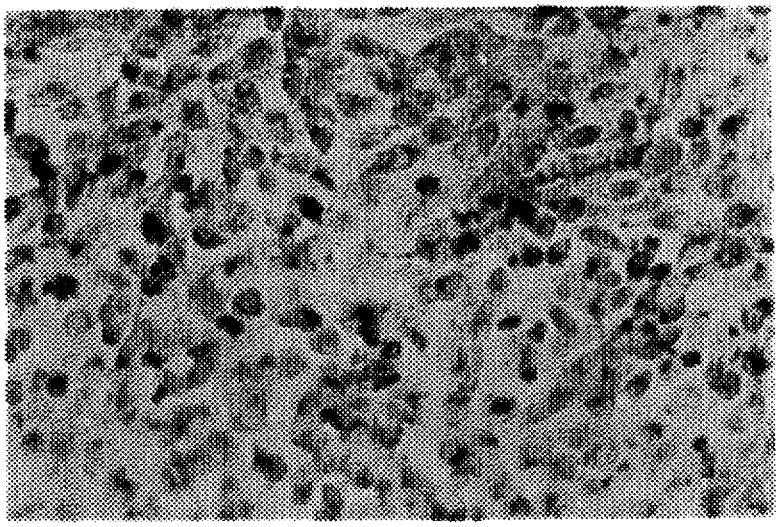

FIGS. 50(a) and (b) are like FIG. 48, except involving RAT 2 rat fibroblast cells, and comparing transfected cells at (A) with nontransfected cells at (B), Example 71.

Figure 51A:
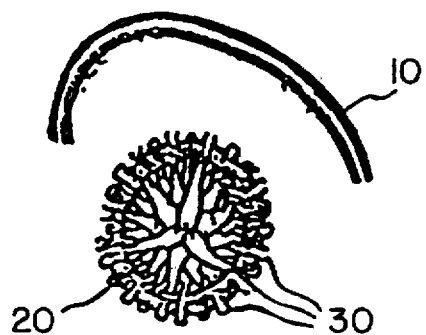
Figure 51B:
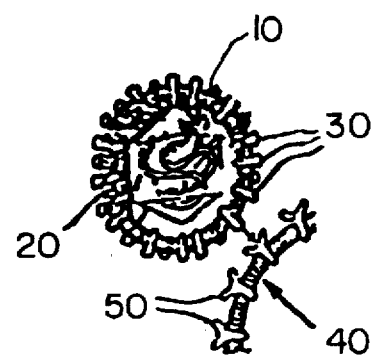
Figure 51C:
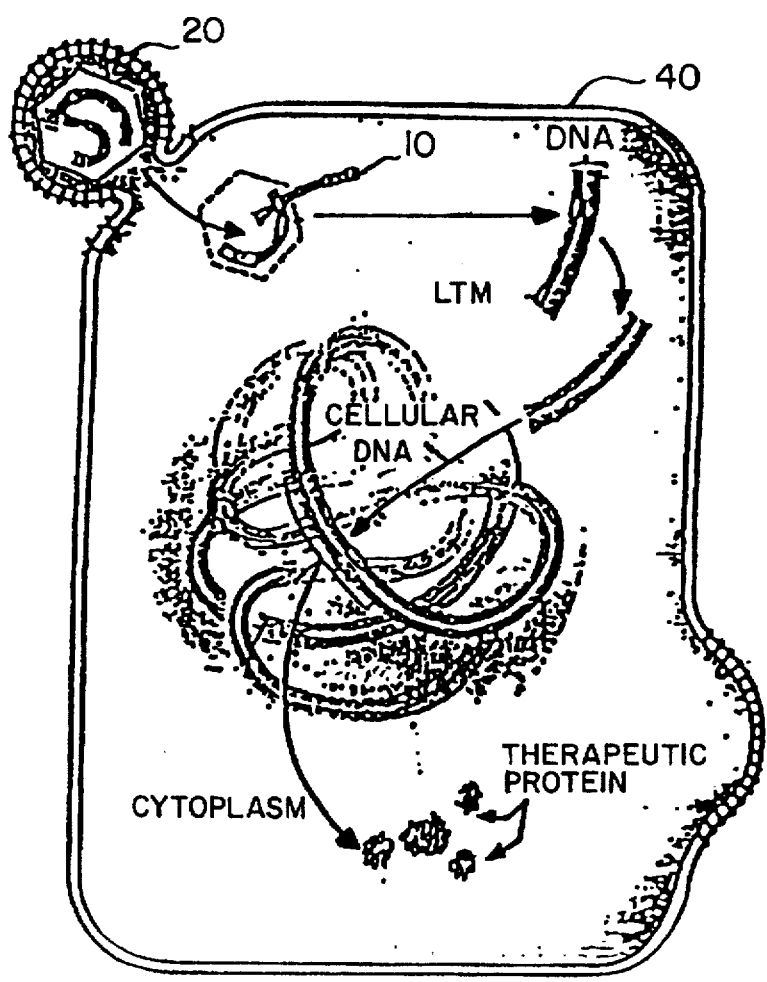

FIGS. 51(a)–(c) is an illustration of the genetic material transfection process.

Figure 52:
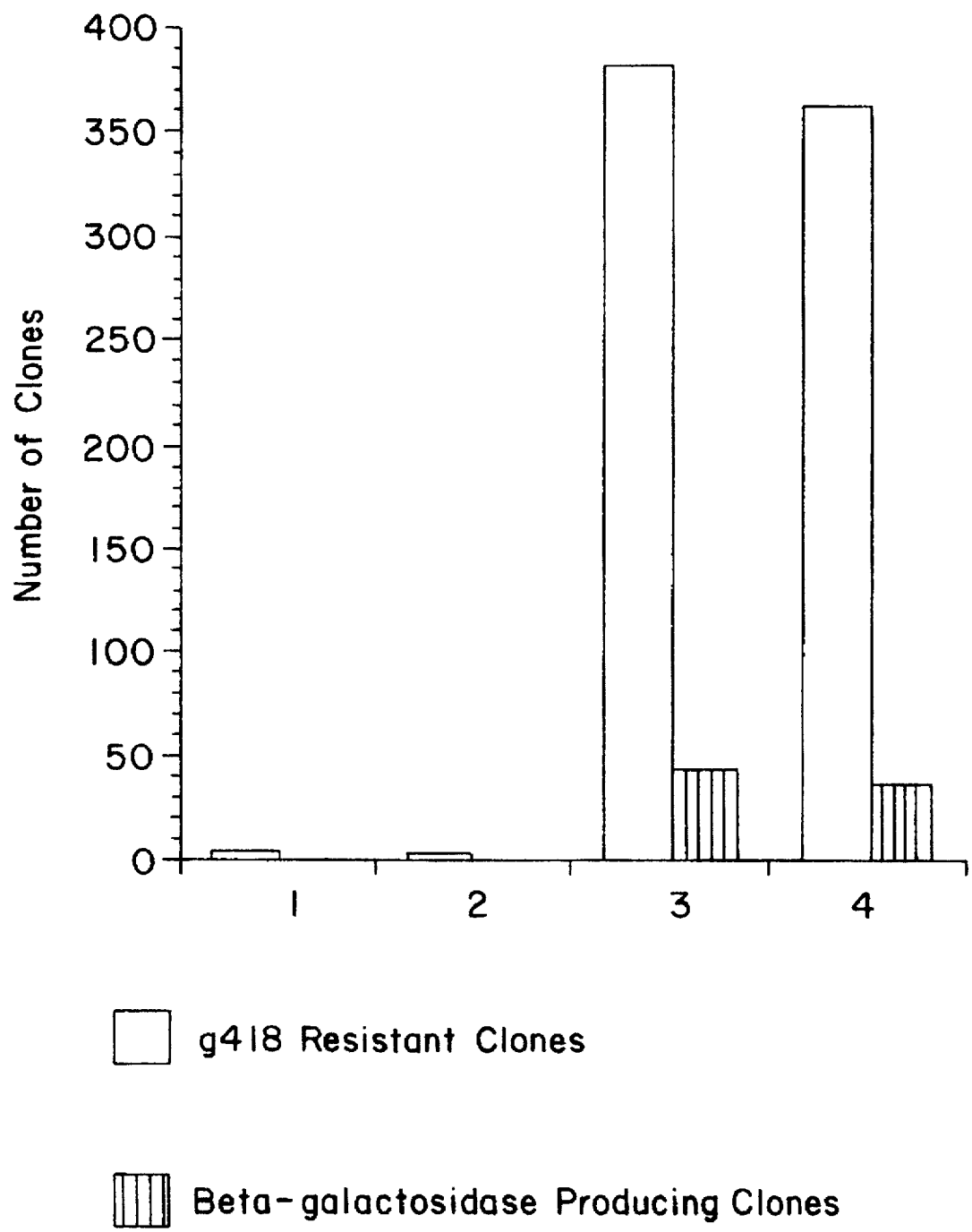

FIG. 52 is a graph of the number of clones obtained from D5 cells transfected with RSV-β-gal-NEO plasmid. Resistant cell clones were selected with geneticin (G418) antibiotic (Gibco/BRL) after transfection into the parent cells was performed using several different techniques, including the claimed invention, Example 72. The vertical axis is the number of clones; and the numbers on the horizontal axis are the Example 72 numbers identifying the DNA quantities and transfection conditions for those samples. The open bars represent G418 resistant clones; and the vertical hatched bars represent β-galactosidase enzyme producing clones.

Figure 53:
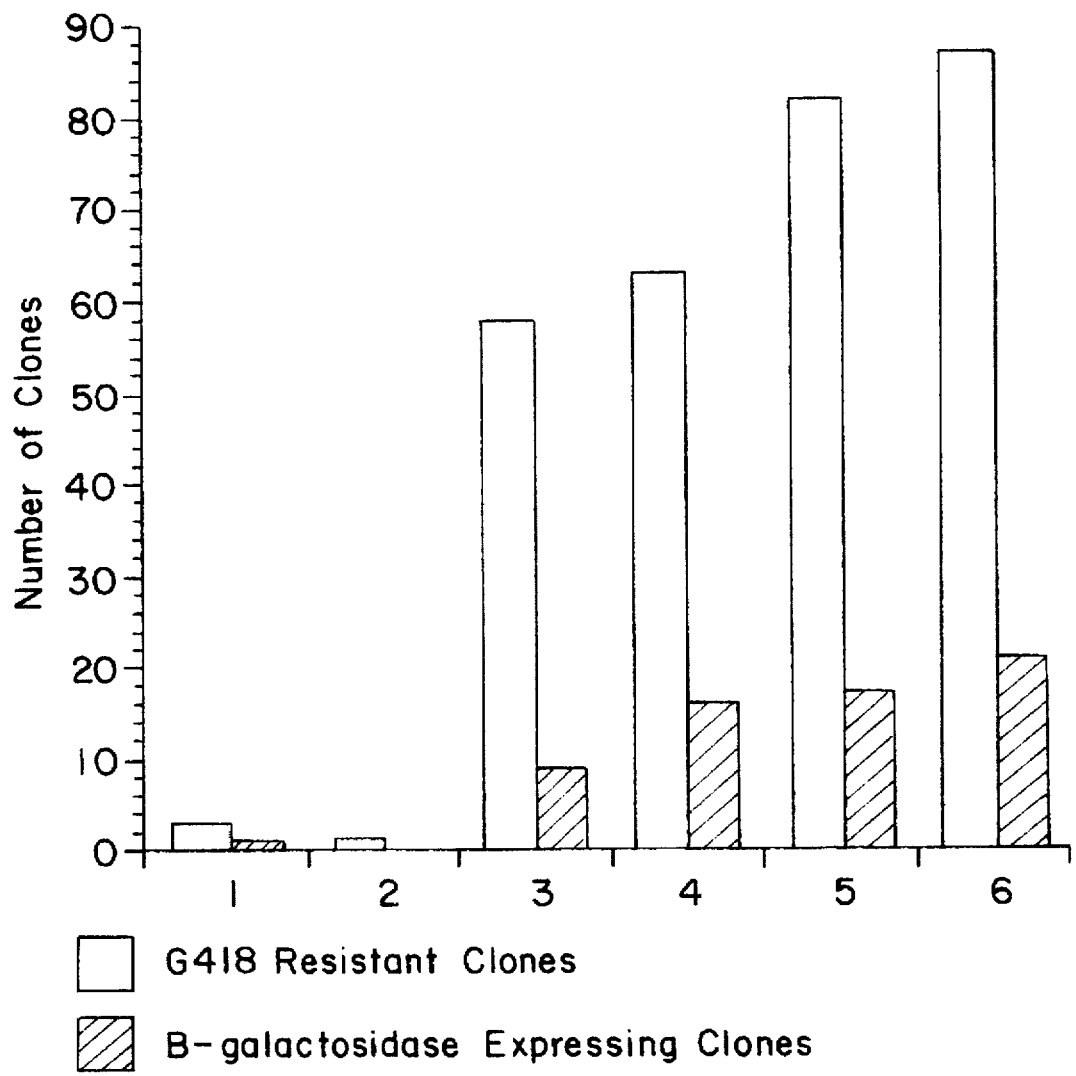

FIG. 53 is a graph comparing the number of clones obtained from RAT2 cells transfected with RSV-β-gal-NEO plasmid using several different techniques, including the claimed invention, Example 72. The clones were selected with geneticin (G418) for neomycin resistance and subsequently evaluated for β-galactosidase activity. The vertical axis is the number of clones; and the numbers on the horizontal axis are the Example 72 sample numbers for the DNA quantities and transfection conditions for those samples. The open bars represent G418 resistant clones; and the diagonal hatched bars represent β-galactosidase expressing clones.

Figure 54:
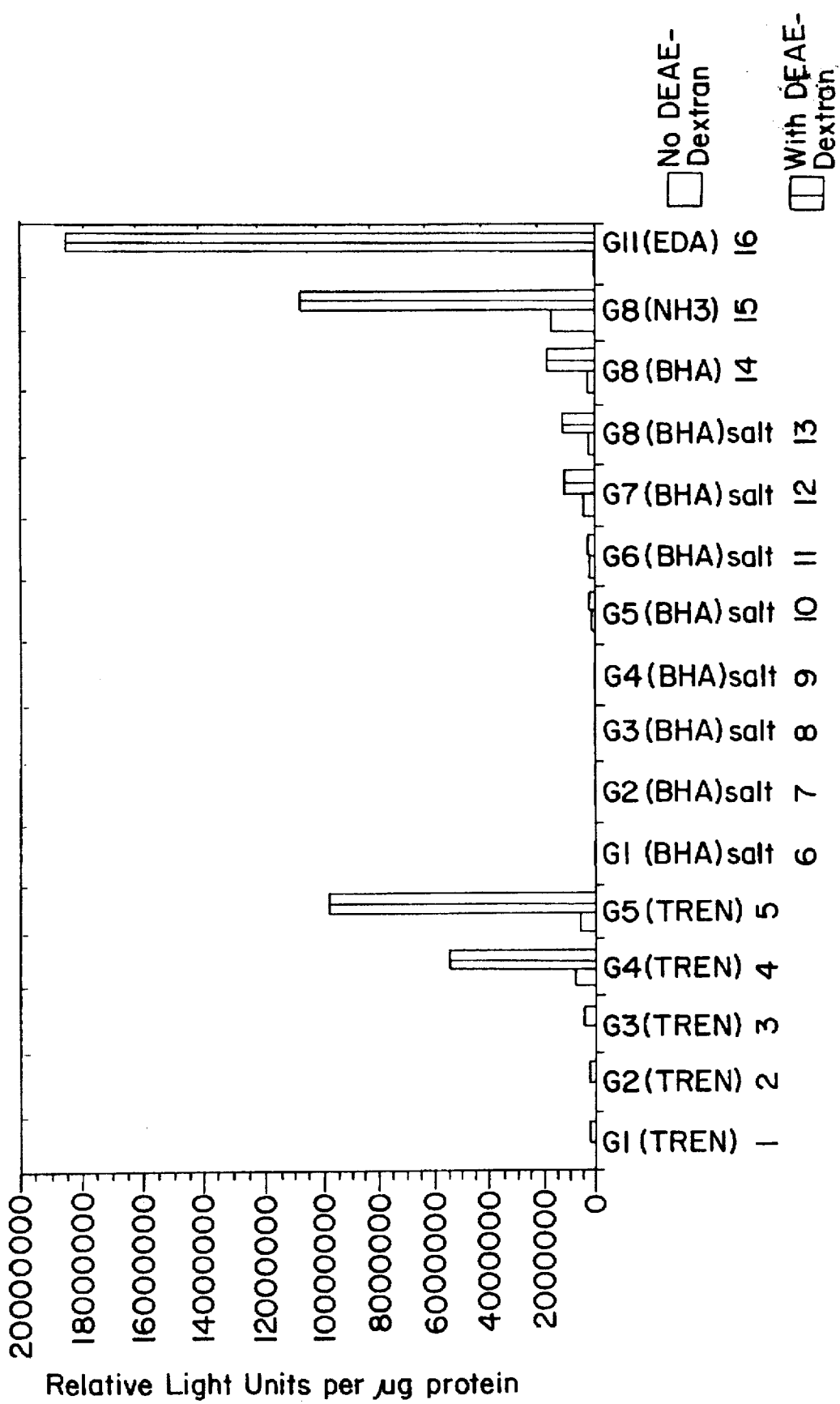
Figure 55A:
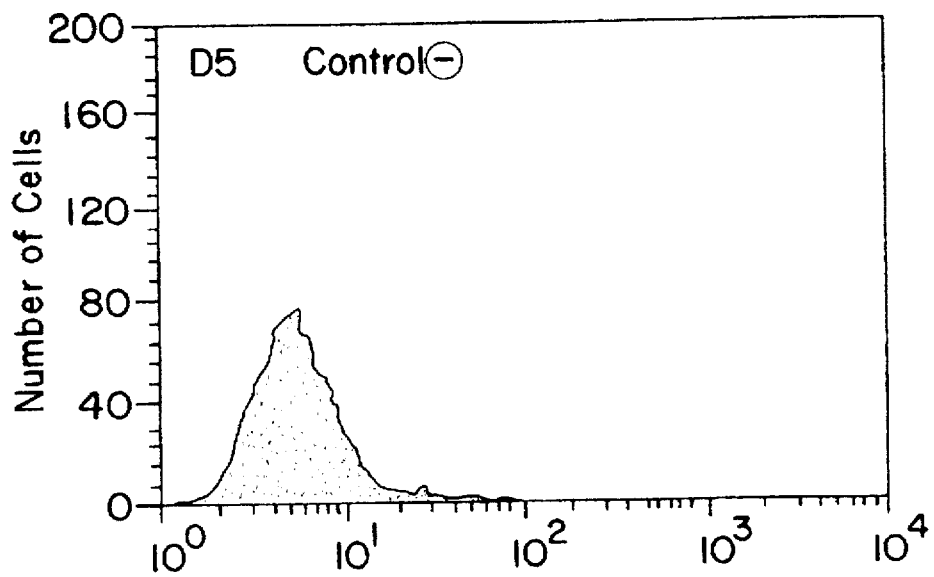
Figure 55B:
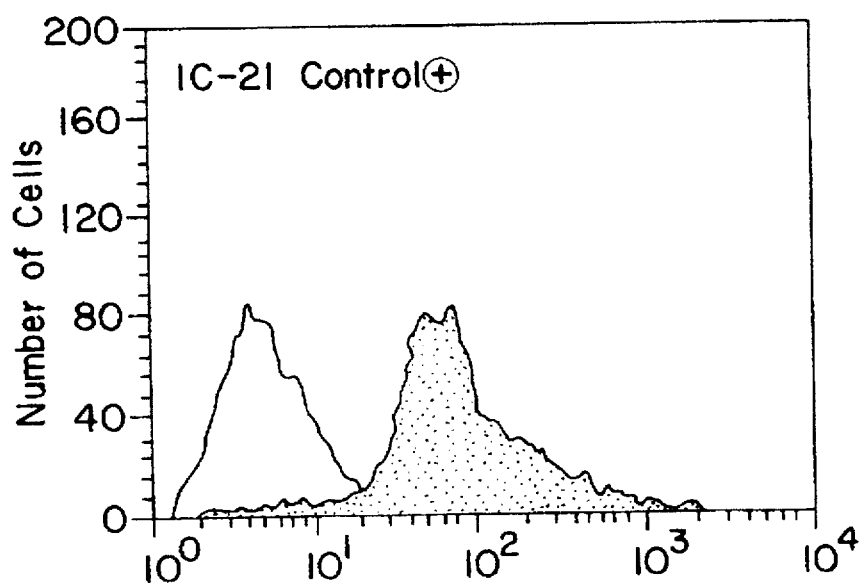
Figure 55C:
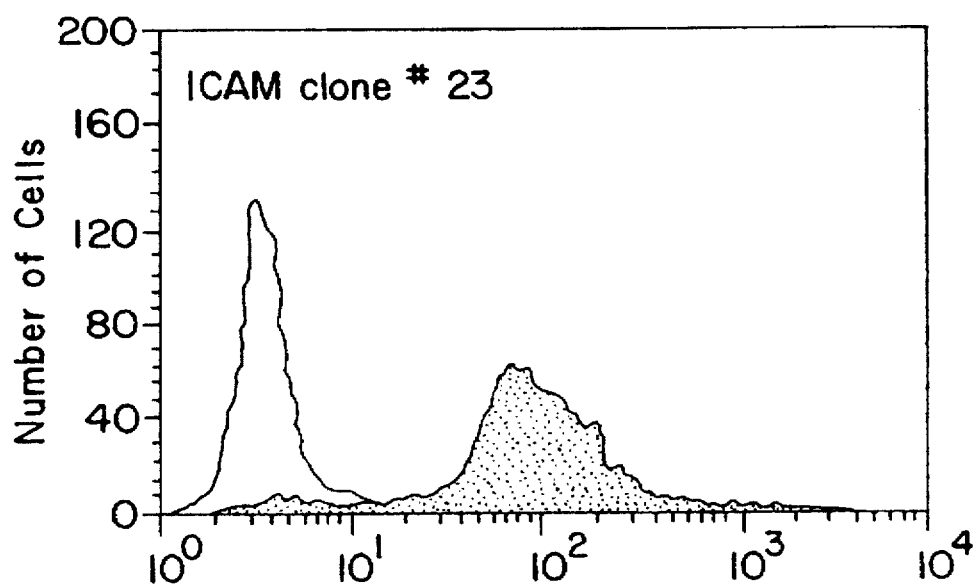
Figure 55D:
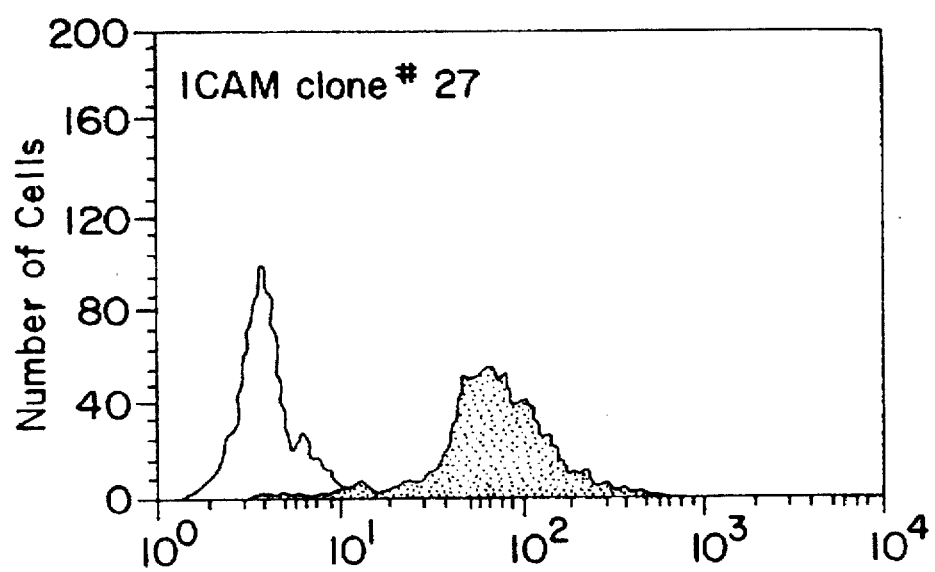
Figure 55E:
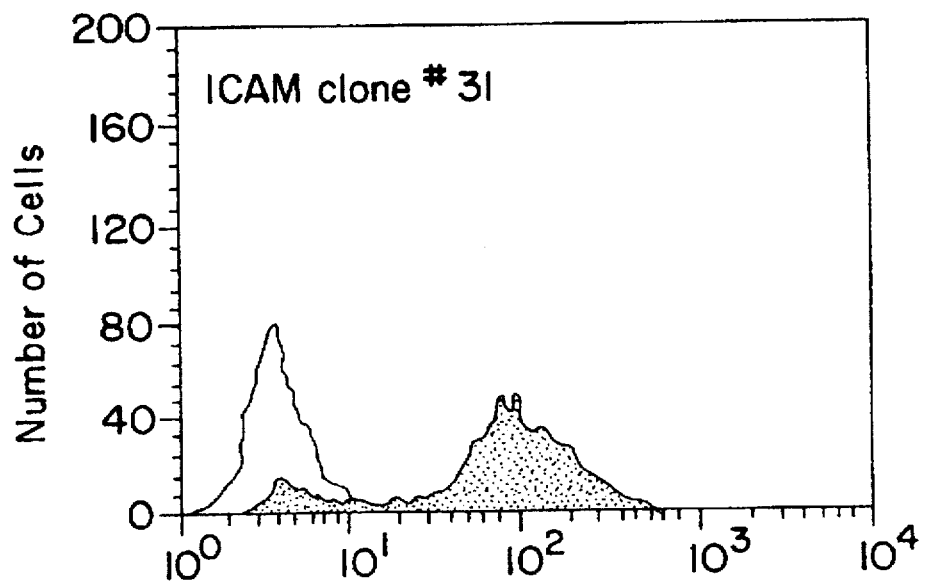
Figure 55F:
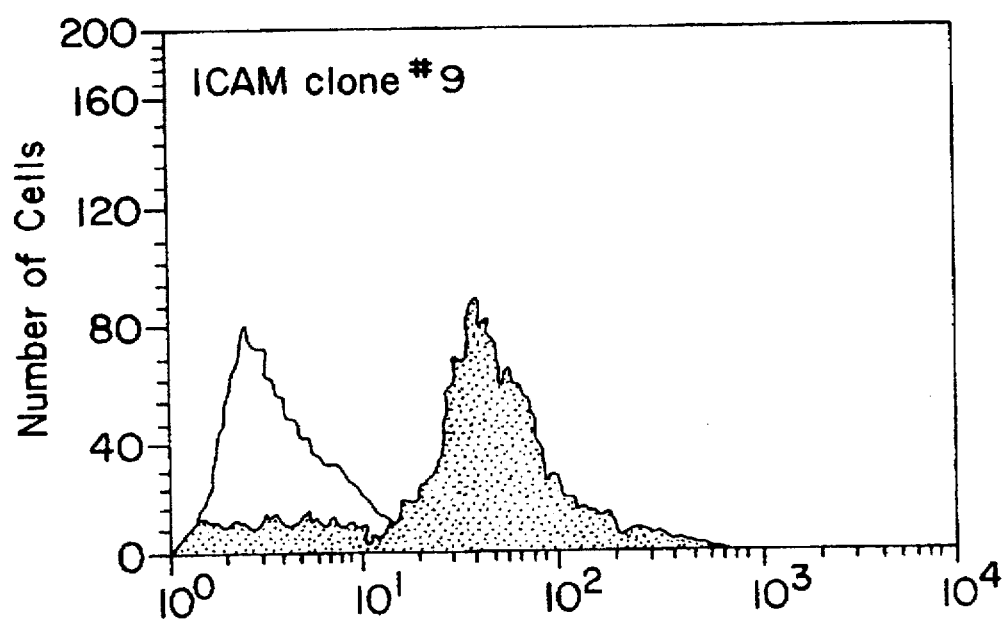

FIG. 54 is a graph showing production of permanently transfected MSU 1.2 cells with EBV-A DNA plasmid. The vertical axis shows hygromycin B resistant colonies per $1 \times 10^6$ cells; and the horizontal axis are sample numbers (as listed in Example 72).

FIGS. 55A–F show a tracing of FACS analysis (fluorescence) in various cell clones transfected with an ICAM expression plasmid. In all of the Figures the vertical axis are the number of cells and the horizontal axis is the amount of ICAM expressed (fluorescence), Example 72.

FIG. 56 shows LUCIFERASE™ activity in RAT2 cells after transfection with pH controlled dendrimer aggregate at a DNA:dendrimer charge ratio of 1:10. The vertical axis is the relative light units per µg protein. The horizontal axis is the sample number used in the test, Example 74.

FIG. 57 shows LUCIFERASE™ activity in RAT2 cells after transfection using lysine modified dendrimers and non-modified dendrimers, both in the presence of DEAE-dextran at a DNA:dendrimer charge ratio of 1:10. The vertical axis is relative light units per µg protein; and the horizontal axis is samples used in the test, Example 75.

FIG. 58 shows the transfection results for two cell lines (COS1 and RAT2), each transfected with various dendrimers, polydisperse dendrimers, and other transfection agents. The vertical axis is relative light units per 3 µg cellular protein; and the horizontal axis is the sample number and charge ratio for the various transfection agents used, Example 76.

FIGS. 59 1–5 comprise photographs of stained cell cultures of mouse melanoma D5 cells, whose parent cells were transfected with RSV-β-gal plasmid DNA. Stable transformants (colonies) are selected with G418 (Example 72). The transfection vehicles used in the parent cells in each of the numbered cultures are:

1. 10 µg DNA with calcium phosphate
2. 10 µg DNA with DEAE-dextran
3. 5 µg DNA with 0.5 µM G8 ($NH_3$)
4. 10 µg DNA with 0.5 µM G8 ($NH_3$)
5. 5 µg DNA with 0.2 µM G8 ($NH_3$)

FIGS. 60A and B are provided in various numbered panels.

Panel 1 is a photomicrograph of tissue sections of D5 mouse melanoma tumor injected in vivo with 10 µg of RSV-β-gal plasmid DNA complexed with G11 (EDA) dendrimer at a 1:10 DNA:dendrimer charge ratio. Successful transfection of the tumor cells is confirmed by the presence of D5 cells expressing β-gal, which is documented by the dark (blue) stain visible in Panel 1, Example 77.

Panel 2 is a photomicrograph of the control for the Panel 1 tissue, in that the D5 mouse melanoma tumor was injected with G11 (EDA) dendrimer only, Example 77.

Panels 3, 4 and 5 are electron-micrographs of the following DNA:dendrimer complexes, Example 43:

Panel 3—DNA with G11 (EDA) dendrimer at a DNA-:dendrimer charge ratio of 1:10;

Panel 4—same as for Panel 3, but with subsequent addition of DEAE-dextran; and

Panel 5—DNA with a polydisperse size mixture of dendrimers at a DNA:dendrimer charge ratio of 1:10.

FIGS. 61A and 61B are graphs comparing transfection using different dense star dendrimers or combinations thereof at different charge ratios and under three different conditions: transfections using a genetic material:dendrimer complex alone (speckle bars); the same genetic material-:dendrimer complexes in the presence of DEAE-dextran (diagonally hatched bars); and the same genetic material-:dendrimer complexes in the presence of chloroquine (solid bars). The resulting data as graphed in FIG. 61A shows that COS1 cells were transfected and in FIG. 61B, RAT2 cells were transfected. The vertical axis indicates the relative light units per 3 μg of protein. The numbers on the horizontal axis are the genetic material:dendrimer complex sample numbers from Example 73.

Figure 62:
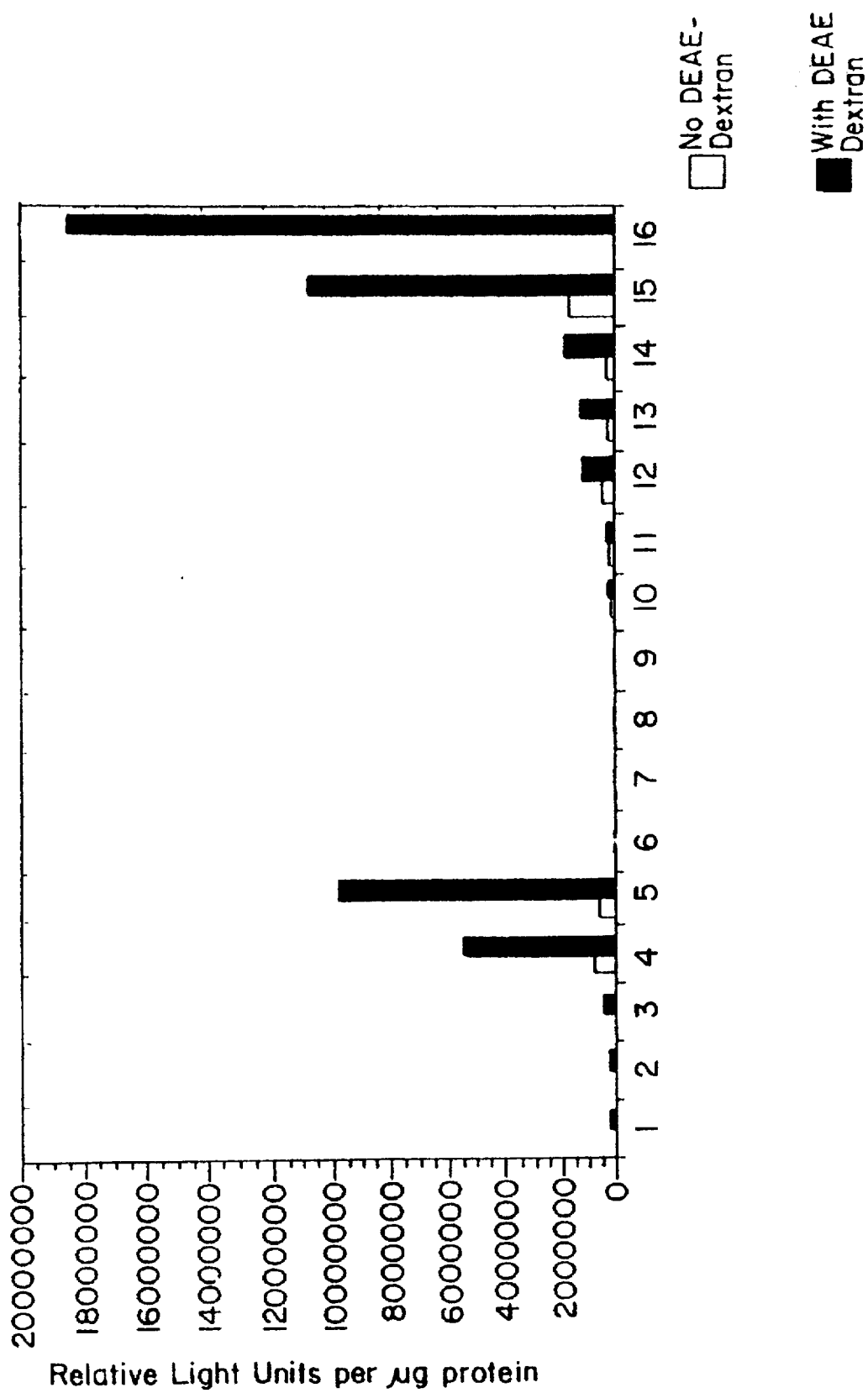

FIG. 62 is a graph comparing transfection using lysine-based, unsymmetrically branched dendrimers to transfection using dense star dendrimers, Example 78. The vertical axis is the relative light units per μg of protein; and the horizontal axis is the dendrimer used. The open bars represent no DEAE-dextran; and the solid bars represent with DEAE-dextran.

DETAILED DESCRIPTION OF THE INVENTION

Figure 1:
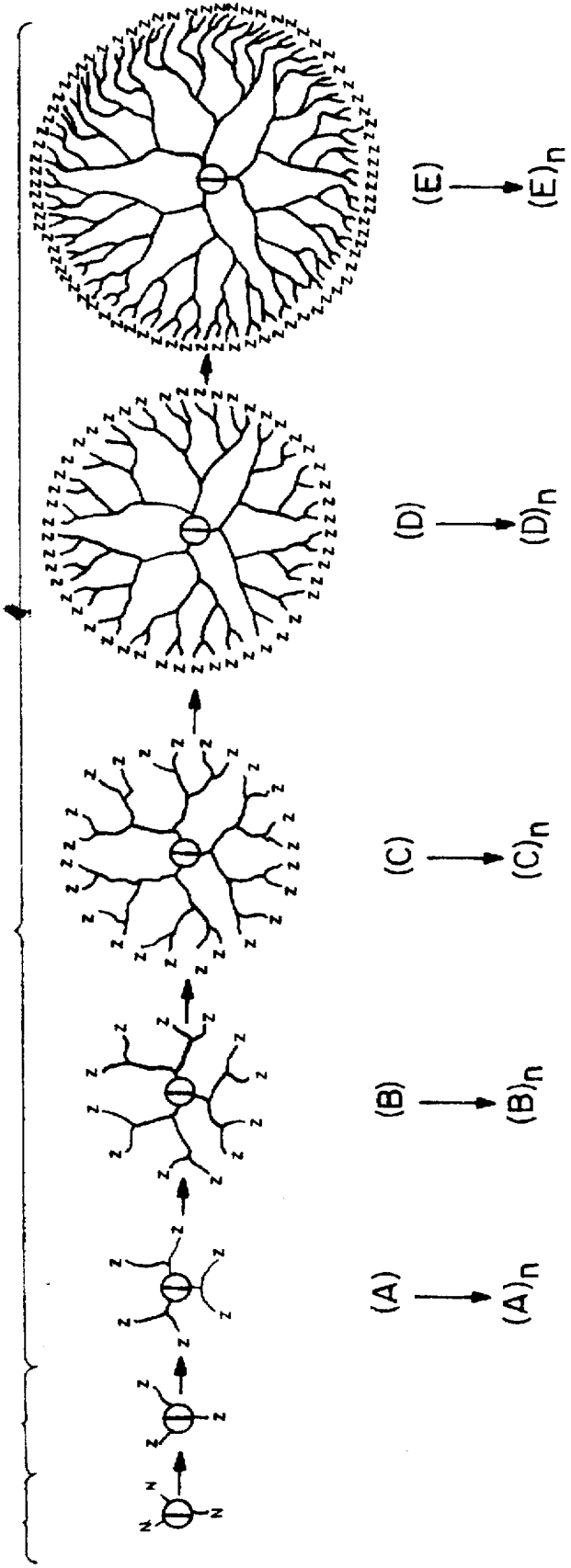
FIGS. 1A–E depict various generations of STARBURST™ dendrimers.

The STARBURST™ polymers are illustrated by FIG. 1 wherein the circled I [herein "core (I)"] represents an initiator core (in this figure a tri-functional initiator core shown by the far left drawing); Z represents a terminal group, shown in the first instance by the second drawing from the left, referred to as a star branched oligomer; A, B, C, D, and E represent particular molecular generations of STARBURST™ dendrimers; and $(A)_n$, $(B)_n$, $(C)_n$, $(D)_n$, and $(E)_n$ represent STARBURST™ bridged dendrimers.

The STARBURST™ dendrimers are unimolecular assemblages that possess three distinguishing architectural features, namely, (a) an initiator core, (b) interior layers (generations, G or Gen) composed of repeating units, radially attached to the initiator core, and (c) an exterior surface of terminal functionality (i.e., terminal functional groups) attached to the outermost generation. The size and shape of the STARBURST™ dendrimer molecule and the functional groups present in the dendrimer molecule can be controlled by the choice of the initiator core, the number of generations (i.e., tiered structure that is formed by each generation when it advances to the next generation) employed in creating the dendrimer, and the choice of the repeating units employed at each generation. Since the dendrimers can be isolated at any particular generation, a means is provided for obtaining dendrimers having desired properties. To have the properties of a dense star dendrimer all of the above three architectural features must be present. These features have been discussed further by Petar R. Dvornic and Donald A. Tomalia in *Chem. in Britain*, 641–645, August 1994. As used in this application, the dendrimers may be indicated by their generation number and the initiator core used, e.g., G7 (EDA) dendrimer.

The choice of the STARBURST™ dendrimer components affects the properties of the dendrimers. The initiator core type can affect the dendrimer shape, producing (depending on the choice of initiator core), for example, spheroid-shaped dendrimers, cylindrical or rod-shaped dendrimers, ellipsoid-shaped dendrimers, or mushroom-shaped dendrimers. Sequential building of generations (i.e., generation number and the size and nature of the repeating units) determines the dimensions of the dendrimers and the nature of their interior.

Because STARBURST™ dendrimers are branched polymers containing dendritic branches having functional groups distributed on the periphery of the branches, they can be prepared with a variety of properties. For example, the macromolecules depicted in FIG. 2A (such as Denkewalter, U.S. Pat. No. 4,289,872), and the present STARBURST™ dendrimers, such as those depicted in FIG. 2B have distinctly different properties due to the branch length. The dendrimer type shown in FIG. 2A possesses unsymmetrical (unequal segment) branch junctures, exterior (i.e., surface) groups (represented by Z'), and interior moieties (represented by Z) but much less internal void space. The preferred dendrimer type shown in FIG. 2B possesses symmetrical (equal segment) branch junctures with surface groups (represented by Z'), two different interior moieties (represented respectively by X and Z) with interior void space which varies as a function of the generation (G). The dendrimers such as those depicted in FIG. 2B can be advanced through enough generations to totally enclose and contain void space, to give an entity with a predominantly hollow interior and a highly congested surface.

It is the tiered structure that is the essence of the STARBURST™ dendrimers rather than the elemental composition. Therefore, the repeat units may be composed of a combination of any elements, so long as these units possess the properties of multiplicity and are assembled into the tiered structure as described herein. These repeat units may be composed entirely of elements that are commonly seen in polymeric structures, such as carbon, hydrogen, oxygen, sulfur, nitrogen, and silicon, or may be composed of less traditional elements, provided that these repeat units allow a stable branched structure to be constructed. For example, metalloids and transition metals are well known in the art to form stable covalent compounds and complexes with organic moieties. These stable covalent compounds and complexes with organic moieties can exist as branched materials such as, for example, boranes, borates, germanes, stannanes, and plumbanes, or non-branched linkages such as, for example, dialkyl zincs or mercuries. The use of appropriate ligands can make a transition metal, such as cobalt, function as a branching unit (by connecting three separate ligands) or a non-branched linkage (by connecting two separate ligands). Therefore, branched structures fitting the patterns described herein and incorporating any element are within the scope of the present invention.

Also, STARBURST™ dendrimers, when advanced through sufficient generations exhibit "STARBURST™ dense packing" where the surface of the dendrimer contains sufficient terminal moieties such that the dendrimer surface becomes congested and encloses void spaces within the interior of the dendrimer. This congestion can provide a molecular level barrier which can be used to control diffusion of materials into or out of the interior of the dendrimer.

Surface chemistry of the dendrimers can be controlled in a predetermined fashion by selecting a repeating unit which contains the desired chemical functionality or by chemically modifying all or a portion of the surface functionalities to create new surface functionalities. For example, these surfaces may either be targeted toward specific sites or made to resist uptake by particular organs or cells, e.g. by reticuloendothelial cells.

In an alternative use of the STARBURST™ dendrimers, the dendrimers can themselves be linked together in a variety of manners (included in the term "associated with") to create polydendritic moieties (STARBURST™ bridged dendrimers or dendrimer aggregates) or dense star dendrimer aggregates which are also suitable as carriers in the conjugates.

In addition, the dendrimers can be prepared so as to have deviations from uniform branching in particular generations, thus providing a means of adding discontinuities (i.e., deviations from uniform branching at particular locations within the dendrimer) and different properties to the dendrimer.

The STARBURST™ polymers employed in the STARBURST™ conjugates of the present invention can be prepared according to methods known in the art, for example, U.S. Pat. No. 4,587,329, the disclosure of which is hereby incorporated by reference. Polyamine dendrimers may be prepared by reacting ammonia or an amine having a plurality of primary amine groups or secondary amine groups with N-substituted aziridine, such as N-tosyl or N-mesyl aziridine, to form a protected first generation polysulfonamide. The first generation polysulfonamide is then activated with acid, such as sulfuric, hydrochloric, trifluoroacetic, fluorosulfonic or chlorosulfonic acid, to form the first generation polyamine salt. Preferably, the desulfonylation is carried out using a strong acid which is volatile enough to allow removal by distillation, such as hydrochloric acid. The first generation polyamine salt can then be reacted further with N-protected aziridine to form the protected second generation polysulfonamide. The sequence can be repeated to produce higher generation polyamines.

Polyamidoamines can be prepared by first reacting ammonia (or an amine having a plurality of primary and/or secondary amine groups) with methyl acrylate under conditions sufficient to cause the Michael addition of one molecule of the ammonia to three molecules of the methyl acrylate to form the core adduct. Following removal of unreacted methyl acrylate, this compound is reacted with excess ethylenediamine under conditions such that one amine group of the ethylenediamine molecule reacts with the methyl carboxylate groups of the core adduct to form a first generation adduct having three amidoamine moieties. Following removal of unreacted ethylenediamine, this first generation adduct is then reacted with excess methyl acrylate under Michael's addition conditions to form a second generation adduct having terminal methyl ester moieties. The second generation adduct is then reacted with excess ethylenediamine under amide forming conditions to produce the desired polyamidoamine dendrimer having ordered, second generation dendritic branches with terminal amine moieties. Similar dendrimers containing amidoamine moieties can be made by using organic amines as the core compound, e.g., ethylenediamine which produces a tetra-branched dendrimer or diethylenetriamine which produces a pent-abranched dendrimer.

To prepare anhydrous STARBURST™ polyethyleneimines, after acid cleavage of the sulfonamide bonds, a solvent which will form an azeotrope with water, such as benzene, toluene, xylene or mesitylene, preferably toluene, can be added and the resulting water/solvent azeotrope removed by azeotropic distillation, such as by heating the mixture to reflux with water removal carried out by a Dean-Stark trap. Alternatively, chlorinated solvents in which anhydrous polyethyleneimine is soluble, such as chloroform, can be used in the drying step. The addition of a chlorinated solvent or solvent which forms an azeotrope with water, avoids the necessity of having to heat the polymer at temperatures which char or degrade the polymer. Anhydrous polyethyleneimines are particularly useful as carriers for antigenic materials (e.g., antibodies or antibody fragments).

Dendrimers can be prepared having highly uniform size and shape and most importantly allow for a greater number of functional groups per unit of surface area of the dendrimer, and can have a greater number of functional groups per unit of molecular volume as compared to other polymers which have the same molecular weight, same core and monomeric components and same number of core branches as the STARBURST™ polymers. The increased functional group density of the dense STARBURST™ polymers may allow a greater quantity of material to be carried per dendrimer. Since the number of functional groups on the dendrimers can be controlled on the surface and within the interior, it also provides a means for controlling, for example, the amount of bioactive agent to be delivered per dendrimer. In a particularly preferred embodiment of the present invention, the STARBURST™ polymers, particularly the STARBURST™ dendrimers, are targeted carriers of bioactive agents capable of delivering the bioactive agents to a particular target organ or to a particular determinant or locus in a target organism.

An analogy can be made between early generation STARBURST™ dendrimers (i.e., generation=1–7) and classical spherical micelles. The dendrimer-micelles analogy was derived by comparing features which they had in common such as shape, size and surface characteristics.

TABLE I

| Parameter | Regular Classical Micelles | Starburst Dendrimers |
| --- | --- | --- |
| Shape | Spherical | Spherical |
| Size (diameter) | 20–60 Å | 17–64 Å |
| Surface aggregation number | 4–202 | Z = 6–192 (Z is the number of surface groups) (generation = 2–7) |
| area/surface group ($Å^2$) | 130–80 $Å^2$ | 127–75 $Å^2$ |

($Å^2 = 10^{-1}$ nm; $10^{-1} = 10^{-1}$ nm$^2$)

In Table I, the shape was verified by scanning transmission electron microscopy (STEM). The size was verified by intrinsic viscosity [η] measurements and size exclusion chromatography (SEC). The surface aggregation numbers were verified by titrimetry and high field NMR. The area/surface group was calculated from SEC hydrodynamic measurements.

The first five generations of STARBURST™ polyamidoamine (PAMAM) dendrimers are microdomains which very closely mimic classical spherical micelles in nearly every respect (i.e., shape, size, number of surface groups, and area/surface groups). A major difference, however, is that they are covalently fixed and robust compared to the dynamic equilibrating nature of micelles. This difference is a significant advantage when using these microdomains as encapsulation devices.

As further concentric generations are added beyond five, congestion of the surface occurs. This congestion can lead to increased barrier characteristics at the surface and manifests itself as a smaller surface area per head (surface) group as shown in Table II.

TABLE II

PAMAM Dendrimer Features vs. Generation

| Generations | 1 | 2 | 3 | 4 | 5 | 6 | 7 | 8 | 9 |
|---|---|---|---|---|---|---|---|---|---|
| # of surface groups, Z | 3 | 6 | 12 | 24 | 48 | 96 | 192 | 384 | 768 |
| Molecular wt. | 275 | 875 | 2411 | 5147 | 10,619 | 21,563 | 43,541 | 87,227 | 174,779 |
| Diameter* measured SEC | 10.4 Å | 15.8 Å | 22 Å | 31 Å | 40 Å | 53 Å | 67 Å | 76 Å | 88 Å |
| Surface area per dendrimer | 366 Å² | 783 Å² | 1519 Å² | 3018 Å² | 5024 Å² | 8,820 Å² | 14,096 Å² | 18,136 Å² | 24,328 Å² |
| Surface area per Z group | 122 Å² | 131 Å² | 127 Å² | 126 Å² | 104 Å² | 92 Å² | 73 Å² | 47 Å² | 32 Å² |
| Distance between Z groups | 12.4 Å | 12.8 Å | 12.7 Å | 12.6 Å | 11.5 Å | 10.8 Å | 9.8 Å | 7.75 Å | 6.28 Å |
| Void Volume | 311.6 Å³ | 1,470.2 Å³ | 4,737.9 Å³ | 11,427.0 Å³ | — | — | — | — | — |

*Hydrodynamic diameters determined by size exclusion chromatogaphy measurements calibrated against monodisperse $\left(\frac{Mw}{Mn} = 1.02\right)$ polyethyleneoxide standards.

$1 \text{ Å} = 10^{-1} \text{ nm}; 1 \text{ Å}^2 = 10^{-2} \text{ nm}^2; 1 \text{ Å}^3 = 10^{-3} \text{ nm}^3$.

For example, amine terminated generations 5.0, 6.0, 7.0, 8.0 and 9.0 have decreased surface areas of 104, 92, 73, 47 and 32 Å² per Z group, respectively. This characteristic corresponds to a transition from a less congested surface to a more congested micelle-like surface with a bi-layer/monolayer barrier-like surface normally associated with vesicles (liposomes) or Langmuir-Blodgett type membranes.

If this surface congestion is occurring, a change in physical characteristics and morphology should be observed as the generations increase from the intermediate generations (G6–G8) to the more advanced generations (G9 or G10). The scanning transmission electron micrographs (STEM) for generations (G)=7.0, 8.0 and 9.0 were obtained after removing the methanol solvent from each of the samples to provide colorless, light yellow solid films and followed by staining with osmium tetroxide. The morphological change predicted occurred at the generation (G)=9.0 stage. The hollow interior at G=9.0 measures about 63 Å in diameter and is surrounded by a darkened rim which is about 22 Å thick. Apparently methanolic solvent has been entrapped within the 22 Å outer membrane-like barrier to provide the colorless interior. Thus, at G=9.0, the STARBURST™ PAMAM is behaving topologically like a vesicle (liposome). However, this STARBURST™ is an order of magnitude smaller and very monodispersed compared to a liposome and is much more physically stable than a liposome. Consequently, the present dendrimers have a large enough void interior to molecularly encapsulate solvent filled void spaces of as much diameter as about 63 Å (volume about 131,000 Å³) or more. These micelle sized prototypes appear to behave like a covalently fixed liposome at this advanced generation stage. This behavior enables these prototypes to have additional capability as carriers for, for example, non-chelating radionuclides in STARBURST™ antibody conjugates for the treatment of various mammalian diseases.

Since the number of functional groups on the dendrimers can be controlled both on the surface and within the interior, it also provides a means for controlling the amount of carried material to be delivered per dendrimer. In one embodiment, the dendrimers are targeted carriers of agents, capable of delivering the carried material, for example, a bioactive agent, to, for example, a plant or pest or a particular determinant or locus in a target organism.

Dendrimers suitable for use in the conjugates of the present invention include the dense star polymers or STARBURST™ polymers described in U.S. Pat. Nos. 4,507,466, 4,558,120, 4,568,737 and 4,587,329, which are hereby incorporated by reference.

In particular, the preferred embodiment concerns a STARBURST™ conjugate which comprises at least one STARBURST™ polymer associated with at least one carried agricultural, pharmaceutical, or other material. STARBURST™ conjugates included within the scope of the present invention include those represented by the formula:

$$(P)_x{}^*(M)_y \tag{I}$$

wherein:

each P represents a dendrimer;

x represents an integer of 1 or greater;

each M represents a unit (for example, a molecule, atom, ion, and/or other basic unit) of a carried material, said carried material can be the same carried material or a different carried material, preferably the carried material is a bioactive agent;

y represents an integer of 1 or greater; and

* indicates that the carried material is associated with the dendrimer; and with the proviso that the carried material maintains its effectiveness.

In Formula (I) above P may be a dense star polymer or dendritic polymer when the carried material is a biological response modifier, especially genetic material.

Preferred STARBURST™ conjugates of Formula (I) are those in which M is a drug, pesticide, radionuclide, chelant, chelated metal, toxin, antibody, antibody fragment, antigen, signal generator, for example, fluorescing entities, signal reflector, for example, paramagnetic entities, or signal absorber, for example, electron beam opacifiers, fragrance, pheromones, or dyes. The terms "signal generator" and "signal absorber" are well known to one skilled in the art. A signal generator may be defined as an entity which is capable of emitting a detectable amount of energy in the form of electromagnetic radiation (such as X-rays, UV radiation, IR radiation, visible radiation and the like) and include phosphorescent and fluorescent entities (e.g., luciferase and alkaline phosphatase) and bioluminescent markers, and gamma and X-ray emitters, or matter (such as neutrons, positrons, β-particles, α-particles, and the like) and include radionuclides, positron emitters and the like. A signal absorber may be defined as an entity which absorbs a detectable amount of energy in the form of electromagnetic radiation or matter. Some examples are dyes, contrast agents, and boron (which absorbs neutrons). A given entity can be both a signal absorber and a signal generator, i.e., fluorescent or phosphorescent substances can absorb light and/or emit light, sometimes after exposure to light such as fluorine containing labels used in DNA sequencing; boron absorbs neutrons and emits radiation, paramagnetic particles can be used in the capture of targeted molecules and emission of energy, and many other such examples. The term pheromone is well known to those skilled in the art and is defined and exemplified, for example, in the McGraw-Hill *Encyclopedia of Science & Technology*, 7th ed., Vol. 13, pp 360–361; and "Insect Pheromone Technology:Chemistry and Applications", ACS Symposium Series 190 (1982). Examples of suitable fragrances, such as perfumes and flavors, are well known to those skilled in the art, and are illustrated and defined further in *Perfume and Flavor Chemicals*, Vols. I and II, by Steffen Arctander, pub. Montclair, N.J. (1969). Dyes and dye moieties are well known to those skilled in the art, and are illustrated and defined in, for example, *Webster's Third New International Dictionary*, pp 706–710, pub. G. C. Merriam Company (1981); Kirk-Othmer *Encyclopedia of Chemical Technology*, Vol. 8, pp 151–406, 3rd ed., pub. John Wiley & Sons (1979). It is particularly preferred that x=1 and y=2 or more.

Also included are STARBURST™ conjugates of Formula (I) wherein the STARBURST™ dendrimers are covalently linked together, STARBURST™ bridged dendrimers, optionally via linking groups, so as to form polydendritic assemblages (i.e., where x>1). Uses of these STARBURST™ bridged dendrimers include topical controlled release agents, radiation synovectomy, and others.

As used herein, "associated with" means that the carried material(s) can be physically encapsulated or entrapped within the core of the dendrimer, dispersed partially or fully throughout the dendrimer, or attached or linked to the dendrimer or any combination thereof, whereby the attachment or linkage is by means of covalent bonding, hydrogen bonding, adsorption, absorption, metallic bonding, van der Waals forces or ionic bonding, or any combination thereof. The association of the carried material(s) and the dendrimer (s) may optionally employ connectors and/or spacers to facilitate the preparation or use of the STARBURST™ conjugates. Suitable connecting groups are groups which link a targeting director (i.e., T) to the dendrimer (i.e., P) without significantly impairing the effectiveness of the director or the effectiveness of any other carried material(s) (i.e., M) present in the STARBURST™ conjugate. These connecting groups may be cleavable or non-cleavable and are typically used in order to avoid steric hindrance between the target director and the dendrimer, preferably the connecting groups are stable (i.e., non-cleavable). Since the size, shape and functional group density of the STARBURST™ dendrimers can be rigorously controlled, there are many ways in which the carried material can be associated with the dendrimer. For example, (a) there can be covalent, coulombic, hydrophobic, or chelation type association between the carried material(s) and entities, typically functional groups, located at or near the surface of the dendrimer; (b) there can be covalent, coulombic, hydrophobic, or chelation type association between the carried material(s) and moieties located within the interior of the dendrimer; (c) the dendrimer can be prepared to have an interior which is predominantly hollow allowing for entrapment (e.g., physically within or by association with the interior moieties of the dense star dendrimer) of the carried materials within the interior (void volume), (e.g., magnetic or paramagnetic cores or domains created by the chelation and reduction of metal ions to the zero valence state within the dendrimer), these dendrimers containing magnetic interiors can be used for harvesting various bioactive entities that can be complexed with various dendrimer surfaces by use of magnets and the like, wherein the release of the carried material can optionally be controlled by congesting the surface of the dendrimer with diffusion controlling moieties; or (d) various combinations of the aforementioned phenomena can be employed.

Dendrimers, herein represented by "P", include the dense star polymers described in U.S. Pat. Nos. 4,507,466, 4,558, 120, 4,568,737 or 4,587,329.

In a preferred embodiment, the carried materials, herein represented by "M", are pharmaceutical materials. Such materials which are suitable for use in the STARBURST™ conjugates include any materials for in vivo, ex vivo or in vitro use for diagnostic or therapeutic treatment of mammals which can be associated with the dense star dendrimer without appreciably disturbing the physical integrity of the dendrimer, for example, but not limited to:

drugs, such as, but not limited to, antibiotics, analgesics, antihypertensives, cardiotonics, and the like; examples are acetaminophen, acyclovir, alkeran, amikacin, ampicillin, aspirin, bisantrene, bleomycin, neocardiostatin, chloroambucil, chloramphenicol, cytarabine, daunomycin, doxorubicin, fluorouracil, gentamycin, ibuprofen, kanamycin, meprobamate, methotrexate, novantrone, nystatin, oncovin, phenobarbital, polymyxin, probucol, procarbazine, rifampin, streptomycin, spectinomycin, symmetrel, thioguanine, tobramycin, trimethoprim, and valban;

toxins, such as, but not limited to, diphtheria toxin, gelonin, exotoxin A, abrin, modeccin, ricin, or toxic fragments thereof;

metal ions, such as, but not limited to, the metals in the Periodic Table Groups VIIIA (Fe, Co, Ni, Ru, Rh, Pd, Os, Ir, Pt), IVB (Pb, Sn, Ge), IIIA (Sc, Y, lanthanides and actinides), IIIB (B, Al, Ga, In, Tl), IA alkali metals (Li, Na, K, Rb, Cs, Fr), and IIA alkaline-earth metals (Be, Mg, Ca, Sr, Ba, Ra) and transition metals;

radionuclides, such as, but not limited to, those generated from actinides or lanthanides or other similar transition elements or from other elements, such as $^{47}$Sc, $^{67}$Cu, $^{67}$Ga, $^{82}$Rb, $^{89}$Sr, $^{88}$Y, $^{90}$Y, $^{99m}$Tc, $^{105}$Rh, $^{109}$Pd, $^{111}$In, $^{115m}$In, $^{125}$I, $^{131}$I, $^{140}$Ba, $^{140}$La, $^{149}$Pm, $^{153}$Sm, $^{159}$Gd, $^{166}$Ho, $^{175}$Yb, 177Lu, 186Re, $^{188}$Re, $^{194}$Ir, and $^{199}$Au, preferably $^{88}$Y, $^{90}$Y, $^{99m}$Tc, $^{125}$I, $^{131}$I, $^{153}$Sm, $^{166}$Ho, $^{177}$Lu, $^{186}$Re, $^{67}$Ga, $^{111}$In, $^{115m}$In, and $^{140}$La;

signal generators, which include anything that results in a detectable and measurable perturbation of the system due to its presence. A signal generator may be defined as an entity which emits a detectable amount of energy in the form of electromagnetic radiation (such as X-rays, ultraviolet (UV) radiation, infrared (IR) radiation and the like) and include phosphorescent and fluorescent entities, and gamma and X-ray emitters, or matter (such as neutrons, positrons, β-particles, α-particles, and the like) and include radionuclides, positron emitters and the like; such as, but not limited to, fluorescing entities, phosphorescence entities and radiation, such as radionuclides, particles and radiation sources, and nucleotides, toxins or drugs labeled with one or more of any of the above, including but not limited to signal generators;

signal reflectors, such as, but not limited to, paramagnetic or magnetic entities, for example, Fe, Gd, or Mn, nitroxyl radicals, NMR shift reagents such as Eu or Pr salts;

chelated metal, such as, but not limited to, any of the metals or their ions given above, whether or not they are radioactive, i.e., contrast agents, paramagnetic or magnetic entities, metals ions, when associated with a chelant;

signal absorbers may be defined as an entity which absorbs a detectable amount of energy in the form of electromagnetic radiation or matter. Some examples are dyes, contrast agents, electron beam opacifiers, aromatic UV absorber, and boron (which absorbs neutrons). A given entity can be both a signal absorber and a signal generator, i.e., fluorescent or phosphorescent substances can absorb light and emit light; boron absorbs neutrons and emits radiation, and many other such examples; e.g., such as, but not limited to, contrast agents, for example, Gd, Mn or Fe, and electron beam opacifiers such as Pb or Fe;

antibodies, including monoclonal antibodies and anti-idiotype antibodies;

antibody fragments;

hormones;

biological response modifiers, i.e., bioactive agents which alter the response of the organism to stimuli, such as, but not limited to, interleukins, interferons, tumor necrosis factor, granulocyte colony stimulating factor, viruses, viral fragments and other genetic materials;

diagnostic opacifiers, such as a signal absorbers above, biological stains and the like;

fluorescent moieties; and scavenging agents such as chelants, antigens, antibodies or any moieties capable of selectively scavenging therapeutic or diagnostic agents.

In another embodiment, the carried materials, herein represented by "M", are agricultural materials. Such materials which are suitable for use in the STARBURST™ conjugates include any materials for in vivo, ex vivo or in vitro treatment, diagnosis, or application to plants or non-mammals (including microorganisms) which can be associated with the STARBURST™ dendrimer without appreciably disturbing the physical integrity of the dendrimer. For example, the carried materials can be toxins, such as, but not limited to, diphtheria toxin, gelonin, exotoxin A, abrin, modeccin, ricin, or toxic fragments thereof;

metal ions, such as described above for pharmaceutical carried materials;

radionuclides, such as those generated from actinides or lanthanides or other similar transition elements or from other elements, such as $^{47}$Sc, $^{67}$Cu, $^{67}$Ga, $^{82}$Rb, $^{89}$Sr, $^{88}$Y, $^{90}$Y, $^{99m}$Tc, $^{105}$Rh, $^{109}$Pd, $^{111}$In, $^{115m}$In, $^{125}$I, $^{131}$I, $^{140}$Ba, $^{140}$La, $^{149}$Pm, $^{153}$Sm, $^{159}$Gd, $^{166}$Ho, $^{175}$Yb, $^{177}$Lu, $^{186}$Re, $^{188}$Re, $^{194}$Ir and $^{199}$Au, or those as described above for pharmaceutical carried materials;

signal generators, which includes anything that results in a detectable and measurable perturbation of the system due to its presence, such as fluorescing entities, phosphorescence entities and radiation, or those as described above for pharmaceutical carried materials;

signal reflectors, such as paramagnetic entities, for example, Fe, Gd, or Mn, or those as described above for pharmaceutical carried materials;

signal absorbers, such contrast agents and as electron beam opacifiers, for example, Fe, Gd, or Mn or those as described above for pharmaceutical carried materials;

pheromones or hormones;

biological response modifiers, such as interleukins, interferons, viruses, viral fragments and other genetic materials; pesticides, including antimicrobials, algicides, anthelmintics, acaridicides, insecticides, attractants, repellents, herbicides and/or fungicides, such as acephate, acifluorfen, alachlor, atrazine, benomyl, bentazon, captan, carbofuran, chloropicrin, chlorpyrifos, chlorsulfuron, cyanazine, cyhexatin, cypermethrin, 2,4-dichlorophenoxyacetic acid, dalapon, dicamba, diclofop methyl, diflubenzuron, dinoseb, endothall, ferbam, fluazifop, glyphosate, haloxyfop, malathion, naptalam, pendimethalin, permethrin, picloram, propachlor, propanil, sethoxydim, temephos, terbufos, trifluralin, triforine, zineb, and the like; and scavenging agents such as chelants, chelated metal (whether or not they are radioactive) or any moieties capable of selectively scavenging therapeutic or diagnostic agents.

In another embodiment, the carried material, herein represented by "M", are immuno-potentiating agents. Such materials which are suitable for use in the STARBURST™ conjugates include any antigen, hapten, organic moiety or organic or inorganic compounds which will raise an immune response which can be associated with the STARBURST™ dendrimers without appreciably disturbing the physical integrity of the dendrimers. For example, the carried materials can be synthetic peptides used for production of vaccines against malaria (U.S. Pat. No. 4,735,799), cholera (U.S. Pat. No. 4,751,064) and urinary tract infections (U.S. Pat. No. 4,740,585), bacterial polysaccharides for producing antibacterial vaccines (U.S. Pat. No. 4,695,624) and viral proteins or viral particles for production of antiviral vaccines for the prevention of diseases such as AIDS and hepatitis.

The use of STARBURST™ conjugates as carriers for immuno-potentiating agents avoids the disadvantages of ambiguity in capacity and structure associated with conventionally known or synthetic polymer conjugates used to give a macromolecular structure to the antigen-carrier. Use of the STARBURST™ dendrimers as carriers for immuno-potentiating agents, allows for control of the size, shape and surface composition of the conjugate. These options allow optimization of antigen presentation to an organism, thus resulting in antibodies having greater selectivity and higher affinity than the use of conventional adjuvants. It may also be desirable to connect multiple antigenic peptides or groups to the STARBURST™ dendrimer, such as attachment of both T- and B-cell epitopes. Such a design would lead to improved vaccines.

It may also be desirable to conjugate pesticides or pollutants capable of eliciting an immune response, such as those containing carbamate, triazine or organophosphate constituents, to a STARBURST™ dendrimer. Antibodies produced to the desired pesticide or pollutant can be purified by standard procedures, immobilized on a suitable support and be used for subsequent detection of the pesticide or pollutant in the environment or in an organism.

In a further embodiment, the carried materials, herein represented by "M", which are suitable for use in the STARBURST™ conjugates include any materials other than agricultural or pharmaceutical materials which can be associated with the STARBURST™ dendrimer without appreciably disturbing the physical integrity of the dendrimer, for example:

- metal ions, such as the alkali and alkaline-earth metals, magnetic interiors, or as for the pharmaceutical carried material as defined before;
- signal generators, which includes anything that results in a detectable and measurable perturbation of the system due to its presence, such as fluorescing entities, phosphorescence entities and radiation sources, or as for the pharmaceutical carried material as defined before;
- signal reflectors, such as paramagnetic entities, for example, Fe, Gd, or Mn, or as for the pharmaceutical carried material as defined before;
- signal absorbers, such as contrast agents and an electron beam opacifiers, for example, Fe, pheromone moieties, or as for the pharmaceutical carried material as defined before;
- fragrance moieties;
- dye moieties; and the like; and
- scavenging agents such as chelants or any moieties capable of selectively scavenging a variety of agents.

Preferably the carried materials are bioactive agents. As used herein, "bioactive" refers to an active entity such as a molecule, atom, ion and/or other entity which is capable of detecting, identifying, inhibiting, treating, catalyzing, controlling, killing, enhancing or modifying a targeted entity such as a protein, a gene, glycoprotein, lipoprotein, lipid, a targeted cell, a targeted organ, a targeted organism [for example, a microorganism, plant or animal (including mammals such as humans)] or other targeted moiety.

The STARBURST™ conjugates of Formula (I) are prepared by reacting P with M, usually in a suitable solvent, at a temperature which facilitates the association of the carried material (M) with the STARBURST™ dendrimer (P).

Suitable solvents are solvents in which P and M are at least partially miscible and the solvents are inert to the formation of the conjugate. If P and M are at least partially miscible with each other, no solvent may be required (e.g., the reaction is neat). When desired, mixtures of suitable solvents can be utilized. Examples of such suitable solvents are water, methanol, ethanol, chloroform, acetonitrile, toluene, dimethylsulfoxide and dimethylformamide.

The reaction conditions for the formation of the STARBURST™ conjugate of Formula (I) depend upon the particular dendrimer (P), the carried material (M), and the nature of the bond (*) formed. For example, if P is the PEI (polyethyleneimine) STARBURST™ dendrimer with an alkylene (e.g., methylene) carboxylate surface, M is a radionuclide, e.g., yttrium, then the reaction is conducted at room temperature in water. However, if P is an ester terminated polyamidoamine (PAMAM) STARBURST™ dendrimer, M is aspirin, then the reaction is conducted at room temperature in chloroform. Typically, the temperature can range from room temperature to reflux. The selection of the particular solvent and temperature will be apparent to one skilled in the art.

The ratio of M:P will depend on the size of the dendrimer and the amount of carried material. For example, the molar ratio (ratio of moles) of any ionic M to P usually is 0.1–1,000:1, preferably 1–50:1, and more preferably 2–6:1. The weight ratio of any drug, pesticide, organic or toxin M to P usually is 0.1–5:1, and preferably 0.5–3:1.

When M is a radionuclide, there are three ways the STARBURST™ conjugate can be prepared, namely: (1) P can be used as a chelant. For example, a methylenecarboxylate surface PEI or PAMAM will chelate a metal such as yttrium or indium. (2) A chelate can be covalently bonded to P. For example, an amine terminated PEI STARBURST™ dendrimer can be reacted with 1-(p-isothiocyanatobenzyl) diethylenetriaminepentaacetic acid and then chelated, or a complex such as rhodium chloride chelated with isothiocyanatobenzyl-2,3,2-tet (i.e., 6-[4-(isothiocyanatobenzyl)]-1,4,8,11-tetraazaundecane; disclosed in published European Appln. 0296522) can be reacted. (3) A prechelated radionuclide can be associated with P by hydrophobic or ionic interaction.

Other STARBURST™ conjugates, which are particularly preferred for use with pharmaceutical materials, are those conjugates which contain a target director (herein designated as "T") and which are represented by the formula:

$$(T)_e{}^*(P)_x{}^*(M)_y \qquad (II)$$

wherein:

each T represents a target director;

e represents an integer of 1 or greater; and

P, x, *, M, and y are as previously defined herein; and with the proviso that M maintains its effectiveness.

Preferred among the STARBURST™ conjugates of Formula (II) are those in which M is a drug, pesticide, radionuclide, chelator, chelated metal, toxin, signal generator, signal reflector, or signal absorber. Also preferred conjugates are those conjugates in which e=1 or 2; and those in which x=1 and y=2 or more. Particularly preferred conjugates are those in which x=1, e=1, y=2 or more and M and T are associated with the polymer via the same or different connectors.

Additionally, T and/or M in Formula (II) may be coated or shielded to prevent immunogencity or RES response by, for example, the liver. Agents which can be used for this purpose include polyethylene glycol (PEG) and others known in the art.

The STARBURST™ conjugates of Formula (II) are prepared either by forming T*P and then adding M or by forming P*M and then adding T. Either reaction scheme is conducted under conditions which are not detrimental to the particular conjugate component (such as particular pH, temperatures or salt concentrations) and in the presence of a suitable solvent when required. To control pH, buffers or addition of suitable acid or base is used. The reaction conditions are dependent on the type of association formed (*), the STARBURST™ dendrimer used (P), the carried material (M), and the target director (T). For example, when T is a monoclonal antibody and M is a chelated radionuclide, the T*P association is done through a functional group such as an isothiocyanate in water or in water with an organic modifier such as acetonitrile or dimethylformamide. Usually, the conjugation is done in a buffer at pH 7–10, preferably pH 8.5–9.5. The formed conjugate is then chelated with a radionuclide such as yttrium acetate, preferably at room temperature. Alternatively, P and M can be chelated, usually in water, before conjugation to T. The conjugation with T is carried out in a suitable buffer.

The molar ratio of T:P is preferably 1:1, especially when T is an antibody or an antibody fragment. The molar ratio of M:P will be as before.

Target directors capable of targeting the STARBURST™ conjugates are entities which when used in the STARBURST™ conjugates of the present invention result in at least a portion of the STARBURST™ conjugates being delivered to a desired target (for example, a protein, a gene, glycoprotein, lipoprotein, lipid, a targeted cell, a targeted organ, a targeted organism or other targeted moiety) and include antibodies, preferably monoclonal antibodies, antibody fragments such as Fab, Fab', F(ab')$_2$ fragments or any other antibody fragments having the requisite target specificity, hormones, biological response modifiers; epitopes; chemical functionalities exhibiting target specificity; and the like.

The antibodies or antibody fragments which may be used in preferred STARBURST™ conjugates described herein can be prepared by techniques well known in the art. An example of suitable antibodies are immunoglobulins, such as IgG, IgM, IgA, IgD, and IgE. High specificity monoclonal antibodies can be produced by hybridization techniques well known in the art, see, for example, Kohler and Milstein (1975, *Nature* 256:495–497; and 1976, *Eur. J. Immunol.* 6:511–519). Such antibodies normally may have a highly specific reactivity.

In the antibody targeted STARBURST™ conjugates, antibodies directed against any antigen or hapten may be used. Although conventional polyclonal antibodies may be used, monoclonal antibodies offer several advantages. Selected monoclonal antibodies are highly specific for a single epitope. In addition, large amounts of each monoclonal antibody can be produced by tissue culture (e.g., a hybridoma cell line). Antibodies used in the present invention may be directed against, for example, tumors, bacteria, fungi, viruses, parasites, mycoplasma, differentiation and other cell membrane antigens, polynucleic acids such as DNA or RNA, pathogen surface antigens, toxins, enzymes, allergens, drugs and any biologically active molecules. For a more complete list of antigens see U.S. Pat. No. 4,193,983.

It may be desirable to conjugate more antibodies or fragments to the dendrimer, and in particular instances to use antibodies of different specificities. For example, a bifunctional conjugate which has the ability to localize and bind to a tumor and then scavenge circulating cytotoxic, diagnostic, or biostatic compounds can be designed.

In the absence of a target director (or in the presence of a target director if desired), due to the number of functional groups which can be located at or near the surface of the dendrimer, all (or a substantial portion of) such functional groups can be made anionic, cationic, hydrophobic or hydrophilic to effectively aid delivery of the STARBURST™ conjugate to a desired target of the opposite charge or to a hydrophobic or hydrophilic compatible target.

Preparation of the conjugates of Formula (II) using a P with a protected handle (S) is also intended as a process to prepare the conjugates of Formula (II). The reaction scheme is shown below:

$$S*P \xrightarrow{loading} S*P*M \xrightarrow{deprotection} P*M$$
$$T*P*M \xleftarrow{linking}$$

where

S*P represents the protected dendrimer;

S*P*M represents the protected dendrimer conjugated with M;

P*M represents the deprotected dendrimer conjugated with M (STARBURST™ conjugate);

T*P*M represents the STARBURST™ conjugate linked to the target director.

Suitable solvents can be employed which do not adversely effect P*M. For example when S is t-butoxycarbonyl, and P*M is stable in an aqueous solvent, S can be removed by aqueous acid.

Also preferred when the carried materials are pharmaceutical materials are STARBURST™ conjugates in which the polymer is associated directly, or via connectors; these STARBURST™ conjugates are represented by the formula:

$$[(T)_e-(C')_f]_g*(P)_x*[(C'')_h-(M)_y]_k \qquad (III)$$

wherein:

each C' represents the same or different connecting group;

each C'' represents the same or different connecting group;

g and k each individually represent an integer of 1 or greater;

f and h each individually represent an integer of 0 or greater;

— indicates a covalent bond in instances where a connecting group is present; and P, x, *, M, y, T, and e are as previously defined herein; and with the proviso that M maintains its effectiveness.

Preferred among the STARBURST™ conjugates of Formula (III) are those in which M is a radionuclide, drug, toxin, signal generator, signal reflector or signal absorber. Also preferred are those conjugates in which x=1. Particularly preferred conjugates are those in which x, e, f, h, and y are each 1, and g is 1 or more and k is 2 or more. Most preferred are those conjugates in which x, e, f, h, y and g are each 1, and k is 2 or more. Also particularly preferred are those STARBURST™ conjugates in which M represents a bioactive agent such as a radionuclide, drug, or toxin.

Suitable connecting groups which are represented by C'' are groups which link the carried material to the dendrimer without significantly impairing the effectiveness of the carried material or the effectiveness of the target director(s) present in the STARBURST™ conjugate. These connectors must be stable (i.e., non-clearable) or clearable depending upon the mode of activity of the carried material and are typically used in order to avoid steric hindrance between the carried material and the polymer.

Most preferred are conjugates in which the dendrimer is associated directly, or via connecting group(s), to one antibody or antibody fragment. The polymer in these preferred conjugates may, in addition, be optionally associated either directly, or via connecting group(s), to one or more other carried materials, preferably a radioisotope. Such STARBURST™ conjugates are represented by the formula:

$$[(Antibody)_e-(C')_f]_g*(P)_x*[(C'')_h-(M)_y]_k \qquad (IV)$$

wherein:

each Antibody represents an antibody or antibody fragment capable of interacting with a desired epitope;

— indicates a covalent or coulombic bond in instances where a connecting group is present; and P, x, *, M, T, e, y, C', C'', k, f, and h are as previously defined herein; and with the proviso that M maintains its effectiveness.

For the above synthesis of STARBURST™ dendrimers (P) which have a functional group available for linking (C' or C'') with a targeting director (T), the preferred process requires that the reactive functionality be protected as a synthetic precursor. This protection is preferred because it enables the synthesis of dendrimer or conjugates of very high quality. This process allows for the chemical binding of a unit of carried pharmaceutical material (M) to the terminal functional groups of the STARBURST™ dendrimer (P) in ways which would otherwise result also in reaction with a linking functional group, thus making it impossible to attach to the targeting director (T). Subsequent deprotection or synthetic conversion into the desired linking functional group thus enables the STARBURST™ conjugate to be linked to the targeting director.

One of the preferred "functional groups for linking" (hereafter referred to as a "handle") is an aniline moiety. This group is preferred because it can be used directly for linking to the targeting director, or it can be readily modified

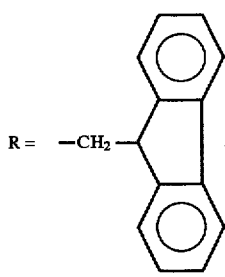

and the phthalimide protecting group,

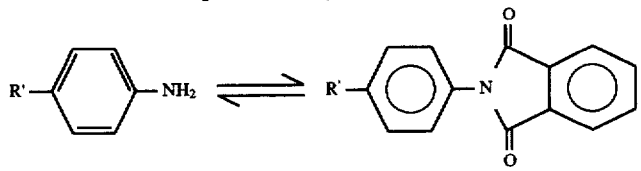

to other functional groups suitable for reaction with the targeting director, e.g., isothiocyanate, isocyanate, semithiocarbazide, semicarbazide, bromoacetamide, iodoacetamide, and maleimide. The aniline moiety is also preferred as a handle for linking with the targeting directors because it can be readily protected for use in STARBURST™ dendrimer synthesis, or the nitro group can be used as a precursor which can be converted into the desired amino function at the end of the synthesis.

There are a number of protecting groups which are suitable for protecting the anilino amino functionality during STARBURST™ dendrimer synthesis. (See Theodora W. Green, *Protective Groups In Organic Synthesis.*, Pub. John Wiley & Son, New York, 1981). A preferred class of protecting groups are the carbamates shown below, wherein R' represents a dendrimer.

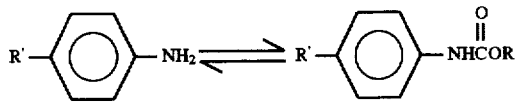

Many carbamates have been used for protection of amines. The most preferred carbamates for STARBURST™ dendrimer synthesis is the t-butoxycarbamate, R=—C(CH$_3$)$_3$. Deprotection is achieved by mild acid hydrolysis. Also preferred is the benzylcarbamate protecting group,

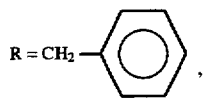

which is preferred when the dendrimer is susceptible to acid hydrolysis. Deprotection is achieved by catalytic hydrogenation.

Other protecting groups which can be used for protecting the reactive moieties at the desired generation level include 9-fluorenylmethylcarbamate Other protecting groups used for amines which are well known in the literature could also be used in this synthetic scheme. The above preferences are given as illustrative examples only but are not the only protecting groups which can be used. Any protecting group which is stable under the reaction conditions and can be removed without altering the integrity of the STARBURST™ dendrimer can be employed.

An alternate process involves the reaction of an activated aryl halide, e.g., 4-nitrofluorobenzene, 2,4-dinitrofluorobenzene, with an amino-function on the agent for conjugation, e.g., STARBURST™ polyethyleneimines (PEI), and subsequent catalytic hydrogenation of the nitro group to the aniline functionality for subsequent conjugation. It is particularly useful for agents, e.g., polyamines, which need further modification prior to use, due to the relative chemical inertness of the nitrophenyl functionality to all non-reducing reaction conditions. Various coupling reagents suitable for the conjugation reaction are well known in the art, such as those discussed in European Published Application 0430863, published Jun. 5, 1991. The more common bifunctional linking agents, e.g., active esters or diisocyanates, which are reactive under a large number of reaction conditions and which would render them usable for conjugation, include:

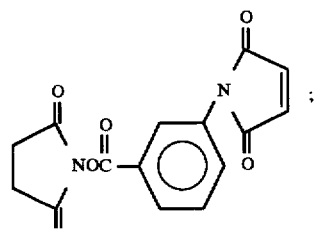

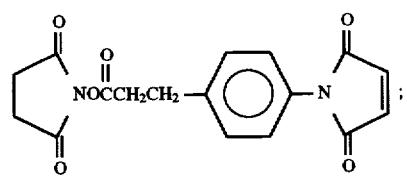

-continued

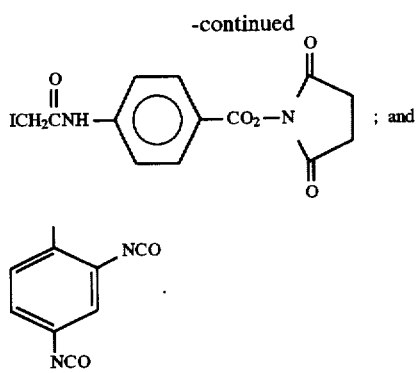

; and

The invention also includes the use of nitro-substituted arylsulphonyl halides to give sulphonamides, e.g., $O_2N$—⟨⟩—$SO_2X$.

The advantage of this process over known processes of introducing an aminophenyl group for conjugation is that it takes place at a late stage of the synthesis. Gansow et al., U.S. Pat. No. 4,472,509, in his process introduced the nitrophenyl group at the first step of a long synthetic procedure, thereby having limitations on the chemistry available.

This process also introduces a handle which is clearly differentiable from the remainder of the molecule. Manabe et al., disclosed that the ring opening of succinic anhydride by residual amines gave a coupling group through which conjugation to an antibody was possible. This method however gave no means of differentiating between any unchelated sites on the polymer, since the chelating groups were the same as the linking group.

The above process can introduce an aminophenyl functionality into any agent containing an amino group which is then conjugated with some bioactive agent, e.g., monoclonal antibody or enzyme. The agent can be conjugated by oxidative coupling to carbohydrates on the bioactive agent, e.g., an antibody. The aminophenyl group also can be converted into an isothiocyanate or isocyanate for subsequent reaction with the pendant amino groups of lysine residues on the bioactive agent.

The present process also provides for direct chelation of lanthanides with STARBURST™ dendrimers, preferably by PEI acetate dendrimer. In contrast, Denkewalter, U.S. Pat. No. 4,289,872, states that just putting acetates on the surface of his polymer works. However, the present reaction shows that PEI acetate, works much better than PAMAM, i.e., surface of iminodiacetates is only part of the story, the nature of the backbone, and branching is very important as well. The PEI acetate has better chelating properties than the PAMAM acetate.

PEI

-continued

PAMAM

Preferred among the STARBURST™ conjugates of Formula (IV) are those in which M is a radionuclide, drug, toxin, signal generator, signal reflector or signal absorber. Also preferred are those conjugates in which x=1. Particularly preferred are those conjugates in which x, e, f, h, and y are each 1, and g is 1 or more and k is each individually 2 or more. Most preferred are those conjugates in which x, e, f, h, y, and g are each 1, and k is 2 or more. Also particularly preferred are those STARBURST™ conjugates in which T represents a monoclonal antibody or an epitope binding fragment thereof; and especially preferred are those in which M represents a bioactive agent such as a radionuclide, drug, or toxin, and T is a target director such as an antibody, monoclonal antibody or antibody fragment, viral fragment, single strand DNA, a polynucleic acid, or a gene fragment, or T is not present.

The STARBURST™ conjugates can be used for a variety of in vitro or in vivo diagnostic applications such as radioimmunoassays, electron microscopy, enzyme linked immunoadsorbent assays, nuclear magnetic resonance spectroscopy, contrast imaging, and immunoscintography, in analytical applications, in therapeutic applications as a carrier of antibiotics, radionuclides, drugs or other agents suitable for use in the treatment of diseases such as cancer, autoimmune diseases, genetic defects, central nervous system disorders, infectious diseases, and cardiac disorders; in biological control applications as a means of delivering pesticides such as herbicides, fungicides, repellents, attractants, antimicrobials or other toxins; or used as starting materials for making other useful agents.

The present invention is also directed to STARBURST™ conjugate compositions in which the STARBURST™ conjugates are formulated with other suitable vehicles. The STARBURST™ conjugate compositions may optionally contain other active ingredients, additives and/or diluents. Injectable compositions of the present invention may be either in suspension or solution form. In solution form the complex is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. The dendrimer drug conjugate also could be incorporated in vesicles or liposomes. Also the conjugate could be encapsulated into polymeric host system that could either be degradable (i.e., lactic-glycolic acid copolymers or a polyanhydride polymer) or nondegradable (ethylene-vinylacetate copolymer). Also the conjugate could be incorporated into a hydrogel matrix comprising either poly(hydroxyethylmethacrylate) or poly(vinylalcohol). A variety of enteric coating systems could be employed to help the dendrimer drug conjugate past through the stomach.

The dendrimer drug conjugate could be formulated into a tablet using binders known to those skilled in the art. Such dosage forms are described in Remington's Pharmaceutical Sciences, 18th edition, 1990, Mack Publishing Company, Easton, Pa. Suitable tablets include compressed tablets, sugar coated tablets, film-coated tablets, enteric-coated tablets, multiple compressed tablets, controlled-release tablets, and the like.

Enteric-coated tablets are particularly advantageous in the practice of the present invention. Enteric coatings are those which remain intact in the stomach, but will dissolve and release the contents of the dosage form once it reaches the small intestine. The purpose of an enteric coating is to delay the release of drugs which are inactivated by the stomach contents, or may cause nausea or bleeding by irritating the gastric mucosa. In addition, such coatings can be used to give a simple repeat-action effect where additional drug that has been applied over the enteric coat is released in the stomachs while the remainders being protected by the coating, is released further down the gastrointestinal tract.

The action of enteric coatings results from a difference in composition of the respective gastric and intestinal environments in regard to pH and enzymatic properties. Although there have been repeated attempts to produce coatings which are subject to intestinal enzyme breakdown, this approach is not popular since enzymatic decomposition of the film is rather slow. Thus, most currently used enteric coatings are those which remain undissociated in the low pH environment of the stomach, but readily ionize when the pH rises to about 4 or 5. The most effective enteric polymers are polyacids having a pK of 3 to 5.

Useful polymers for the preparation of enteric coated tablets includes cellulose acetate phthalate, polyvinyl acetate phthalate, hydroxypropyl methylcellulose phthalate, methacrylic acid ester copolymers and the like.

In the agricultural materials embodiment of the invention, the STARBURST™ conjugates can be formulated with suitable vehicles useful in agriculture such as in treatment of crops or fallow land, or as pesticides, or in treatment of in vivo or in vitro testing of animals. An agriculturally acceptable carrier or diluent which may also be present with one or more STARBURST™ conjugates of the present invention includes those carriers or diluents customarily used in granular formulations, emulsifiable concentrates, solutions, or suspensions such as, for example, toluene, xylene, benzene, phenol, water, methane, hydrocarbons, naphthalene and the like.

The preferred STARBURST™ polymer for use in the STARBURST™ conjugates of the present invention is a polymer that can be described as a STARBURST™ polymer having at least one branch (hereinafter called a core branch), preferably two or more branches, emanating from a core, said branch having at least one terminal group provided that (1) the ratio of terminal groups to the core branches is more than one, preferably two or greater, (2) the density of terminal groups per unit volume in the polymer is at least 1.5 times that of an extended conventional star polymer having similar core and monomeric moieties and a comparable molecular weight and number of core branches, each of such branches of the extended conventional star polymer bearing only one terminal group, and (3) a molecular volume that is no more than about 80 percent of the molecular volume of said extended conventional star polymer as determined by dimensional studies using scaled Corey-Pauling-Koltun (CPK) molecular models. As used herein, the term "dense" as it modifies "star polymer" or "dendrimer" means that it has a smaller molecular volume than an extended conventional star polymer having the same molecular weight. The extended conventional star polymer which is used as the base for comparison with the dense star polymer is one that has the same molecular weight, same core and monomeric components and same number of core branches as the dense star polymer. By "extended" it is meant that the individual branches of the conventional star polymer are extended or stretched to their maximum length. In addition while the number of terminal groups is greater for the dense star polymer molecule than in the conventional star polymer molecule, the chemical structure of the terminal groups is the same.

Dendrimers used in the conjugates of the present invention can be prepared by processes known in the art. The above dendrimers, the various coreactants and core compounds, and process for their preparation can be as defined in U.S. Pat. No. 4,587,329. For example, core compounds may be anything on which further groups may be attached [see FIGS. 1 and 2(B)].

The dendrimers, for use in the conjugates of the present invention, can have terminal groups which are sufficiently reactive to undergo addition or substitution reactions. Examples of such terminal groups include amino, hydroxy, mercapto, carboxy, alkenyl, nitrile, allyl, vinyl, amido, halo, urea, oxiranyl, aziridinyl, oxazolinyl, imidazolinyl, sulfonato, silanyl, phosphonato, crown ethers, bipyridines, chloromethylphenyl, isocyanato and isothiocyanato. The terminal groups can be modified to make them biologically inert, for example, to make them non-immunogenic or to avoid non-specific uptake in the liver, spleen or other organ, e.g., by use of polyethylene glycol (PEG) or polyacylpolyalkyleneimine (i.e., polyacylpolyethyleneimine) groups of various lengths which are attached to the dendrimer surface. The dendrimers differ from conventional star or star-branched polymers in that the dendrimers have a greater concentration of terminal groups per unit of molecular volume than do conventional extended star polymers having an equivalent number of core branches and an equivalent core branch length. Thus, the density of terminal groups per unit volume in the dendrimer usually is at least 1.5 times the density of terminal groups in the conventional extended star polymer, preferably at least 5 times, more preferably at least 10 times, most preferably from 15 to 50 times. The ratio of terminal groups per core branch in the dense polymer is preferably at least 2, more preferably at least 3, most preferably from 4 to 1024. Preferably, for a given polymer molecular weight, the molecular volume of the dense star polymer is less than 70 volume percent, more preferably from 16 to 60, most preferably from 7 to 50 volume percent of the molecular volume of the conventional extended star polymer.

Preferred dendrimers for use in the conjugates of the present invention are characterized as having a univalent or polyvalent core that is covalently bonded to dendritic branches. Such ordered branching can be illustrated by the following sequence wherein G indicates the number of generations:

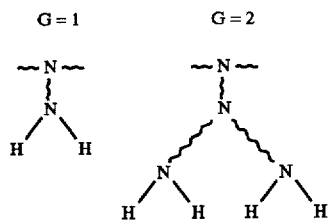

-continued
G = 3

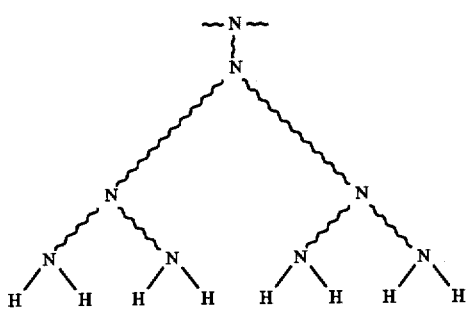

Mathematically, the precise sequencing involved in the preparation of dendrimers leads to precise, predictable stoichiometries within each dendrimer molecule. For example, the number of repeat units within a dendrimer depends on the number of generations (G), the multiplicity of the repeat unit ($N_r$), and the multiplicity of the core molecule or core atom ($N_c$). In a homopolymeric dendrimer, where the same repeat unit is employed throughout the molecule, the total number of repeat units within a dendrimer, its degree of polymerization (DP), is given by:

$$DP = N_c \frac{N_r^G - 1}{N_r - 1}.$$

The total valency or number of terminal moieties on the dendrimer (Y) is given by:

$$Y = N_c N_r^G.$$

Often it is more convenient or intuitive to consider the number of terminal groups on the dendrimer (Z) because each group may contain a multiplicity of valences or a number of valences that varies in subsequent chemical modifications. Therefore, the number of terminal groups is defined by:

of terminal groups per dendrimer $$(Z) = \frac{N_c N_r^G}{\text{multiplicity of terminal group}}$$

This may be illustrated by the amine terminal group, which has a multiplicity of 2 in polyamine synthesis. In this case, the # of terminal groups per dendrimer $$(Z) = \frac{N_c N_r^G}{2}.$$

For subsequent modifications of dendrimers, this number is more convenient because the valency of the amine group depends upon the chemistry employed. For example, a primary amine end group will react readily with only one molecule of ester to form an amide with two molecules of alkylating agent (under mild conditions, e.g., Eschweiler-Clarke conditions) to form a tertiary amine, or with three molecules of alkylating agent (under more rigorous conditions, e.g., reaction with alkyl sulfonates) to form a quaternary amine salt.

Accordingly, the dendrimers of this invention can be represented in its component parts as follows:

$$(\text{Core}) \left\{ (\text{Repeat Unit}) \frac{N_r^{G-1}}{N_r - 1} \left( \begin{array}{c} \text{Terminal} \\ \text{Moiety} \end{array} \right)_{N_r^G} \right\}_{N_c}$$

wherein the Core (I) is an initiator molecule or atom; Terminal Moiety is the atom, molecule or a functional group which occupies the binding sites of the Repeat Unit, e.g., hydrogen or methoxy group of an ester; G and $N_c$ are as defined before; and the Repeat Unit has a valency or functionality of $N_r+1$ wherein $N_r$ is as defined before.

A copolymeric dendrimer which is a preferred dendrimer for the purposes of this invention is a unique compound constructed of polyfunctional monomer units in a highly branched (dendritic) array. The dendrimer molecule is prepared from a polyfunctional initiator unit [core compound, core (I)], polyfunctional repeating units and terminal units which may be the same or different from the repeating units. The core compound is represented by the formula (I) $(Z^c)_{Nc}$ wherein core (I) represents the core, $Z^c$ represents the binding sites available on the core (I) and $N_c$ represents the core functionality or number of binding sites, which is preferably 2 or more, most preferably 3 or more. Thus, the dendrimer molecule comprises a polyfunctional core, (I), bonded to a number ($N_c$) of functional groups, $Z^c$, each of which is connected to the monofunctional tail of a repeating unit, $X^1Y^1(Z^1)_{N^1}$, of the first generation and each of the Z groups of the repeating unit of one generation is bonded to a monofunctional tail of a repeating unit of the next generation until the terminal tier or layer is reached.

In the dendrimer molecule, the repeating units are the same within a single generation i, but may differ from generation to generation. In the repeating unit, $X^1Y^1(Z^1)_{N^1}$, $X^1$ represents the monofunctional tail of the first generation repeating unit, $Y^1$ represents the moiety constituting the first generation, $Z^1$ represents a binding site of the polyfunctional head of the repeating unit of the first generation and may be the same as or different from the binding sites of the core compound, (I) $(Z^c)_{Nc}$, or other generations; and $N^1$ is a number of 2 or more, most preferably 2, 3 or 4, which represents the multiplicity of the polyfunctional head of the repeating unit in the first generation. Generically, the repeating unit is represented by the formula $X^iY^i(Z^i)_{N^i}$ wherein "i" represents the particular generation from the first to the t−1 generation. Thus, in the preferred dendrimer molecule, each $Z^1$ of the first generation repeating unit is connected to an $X^2$ of a repeating unit of the second generation and so on through the generations such that each $Z^i$ group for a repeating unit $X^iY^i(Z^i)_{N^i}$ in generation number "i" is connected to the tail ($X^{i+1}$) of the repeating unit of the generation number "i+1". The final or terminal tier of a preferred dendrimer molecule comprises terminal units, $X^tY^t(Z^t)_{N^t}$ wherein t represents a terminal unit and $X^t$, $Y^t$, $Z^t$ and $N^t$ may be the same as or different from $X^i$, $Y^i$, $Z^i$ and $N^i$ except that there is no succeeding generation connected to the $Z^t$ groups and $N^t$ may be less than two, e.g., zero or one and all these terminal units, $X^tY^t(Z^t)_{N^t}$, need not be identical to each other. Therefore, the preferred dendrimer has a molecular formula represented by $$(I\ (Z^c)_{N_c}) \left\{ (X^iY^i(Z^i)_{N^i})^{t-1}_{\underset{n\ is\ 1}{N_c\prod N_n}} \right\} (X^tY^t(Z^t)_{N^t})^{t-1}_{\underset{n\ is\ 1}{N_c\prod N_n}}$$

wherein i is 1 to t−1; the symbols are as previously defined. The $\prod$ function is the product of all the values between its defined limits. Thus $$\prod_{n=1}^{i-1} N^n = (N^1)(N^2)(N^3)\ldots(N^{i-2})(N^{i-1})$$

which is the number of repeat units, $X^iY^i(Z^i)_{N^i}$, comprising the ith generation of one dendritic branch and when i is 1, then $$\prod_{n=1}^{0} N^n = 1.$$

In copolymeric dendrimers, the repeat unit for one generation differs from the repeat unit in at least one other generation. The preferred dendrimers are very symmetrical as illustrated in structural formulas described hereinafter. Preferred dendrimers may be converted to functionalized dendrimers by contact with another reagent. For example, conversion of hydroxyl in the terminal layer or tier to ester by reaction with an acid chloride gives an ester terminally functionalized dendrimer. This functionalization need not be carried out to the theoretical maximum as defined by the number of available functional groups and, thus, a functionalized dendrimer may not have high symmetry or a precisely defined molecular formula as is the case with the preferred dendrimer.

In a homopolymeric dendrimer, all of the repeat units, $X^iY^i(Z^i)_{N^i}$, are identical. Since the values of all $N^i$ are equal (defined as $N_r$), the product function representing the number of repeat units reduces to a simple exponential form. Therefore, the molecular formula may be expressed in simpler form as:

$$(\textcircled{I}\ (Z^c)_{N_c})\{(X^iY^i(Z^i)_{N^i})_{N_cN_r^{i-1}}\}(X^tY^t(Z^t)_{N^t})_{N_cN_r^{(t-1)}}$$

where $i = 1$ to $t - 1$

This form still shows the distinction between the different generations i, which each consist of $N_cN_r^{(i-1)}$ repeating units $X^iY^i(Z^i)_{N^i}$. Combining the generations into one term gives:

$$(\textcircled{I}\ (Z^c)_{N_c})(X^rY^r(Z^r)_{N_r})_{N_c\frac{N_r^{(t-1)}-1}{N_r-1}}(X^tY^t(Z^t)_{N^t})_{N_cN_r^{(t-1)}}$$

or $$(\textcircled{I}\ (Z^c)_{N_c})\{(X^rY^r(Z^r)_{N_r})\frac{N_r^{(t-1)}-1}{N_r-1}(X^tY^t(Z^t)_{N^t})_{N_r^{(t-1)}}\}_{N_c}$$

Core     Repeat Unit     Terminal Unit wherein $X^rY^r(Z^r)N_r$ is the repeating unit which is used in all generations i. This formula is essentially the same as that on page 68, line 10 with G=t−1.

Consequently, if a polymer compound will fit into these above formulae, then the polymer is a STARBURST™ polymer. Conversely, if a polymer compound will not fit into these above formulae, then the polymer is not a STARBURST™ polymer. Also, to determine whether a polymer is a STARBURST™ polymer, it is not necessary to know the process by which it was prepared, but only whether it fits the formulae. The formulae also demonstrate the generations (G) or tiering of dendrimers.

The foregoing mathematical formulae are based on referring to the first iteration of reactions about the core reactant as generation 1. Thus, for a polyamidoamine dense star dendrimer, the reaction product of methyl acrylate with the ammonia core would be referred to as generation 0.5 and the subsequent reaction product of EDA with methyl acrylate would be referred to as generation 1.0.

In a variation on that nomenclature, the first iteration is referred to as generation 0 instead of generation 1. The reaction product of methyl acrylate with the ammonia core would be generation −0.5, and the subsequent reaction product of EDA with the methyl acrylate would be generation 0. Under this alternative nomenclature, all of the generational numbers used elsewhere in this application would be reduced by 1.

Under this revised nomenclature, the formula for the degree of polymerization (DP) becomes:

$$DP = N_c \left( \frac{N_r^{G+1} - 1}{N_r - 1} \right)$$

The formula for the number of terminal moieties on the dendrimer (Y) is:

$$Y = N_c N_r^G$$

where Y can be converted to Z (number of terminal groups/dendrimer) by dividing by the multiplicity of the terminal group as described hereinbefore.

The number of dendrimer branch cells ($N_{BC}$) is expressed as follows:

$$N_{BC} = N_c \left( \frac{N_r^G - 1}{N_r - 1} \right)$$

The theoretical molar mass (M) can then be expressed:

$$M = M_c + N_c \left[ M_{RU} \left( \frac{N_r^{G+1} - 1}{N_r - 1} \right) + M_t N_r^{G+1} \right]$$

or $$M = M_c + N_c \left[ M_{BC} \left( \frac{N_r^G - 1}{N_r - 1} \right) + M_t N_r^G \right]$$

where $M_c$ is the molar mass of the initiator core, $M_{RU}$ is the molar mass of the repeating units, $M_{BC}$ is the molar mass of the branch cells and $M_t$ is the molar mass of the terminal units.

Clearly, there are several ways to determine the ratio of agent (M) to dendrimer (P) which depend upon how and where the association of P*M occurs. When there is interior encapsulation, the weight ratio of M:P usually is 10:1, preferably 8:1, more preferably 5:1, most preferably 3:1. The ratio can be as low as 0.5:1 to 0.1:1. When interior stoichiometry is used, the weight ratio of M:P is the same as for interior encapsulation. When exterior stoichiometry is determined, the mole/mole ratio of M:P is given by the following formulae:

| M | : | P |
|---|---|---|
| (A) 5 $N_cN_sN_r^{t-1}$ | | 1 |
| (B) 3 $N_cN_sN_r^{t-1}$ | | 1 |
| (C) 1 $N_cN_sN_r^{t-1}$ | | 1 | where $N_c$ means the core multiplicity, $N_t$ means the average terminal group multiplicity, and $N_r$ means branch juncture multiplicity. The $N_cN_tN_r^{t-1}$ term will result in the number of terminal moieties. Thus, for example, (A) above may result when proteins, enzymes or highly charged molecules are on the surface; (B) above when it is aspirin, 2,4-D or octanoic acid; (C) above when converting surface ester groups to carboxylate ions or groups.

Figure 3:
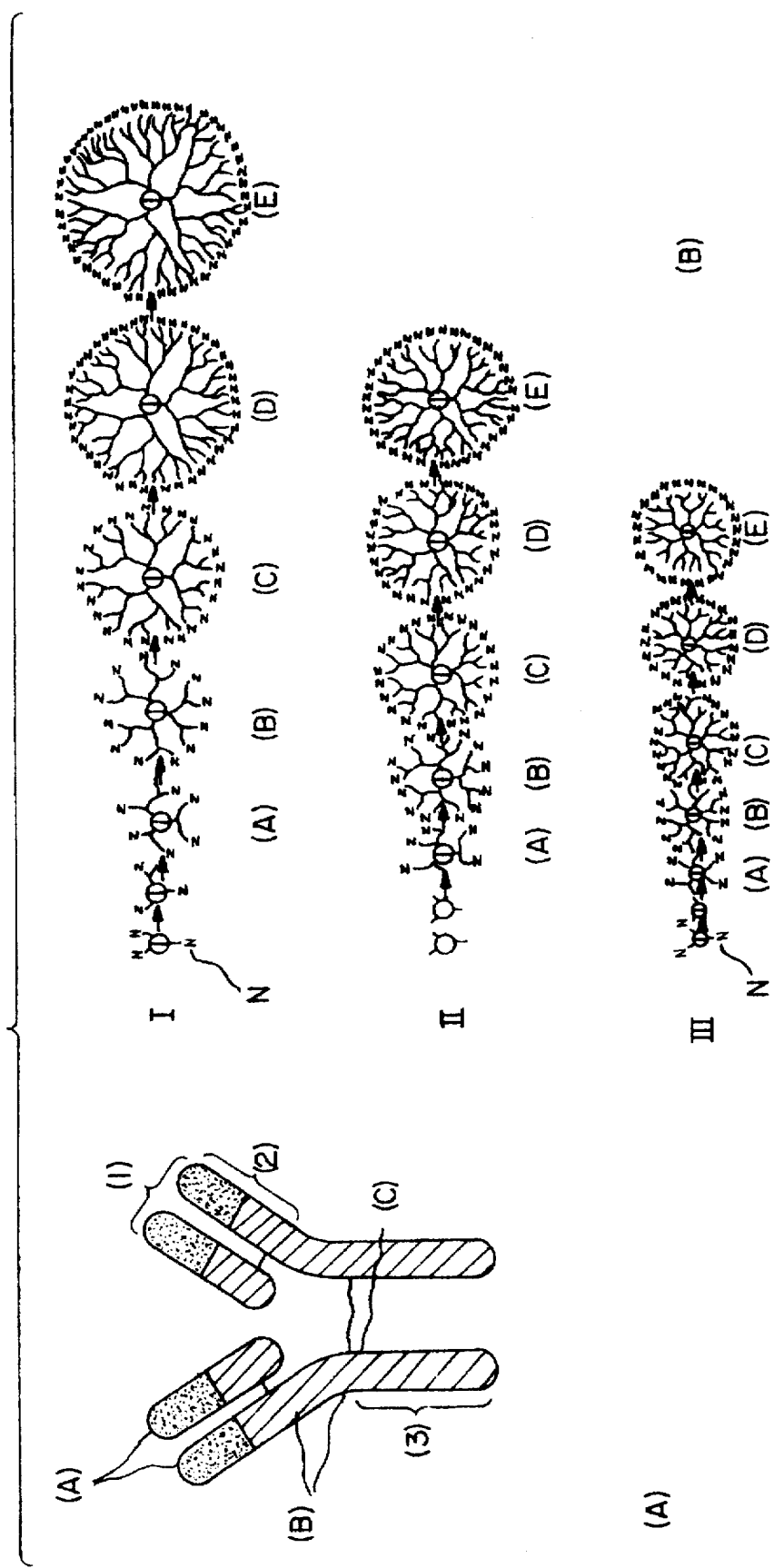
FIG. 3 depicts various dendrimer family sizes |A–E in I, II, III of (B)| relative to antibody dimensions (A).
Figure 4:
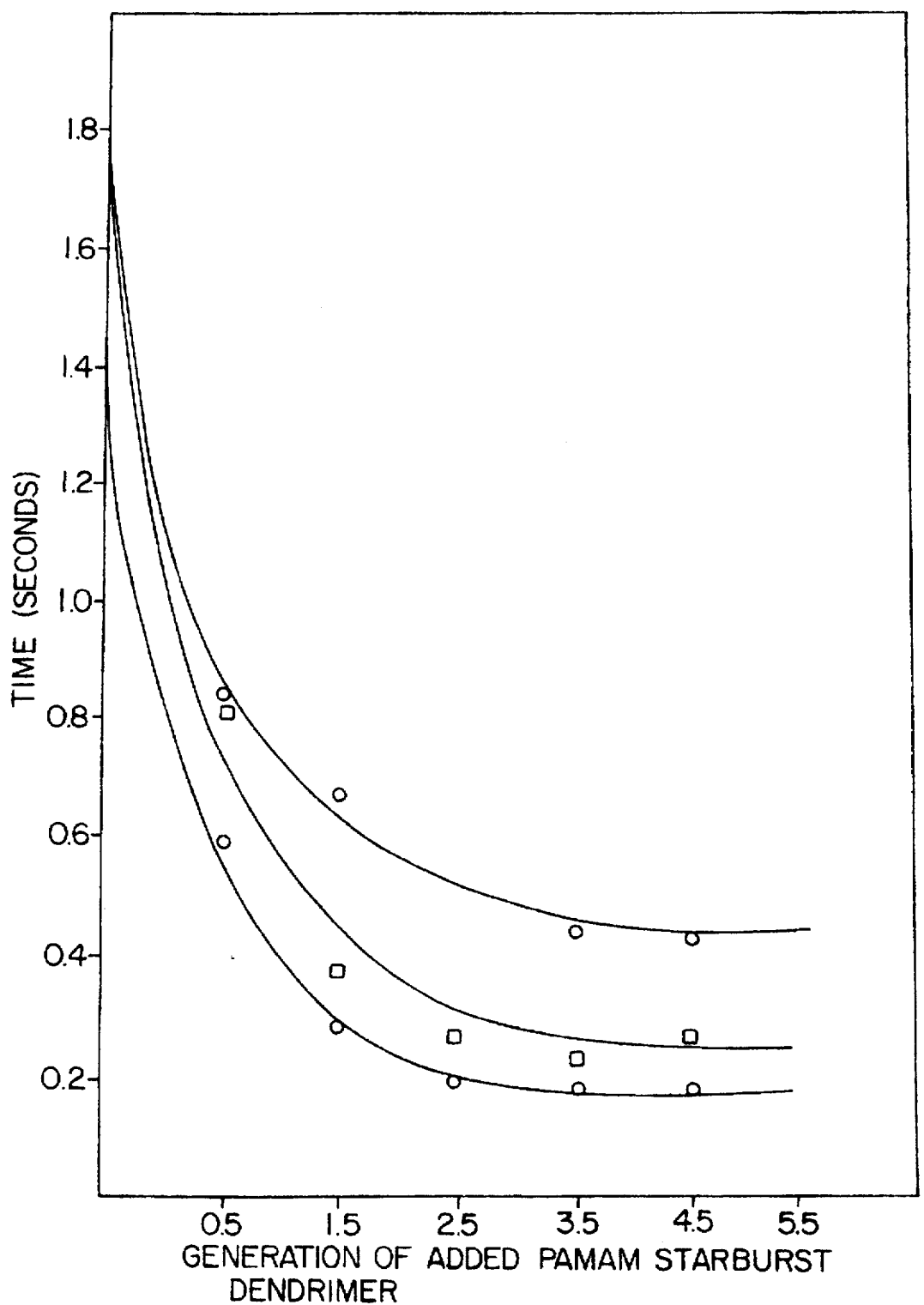
FIG. 4 shows carbon-13 spin lattice relaxation times ($T_1$) for aspirin incorporated into various dendrimer generations.

Of course other structures of various dimensions can be readily prepared by one skilled in the art by appropriately varying the dendrimer components and number of generations employed. A roughly scaled comparison of three different dendrimer series relative to an IgG antibody is seen in FIG. 3. The series of drawings indicated by FIG. 3(B) I shows the STARBURST™ polyamidoamines (PAMAM); by II shows the STARBURST™ polyethers (PE); and by III shows the STARBURST™ polyethyleneimines (PEI). In a manner similar to that of FIG. 1, all three series (I, II and III) have their far left drawing showing the initiator core, the next drawing from the left showing the starbranch oligomer, and the remaining drawings showing the STARBURST™ oligomers, and respective STARBURST™ bridged dendrimers. It can be seen that in these series of scale drawings that the dendrimer dimensions are close to and in fact smaller than those noted for the whole IgG antibody FIG. 3(A). The IgG antibody is shown to the far left in FIG. 3. The scale is 1 mm=3.5 Å. In FIG. 3(A) the variable region is shown by (A); the constant region by (B); and the carbohydrate attachment sites by (C). Approximate measurements shown on FIG. 3 follow: (1) is 35–40 Å; (2) is 70 Å; and (3) is 60 Å. These dimensional properties are preferred for instance where targeting involves exiting from the vascular system. Therefore dendrimer diameters of 125 Angstrom units or less are particularly preferred in that they may allow exiting from the vascular system to targeted organs serviced by continuous or fenestrated capillaries. These dimensions are significant in that they are small compared to the size of a potential targeting component such as an antibody (see FIG. 3). A linear polymer of comparable molecular weight would have a radius of gyration, (in its fully extended form), that would be much larger than the same molecular weight dendrimer. A linear polymer of this type would be expected to adversely affect the molecular recognition properties of many accepted targeting components. It is also desirable that the conjugates be of minimum molecular volume so as not to discourage extravascularisation, e.g., by coupling Fab, Fab', Fab'$_2$ or single chain or portions thereof, or other appropriate antibody fragment to low molecular volume dendrimers.

Dendrimers are desirable for the delivery of radionuclides or strongly paramagnetic metal ions to tumor sites because of their ability to chelate a number of metal ions in a small volume of space. Coupling to antibodies or antibody fragments which are specific for tumors may deliver a number of metals per antibody, with only a single modification to the antibody.

Linking target directors to dendrimers is another aspect of the present invention. In preferred embodiments of the present invention, particularly where it is desired to use an antibody as a target director, a reactive functional group such as a carboxyl, sulfhydryl, reactive aldehyde, reactive olefinic derivative, isothiocyanato, isocyanato, amino, reactive aryl halide, or reactive alkyl halide can conveniently be employed on the dendrimer. The reactive functional groups can be introduced to the dendrimer using known techniques, for example:

(1) Use of a heterofunctional initiator (as a starting material for synthesizing the dendrimer) which has incorporated into it functional groups of different reactivity. In such heterofunctional initiator at least one of the functional groups will serve as an initiation site for dendrimer formation and at least one of the other functional groups will be available for linking to a target director but unable to initiate dendrimer synthesis. For example, use of protected aniline allows further modification of $NH_2$ groups within the molecule, without reacting the aniline $NH_2$.

The functional group which will be available for linking to a target director may be part of the initiator molecule in any one of three forms; namely:

(a) In the form in which it will be used for linking with the target director. This is possible when none of the synthetic steps involved in the dendrimer synthesis can result in reaction at this center.

(b) When the functional group used for linking to the targeting director is reactive in the synthetic steps involved in the dendrimer synthesis, it can be protected by use of a protecting group, which renders the group unreactive to the synthetic procedures involved, but can itself be readily removed in a manner which does not alter the integrity of the remainder of the macromolecule.

(c) In the event that no simple protecting group can be formed for the reactive functionality to be used for linking with the targeting director, a synthetic precursor can be used which is unreactive in all the synthetic procedures used in the dendrimer synthesis. On completion of the synthesis, this functional group must be readily convertible into the desired linking group in a manner which does not alter the integrity of the remainder of the macromolecule.

(2) When coupling (covalently) the desired reactive functional group onto a preformed dendrimer, the reagent used must contain a functionality which is readily reacted with the terminal functional groups of the dendrimer. The functional group to be ultimately used to link with the targeting agent can be in its final form, as a protected functionality, or as a synthetic precursor. The form in which this linking functionality is used depends on its integrity during the synthetic procedure to be utilized, and the ability of the final macromolecule to withstand any conditions necessary to make this group available for linking. Examples of suitable linking agents may be found in the art, for example European Published Application 0430863, published Jun. 5, 1991. For example, the preferred route for PEI uses.

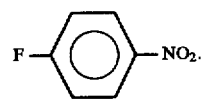

Examples of heterofunctional initiators for use in (1) above, include the following illustrative examples:

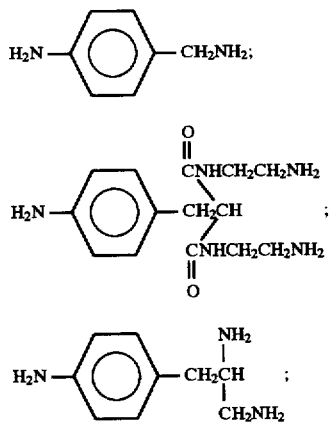

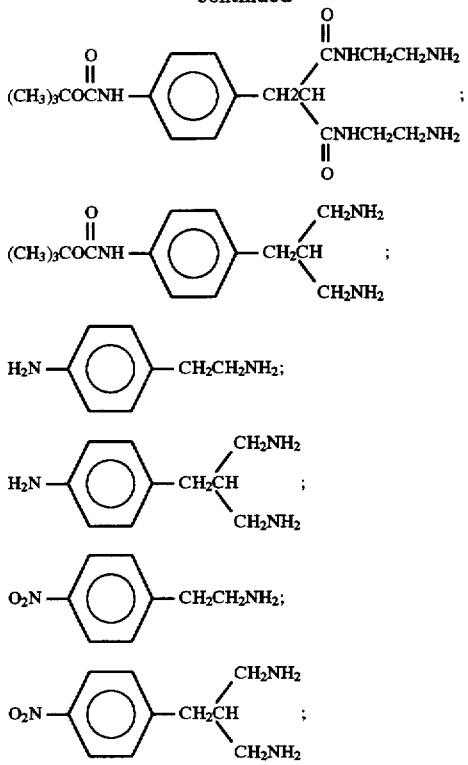

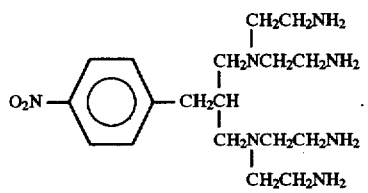

There are several chemistries of particular importance:
1) STARBURST™ Polyamidoamines ("PAMAM") Chemistry;
2) STARBURST™ Polyethyleneimines ("PEI") Chemistry;
3) STARBURST™ PEI compound with a surface of PAMAM;
4) STARBURST™ polyether ("PE") chemistry.

Modifications of the dendrimer surface functionalities may provide other useful functional groups such as the following:

—OPO$_3$H$_2$, —PO$_3$H$_2$, —PO$_3$H$^{(-1)}$, —PO$_3^{(-2)}$, —CO$^{(-1)}$, —SO$_2$H, —SO$_2^{(-1)}$, —SO$_3$H, —SO$_3^{(-1)}$, —NR$^1$R$^2$, —R$^5$, —OH, —OR$^1$, —NH$_2$, polyethers, perfluorinated alkyl,

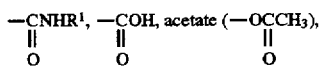

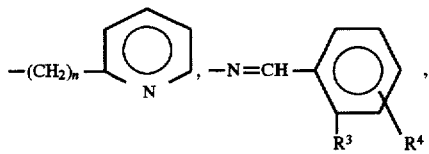

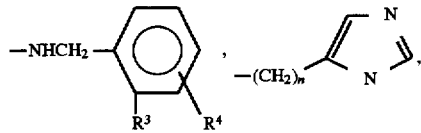

wherein:
R represents alkyl, aryl or hydrogen;
R$^1$ represents alkyl, aryl, hydrogen, or

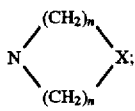

R$^2$ represents alkyl, aryl, or

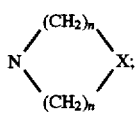

R$^3$ represents —OH, —SH, —CO$_2$H, —SO$_2$H, or —SO$_3$H;
R$^4$ represents alkyl, aryl, alkoxy, hydroxyl, mercapto, carboxyl, nitro, hydrogen, bromo, chloro, iodo, or fluoro;
R$^5$ represents alkyl;
X represents NR, O or S; and
n represents the integer 1, 2 or 3;
polyethers; or other immuno insensitive moieties
wherein for all the above, alkyl is a linear or branched C$_1$–C$_{18}$ hydrocarbon and aryl is a benzyl or naphthyl which may be substituted with one or more C$_1$–C$_4$ alkyl, bromo, chloro, iodo, fluoro, or trifluoromethyl moieties.

The choice of functional group depends upon the particular end use for which the dendrimer is designed. For example, a dendrimer having 1,4,7,10-tetraazacyclododecane-1,4,7,10-tetraacetic acid (DOTA) or 1,4,7-tris-(carbomethoxymethyl)-1,4,7,10-tetraazacyclododecane (DO3A methyl ester) as the functional group can be used as carriers for magnetic resonance imaging or as nuclear magnetic resonance reagents.

These functionalized dendrimers are prepared, for example, by reacting the functionalizing group, such as DO3A methyl ester, with an epoxide or epoxide substituted with a C$_1$–C$_{18}$ alkyl group to form a hydroxyethylated product. The hydroxyethylated product is reacted with a coupling agent, such as dicyclohexyl carbodiimide (DCC), and then reacted with a PAMAM STARBURST™ polymer. A dendrimer having DOTA as a functional group can be prepared by using an isothiocyanate derivativized DOTA, such as, 1-[1-carboxy- 3(4'-isothiocyanatophenyl)propyl]-4,7,10-tris(carboxymethyl)-1,4,7,10-tetraazacyclododecane, with a PAMAM STARBURST™ polymer. Other suitable chelates can be added by known synthetic techniques. When desired, a lanthanide ion or pseudolanthanide ion can be incorporated by conventional methods.

Linking of antibodies to dendrimers is another aspect of the present invention. Typically, the antibodies or antibody fragments are linked to the dendrimer by techniques well known in the art such as attachment between a functional group on the dendrimer and moieties such as carbohydrate, amino, carboxyl, or sulfhydryl functionalities present in the antibody or antibody fragment. In some instances connecting groups may be used as connectors or spacers between the dendrimer and antibody or antibody fragment. The attachment of the dendrimer to the antibody or antibody fragment should be performed in a manner which does not significantly interfere with the immunoreactivity of the antibody or antibody fragment, that is, by binding the antibody or antibody fragment via a functionality in the antibody or antibody fragment which is not a part of the antigen recognition and binding site.

CARRYING GENETIC MATERIAL AND TRANSFECTION

A. Introduction

The transfer of genetic material into cells has many potential uses as therapeutic and/or diagnostic agents for human illness. Genetic material can be transfected, and subsequently transcribed and expressed, to make new proteins within cells, replacing either aberrant or absent proteins caused by genetic errors. In additions smaller pieces of genetic material, including either DNA or RNA, can be transfected into cells to act as enzymes that can alter cell function or edit specific messenger RNA's to correct other types of genetic defects. Synthetic genetic material, such as modified forms of antisense oligonucleotides, can be transferred into cells to block the production of specific proteins. This may be useful in suppressing cells that grow abnormally, such as cancer cells, or in the alteration of normal cell functions, such as immunosuppression for organ transplantation. Small pieces of genetic material, such as aptimers, can also function as drugs, and the transfer of these forms of nucleic acids can specifically alter cellular functions in a manner similar to a pharmaceutical.

The most important part of gene transfer therapeutics is the carrier or modality with which the genetic material is transferred to cells. The transfer is a complicated process, involving a number of different steps. The first function of the carrier is to bind and protect the DNA from hydrolysis or enzymatic digestion. The carrier must then facilitate the transfer of the genetic material into the cell. Once in the cell, the carrier should protect the DNA from degradation in endosomes and direct the material to specific compartments within the cell. These compartments might include the nucleus, either for incorporation of the genetic material into chromosomes or for the transient expression of the transferred genetic material through transcription and translation. In contrast, there may be a requirement for transport to the cytoplasmic endoplasmic reticulum for functions such as ribosome editing or interruption of protein production through anti-sense inhibition. Once in the appropriate compartment, the genetic material also must be released from the carrier to allow it to function. Thus, the ability to protect, transfer and allow the genetic material to function are all crucial features of an appropriate carrier for gene therapy.

Besides the many activities the carrier of the genetic material must perform, there are certain things that are important to avoid in a carrier. The carrier must not be immunogenic and should not induce an immune response to the carried DNA if administered in vivo. In addition, it should not form insoluble complexes with the DNA that prevent its administration or the ability to effectively reach its cellular target, whether it be in tissue culture or within an individual. Importantly, the carrier should not be toxic to cells in vitro or to organisms in vivo, as this would markedly reduce the amount of material that could be administered and could be potentially dangerous.

There are two general forms of transfer for genetic material. Both require binding and protecting genetic material, transfer of genetic material into the cell and release of the material for functional activity. However, there is a major difference between the two forms of transfer. One form uses a carrier that binds nonspecifically to cells through charge or other interaction, and transfers DNA into essentially all cells it contacts. This might occur in vitro or in vivo in a closed space, such as a joint. A carrier of this type is particularly important in therapies where cells are transfected in tissue culture and reintroduced into an individual. This "ex vivo" therapy is very useful in a number of different disease states and requires that the carrier be highly efficient in binding and transferring genetic material into almost all cells with which it interacts. The other type of carrier specifically targets itself to only certain cell types. A target director coupled to this carrier facilitates the specific interaction between a target on a cell and the DNA carrier complex that facilitates uptake into targeted cells. Using this carrier, non-specific transfection of cells is not desirable as expression or action of the transfected genetic material within non-targeted cells may be detrimental. Target directors may also increase transfection of cells in vitro for ex vivo therapeutic or diagnostic purposes through enhanced binding and transfer into cells. In this case, the adverse affects of non-specific transfection are not an issue since all cells in culture are targeted.

The art of gene therapy is advancing at a rapid rate. Numerous articles and text books have been written describing techniques for gone therapy. *Recombinant DNA*, second edition, by James D. Watson, oral., 1992, distributed by W. H. Freeman and Company, New York is one such book.

The dense star polymers of the present invention may be complexed with genetic material and used for gene therapy in mammalian organisms, e.g., humans. A method for preventing or treating a disease comprises transfecting a mammalian cell with a dense star polymer complexed with genetic material. As discussed earlier, genetic material may be transfected into cells for a variety of reasons including the production of proteins within cells, altering cell function, correcting genetic defects function as drugs, and the like. Thus, genetic diseases or conditions, in particular, may be prevented or treated using the complex of the dense star polymer and genetic material of the present invention.

The amount of genetic material used in the genetic material:dendrimer complex solution is sufficient to achieve the desired prophylactic, therapeutic or diagnostic effect. This amount will vary as a function of the effect sought, the ease with which target cells are successfully transfected, the efficiency of any target director attached to the dendrimer, and the mode of administration of the complex, i.e., in vitro, ex vivo, in vivo, and, if in vivo, intravenous, topical or direct injection into a particular tumor, organ, gland or other tissue.

Once the amount of genetic material and its charge has been determined, the amount of dendrimer used is then determined as a function of the genetic material:dendrimer charge ratio selected. Sufficient dendrimer is used in the solution to give the desired charge ratio. The charge ratio selected will vary as a function of the same variables which affect the solution concentration of genetic material, as well as with whether or not DEAE-dextran or glycerol is used to synergistically enhance transfection. Generally speaking, the genetic material:dendrimer charge ratio may be from about 10:1 to about 1:10,000 (possibly even lower), but more preferably from about 3:1 to 1:1,000, 1:1 to 1:100, 1:1 to 1:15, or 1:5 to 1:10, as a function of the above variables.

A method for introducing human genes into mammalian cells to avoid substantial gene rearrangement or other alterations that may affect gene expression may be conducted by transfecting a mammalian cell with a dendritic polymer(s), preferably a dense star dendrimer, complexed with genetic material.

Gene transfer can be effected by transfecting a variety of cell types such as hematopoietic cells, skin fibroblasts, hepatocytes and the like. Thus, a method for preventing or treating a genetic disease may comprise transfecting a dense star polymer complexed with genetic material into a hematopoietic stem cell, skin fibroblast cell, hepatocyte, or the like, administering the transfected cell into a mammalian organism and expressing said cell to obtain a prophylactic or therapeutic effect.

The transfection as discussed in the present invention can be used for a variety of purposes, including in vitro, in vivo and ex vivo uses. Further, the in vitro use of the complex of dense star polymers and genetic material of the present invention can be useful in detecting or diagnosing various conditions. A method for diagnosing a disease or condition in a mammalian organism may be detected or diagnosed using the complex of the dense star polymer and genetic material of the present invention.

The dendrimer-genetic material complex as described herein can also be considered a "conjugate" of the present invention as that term is broadly used herein. The dendrimer (or dense star polymer, P) is associated with a carried biological response modifier, M, which is a bioactive material, and in this instance is a genetic material, to form a conjugate of the present invention. A target director, T, may also be present. This allows for the directed delivery of the genetic material to specific cells, and these unique features are discussed further hereinafter.

The function of dendrimers as the carrier for the transfer of genetic material is discussed below. Examples are provided for both non-specific transfection of cells and specific targeted transfection. Little toxicity or immunogenicity are observed in either application. Thus, dendrimer carriers can encompass all the types of necessary carriers required for gene transfer therapy.

As indicated earlier, the dense star polymers of the present invention can be used as carriers for agricultural materials, including gene transfer.

There are a variety of prior art methods for transfecting genetic material into plant cells. One method involves the use of Agrobacterium sp. In a typical procedure, the gene is introduced into plant cells by first inserting it into the cloning site of a plasmid that can replicate in *E. coli* and contains a segment of T-DNA (a DNA found in the Ti plasmids naturally occurring in agrobacteria). The resulting intermediate shuttle vector is then introduced into *E. coli* cells, and transformants are selected by resistance to ampicillin, encoded within pBR 322 sequences. Next, the plasmid is transferred from the *E. coli* cell to an Agrobacterium cell by mating. Once inside the Agrobacterium, the plasmid integrates into the Ti plasmid by means of homologous recombination of the T-DNA sequences on the two plasmids. This process places the entire integrative plasmid (the plasmid integrated into the Ti plasmid) between the left and right boundaries of the T-DNA. Plasmids that fail to integrate do not accumulate because they lack an origin of replication for Agrobacterium. Agrobacteria containing the recombinant Ti plasmid are selected and used to infect plant cells. Plant cells that have taken up the T-DNA are identified by the plant selectable marker NPTII, which confers resistance to kanamycin. These cells also contain the cloned gene of interest.

In addition, genetic material is transfected into plant cells via viral vectors. Viral vectors are viruses that are evolutionarily adapted to distribute genes throughout an infected plant. If the viral genome includes a foreign gene, then that too will spread systemically throughout the plant. Viral vectors can circumvent the problems of delivering genes to monocoty edons, which are less susceptible to agrobacteria. Genetic material can replace the coat protein-coding region in the A component of a geminivirus (e.g., tomato golden mosaic virus) genome. These are DNA viruses with genomes made up of two single-stranded DNA molecules that each go through a double-stranded replicative form. The A molecule alone can replicate in plant cells, but the B molecule is required for infectivity. Both A and B genes must be present in a cell for productive viral infection.

Other methods for transfecting genetic material into plant cells involves introduction of the genetic material directly into cells using physical means. One physical method of introducing genetic material into a plant cell uses electroporation. Typically, a high concentration of plasmid DNA containing the genetic material is added to a suspension of protoplasts and the mixture shocked with an electrical field of 200 to 600 V/cm. Following electroporation, the protoplasts are grown in tissue culture for one to two weeks before beginning selection for cells that have taken up the DNA. Normally, this process attains an efficiency of between 0.1 and 1 percent.

Another method of physically introducing genetic material into plant cells involves the use of minute metal (such as tungsten) beads coated with the relevant DNA. These beads, i.e., microspheres 1 µm in diameter, are shot directly into the cells. The DNA is simply precipitated onto the surface of the beads, which are fired from the "gun" with velocities of about 430 meters per second. The targets may include suspension cultures of embryonic cells plated on filters and intact leaves and seeds. Cells in the direct line of fire are killed, but there is a concentric zone of cells where the projectiles penetrate the cells without killing them. Morphological analysis of leaves bombarded with a β-glucuronidase (GUS) reporter gene vector show that the tungsten particles can penetrate at least one layer of tissue, the leaf epidermis, to reach the mesophyll. DNA-coated microspheres have also been used to introduce genetic material into chloroplasts.

The dendritic polymers, and especially the dense star polymers, of the present invention offer significant advantages when used in the transfection of genetic material into plant cells. The prior art techniques, for instance, can be modified to allow the dense star polymer (e.g., dense star dendrimer) along with the genetic material to transfect the cell thereby providing the advantages set forth above. In particular, electroporation or minute metal beads can be used to allow transfection of the dense star polymer and genetic material into plant cells.

The Dendrimer

The present invention concerns, in one aspect, the concept of carrying genetic material on dendritic polymers, and/or effecting transfection with such complexes. In the broader aspects, the term "dendritic polymer" as used herein is not intended to be limited to dense star polymers, though it does include dense star polymers. A "dendritic polymer" is a polymer exhibiting regular dendritic branching, formed by the sequential or generational addition of branched layers to or from a core. The term "dendritic polymer" encompasses "dendrimers," which are characterized by a core, at least one interior branched layer, and a surface branched layer. (See Petar R. Dvornic and Donald A. Tomalia in *Chem. in Britain*, 641–645, August 1994.) A "dendron" is a species of dendrimer having branches emanating from a focal point which is or can be joined to a core, either directly or through a linking moiety to form a dendrimer. Many dendrimers comprise two or more dendrons joined to a common core. However, the term dendrimer is used broadly to encompass a single dendron.

Dendritic polymer includes, but is not limited to, symmetrical and unsymmetrical branching dendrimers, cascade molecules, arborols, and the like, though the most preferred dendritic polymers are dense star polymers. The PAMAM dense star dendrimers disclosed herein are symmetric, in that the branch arms are of equal length. The branching occurs at the hydrogen atoms of a terminal —$NH_2$ group on a preceding generation branch. The lysine-branched dendrimers of Example 78 are unsymmetric, in that the branch arms are of a different length. One branch occurs at the epsilon nitrogen of the lysine molecule, while another branch occurs at the alpha nitrogen, adjacent the reactive carboxy group which attaches the branch to a previous generation branch.

Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

Dendritic polymers include bridged dendrimers and dendrimer aggregates. Dendritic polymers encompass both generationally monodisperse and generationally polydisperse solutions of dendrimers. The dendrimers in a monodisperse solution are substantially all of the same generation, and hence of uniform size and shape. The dendrimers in a polydisperse solution comprise a distribution of different generation dendrimers. In the preferred embodiment, the polydisperse dendritic polymers comprise dendrimers of at least three different generations ranging in size from about 22 to about 110 Å. Samples P and Q of Example 42 are exemplary of such polydisperse dendritic polymers.

Dendritic polymers also encompass surface modified dendrimers. For example, the surface of a PAMAM dendrimer may be modified by the addition of an amino acid, e.g., lysine.

It should be understood that reference to any particular type of dendritic polymer as a "polymer," e.g., a "dense star polymer," and "unsymmetrical dendritic polymer," a "cascade polymer" is also intended to encompass bridged dendrimers of that type, dendrimer aggregates of that type, polydisperse dendrimers of that type, and surface modified dendrimers of that type.

When the carried material is genetic material, the surface of the dendrimer is preferably comprised of a predominance of positively charged functional groups. More preferably, such positive functionality is achieved by providing amino terminal groups at the dendrimer surface. Positively charged functional groups can also be introduced on the surface chemically (e.g., quaternary amines). Such amino functionality is provided by the polyamine, polyamidoamine, and polyalkyleneimine (e.g., polyethyleneimine and polypropyleneimine) dendrimers described above, although it can be achieved in other ways.

Broadly, dendrimers used for carrying genetic materials are spherical, ellipsoidal or rod-like in configuration. Their narrowest cross-sectional diameter(s) are preferably at least 50 angstroms (Å). This dimension corresponds approximately to the diameter of a generation 6 ammonia core [G6 ($NH_3$)] PAMAM dendrimer or a generation 6 ethylenediamine core [G6 (EDA)] dendrimer (which is somewhat larger than the ammonia core dimension). (See Example 44, FIGS. 12 and 13; Example 45, FIG. 14, and Example 42, FIG. 19.) The upper limit of this dimension has not been tested, though it is known that G11 (EDA) PAMAM dendrimers, with a diameter of approximately 110 Å, show excellent transfection. Based on data showing that aggregates of dendrimers up to about 1,000 Å in diameter transfect sufficiently while aggregates of 2,000–5,000 Å do not; it is believed that the dendrimer particles could have diameters as great as about 1,000 Å, or smaller particles agglomerated could have diameters as great as about 1,000 Å, preferably from 50 to 110 Å. These diameters are generally considered macromolecular dimensions, and hence these dendrimers are referred to as dendritic macromolecules.

Dendrimers with smaller diameters also can be employed to transfect cells with genetic material, however the best results are obtained if the smaller DNA:dendrimer complex is subsequently associated with larger dendrimers that have about a 50 Å diameter at their narrowest diameter dimension. (See Example 46, FIGS. 15 and 16.) In Example 46 (FIGS. 15 and 16), excellent transfection was achieved by complexing DNA with a G5 (EDA) dendrimer or G5 ($NH_3$) dendrimer (diameter approximately 40 Å), followed by adding a G9 (EDA) dendrimer or G9 ($NH_3$) dendrimer (diameter approximately 90 Å) to the complex. Interestingly, the reverse order does not appear to be as effective.

When used in this sequential manner, it is believed that the smaller dendrimers can have as their narrowest diameters, diameters as low as of about 22 Å, i.e., corresponding to a G3 ($NH_3$) PAMAM dendrimer. The dendrimers below about generation 3 (G3) do not appear to independently complex DNA. The larger dendrimer can have as its smallest diameter, diameters as low as from about 50 Å up to about 1,000 Å.

Combinations of two different size dendrimers complexed with DNA also can enhance transfection. This is particularly true when the mix of dendrimers are polydispersed in size,i.e., those having particle sizes ranging from about 22 to about 110 Å. Samples P and Q of Example 42 are exemplary of such polydisperse compositions.

A spheroidal dendrimer can be made by starting the generational reaction sequence with a generally spherical initiator or core material, most preferably having three reactive sites projecting from the core, generally equal distance from each other, e.g., ammonia. (gee, for example, European publication 0 115 771, and U.S. Pat. Nos. 4,507, 466, 4,558,120, 4,568,737, 4,631,337, 4,587,329 and 4,737, 550.) The dendrimer can be given an elongated ellipsoidal or rod-like configuration by starting with an elongated, polymeric core having a plurality of reactive sites projecting radially from the core at various points along its length, e.g., polyethyleneimine. (See, for example, European publication 0 234 408, and U.S. Pat. No. 4,694,064.) An ellipsoidal dendrimer starts with a shorter core material than the core used for the rod dendrimer, e.g., ethylenediamine (EDA).

In a spherical dendrimer, the diameter of the sphere preferably falls within the preferred diameter ranges described above. In an ellipsoidal dendrimer or a rod-shaped dendrimer, the diameter of the right cross section of the ellipsoid or rod would preferably have the preferred diameter(s) referred to above. The right cross section does not have to be a perfect circle, and hence may have diameters of varying lengths, depending on where taken across the cross section. Lengths of up to 1,000 Å are contemplated.

The bridged dendrimers may also be useful for carrying genetic material. These structures can vary in shape considerably, but basically are formed by associating adjacent dense star dendrimers with one another, especially through a covalent bond, but non-covalent interactions are also possible. Four or five smaller spherical, ellipsoid or rod-shaped dendrimers might be bridged together to form an aggregate unimolecular structure, that has the transfection efficiency of a higher generation dendrimer.

An interesting variation on a bridged dendrimer concept involves the formation of macromolecular clusters where a DNA or RNA material serves as the non-covalent lattice between separate dendrimers, where the lattice is formed, for example, on the basis of electrostatic interactions. This model appears to approximate the complex of Example 46 discussed above, in which DNA is first complexed with a smaller dendrimer (e.g., G5), with the DNA:dendrimer complexes subsequently blended with a larger diameter dendrimer (eg., G9), as in FIGS. 15 and 16.

Larger diameter aggregates of dendrimers are formed by attracting amino-terminated dendrimers around a core of carboxylate-terminated dendrimers. Depending on the charge ratio of the two classes of dendrimers used in the formulation and also the concentration that they are prepared at, different types of dendrimer aggregates are formed. The transfection efficiency seems to be the greatest when the amino-terminated dendrimer and carboxylate-terminated dendrimer are present in a dendrimer:dendrimer positive charge to negative charge ratio of preferably from about 25:1 to about 100:1, which results in formation of aggregates that have an overall positive charge (Example 74). When the appropriate ratios are used, the transfection efficiency can be greater than that observed with the parent amino-terminated dendrimer used at the same DNA:dendrimer charge ratio and in the presence of DEAE-dextran (which also acts to enhance the transfection efficiency).

Full generation (amino-terminated) and half generation carboxylate-terminated dendrimers form dendrimer aggregates at about pH 6–9, depending on the ratio of amino-terminated and carboxylate-terminated dendrimers, as well as sample concentrations. At pH>9, the protonated primary amines of the full generation dendrimers start to deprotonate, thus breaking down the aggregates. At pH<6, the carboxylates and interior tertiary amines of the half generation dendrimers are being protonated, resulting in the formation of zwitterions within the half generation dendrimers, and, thus dissociate the aggregates as well. To our knowledge, the PAMAM dendrimer aggregate is the only material that possess this unique property.

It is known that the pH outside the cell is 7.2 and inside the cell is about 5.0. Therefore, it is reasonable to design and prepare higher molecular weight dendrimer aggregates from the lower generation dendrimers at pH 7.4 so that the dendrimer aggregate sizes are large enough to efficiently complex the DNA molecules. However, in order to bind DNA, these dendrimer aggregates have to carry net positive charges, which means the full generation dendrimers have to be in large excess over the half generation dendrimers. One of the interesting features of this delivery system is that after the complex enters into the cell, the dendrimer aggregates will be broken apart due to the lower pH of the cell's interior. This dissociation could also enhance transfection efficiency.

The covalent modification of a PAMAM dendrimers surface amino groups with an amino acid, lysine, showed a surprising and unique enhancement of transfection efficiency (Example 75, FIG. 57). Using a lysine-modified G7 (NH$_3$) dendrimer complexed to the plasmid results in a greatly enhanced expression of the luciferase gene in comparison to an unmodified G7 (NH$_3$) dendrimer, and furthermore, the complexes formed with the lysine-modified G7 (NH$_3$) dendrimer show transfection equivalent to that of a G10 (NH$_3$) dendrimer (all experiments were conducted at a DNA:dendrimer charge ratio of 1:10 and in the presence of DEAE-dextran). This experiment suggests that increasing the charge density of the dendrimers influences the transfection process since the pK$_a$ of the epsilon amino group is 10.53 in comparison to the approximate pK$_a$ of 9 for the terminal amino groups of a PAMAM dendrimer. Other surface modifications could also be expected to enhance transfection in a similar or even greater manner.

C. Description of Non-specific Transfection Activities of Dendrimers

The exact mechanism of non-specific (i.e., non-target directed) transfection of cells by DNA:dendrimer complexes is not known, however, several things are apparent. While not wishing to be bound by any theory, we believe that the DNA binds to the dendrimer on the basis of charge interaction and that the most efficient transfection occurs when the complex is formed in positive charge excess. The interaction between the DNA:dendrimer complex and the cell is likely due to the positively charged complex binding to negatively charged phospholipids on the surface of the cells. Transfection in the presence of serum or failing to wash the serum off the surface of the cells appears to prevent transfection by neutralizing cell-surface charges, thus preventing adherence of the complexes to cells. It is of interest that certain types of DNA:dendrimer complexes work better for the non-specific transfection of particular cells. This finding suggests that there are differences in the surface of cells that facilitate interactions with certain types of DNA:dendrimer complexes. Potentially, different dendrimers may have to be used or developed for the most efficient transfection of different types of cells.

It is also possible that, given the marked differences in size of the forms of genetic material used in gene transfer therapy, different sizes and charge densities of dendrimers may be necessary for efficient, non-specific transfection of the different forms of genetic material. In theory, a genetic material:dendrimer complex that binds to cells effectively on the basis of charge interaction may be very different for small pieces of genetic material, such as oligonucleotides of only a few bases in length, and larger pieces of genetic material, such as large DNA plasmids. In general, one would require that the genetic material forms a small complex that has a high density positive charge on its surface for transfection based on charge interaction. In this realm, using smaller dendrimers followed by larger dendrimers or using polydispersed dendrimers may be important in forming unique complexes that are most efficient for DNA transfer. Also the addition of DEAE-dextran or glycerol to the transfection buffer after the formation of the DNA:dendrimer complex shows surprising and unexpected enhancement of cell transfection. The addition of other agents in transfection buffers, such as chloroquine, that can either aid in the release of the DNA from endosomes or prevent its degradation in endosomes, also may be of value in enhancing transfection with dendrimer complexes. However, these findings may be unique for non-specific transfection in vitro, with different conditions or combinations of materials, such as fusogenic peptides, being more effective in enhancing transfection in vivo or with target-directed dendrimer carriers.

D. Genetic Material and Complexing It with Dendrimer to Form a Conjugate

Genetic materials are nucleotide based materials, including without limitation, viruses and viral fragments, plasmids, phages, cosmids, genes and gene fragments (i.e., exons, introns), deoxyribonucleic acid (DNA) both single and double stranded, ribonucleic acid (RNA), ribosomal RNA (rRNA), catalytic RNA (cRNA), small nuclear RNA (snRNA), messenger RNA (mRNA), transfer RNA (tRNA), DNA and RNA oligonucleotides (both single and double stranded) or oligomers and (anti-sense) oligonucleotides, protein nucleic acids (PNA), and substituted nucleic acid oligonucleotides. Genetic material, especially viruses and viral fragments, may be complexed or coupled with some protein. The term genetic materials is also intended to include "modified nucleotides" as described more fully below. The nucleotides may be modified to render them more resistant to enzymatic degradation, enhance cellular uptake, or for other purposes. In order to improve uptake by cells and/or resistance to enzymatic degradation, scientists have replaced the negative oxygen on the phosphodiester backbone with methyl or sulfur, creating methylphosphonates or phosphoryl thioates. This will result in an enzyme-resistant synthetic oligonucleotide derivative strand possessing enduring integrity when commingled with a cellular biological material. Nuclease-resistant strands may also be produced by including 2'-O-allyl groups in the synthetic oligo strands. Phosphoryl dithioates have also been created. Modification by creating phosphate esters and phosphoryl amidates has been accomplished.

Another type of modification which has been investigated is replacement of the phosphodiester bridge between nucleotides with an entirely different group, such as a siloxane bridge, carbonate bridge, carboxymethyl ester bridge, acetamide bridge, carbamate bridge, thioether bridge, and peptide bridge. Besides replacing the phosphate bridge, one can replace the sugar and phosphate residues by a synthetic polymer and thus obtain a plastic DNA. The nucleoside units themselves can be modified.

The term "genetic material" as used throughout this text is intended to encompass nucleotide segments modified in any of the above suggested ways and other ways. In general, in the ensuing description of the invention, the term "oligonucleotide" will be applied to all short forms of genetic material.

Genetic materials (i.e., nucleic acids) can vary in length dramatically from three bases (about 10 Å) for a codon to 10 billion Å or one meter for human DNA. Many different forms of genetic materials have potential uses in genetic therapies. [For example, such ranges are: a typical human gene is approximately 34 microns ($\mu$) (340,000 Å) in length; the average length of an $E.\ coli$ mRNA is about one-half of a micron ($\mu$); and tRNA, which is believed to be the smallest of the RNA molecules, is typically about 0.003 microns ($\mu$).] Potentially, any genetic material can be used in the present invention.

The conjugates of genetic material and dendrimer are referred to as complexes. A "complex" as that term is used herein refers to a type of conjugate of dendrimer and carried material in which association between the carried material and the dendrimer is effected through ionic bonding, van der Waals forces, hydrogen bonding, metallic bonding or any combination thereof. In a complex, the carried material is not associated with dendrimer through covalent bonding.

The uptake of DNA:dendrimer complexes by cells has been demonstrated for relatively low molecular weight, single-stranded DNA nucleotides (Example 47, FIGS. 20 and 21), as well as high molecular weight DNA. Gene transfer and expression also has been demonstrated in FIG. 22, for circular or supercoiled DNA and linear DNA (Example 48, FIG. 22), and in other experiments and figures for entire genes and longer DNA segments (e.g., 6.5 kb). This uptake that is observed with DNA:dendrimer is facilitated over the cellular entry that occurs with DNA alone, and is an active, energy dependent process of the target cell (Example 47).

In order to attach the genetic material to the dendrimer, the dendrimer, preferably already targeted for in vivo use in the manner described below, is mixed with the genetic material in an aqueous solution at room temperature (20°–40° C.) at a pH from about 5 to about 10. The negatively charged nucleic acid complexes with the positively charged surfaces of dendrimer macromolecules form a lattice structure.

Genetic material, such as DNA, form stable complexes with dendrimers at genetic material to dendrimer charge ratios as high as about 10:1, with more complexing occurring at charge ratios of about 2:1 and below. (In Example 42, efficient transfection is seen for Sample 4 at a charge ratio of 1:0.6; see Table XIV, FIGS. 18 and 32. This charge ratio also permits complete DNA complexing when assayed in an agrose gel.) At lower charge ratios, e.g., 1:10 or 1:100, the complexes continue to be very stable (see Example 49, FIG. 23) and transfection is observed even in the absence of DEAE-dextran (Example 56 and FIG. 30). Complexing is minimal at charge ratios of DNA:dendrimer above about 40:1, as indicated in Example 49, FIGS. 23(A)–(D). At the other end of the charge ratio range, good transfection results are seen for some dendrimers at DNA:dendrimer charge ratios of about 1:1,000 and for some as low as about 1:10,000 (Example 56, FIG. 30). It is possible that with other dendrimer systems charge ratios as low as 1:1,000,000 may be effective in mediating transfection.

The charge ratio appears to be the defining factor in the formation of the DNA:dendrimer complexes as is indicated in Example 50 (FIG. 24), where at the same molar ratio, 1:16, a G11 (EDA) dendrimer, having greater surface charge than a G8 ($NH_3$) dendrimer, forms a stable complex with DNA, while a G8 ($NH_3$) dendrimer mixed with DNA at the same molar ratio does not. This indicates that complex formation is more dependent on charge ratio than molar ratio.

DNA:dendrimer complexes are remarkably stable and water soluble over a fairly wide pH range, i.e., 5.2–9.8 (Example 51, FIG. 25) and in a wide range of salt concentrations, i.e., 0–1.5M (Example 52, FIG. 26). Complexing the genetic material with dendrimer protects it from digestion in the presence of either restriction endonuclease enzymes or cellular nucleases (Example 53, FIG. 27 and Example 54, FIG. 28). This makes these complexes suitable for the transfection of cells in vivo.

The amount of genetic material per cell that can be transfected using DNA:dendrimer complexes can vary, and to a point, increasing the concentration of genetic material tends to increase the extent of transfection (Example 55, FIG. 29). At a given charge ratio, transfection appears to be greater at 5 micrograms ($\mu$g) of plasmid DNA per culture well (about 200,000 cells), than at 1 $\mu$g of plasmid DNA, though this effect appears to plateau at 10 $\mu$g of plasmid DNA per well.

It is believed that genetic material:dendrimer solutions in which the concentration of genetic material is from about 1.0 to about 10.0 $\mu$g/ml are useful in vitro and in vivo. The in vivo concentration used will of course vary as a function of the mode of administration. A more concentrated solution would be used for intravenous injection, given the dilution which will occur in the bloodstream. A more dilute solution could be used for site specific administration, e.g., for injection directly into a tumor or an organ.

Thus, sufficient genetic material to yield a final concentration from about 1.0 to about 10.0 μg/mL is mixed in water with sufficient dendritic polymer being substantially positive surface functionality to yield a genetic material, dendritic polymer charge ratio from about 10:1 to about 1:10,000, more preferably from about 3:1 to about 1:1,000, or more preferably from about 1.5:1 to about 1:100, or from about 1:1 to about 1:15, or from about 1:5 to about 1:10, as a function of variables discussed above. The mixing is done at a pH from about 5 to about 10 and at a temperature from about 20° to about 40° C.

Generally speaking, the genetic material:dendrimer charge ratio may be from about 10:1 to about 1:10,000) possibly even lower), but more preferably between about 5:1 or even 3:1 to 1:10,000. The ratio selected within that range may vary as a function of whether or not an enhancing agent such as DEAE-dextran, glycerol or chloroquine is used, or whether a target director is used. While the foregoing broad ranges are still applicable, the preferable charge ratio range when no enhancer is used is from about 1:5 to about 1:10,000, more preferably 1:10 to about 1:10,000. Similarly when an enhancer is used, the preferable charge ratio range is from about 5:1 to about 1:10,000, preferably from about 1:1 to about 1:100, more preferably from about 1:1 to about 1:15, and most preferably from about 1:5 to about 1:10. Finally when a target director is used, it is believed that higher charge ratios can be used with better effect than for non-directed transfection. Thus, the preferable range is believed to be from about 10:1 to about 1:10, more preferably from about 3:1 to about 1:10, more preferably from about 1:1 to about 1:10 and in some circumstances most preferably about 1:1. These ranges are discussed more fully below.

Typically, the complexes are initially mixed at genetic material concentrations from about 1.0 to about 10.0 μg per 20 μL, and then diluted fifty-fold to the final concentration of 1.0 to 10.0 μg of genetic material per mL. Either the initial more concentrated or the final genetic material:dendritic polymer solutions could be packaged as suitable diagnostic or pharmaceutical compositions.

Enhancing Transfection

One can effect transfection of a cell with genetic material using dendritic polymers alone, but primarily with larger (>G8) dendrimers at lower genetic material to dendrimer charge ratios, e.g., about 1:5 and lower, preferably lower than about 1:10, (Example 56, FIGS. 30 and 31). Transfection using dendrimer and genetic material alone can be enhanced by first complexing the genetic material with a lower generation dendrimer, e.g., G5, followed by adding a larger dendrimer,e.g., G9, as discussed above (see Example 46, FIGS. 15 and 16). This tends to work best where the second dendrimer is used at a concentration from about 0.1 to about 10 micromolar, although the specific concentration may vary depending on dendrimer type (compare FIGS. 15 and 16). The first dendrimer and its complexed genetic material are used at concentrations sufficient to complex about 1 μg genetic material per test well.

Complexes transfecting cells nonspecifically should achieve two conflicting goals; the first is to compact DNA as densely as is possible and, at the same time, have a large positive charge density on the surface of the complex to mediate binding to negatively charged phospholipids on cell membranes. This requirement for dual activity suggests that a polydispersed size mix of dendrimers might be of value in non-specific transfection with the smaller dendrimers helping to compact DNA while the larger ones mediate binding to cells. This also may help to create smaller sized DNA-:dendrimer complexes, as the lower generation dendrimers would disrupt the regular lattice formed by the larger dendrimers and DNA. Concepts such as these are supported by data set forth in the electron-micrographs (i.e., FIG. 60, Panels 3, 4 and 5), that demonstrate small, compacted DNA complexes when polydispersed-sized dendrimers are employed as compared to massive DNA:dendrimer complexes produced with large dendrimers alone.

Transfection also can be enhanced through the addition of a variety of agents to the transfection buffer. Unexpectedly, synergistic transfection results are obtained when DEAE-dextran is present in the transfection buffer with the complex of genetic material and dendrimer. The genetic material:dendrimer charge ratio is from about 5:1 to about 1:10,000, preferably about 1:1 to about 1:100, more preferably from about 1:1 to about 1:15, and most preferably from about 1:5 to about 1:10. (Example 56, FIG. 30; Example 57, FIG. 32; Example 58, FIG. 33; Example 59, FIG. 34; Example 42, FIG. 17.) The DEAE-dextran concentration should preferably be within a relatively narrow range from about 0.125 to 2 micromolar, and more preferably from about 0.25 to about 1 micromolar (Example 60, FIG. 35). The genetic material must also be complexed to the dendrimer before being placed in the DEAE-dextran solution for the enhancement of transfection to occur. When this is done, transfection in the presence of DEAE-dextran by DNA:dendrimer complexes at charge ratios from about 1:1 to about 1:100, more preferably from about 1:5 to about 1:10, is more effective by orders of magnitude than transfection with DNA:dendrimer complexes alone in a wide variety of different types of cells (Example 61, FIG. 36). This is true even in difficult to transfect cell lines (Example 62, FIG. 37). It is also more effective than transfection using other agents such as the LIPOFECTIN™ and LIPOFECTAMINE™ (Examples 61–63, FIGS. 36–38).

Typically, the genetic material:dendrimer complex is allowed to stand 3–5 minutes after forming before being combined with DEAE-dextran. Although the DEAE-dextran can be added either to the more concentrated complex solution (i.e., the 1–10 μg genetic material/20 μL solution) or to the transfection buffer, it is preferable that it be added to the latter, with which the more concentrated genetic material:dendrimer complex solution is then diluted.

In vitro transfection has been known to be enhanced by using a conventional cell perturbation ingredient. In the present invention, DEAE-dextran appears to be acting as more than a cell perturbation agent as can be seen from Example 64, FIG. 39, in which the effects of DEAE-dextran and the cell perturbation agent DMSO are compared. DMSO alone appears to have little impact on transfection with DNA:dendrimer complexes as compared to the effect of DEAE-dextran. Interestingly, DMSO does seem to synergistically enhance the effect of DEAE-dextran when the two are used together, suggesting that the effect of the DEAE-dextran involves actions other than cell perturbation.

Because the addition of DEAE-dextran or other agents to the DNA:dendrimer complex (after it has been formed) has been shown to be effective in enhancing transfection in a unique manner, another type of experiment was conducted to further understand the role of this agent in enhancing non-specific transfection. Electronmicrographs were taken of DNA:dendrimer complexes with and without the addition of DEAE-dextran. The addition of the DEAE-dextran or the use of polydispersed mixes of dendrimers reduced the size of DNA:dendrimer complexes dramatically (i.e., FIG. 60, Panels 3, 4 and 5). This provides a rationale why these agents would enhance transfection since it is likely that the smaller size complexes that are achieved with these agents makes them much more likely to gain access into the cells and achieve transfection.

The DNA:dendrimer complexes must contain an electrodense positive charged material, to act as a focal point for binding to negatively charged phospholipids on the cell surface. This is best achieved by using higher generation dendrimers, that have greater surface charge density. Unfortunately, these dendrimers tend to complex DNA into large aggregates or macrolatices from about 2,000 to 5,000 Å that are difficult for a cell to pinocytose.

DEAE-dextran acts as a dispersant that reduces the large aggregate into smaller complexes, that still retain the charge dense dendrimer on their surface for binding to the cells. Polydisperse dendritic polymers i.e., mixtures of particles of varying dimensions from about 22 to about 110 Å (see e.g., samples P and Q of Example 42) tend not to form the 2,000 to 5,000 Å aggregates. Instead, they seem to form aggregates of no greater than up to about 1,000 Å, which facilitates efficient transfection of genetic material without the use of DEAE-dextran. A comparison of electron micrographs for complexes of genetic material with a uniformly sized dendrimer G10 (EDA) with (FIG. 60, Panel 4) and without (FIG. 60, Panel 3) DEAE-dextran added, shows the substantial difference in aggregate size. An electron micrograph for a genetic material complexed with a polydisperse dendrimer (FIG. 60, Panel 5) shows aggregates more comparable to those seen in FIG. 60, Panel 4.

Surprisingly, glycerol, like DEAE-dextran, also seems to synergistically enhance transfection of genetic material in genetic material:dendritic polymer complexes. The transfection solution concentration of the glycerol is preferably from about 2 to 10% by weight, more preferably from about 2 to about 5%. It appears to serve a dispersing function comparable to that of DEAE-dextran.

Chloroquine also enhances transfection, and does so with surprising synergy, whether used alone as an enhancer, or in conjunction with DEAE-dextran. Although not wishing to be bound by any specific theory, it is believed that chloroquine acts in a completely different manner from that of DEAE-dextran. It is believed that chloroquine neutralizes endosomes, thus preventing the sequestration and rapid degradation of genetic material:dendrimer complexes. This allows the genetic material to be transcribed and translated to a greater extent than if it had been transfected either alone or solely in the presence if DEAE-dextran without the addition of chloroquine (see FIGS. 61A and 61B, and Example 73). Because there are differences between cells in their ability to trap complexes in endosomes, the enhancing effect of chloroquine does vary significantly between different cell lines, as is illustrated by the difference in results for the transfection of COS1 cells (FIG. 61A) and RAT2 cells (FIG. 61B).

Introducing random negative functionality onto the dense star polymer surface will also affect transfection (Example 67, FIG. 43). Such negative functionality is achieved by randomly interspersing a predominantly positively charged surface (e.g., having amino surface functionality) with carboxy groups. Dendrimers with both positive (cationic) and negative (anionic) functionality are sometimes referred to herein as dendrimers with zwitterionic surfaces. Reduction of overall positive surface charge, in general, seems to decrease transfection efficiency, except perhaps at lower charge ratios, e.g., 1:10 as compared to 1:5 or 1:1 (FIG. 43).

F. Target Directed Transfection

Incorporation of target directors into the dendrimer-genetic material complex not only directs the complex to a desired cell, but may also enhance transfection of cells with the target moiety (Example 65, FIG. 40). Sufficient target director is attached to the macromolecule to attract and attach it to receptor sites on the cellular material to be transfected, but not to decrease surface charge to the point that DNA complexation does not occur. As a result, target director attachment is accomplished in such a way, or in such proportionally small quantities relative to functional groups on the surface of the macromolecule, that the target director does not significantly interfere with the cationic character of the dendritic polymer surface. Hence the ability of the dendrimer to form stable complexes with DNA (at the prior mentioned charge ratios) and is not compromised by the presence of target director (Example 65, FIG. 41).

The use of target directors in conjunction with the dendrimer-genetic material conjugate is one of the most important preferred aspects of the invention. The fact that non-targeted transfection does not occur as effectively at charge ratios of DNA:dendrimer above about 1:10 or 1:5 without enhancement may be due to the fact that these complexes do not have enough positive charge to bind to negatively charged phospholipids on the surface of cells. Importantly, the complex formed in these higher genetic material:dendrimer charge ratios (i.e., 1:10 to 1:1, or possibly even 3:1 or as high as 10:1) can still be targeted to transfect specific cells by a target director. Non-intended transfection of randomly encountered cells (which might be undesirable under many circumstances) is avoided when DNA:dendrimer complexes are produced in this manner at these higher charge ratios or when serum is present (Example 66, FIG. 42). Where a target director is used, a charge ratio of 1:1 may be preferred in many applications.

The use of a target director is very important to in vivo transfection of genetic material into cells. DEAE-dextran, while not toxic for purposes of in vitro use, would not be suitable for in vivo use as a transfection enhancer. Dendrimer-genetic material complexes, with or without an enhancing agent, do not significantly transfect cells in the presence of serum (Example 66, FIG. 42). A target director, promoting binding of the genetic material-dendrimer complex to specifically targeted cells, facilitates transfection of the genetic material into those cells even in the presence of serum.

Target directors or modified dendrimer surfaces may also be used with the dendrimer-genetic material complex in the presence of DEAE-dextran in vitro to augment transfection. The presence of target directors such as the galactose trisaccharide on the dendrimers appears to significantly enhance transfection of genetic material in cells expressing the receptor for this sugar. This is compared to transfection achieved using unconjugated G11 (EDA) PAMAM dendrimer. (See FIG. 40.)

Suitable target directors include any material which binds with specificity and high affinity, such as, for example, antibodies, antibody fragments such as Fab, Fab', F(ab')$_2$ fragments, single chain antibodies, or any other antibody fragments having the requisite target specificity, glycoproteins, proteins, glycolipids, hormones, additional biological response modifiers, epitopes, cell nutrients, chemical functionalities exhibiting target cell specificity and the like. A number of avenues will be apparent to those skilled in the art for linking a target director to the dendrimer.

One method for the attachment of a preferred target director, biotin, to a dendrimer having an amino functional surface is illustrated schematically below:

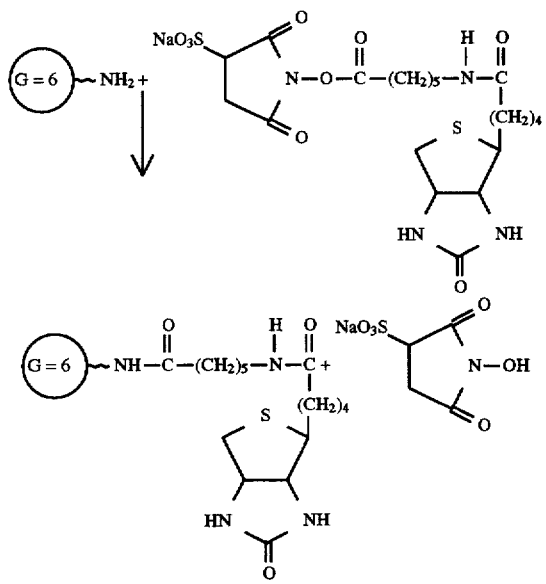

The attachment of pyruvic acid, another potential target director, to a dendrimer having an amino functional surface proceeds according to the following reaction showing the coupling of 64 pyruvates to G5 dendrimers:

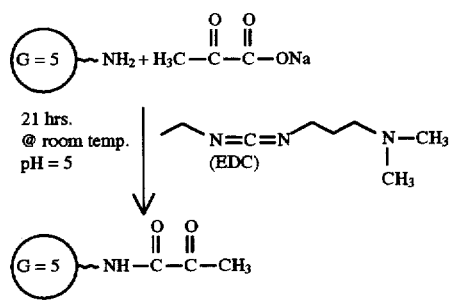

The degree of functionalization of the dendrimer with the target director is minimal, in order to minimize interference of the target director with the overall cationic surface character of the dendrimer. Thus, the stoichiometric ratio of target director to dendrimer macromolecule is from about 1:1 to about $N_cN_b^{G-1}$:1. (Where $N_c$ and G are defined as before and $N_b$ is the branch multiplicity.) On a dendrimer where $N_c=3$, $N_b=2$, this requires the use of only one to $N_cN_b^{G-1}$ terminal groups, leaving $N_cN_b^{G-1}$ to 1 terminal groups available to provide positive character (e.g., amino) functionality and interspersed negative carboxylic functional groups in some cases. The dendrimer's consistent structure, especially for dense star polymers and dendrimers, allows for conjugation with extreme precision that is not achieved with other types of materials. This precision makes possible the production of targeted dendrimers that maintain the capability to bind and carry genetic material.

Just as individual dendrimer molecules can be differentiated by attaching a targeting moiety, so too such aggregates can be differentiated. One might attach a targeting moiety to all dendrimers in the aggregate, or only to one or a portion of them, which are then aggregated with other non-differentiated dendrimers. After mixing the two types under the mild physiological conditions (i.e., pH 7.4), the two types will associate together based on electrostatic interactions. This novel method offers not only a novel way to synthesize the differentiated dendrimer aggregates, but also provides a system that can deliver the targeting moieties at physiological conditions.

Use of the Genetic Material-Dendrimer Conjugates

The genetic material-dendrimer conjugates of the present invention can be employed for DNA transfer either in vivo or in vitro. In vivo use involves introduction of the conjugate into the blood stream to reach a targeted cell, as for example, DNA:dendrimer complexes injected into the portal vein to reach hepatocytes. Also, the complexes can be injected into a particular localized area of interest, such as a joint space or the peritoneal cavity, to locally transfect cells. Transdermal introduction of the conjugate into the body may also be employed, and as with other techniques can be used in a manner similar to introducing pharmaceuticals into the body.

A target director on the dendrimer facilitates direction and binding of the conjugate to a cell surface receptor and its subsequent transfection via endocytosis. FIG. 51 illustrates the hypothetical process of a targeted DNA:dendrimer complex in transfecting a cell. At "A," DNA (10) is complexed and compacted with a number of dense star dendrimers (20) with attached target director (30). At "B," the conjugate (10-20-30) has attached to a cell (40) at receptors (50) via target director (30). At "C," transfection is taking place, as DNA (10) disassociation from dendrimer (20) is illustrated, which facilitates subsequent transcription and translation.

Radionuclide studies indicate that a substantial portion of the transfected genetic material enters the nucleus of eukaryotic cells (Example 70, FIGS. 47, A–F). The product of dendrimer transfected genetic material shows excellent substantivity (Example 68, FIG. 44). LUCIFERASE™ enzymatic activity is pronounced at 21 hours, and is still substantial at 45 hours after transfection, and some activity continues even at 69 hours. Expression of lacZ gene delivered into the cells with RSV-β-gal plasmid and dendrimer is photographically shown in FIGS. 48, 49 and 50 (see also Example 71). The cells expressing lacZ gene are the cells which have been darkened in the figures. Under appropriate conditions, almost every cell is stained documenting that transfection has occurred in almost every cell in culture.

The DNA:dendrimer complexes per se have very low cytotoxicity (Example 69, FIGS. 45 and 46). Normal cell death in culture is about 5 to 10%. The addition of DNA:dendrimer complexes to the cell culture does not significantly increase the rate of attrition. Addition of the DEAE-dextran with the DNA:dendrimer complex does increase toxicity, but not sufficiently to prevent its use in vitro. (FIGS. 45 and 46.) The foregoing has been demonstrated for a variety of different types of cells (ibid).

Genetic material transfected in accordance with the present invention can be permanently incorporated into the chromosomal DNA of the cell, and is successfully reproduced and carried forward into subsequent generation clones (Example 72, FIGS. 52 and 53). Genes expressing G418 (neomycin) resistance and β-galactosidase were successfully transfected into D5 and RAT2 cell lines using the techniques of the present invention. Both genes were delivered on a single RSV-β-gal-NEO plasmid. These cell lines replicate every 24 hours. Four weeks after transfection, the newly generated clones continued to express neomycin resistance and β-galactosidase. The results obtained using the techniques of the present invention are strikingly superior, as compared to prior art techniques, such as mediation of transfection with calcium phosphate or DEAE-dextran alone. Similar results are obtained when reporter genes from different expression plasmids are co-transfected (e.g., neomycin or β-galactosidase).

Transfection of genetic material can also be achieved using other types of dendritic polymers, other than dense star polymers, i.e., a lysine-based, unsymmetrically branched dendrimer, is demonstrated in Example 73 (FIG. 54). All of the conditions in the preceding discussion of transfection with dense star polymers also govern transfection using other types of dendritic polymers. For example, DEAE-dextran also synergistically enhances such transfection with an asymmetrical lysine dendrimer at charge ratios of 1:5 to 1:10 DNA:dendrimer.

EXAMPLES

The following examples further illustrate the invention but are not to be construed as a limitation on the scope of the invention. The lettered examples concern the preparation of starting materials; the numbered examples concern the preparation of products of this invention.

In the following examples, the following terms and conditions were used unless otherwise specified.

Glossary

Ambient temperature means room temperature or about 20° to about 25° C.

ASGPR means asialoglycoprotein receptor.

BHA means benzhydryl amine.

β-gal means RSV-lacZ.

Binding Buffer means a specific buffer solution as described hereafter under Protocol for Dendrimer-Dextran Transfection, Day 2, Step 1, discussion on preparing the solution.

BOC means t-butoxycarbonyl.

Conc. means concentrated.

Cyt c means the protein, cytoehrome c.

DCC means dicyclohexylcarbodiimide.

DEAE-dextran means a diethylaminoethyl ether of dextran, an electropositively charged polymer.

DMEM means Dulbecco's Modified Eagles Medium.

DMF means dimethylformamide.

DMSO means dimethylsulfoxide.

DO3A means 1,4,7,10-tetraazacyclododecane-1,4,7-triacetic acid.

DOTA means 1,4,7,10-tetraazacyclododecane-1,4,7,10-tetraacetic acid.

DTAF means dichlorotriazinyl fluorescein.

DTPA means diethylenetriaminepentaacetic acid.

DTPMP means diethylenetriaminepentamethylenephosphonic acid.

DTT means 1,4-dithiothreitol.

EBV means Epstein-Barr virus.

EBV-A means expression plasmid producing a hygromycin B phosphotransferase protein that inactivates HYGROMYCIN B™ antibiotic from a kinese gene driven by the EBV promotor.

EDA means ethylenediamine.

EDAC means 1-ethyl-3-(3-dimethylaminopropyl) carbodiimide.

EDC means 1-(3-dimethylaminopropyl)-3-ethylcarbodiimide.

EDTA means ethylenediaminetetraacetic acid.

FACS analysis means fluorescence activated cell sorting.

FITC means fluorescein isothiocyanate.

G or Gen means the generation of the dendrimer.

GC means gas chromatography.

GGE means gradient gel electrophoresis.

HBS means Hanks buffered saline.

HEPES=N-2-hydroxyethylpiperazine-N'-2-ethanesulfonic acid.

HOBT means N-hydroxybenzotriazole.

HPLC means high performance liquid chromatography.

HRP means horse-radish peroxidase.

HYGROMYCIN B™ is an aminoglycosidic antibiotic produced by Streptomyces hygroscopicus.

ICAM means intercellular cell adhesion molecule.

Immunoglobulins means IgG, IgM, IgA, IgD, and IgE, including Fab, F(ab')$_2$ and other fragments.

LC means liquid chromatography.

LUCIFERASE™ means an enzyme produced from the firefly luciferase gene, the enzyme available from Promega, Madison, Wis., U.S.

LUCIFIREN™ means a substrate for measuring LUCIFERASE™ enzymatic activity.

$MB^+$ means a cationic form of the dye, methylene blue.

NHS-LC-biotin means a standard spacer with linker used with biotin.

NMP means N-methylpyrrolidinone.

Overnight means from about 9 to 18 hours.

PAMAM means polyamidoamine.

PBS means phosphate buffered saline (purchased from Sigma Chemical), containing 120 mM NaCl, 2.7 mM KCl and 10 mM phosphate buffer, pH 7.4.

PEI means polyethyleneimine.

$P_i$ means inorganic phosphate (used in buffers)

PTFE means polytetrafluoroethylene.

RSV-β-gal-NEO means expression plasmid producing β-galactosidase protein from the lacZ gene and aminoglycoside phosphotransferase protein from the APH gene (NEO) driven by the RSV promoter.

RSV-lac means expression plasmid producing β-galactosidase protein from the lacZ gene driven by a RSV promoter.

RSV-luc means a reporter plasmid expressing firefly luciferase gene driven by the RSV promoter.

SDS means soduim dodecylsulfate.

SP-Sephadex™ C-25 resin is a cation exchange resin having sulfonic acid functionality, sold by Pharmacia, Inc.

TREN means tris-(2-aminoethyl)amine.

THF means tetrahydrofuran.

TLC means thin layer chromatography.

TMB means 3,3',5,5'-tetramethylbenzidine.

TRIS glycine means N-[2-hydroxy-1,1-bis(hydroxymethyl)ethyl]glycine.

TRIS means tris amine buffer, i.e. tris(hydroxymethyl) aminomethane.

Triton X-100 means octoxynol-9, is the ethoxylated alkylphenol that conforms generally to the formula $C_8H_{17}C_6H_4(OCH_2CH_2)_n$ where n has an average value of 9 (purchased from Rohm and Hass), a surfactant.

X-gal means 5-bromo-4-chloro-3-indolyl-β-D-galactoside.

General Experimental

Mass spectra were obtained on either a Finnigan TSQ mass spectrometer ($Q^1MS$ mode) or a VG ZAB-MS high resolution mass spectrometer (fast atom bombardment with xenon, using 3:1 dithiothreitol:dithioerythritol).

$^1H$ and $^{13}C$ NMR spectra were obtained using a Varian VXR-300, Bruker APC 300, IBM/Bruker NR-80 or a Jeol FX400 spectrometer. All spectra were obtained at 30° C. unless otherwise noted. $^1H$ NMR was done at 300 MHz, 80 MHz or 400 MHz, respectively to the equipment listed above; $^{13}C$ NMR was done at 75 MHz, 20 MHz or 100 MHz, respectively to the equipment listed above. The values for the NMR are δ versus TMS (tetramethylsilane) or when $D_2O$ was the solvent versus DSS (2,2-dimethyl-2-silapentane-5-sulfonic acid, sodium salt).

Infrared spectra (IR) were recorded on a Nicolet 5SX FT/IR instrument.

For the chromatography procedures, most solvents were Fisher HPLC grade materials. Ammonium acetate was purchased from Aldrich. Water was purified using a Barnstead NANOpure™ water filtration system. Preparative chromatography of organic compounds was performed either by normal gravity chromatography using standard techniques or by flash chromatography as described by C. W. Still et al., *J. Org. Chem.* 43, 2923–24 (1978).

TLC and $R_f$ values are reported using these solvent systems and commercially available, normal phase, silica TLC plates [GHLF 250 micron, Analtech Inc. or Merck Kiesel gel 60F$_{254}$]. Preparative column chromatography was done using Merck grade 60, 60 Å silica gel.

All percentages are by weight unless stated otherwise.

pH star is a mechanical device that measures and adjusts the pH of a solution to a predetermined, desired value by addition of the appropriate amount of a preselected acid and/or base.

Some solids were dried using a rotary evaporator (Buchi 461) and/or a vacuum oven at a temperature of about 55°–60° C. for several hours. In addition, a Virtis model 10-010 automatic freezer dryer or Speed Vac™ concentrator was used for solvent removal.

HPLC columns used were: Hand-packed Q-Sepharose™ (Pharmacia) either 1.5 cm×25 cm or 2.5 cm×25 cm; Zorbax™ BIO Series GF-250 (9.4 mm×25 cm) from DuPont Instruments; Vydac™ (Trademark of the Separations Group, Hesperia, Calif.) protein C-4 (4.6 mm×25 cm) from the Separation Group (Hesperia, Calif.); Mono-Q™ and SP-Sephadex™ (Tradename of Pharmacia Biotechnology Products) from Pharmacia; Sep-Pak™ (Tradename of Waters Associates) C-18 cartridge was purchased from Waters Associates (Milford, Mass.); Sephadex™ G-25 disposable columns (2.2 mL) from Isolab Inc. (Akron, Ohio), Centricon™-30 (Tradename of Amicon Division, W. R. Grace & Co., Danvers, Mass.) microconcentrators from Amicon; and Spherisorb™ ODS-1 (Tradename of Phase Separations, Ltd.).

For centrifugation and concentration, a Sorvall RT 6000B (refrigerated centrifuge of DuPont) was used. A Speed Vac concentrator (Savant Instruments Inc., Hicksville, N.Y.) was employed for removal of volatile solvents.

Example A

Preparation of 2-Carboxamido-3-(4'-nitrophenyl) propanamide p-Nitrobenzyl malonate diethylester (2.4 grams (g), 8.13 mmole) was dissolved in 35 mL of methanol. The solution was heated to 50°–55° C. with stirring and a stream of anhydrous ammonia was bubbled through the solution for 64 hours. The solution was cooled and the white, flocculent product was filtered and recrystallized from 225 mL of boiling methanol to afford 1.85 g (7.80 mmole) of bis-amide in 96% yield [mp=235.6° C.(d)].

The title structure was confirmed by MS, $^1$H and $^{13}$C NMR spectroscopy.

| Anal: Calc. for $C_{10}H_{11}O_4N_3$ | | | |
|---|---|---|---|
| | C | H | N |
| Theo: | 50.63 | 4.69 | 17.72 |
| Found: | 50.75 | 4.81 | 17.94 |

Example B

Preparation of 1-Amino-2-(aminomethyl)-3-(4'-nitrophenyl)propane

2-Carboxamido-3-(4'-nitrophenyl)propanamide (2.0 g, 8.43 mmole) was slurried in 35 mL of dry THF under a nitrogen atmosphere with stirring. To this mixture was added borane/THF complex (106 mL, 106 mmole) via syringe. The reaction mixture was then heated to reflux for 48 hours during which time the suspended amide dissolved. The solution was cooled and the THF was removed in vacuo using a rotary evaporator. The crude product and borane residue was dissolved in 50 mL of ethanol and this solution was purged with anhydrous hydrogen chloride gas. The solution was refluxed for 1 hour and the solvent removed in vacuo. The crude hydrochloride salt was dissolved in 15 mL of deionized water and extracted with two 50 mL portions of methylene chloride. The aqueous layer was cooled in an ice bath under an argon blanket and 50% sodium hydroxide was slowly added until basic, pH=11.7. The basic aqueous layer was extracted with four 25 mL portions of methylene chloride and these combined extracts were evaporated using a rotary evaporator to give 1.45 g of amber colored oil. This oil was triturated with diethyl ether (50 mL) and filtered under pressure through a short silica gel (grade 62 Aldrich) column. The column was washed with 100 mL of ether and the combined filtrates were vacuum evaporated giving 1.05 g (5.02 mmole) of the titled diamine as a clear oil [mp= 275°–278° C.(d) bis HCl salt].

The title structure was confirmed by MS, $^1$H and $^{13}$C NMR spectroscopy.

| Anal: Calc. for $C_{10}H_{17}N_3O_2Cl_2$ | | | |
|---|---|---|---|
| | C | H | N |
| Theo: | 42.57 | 6.07 | 14.89 |
| Found: | 43.00 | 6.14 | 15.31 |

Example C

Preparation of 1-Amino-2-(aminomethyl)-3-(4'-aminophenyl)propane

Borane/THF solution (70 mL, 70 mmole) was added under nitrogen via a cannula needle to a flask containing 4-aminobenzyl malonamide (1.5 g, 7.24 mmole) with stirring. The solution was brought to reflux for 40 hours. The colorless solution was cooled and excess THF was removed by rotary evaporation leaving a clear gelatinous oil. Methanol (50 mL) was cautiously added to the oil with notable gas evolution. Dry hydrogen chloride was bubbled through the suspension to effect dissolution and the solution was then refluxed for 1 minute. The methanol/HCl solution was removed by rotary evaporation and the resulting hydrochloride salt was carried through the same dissolution/reflux procedure again. The hydrochloride salt obtained was dissolved in 10 mL of water and cooled in an ice bath under argon. Conc. sodium hydroxide (50%) was added slowly with stirring to pH=11. The aqueous portion was then extracted with 2×100 mL portions of chloroform which were combined and filtered through a short silica gel plug without drying. The solvent was removed in vacuo (rotary evaporator) affording the title compound (0.90 g, 5.02 mmole) in 70% yield ($R_f$=0.65—CHCl$_3$/MeOH/NH$_4$OH concentrated—2/2/1). The title structure was confirmed by $^1$H and $^{13}$C NMR spectroscopy and used without further purification.

Example D

Preparation of 6-(4-Aminobenzyl)-1,4,8,11-tetraaza-5,7-dioxoundecane

4-Aminobenzyl malonate dimethylester (2.03 g, 8.43 mmole) was dissolved in 10 mL of methanol. This solution was added dropwise to a stirred solution of freshly distilled ethylenediamine (6.00 g, 103.4 mmole) in 10 mL of methanol under nitrogen over a 2 hour period. The clear solution was stirred for 4 days and TLC analysis indicated total conversion of diester ($R_f$=0.91) to the bis-amide ($R_f$= 0.42–20% concentrated NH$_4$OH/80% ethanol). This material was strongly ninhydrin positive. The methanol and excess diamine were removed on a rotary evaporator and the resulting white solid was vacuum dried ($10^{-1}$ mm, 50° C.) overnight to afford crude product (2.45 g, 8.36 mmole) in 99% yield. An analytical sample was recrystallized from chloroform/hexane, MP=160°–161° C. The mass spectral, $^1$H and $^{13}$C NMR data were consistent with the structure of the titled compound.

Example E

Reaction of Mesyl Aziridine with 1-Amino-2-(aminomethyl)-3-(4-nitrophenyl)propane 1-Amino-2-(aminomethyl)-3-(4-nitrophenyl)propane (400 mg, 1.91 mmole, >96% pure) was dissolved in 10.5 mL of absolute ethanol under nitrogen. Mesyl aziridine (950 mg, 7.85 mmole) was added to the stirred diamine solution as a solid. The reaction was stirred at 25° C. for 14 hours using a magnetic stirrer and during this period a white, gummy residue formed on the sides of the flask. The ethanol was decanted and the residue was triturated with another 15 mL portion of ethanol to remove any unreacted aziridine. The gummy product was vacuum dried (101 mm, 25° C.) to afford the tetrakis methyl sulfonamide (1.0 g, 1.44 mmole) in 75% yield ($R_f$=0.74—NH$_4$OH/ethanol—20/80). The titled structure was confirmed by $^1$H and $^{13}$C NMR spectroscopy.

Example F

Preparation of 2-(4-Nitrobenzyl)-1,3-(bis-N,N-2-aminoethyl)diaminopropane

The crude methylsulfonamide from Example E (650 mg, 0.94 mmole) was dissolved in 5 mL of nitrogen purged, conc. sulfuric acid (98%). This solution was maintained under nitrogen and heated to 143°–146° C. for 27 minutes with vigorous stirring. A slight darkening was noted and the cooled solution was poured into a stirred solution of ether (60 mL). The precipitated white salt cake was filtered and immediately dissolved in 10 mL of deionized water. The pH of the solution was adjusted to pH=11 with 50% NaOH under argon with cooling. The resulting solution was mixed with 90 mL of ethanol and the precipitated inorganic salts were filtered. The solvent was removed from the crude amine under reduced pressure and to the resulting light brown oil was added 190 mL of toluene under nitrogen. The mixture was stirred vigorously and water was removed through azeotropic distillation (Dean-Stark trap) until the remaining toluene acquired a light yellow color (30–40 mL remaining in pot). The toluene was cooled and decanted from the dark, intractable residues and salt. This solution was stripped of solvent in vacuo and the resulting light yellow oil was vacuum dried (0.2 mm, 35° C.) overnight affording 210 mg of the title product (60%) which was characterized by MS, $^1$H and $^{13}$C NMR spectroscopy.

Example G

Preparation of a STARBURST™ polymer (containing an aniline derivative) of one half generation represented by the following scheme

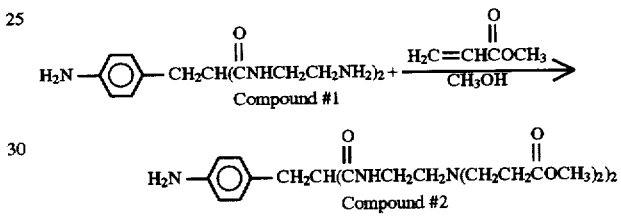

Methyl acrylate (2.09 g, 24 mmole) was dissolved in methanol (15 mL). The compound 6-(4-aminobenzyl)-1,4,8,11-tetraaza-5,7-dioxoundecane (1.1 g, 3.8 mmole) (i.e., Compound #1, the preparation of this compound is shown in Example D) was dissolved in methanol (10 mL) and was added slowly over 2 hours with rigorous stirring to the methyl acrylate solution. The reaction mixture was stirred for 48 hours at ambient temperatures. The solvent was removed on the rotary evaporator maintaining the temperature below 40° C. The ester (Compound #2) was obtained as a yellow oil (2.6 g). No carboxyethylation of the aniline function was observed.

Example H

Preparation of a STARBURST™ polymer (containing an aniline moiety) of one generation; represented by the following scheme

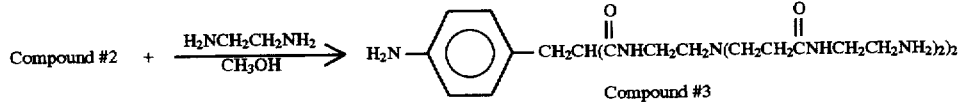

The ester (Compound #2) (2.6 g, 3.7 mmole) was dissolved in methanol (100 mL). This was carefully added to a vigorously stirring solution of ethylenediamine (250 g, 4.18 mole) and methanol (100 mL) at such a rate that the temperature did not rise above 40° C. After complete addition the reaction mixture was stirred for 28 hours at 35°–40° C. (heating mantle). After 28 hours no ester groups were detectable by infrared spectroscopy. The solvent was removed on the rotary evaporator at 60° C. The excess ethylenediamine was removed using a ternary azeotrope of toluene-methanol-ethylenediamine. Finally all remaining toluene was azeotroped with methanol. Removal of all the methanol yielded 3.01 g of the title product (Compound #3) as an orange glassy solid.

Example I

Preparation of a STARBURST™ polymer (containing an aniline moiety) of one and one half generations represented by the following scheme

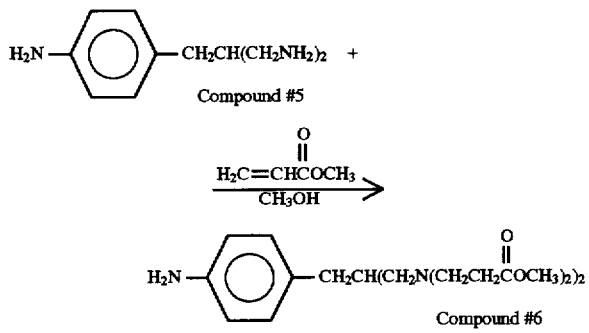

Compound #4

The amine (Compound #3) (2.7 g, 3.6 mmole) was dissolved in methanol (7 mL) and was added slowly over one hour to a stirred solution of methyl acrylate (3.8 g, 44 mmole) in methanol (15 mL) at ambient temperatures. A slight warming of the solution was observed during the addition. The solution was allowed to stir at ambient temperatures for 16 hours. The solvent was removed on a rotary evaporator at 40° C. After removal of all the solvent and excess methyl acrylate the ester (Compound #4) was obtained in 4.7 g yield as an orange oil.

Example J

Preparation of a STARBURST™ polymer (containing an aniline moiety) of one half generation represented by the following scheme

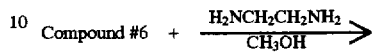

Compound #5

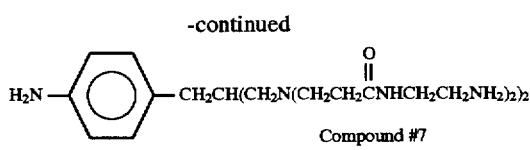

Compound #6

The triamine (Compound #5, the preparation of this compound is shown in Example C) (0.42 g, 2.3 mmole) was dissolved in methanol (10 mL) and was added dropwise over one hour to methyl acrylate (1.98 g, 23 mmole) in methanol (10 mL). The mixture was allowed to stir at ambient temperatures for 48 hours. The solvent was removed on a rotary evaporator, maintaining the temperature at no higher than 40° C. The excess methyl acrylate was removed by repeated azeotropic distillation with methanol. The title ester (Compound #6) was isolated as an orange oil (1.24 g).

Example K

Preparation of a STARBURST™ polymer (containing an aniline moiety) of one generation; represented by the following scheme

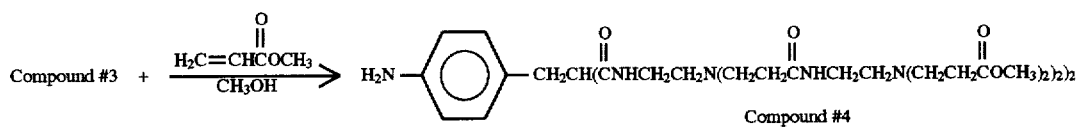

-continued

Compound #7

The ester (Compound #6) (1.24 g, 2.3 mmole) was dissolved in methanol (50 mL) and was added dropwise over two hours to ethylenediamine (73.4 g, 1.22 mole) in methanol (100 mL). A small exotherm was noted, vigorous stirring was maintained. The solution was left to stir at ambient temperatures for 72 hours. The solvent was removed on a rotary evaporator at 60° C. The excess ethylenediamine was removed using a ternary azeotrope of toluene-methanol-ethylenediamine. Finally all remaining toluene was removed with methanol, and then pumping down with a vacuum pump for 48 hours gave the title amine (Compound #7) (1.86 g) as a yellow/orange oil.

Example L

Preparation of a STARBURST™ polymer (containing an aniline moiety) of one and one half generations (G1.5); represented by the following scheme

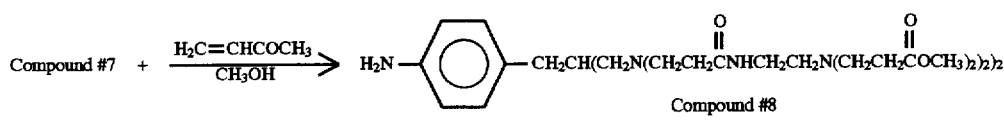

Compound #8

The amine (Compound #7) (1.45 g, trace of methanol remained) was dissolved in methanol (100 mL) and was added slowly over 1½ hours to a stirred solution of methyl acrylate (5.80 g) in methanol (20 mL). The solution was allowed to stir for 24 hours at room temperature. Removal of the solvent followed by repeated azeotropic distillation with methanol enabled the removal of all the excess methyl acrylate. After pumping down on a vacuum pump for 48 hours the title ester (Compound #8) was isolated as an orange oil (2.50 g, 1.8 mmole).

Example M

Hydrolysis of (G4.5) dendrimer and preparation of calcium salt 4.5 Generation PAMAM (ester terminated, initiated from $NH_3$) (2.11 g, 10.92 meq) was dissolved in 25 mL of $NH_3$ and to it was added 10% NaOH (4.37 mL, 10.92 meq) (pH=11.5–12). After 24 hours at room temperature, the pH was about 9.5. After an additional 20 hours, the solution was removed using a rotary evaporator, 50 mL of toluene added, and evaporated again.

The resulting oil was dissolved in 25 mL of methanol and precipitated as a white gum upon addition of 75 mL of diethyl ether. The liquid was decanted, and the gum was rotary evaporated to give a very fine off-white powder which upon further drying gives 2.16 g of product (98% yield). No ester groups were found upon NMR and infrared analysis.

The sodium salt of 4.5 Generation PAMAM (ester terminated, initiated from $NH_3$) was replaced by the calcium salt via dialysis. The sodium salt (1.03 g) was dissolved in 100 mL of water and passed through hollow fiber dialysis tubing (cut off=5000) at 3 mL/minute. The exterior of the tubing was bathed in 5% $CaCl_2$ solution. This procedure was then repeated.

The resulting solution was again dialyzed, this time against water, then repeated two additional times.

Evaporation provided 0.6 g of wet solid, which was taken up in methanol (not totally soluble) and is dried to give 0.45 g of the title product as off-white crystals.

$C_{369}H_{592}O_{141}N_{91}Ca_{24}$ M Wt.=9526.3

|        | C     | H    | N     | Ca    |
| ------ | ----- | ---- | ----- | ----- |
| Theo:  | 46.5  | 6.32 | 13.38 | 10.10 |
| Found: | 47.34 | 7.00 | 13.55 | 8.83  |

Example N

Preparation of dendrimers with terminal carboxylate groups

Half-generation STARBURST™ polyamidoamines were hydrolyzed to convert their terminal methyl ester groups to carboxylates. This generated spheroidal molecules with negative charges dispersed on the periphery. The dendrimers hydrolyzed ranged from 0.5 generation (three carboxylates) to 6.5 generation (192 carboxylates).

The products could be generated as $Na^+$, $K^+$, $Cs^+$ or $Rb^+$ salts.

Example O

N-t-butoxycarbonyl-4-aminobenzyl malonate dimethylester

4-Aminobenzyl malonate dimethylester (11.62 g, 49 mmol) was dissolved in 50 mL of t-butanol:water (60:40 v:v) with stirring. Di-t-butoxydicarbonate (19.79 g, 90 mmol) was added and the reaction mixture stirred overnight. The butanol was removed on a rotary evaporator, resulting in a yellow suspension of the product in water. Extraction into methylene chloride, drying ($MgSO_4$) and evaporation gave a yellow oil (21.05 g, contaminated by di-t-butoxydicarbonate). Recrystallization from 2-propanol:water (75:25) yielded pale yellow crystals (11.1 g, 33 mmol, 67%) of title product. The structure was confirmed by $^{13}C$ NMR spectroscopy and purity checked by HPLC analysis (Spherisorb™ ODS-1, 0.05M $H_3PO_4$ pH 3: $CH_3CN$ 55:45). The material was used without further purification.

Example P

N-t-butoxycarbonyl-6-(4-aminobenzyl)-1,4,8,11-tetraaza-5,7-dioxoundecane

N-t-butoxycarbonyl-4-aminobenzyl malonate dimethylester (8.82 g 26 mmol), prepared in Example O, was dissolved in 50 mL of methanol. This solution was added dropwise (2 hours) to a solution of freshly distilled ethylenediamine (188 g 3.13 mole) and 20 mL of methanol, under a nitrogen atmosphere. The solution was allowed to stir for 24 hours. The ethylenediamine/methanol solution was removed on a rotary evaporator. The residue was dissolved in methanol and toluene added. Solvent removal on the rotary evaporator gave the crude product as a white solid (10.70 g contaminated with ethylenediamine). The sample was divided into two samples for purification. Azeotropic removal of ethylenediamine with toluene, using a soxhlet extractor with sulphonated ion exchange beads in the thimble to trap the ethylenediamine, resulted in partial decomposition of the product, giving a brown oil. The remaining product was isolated as a white solid from the toluene on cooling (2.3 g approximately 50 percent). Analysis of a 10 percent solution in methanol by GC (Column, Tenax 60/80) showed no ethylenediamine detectable in the sample (<0.1 percent). The second fraction was dissolved in methanol to give a 10 percent solution (by weight) and purified from the ethylenediamine by reverse osmosis, using methanol as the solvent. (Filmtec™ FT-30 membrane and an Amicon™ TC1R thin channel separator; the EDA crossing the membrane.) The product was isolated as a white solid (2.7 g), in which no detectable amounts of ethylenediamine could be found by GC. The $^{13}C$ NMR data and HPLC analysis (Spherisorb™ ODS-1, 0.05M $H_3PO_4$ pH 3:$CH_3CN$ 55:45) were consistent with the proposed title structure. The product was used with no further purification.

Example Q

Preparation of a STARBURST™ dendrimer of one half generation (G0.5) from N-t-butoxycarbonyl-6-(4-aminobenzyl)-1,4,8,11-tetraaza-5,7-dioxoundecane N-t-butoxycarbonyl-6-(4-aminobenzyl)-1,4,8,11-tetraaza-5,7-dioxoundecane (5.0 g 13 mmol), prepared in Example P, was dissolved in 100 mL of methanol. Methyl acrylate (6.12 g, 68 mmol) was added and the solution stirred at ambient temperatures for 72 hours. The reaction was monitored by HPLC (Spherisorb™ ODS1, acetonitrile: 0.04M ammonium acetate 40:60) to optimize conversion to the desired product. The solution was concentrated to 30 percent solids, and methyl acrylate (3.0 g, 32 mmol) was added. The reaction mixture was stirred at ambient temperatures until no partially alkylated products were detectable by HPLC (24 hours). Removal of the solvent at 30° C. by using a rotary evaporator, and pumping down at 1 mm Hg for 24 hours gave the product as yellow viscous oil, yield 7.81 g. The $^{13}C$ NMR data was consistent with the title structure. The product was used without further purification.

Example R

Preparation of a STARBURST™ dendrimer of one full generation (G1.0) from N-t-butoxycarbonyl-6-(4-aminobenzyl)-1,4,8,11-tetraaza-5,7-dioxoundecane The half generation product (Example Q) (7.70 g, 10.45 mmol) was dissolved in 75 mL of methanol and added dropwise over 2 hours to a stirred solution of ethylenediamine (400 mL, 7.41 mol) and methanol (50 mL). The reaction mixture was stirred at ambient temperatures for 48 hours. The ethylenediamine and methanol were removed by rotary evaporation to give a yellow oil (11.8 g contaminated with ethylenediamine). The product was dissolved in 90 mL of methanol, and purified from the ethylenediamine by reverse osmosis (Filmtec™ FT-30 membrane and Amicon™ TC1R thin channel separator, methanol as solvent). After 48 hours, no ethylenediamine could be detected by GC (Column, Tenax™ 60/80). Removal of the solvent on a rotary evaporator, followed by pumping down on a vacuum line for 24 hours gave the product as a yellow glassy solid (6.72 g). Analysis by HPLC, PLRP-S column, acetonitrile:0.015M NaOH, 10–20 percent gradient in 20 min.) and $^{13}$C NMR analysis was consistent with the title structure.

Example S

Preparation of a STARBURST™ polymer of one and one half generation (G1.5) from N-t-butoxycarbonyl-6-(4-aminobenzyl)-1,4,8,11-tetraaza-5,7-dioxoundecane The one generation product (Example R) (2.14 g, 25 mmol) was dissolved in 12.5 mL of methanol, and methyl acrylate (3.5 g, 39 mmol) in 5 mL of methanol was added. The solution was stirred at ambient temperatures for 48 hours, monitoring the progress of the reaction by HPLC (Spherisorb™ ODS-1, acetonitrile: 0.04M ammonium acetate, 60:40). A second aliquot of methyl acrylate was added (3.5 g 39 mmol) and the reaction mixture stirred at ambient temperatures for a further 72 hours. Removal of the solvent on the rotary evaporator gave the title product as a yellow oil (3.9 g) after pumping down overnight with a vacuum pump. The product was used with no further purification.

Example T

Preparation of a STARBURST™ polymer of two full generations (G2.0) from N-t-butoxycarbonyl-6-(4-aminobenzyl)-1,4,8,11-tetraaza-5,7-dioxoundecane The one and one half generation product (Example S) (3.9 g, 2.5 mmol) was dissolved in 50 mL of methanol, and was added dropwise over 2 hours to a stirred solution of ethylenediamine (600 g, 10 mol) and methanol (50 mL). The solution was stirred at ambient temperature under an atmosphere of nitrogen for 96 hours. The ethylenediamine/ methanol was removed on the rotary evaporator to give a yellow glassy solid (4.4 g contaminated with ethylenediamine). A 10 percent solution of the product was made in methanol, and purified from the ethylenediamine by reverse osmosis (Filmtec™ FT-30 membrane and an Amicon™ TC1R thin channel separator) until no ethylenediamine could be detected by GC (Column, Tenax 60/80). Removal of the solvent gave the product as a yellow glassy solid (3.52 g). The $^{13}$C NMR data and HPLC analysis (PLRP-S column, acetonitrile:0.015M NaOH, 10–20 percent gradient in 20 minutes) were consistent with the title structure.

Example U

Reaction of the two generation (G2.0) STARBURST™ polymer with Bromoacetic Acid to give a methylene carboxylate terminated STARBURST™ dendrimer The second generation product (Example T) (0.22 g, 0.13 mmol) was dissolved in 15 mL of deionized water and the temperature equilibrated at 40.5° C. Bromoacetic acid (0.48 g, 3.5 mmol) and lithium hydroxide (0.13 g, 3.3 mmol) were dissolved in 5 mL of deionized water, and added to the reaction mixture. The reaction pH was carefully maintained at 9, with the use of a pH stat (titrating with 0.1N NaOH), at 40.5° C. overnight. Monitoring by reverse phase HPLC, (Spherisorb™ ODS-1 column, eluent 0.25M $H_3PO_4$ pH 3 [NaOH]; acetonitrile 85:15) confirmed the synthesis of predominantly a single component.

Example V

Preparation of Isothiocyanato functionalized second generation (G2.0) methylene-carboxylate terminated STARBURST™ dendrimer Five mL of a 2.8 mM solution of the second generation methylenecarboxylate terminated STARBURST™ dendrimer (Example U) was diluted with 20 mL water and the pH adjusted to 0.5 with conc. hydrochloric acid. After one hour at room temperature the mixture was analyzed by HPLC to verify the removal of the butoxycarbonyl group and then treated with 50 percent sodium hydroxide to bring the pH to 7. A pH stat (titrating with 0.1N NaOH) was used to maintain the pH at 7 and 225 µL thiophosgene was added. After 15 minutes at room temperature the pH of the mixture was adjusted to 5 with 1N HCl. The mixture washed with chloroform (20 mL×2) then concentrated on a rotary evaporator at reduced pressure. The residue recovered, 0.91 g, is a mixture of the isothiocyanate and salts.

Example W

Preparation of second generation (G2.0) STARBURST™ polyethyleneimine-methane sulfonamide To a solution of 125 g N-methanesulfonylaziridine in 50 mL ethanol was added 25.0 g tris(2-aminoethyl)amine. The solution was stirred at room temperature for 4 days. Water was added to the reaction mixture as needed to maintain the homogeneity of the solution. The solvent was removed by distillation in vacuo to give the 2nd generation STARBURST™ PEI-methane sulfonamide as a yellow glass (161 g).

Example X

Cleavage of methane sulfonamides to form second generation (G2.0) STARBURST polyethyleneimine A solution of 5.0 g of second generation STARBURST™ PEI-methane sulfonamide, from Example W in 20 mL of 38 percent HCl was sealed in a glass ampule. The ampule was heated at 160° C. for 16 hours, then cooled in an ice bath and opened. The solvent was removed by distillation in vacuo and the residue dissolved in water. After adjusting the pH of the solution to greater than or equal to 10 with 50 percent NaOH, the solvent was removed by distillation in vacuo. Toluene (150 mL) was added to the residue and the mixture heated at reflux under a Dean-Stark trap until no more water could be removed. The solution was filtered to remove salts and the filtrate concentrated in vacuo to give 1.9 g second generation STARBURST™ PEI as a yellow oil.

Example Y

Preparation of third generation (G3.0) STARBURST™ polyethyleneimine-methane sulfonamide To a solution of 10.1 g second generation STARBURST™ PEI, from Example X, in 100 mL ethanol was added 36.6 g N-methanesulfonylaziridine. The solution was stirred at room temperature for 1 week. Water was added as needed to maintain the homogeneity of the solution. The solvent was removed by distillation in vacuo to give third generation STARBURST™ PEI-methane sulfonamide as a yellow glass (45.3 g).

Example Z

Cleavage of methane sulfonamides to form 3rd generation (G3.0) STARBURST™ polyethyleneimine The methane sulfonamide groups of third generation STARBURST™ PEI-methane sulfonamide (5.0 g), from Example Y, were removed by the same procedure as described for the second generation material in Example X to give 2.3 g third generation STARBURST™ PEI as a yellow oil.

Example AA

Reaction of a third generation (G3.0) STARBURST™ polyethyleneimine with (4-fluoro)nitrobenzene The third generation STARBURST™ polyethyleneimine (Example Z) (1.06 g, 1.2 mmol) was dissolved in 12 mL of absolute ethanol. (4-Fluoro)nitrobenzene (120 μL, 1.2 mmol) was added and the reaction mixture refluxed overnight. The solvent was removed on the rotary evaporator, and the bright yellow oil dissolved in water. The aqueous solution was washed with chloroform to remove any unreacted (4-fluoro)nitrobenzene. Removal of the water gave the product as a deep yellow oil (0.80 g). The $^{13}$C NMR spectrum was consistent with the title structure. (No attempt was made to determine the nature of the statistical distribution). The product was used without further purification.

Example BB

Reaction of the nitrophenyl derivative of the third generation (G3.0) STARBURST™ polyethyleneimine with glycolonitrile The nitrophenyl derivative of the third generation STARBURST™ polyethyleneimine (Example AA) (0.80 g) was dissolved in 20 mL of deionized water. Sodium hydroxide (2.80 g, 50 percent w/w) was added to the stirred solution, and the solution purged with nitrogen, venting through a sodium hydroxide scrubber. Glycolonitrile (2.85 mL of a 70 percent aqueous solution) was added at ambient temperatures. A yellow precipitate was observed to form after a few minutes. After two hours, the temperature was slowly raised to a reflux, and the solution maintained at a reflux with a nitrogen purge for 24 hours. Removal of the water gave the product as a yellow solid contaminated with glycolic acid and sodium hydroxide. The $^{13}$C NMR spectrum was consistent with the title structure. The product was used without further purification.

Example CC

Hydrogenation of the nitrophenyl derivative to the aminophenyl methylenecarboxylate terminated third generation (G3.0) STARBURST™ polyethyleneimine The yellow solid from Example BB (1.70 g) was dissolved in 10 mL of deionized water, the resulting pH of the solution was approximately 11. Palladium on charcoal (200 mg of 5 percent Pd/C) was added to the reaction mixture in a glass Parr shaker bottle. The reaction mixture was placed under a pressure of 40 psi (275 kPa) of hydrogen, and shaken at ambient temperature in a Parr hydrogenation apparatus, for 6 hours. The reaction mixture was then filtered through a 0.5 μm Millipore™ filter to remove the Pd/C and the solvent removed in vacuo and was gel filtered through a Biogel P2 resin (25 g swollen with water). Acidification with HCl resulted in an orange brown solution, which was purged with nitrogen overnight. Removal of the solvent in vacuo gave the title product as the hydrochloride salt which was a pale brown solid (3.98 g, contaminated with NaCl and glycolic acid, maximum theoretical amount of product 1.15 g). The product was used with no further purification.

Example DD

Preparation of 4-isothiocyanatophenyl methylenecarboxylate terminated third generation (G3.0) STARBURST™ polyethyleneimine The product from Example CC (3.98 g) was dissolved in 15 mL of deionized water and an aliquot (2.5 mL) of this solution was diluted with 10 mL water. The pH of the solution was adjusted to 7 with sodium hydroxide. A pH stat (titrating with 1N NaOH) was used to maintain the pH and 200 μL thiophosgene was added. After 10 minutes the pH of the mixture was adjusted to 4 with hydrochloric acid. Water was removed on a rotary evaporator at reduced pressure (a small amount of n-butanol was added to prevent foaming). The residue was washed with methylene chloride and then dried. The crude title product (0.95 g) a mixture of isothiocyanate (0.14 g) and salts was used without further purification.

Example EE

Preparation of a methylenecarboxylate-terminated second generation (G2.0) STARBURST™ polyamidoamine (initiated from ammonia)

The second generation STARBURST™ polyamidoamine (2.71 g, 2.6 mmol) and bromoacetic acid (4.39 g, 31.6 mmol) were dissolved in 30 mL of deionized water and the pH adjusted to 9.7 with 5N NaOH using a pH stat. The reaction was maintained at this pH for a half hour, and the temperature was slowly raised to 60° C. and was maintained at 60° C. for three hours at constant pH. The pH was raised to 10.3, and the reaction mixture remained under control of the pH stat at ambient temperatures overnight. The reaction mixture was refluxed for a further four hours prior to work up. Removal of the solvent, and azeotropic distillation the final traces of water with methanol gave the title product as a pale yellow powder (8.7 g, contaminated with sodium bromide). The $^{13}$C/NMR spectrum was consistent with the title structure (with some contamination due to a small amount of defected material as a result of some monoalkylation).

Example FF

Preparation of a methylenecarboxylate terminated second generation (G2.0) STARBURST™ polyethyleneimine (initiated from ammonia)

The second generation STARBURST™ polyethyleneimine (2.73 g, 6.7 mmol), from Example X, and bromoacetic acid (11.29 g 81 mmol) were dissolved in 30 mL of deionized water. The pH was slowly raised to pH 9.5 maintaining the temperature below 30° C. The temperature was raised slowly to 55° C., and the reaction pH maintained at 9.5 for 6 hours with the aid of a pH stat (titrating with 5N NaOH). The pH was raised to 10.2, and maintained at that pH overnight. Removal of the solvent on a rotary evaporator, and azeotropic distillation of the final traces of water using methanol, gave the title product as a yellow powder (17.9 g, contaminated with sodium bromide). The $^{13}$C NMR spectrum was consistent with the title structure (with some contamination due to a small amount of defected material as a result of some monoalkylation).

Example GG

Preparation of 3.5, 4.5, 5.5 and 6.5 generation STARBURST™ PAMAM

To a 10 weight percent methanolic solution of 2.46 g of third generation PAMAM STARBURST™ was added 2.32 g of methyl acrylate. This mixture was allowed to sit at room temperature for 64 hours. After solvent and excess methyl acrylate removal, 4.82 g of title product (G 3.5) was recovered (105% of theoretical).

Preparation of higher half generation STARBURST™ PAMAM's

Generations 4.5, 5.5 and 6.5 were prepared as described above with no significant differences in reactant concentrations, reactant mole ratios or reaction times.

Example HH

Preparation of 4, 5 and 6 generation STARBURST™ PAMAM

To 2000 g of predistilled ethylenediamine was added 5.4 g of 4.5 generation STARBURST™ PAMAM as a 15 weight percent solution in methanol. This was allowed to sit at room temperature for 48 hours. The methanol and most of the excess ethylenediamine were removed by rotary evaporation under water aspirator vacuum at temperature less then 60° C. The total weight of product recovered was 8.07 g. At this point GC indicated that the product still contained 34 weight percent ethylenediamine. A 5.94 g portion of this product was dissolved in 100 mL methanol and ultrafiltered to remove the residual ethylenediamine. The ultrafiltration was run using an Amicon™ TC1R thin channel recirculating separator equipped with an Amicon™ YM2 membrane. An in-line pressure relief valve was used to maintain 55 psig (380 kPa) pressure across the membrane. The 100 mL was first concentrated to 15 mL by forcing solvent flow exclusively through the membrane. After this initial concentration, the flow was converted to a constant volume retentate recycle mode for 18 hours. After this time, 60 mL of methanol was passed over the membrane to recover product still in the module and associated tubing. The product was stripped of solvent and 2.53 g of fifth generation (G 5.0) STARBURST™ PAMAM was recovered. Analysis by GC indicated 0.3 percent residual ethylenediamine remained in the product Preparation of generation 4 and 6 proceeded as above with the only difference being the weight ratio of ethylenediamine to starting material. To prepare 4th generation this ratio was 200:1 and for 6th generation this ratio was 730:1.

Example II

Modification of polyamidoamine dendrimers by reaction with epoxyoctane

To a solution of 0.50 g of sixth generation PAMAM in 5 mL of methanol was added 0.56 g of epoxyoctane. After 6 days at room temperature, the solvent was evaporated in vacuo to give 0.80 g of colorless oil. The material was soluble in chloroform, toluene or methanol, but not soluble in water. The $^{13}$C-NMR spectrum was in accord with a dendrimer with C-8 alkyl groups attached to its terminal amines.

Example JJ

Modification of polyamidoamine dendrimers by reaction with t-butyl glycidyl ether To a solution of 0.50 g sixth generation (G 6.0) PAMAM in 5 mL methanol was added 0.57 g of t-butyl glycidyl ether. After 6 days at room temperature, the solvent was evaporated in vacuo to give 1.0 g of colorless oil. The material was soluble in chloroform, toluene or methanol, but not soluble in water. The $^{13}$C-NMR spectrum was in accord with a dendrimer with 3-(t-butoxy)-1-propan-2-ol groups attached to its terminal amines

Example KK

Modification of polyamidoamine dendrimers by reaction with epoxyoctadecane

To a solution of 0.50 g of sixth generation (G 6.0) PAMAM in 25 mL of methanol was added 1.1 g epoxyoctadecane. The solution was heated at reflux for 5 days. During the reflux time, a colorless viscous oil precipitated from the solution. The solvent was evaporated in vacuo to give 1.6 g of white foam. The material was soluble in chloroform or toluene, but not soluble in water or methanol. The $^{13}$C-NMR spectrum was in accord with a dendrimer with C-18 alkyl groups attached to its terminal amines.

Example LL

Reaction of STARBURST™ PEI with a hydrophobic epoxide

Into a flask equipped with a magnetic stirrer was added 0.397 g ($2 \times 10^{-4}$ moles) of fourth generation (G 4.0) PEI (NH$_3$ core; MW 1,955) and 2.1 g ($9.6 \times 10^{-3}$ moles) of methyl 10,11-oxoundecanoate (MW 214.3); in 5 mL of methanol. The reaction mixture was stirred at room temperature for 1 day and then warmed at 80° C. for 8 hours to give a brown viscous syrup. Complete ring opening reaction to produce the carbomethoxy terminated, hydrophobic dendrimer was confirmed by NMR analysis and comparison to model systems.

The above hydrophobic dendrimer was converted into a water soluble form by simply combining an equivalent weight of this product with sodium hydroxide in water and heating for 30 to 60 minutes. A homogeneous solution, which showed no detectable carbomethoxy groups, was obtained. Addition of excesses of NaOH or NaCl caused the sodium carboxylate salt to become cloudy and phase out as an oil.

Example MM

Modification of PAMAM Dendrimers with Acrylic Acid
2:1 acrylate: amine (Reaction A)

A 3.84 g quantity of acrylic acid was mixed with 3.84 g of methanol and cooled in an ice bath for 10 minutes. Then, 18.72 g of a 26.7% (w/w) solution of G6 (NH$_3$) PAMAM was added while stirring the acrylic acid solution. The reaction was kept at 4° C. for 15 minutes, blanketed with nitrogen, capped, and allowed to react at room temperature for 5 days.

1:1 acrylate: amine (Reaction B)

A 1.6 g quantity of acrylic acid was mixed with 1.6 g of methanol and cooled in an ice bath for 10 minutes. Then, 18.72 g of a 26.7% (w/w) solution of G6 (NH$_3$) PAMAM was added while stirring the acrylic acid solution. The reaction was kept at 4° C. for 15 minutes, blanketed with nitrogen, capped, and allowed to react at room temperature for 5 days.

0.5:1 acrylate: amine (Reaction C)

A 0.80 g quantity of acrylic acid was mixed with 0.8 g of methanol and cooled in an ice bath for 10 minutes. Then, 18.72 g of a 26.7% (w/w) solution of G6 (NH$_3$) PAMAM was added while stirring the acrylic acid solution. The reaction was kept at 4° C. for 15 minutes, blanketed with nitrogen, capped, and allowed to react at room temperature for 5 days.

0.25:1 acrylate: amine (Reaction D)

A 0.40 g quantity of acrylic acid was mixed with 0.4 g of methanol and cooled in an ice bath for 10 minutes. Then, 18.72 g of a 26.7% (w/w) solution of G6 (NH$_3$) PAMAM was added while stirring the acrylic acid solution. The reaction was kept at 4° C. for 15 minutes, blanketed with nitrogen, capped, and allowed to react at room temperature for 5 days.

Ultrafiltration and Drying

The solvent from the reactions was stripped on a rotary evaporator and the recovered solid was redissolved in approximately 150 mL of water. The 150 mL solution was ultrafiltered with water on a YM3 (MWCO=3000) flatstock membrane until 4 L of permeate was collected. The retentate was stripped of water on a rotoevaporator until a solid or viscous liquid remained. The semi-dry solids were then placed under high vacuum overnight to remove remaining water.

Conclusion

The products of reactions of G6 (NH$_3$) PAMAM ammonia-core dendrimer with acrylic acid in different ratios yield expected products. The products exhibit the charge characteristics consistent with the amount of acrylic acid added. When excess acrylic acid is added, the product approaches that which is obtained in the conventional synthesis of half-generation PAMAM carboxylate salts. As the amount of acrylic acid added is decreased, the analysis of the material is consistent with a positively charged dendrimer with some negatively charged surface groups, or an ampho- teric surface.

Example NN

Conjugating dense star dendrimers with target directors such as biotin, insulin, and avidin, and also including a carried material (fluorescein)

Materials

G4 (NH$_3$) PAMAM STARBURST™ dendrimer and Generation 6.0 STARBURST™ dendrimer were prepared. Fluorescein-5-isothiocyanate (isomer I) (FITC) was obtained from Molecular Probes. Dansyl chloride was obtained from Aldrich Chemical Co. NHS-LC-Biotin and avidin were obtained from Pierce. Dichlorotriazinyl fluorescein (I) and insulin were obtained from Sigma Chemical. All reagents were used without further purification.

I. Biotin/Dendrimer Conjugation Couplings

A. Preparation of Biotin-Dendrimer Conjugates

A stock solution of G6 (NH$_3$) PAMAM dendrimer was made to a concentration of 1.8 mg/mL in 100 mM phosphate buffer of pH 7.0. Another stock solution of G6 (NH$_3$) was made to a concentration of 1.9 mg/mL in H$_2$O. A 1 mL aliquot from each solution was withdrawn and 5 mg of solid NHS-LC-biotin was added to each solution. The vials were vigorously shaken for 5 minutes to dissolve the biotin. The incubation was done at room temperature for 18 hours. Similar reactions were performed with solutions of G4 (NH$_3$) in both phosphate buffer and in H$_2$O. The G4 (NH$_3$) stock solutions were 2.0 mg/mL and 5 mg of NHS-LC-biotin was added to a 1 mL aliquot of each.

Other conjugations were performed with lesser ligand to amine ratios. For example, in an effort to conjugate twenty biotins to a G7 (NH$_3$) PAMAM dendrimer, an 844 µL aliquot of 11.85% G7 dendrimer was added to 0.0244 g of NHS-LC-biotin in 5 mL of borate buffer, pH 9. After 3 hours, the reaction mixture was dialyzed against deionized water to remove unreacted biotin.

Electrophoresis

After 18 hours, 100 µl of each reaction mixture and of each full generation stock solutions were withdrawn for electrophoretic analysis. Ten microliters of 0.1% MB$^+$ with 50% sucrose was added to each solution, and the samples were electrophoresed on a 5–50% T gradient Hylinx™ gel (obtained from Gradipore). The buffer used was 90 mM Tris, 80 mM boric acid, and 2.5 mM EDTA of pH 8.3. Ten microliters of each sample was applied to the gel. The gel was run for 30 minutes at 200 V (constant). Lane assignments were as listed below:

1 G7 (NH$_3$)
2 G6 in P$_i$, (NH$_3$)
3 G6 (NH$_3$) w/biotin in P$_i$
4 G4 in P$_i$, (NH$_3$)
5 G4 (NH$_3$) w/biotin in P$_i$
6 G6 in H$_2$O, (NH$_3$)
7 G6 (NH$_3$) w/biotin in H$_2$O
8 G4 in H$_2$O, (NH$_3$)
9 G4 (NH$_3$) w/biotin in H$_2$O
10 G4 (NH$_3$)
11 Cyt c/G3.5 (NH$_3$)
12 G5 (NH$_3$)

Results and Discussion

Electrophoresis clearly showed retarded mobility of the dendrimers treated with biotin when compared to the migration distance of the unmodified dendrimers. The molecular weight increased due to the covalent attachment of biotin molecules to the dendrimer surface. This causes the dendrimer to migrate a shorter distance due to the sieving effect of GGE which retards higher molecular weight molecules.

The number of biotin molecules attached per dendrimer is not presently known. The distribution of biotin molecules on the dendrimer is statistical, and the sample run is not a single species.

Some reactions were done such that, theoretically, all surface groups on the dendrimer (Z in FIG. 1; Z' in FIG. 2) would be biotinylated. No visible insoluble matter formed during the course of these reactions.

B. Preparation of Dendrimer-Fluorescein (FITC) Conjugates

A 5 mL methanolic solution of 12.7% (w/w) G4 (NH$_3$) core, PAMAM dendrimer was dried under vacuum on a rotary evaporator. Approximately 40 mg (7.4 µmol) of the dried dendrimer was removed and dissolved in 5 mL of 0.1M phosphate buffer of pH 9.0.

Fluorescein isothiocyanate (FITC I) (14.5 mg, 37 µmol) was dissolved in 2 mL of DMSO in the dark. The FITC I solution was added to the stirring dendrimer solution in a dropwise manner over 1 to 2 minutes. The reaction mixture was protected from light and stirred at room temperature for 15 to 20 hours. The solution was maroon colored.

After stirring, the reaction mixture was placed into two Centricon™ microconcentrator tubes (molecular weight cut-off: 3000 Daltons), and was ultrafiltered to remove any unreacted FITC I. Three, 2 mL additions of 0.1M phosphate buffer of pH 9.0 were made during the ultrafiltration. The conjugated fourth generation (ammonia core) dendrimer-FITC I was recovered from the retentate after ultrafiltration.

C. Preparation of Biotinylated/Dendrimer-FITC I Conjugates

Using the 20 mg/mL stock solution of G4 (NH$_3$) PAMAM Starburst™ dendrimer-FITC I (prepared in the previous section), 1 mL of the dendrimer-FITC I stock solution was removed and added to 3 mL of 0.1M phosphate buffer (pH=9.0).

A 10.0 mg (18 mmol) quantity of NHS-LC-biotin was added to 0.5 mL of DMSO and shaken to dissolve.

The NHS-LC-biotin solution was added to the dendrimer solution over 30 seconds and the reaction mixture allowed to stir at room temperature, in the dark, for 4 hours. Then the reaction mixture was removed from the stir plate and transferred to two Centricon™ microconcentrator tubes (molecular weight cutoff: 3,000 Daltons) and ultrafiltered to remove any unbound biotin. Eight, 2 mL additions of 0.1M phosphate buffer of pH 9.0 were made during the ultrafiltration in order to facilitate the purification.

D. Formation of the Biotinylated G4 Dendrimer-FITC I/Avidin Complex

A 3.0 mg (45 µmol) quantity of avidin was dissolved in 1 mL of 10 mM phosphate buffer (pH 7.1).

A 300 µL (10 mg/mL, 450 µmol) quantity of the biotinylated G4 (NH$_3$) dendrimer-FITC I (prepared previously) was added to the avidin solution and gently stirred at room temperature for 4 hours. The reaction mixture was then placed into Centricon™ microconcentrator tubes (molecular weight cutoff: 30,000 Daltons) and ultrafiltered to remove the excess biotinylated dendrimer. Eight, 2 mL additions of 10 mM phosphate buffer of pH 7.1 were made during the ultrafiltration process to facilitate the purification. The resulting biotin-dendrimer/avidin complex was removed from the microconcentrator tubes and stored at −10° C.

E. Preparation of Dendrimer/Dichlorotriazinyl Fluorescein (I)

Approximately 300 µL of G6 (EDA) PAMAM Starburst™ dendrimer (21.5% solids) was added to 700 µL of deionized water and dispersed (64.5 mg, 2.24 µmole). An additional 4 mL of deionized water was added to dilute the dendrimer to a concentration of 12.9 mg/mL.

Dichlorotriazinyl fluorescein (Isomer I) hydrochloride [DTAF(I)] (6.0 mg, 11.3 µmol) was dissolved in 0.5 mL of methanol in the dark, and two drops of triethylamine added. The DTAF(I) solution was added to the stirring dendrimer solution in a dropwise manner over 30 seconds. The reaction mixture was protected from light, and stirred at room temperature for 15 to 20 hours. The solution remained clear and orange throughout the reaction.

After stirring, the reaction mixture was placed into two Centricon™ microconcentrator tubes (molecular weight cutoff: 10,000 Daltons), and was ultrafiltered to remove any unreacted DTAF(I). Fifteen, 2 mL additions of 0.1M phosphate buffer of pH 9.0 were made during the ultrafiltration in order to facilitate the purification. Approximately 3 mL of conjugated G6 (EDA core) dendrimer-DTAF(I) were recovered from the purification.

F. Preparation of Multi-biotinylated/Dendrimer-DTAF(I) Conjugates

Using the 20 mg/mL stock solution of G6 (EDA) PAMAM Starburst™ dendrimer-DTAF(I) (prepared in the previous section), 0.425 mL (8.5 mg, 0.0003 mmol) of the dendrimer-DTAF(I) stock solution was removed and added to 0.575 mL of 0.1M phosphate buffer (pH of 9.0).

An 8.1 mg (0.029 mmol) quantity of NHS-LC-biotin was added to 0.3 mL of DMSO and shaken to dissolve.

The NHS-LC biotin solution was added to the dendrimer solution over a 30 second period and the reaction mixture allowed to mix at room temperature, in the dark for 4 hours.

After 4 hours, the reaction mixture was removed from the stir plate and transferred to two Centricon™ microconcentrator tubes (molecular weight cutoff: 10,000 Daltons) and ultrafiltered to remove any unbound biotin. Eight, 2 mL additions of 0.1M phosphate buffer of pH 9.0 were made during the ultrafiltration in order to facilitate the purification.

II. Insulin/Dendrimer Conjugation Coupling

A. Preparation of Dansylated Dendrimer Conjugate

A 5 mL methanolic solution 12.7% (w/w) G4 (NH$_3$) PAMAM dendrimer solution was dried under vacuum on a rotary evaporator. Approximately 40 mg (7.4 µmol) of the dried dendrimer was removed and dissolved in 5 mL of 0.1M phosphate buffer of pH 9.0.

A 10 mg (0.037 mmol) quantity of dansyl chloride was added to 5 mL of acetone and shaken for 5 to 10 minutes. (This solution was a deep yellow and had traces of solid in it).

The dansyl chloride solution was added to the dendrimer solution over a 30 second period and the reaction flask was placed in a water bath of 40° C. for 90 minutes. During the heating, the reaction mixture was shaken intermittently. (Note that the color of the solution faded from a bright to a faint yellow).

After 90 minutes, the reaction flask was removed from the heat and allowed to cool to room temperature. (Reaction mixture was slightly hazy in appearance). The labelled dendrimer was then purified while keeping it in solution. The reaction was placed on a rotary evaporator and the acetone removed under vacuum at 30°–35° C. This appeared to clarify the solution substantially. The reaction mixture was then transferred into two centrifuge tubes and centrifuged at 5000 rpm for 30 minutes. No additional precipitation was visible following the centrifugation.

The dansylated-fourth generation dendrimer solution was then placed into two Centricon™ microconcentrator tubes (molecular weight cutoff: 3,000 Daltons) and ultrafiltered to remove any unbound dansyl chloride. The ultrafiltrations were also monitored for purity by thin-layer chromatography in order to insure the complete removal of any unreacted dansyl chloride. The filtrate was saved and tested by TLC as follows: Silica gel 60 plates (E. Merck) were used with an ethyl acetate (100%) solvent system (visualization by UV light). While the labelled dendrimer remained at the origin, the remaining dansyl chloride eluted near an R$_f$ of 0.3. Approximately 1 to 2 mL of suspected dansylated dendrimer solution was recovered.

B. Preparation of Insulin/Dansylated Dendrimer Conjugate

In a 2 dram vial, 0.5 mL of dansylated dendrimer (prepared previously) was added to 1.5 mL of deionized water for a 10 mg/mL solution. One mL (10.0 mg 0.0019 mmol) was removed and used for the insulin coupling.

In a second vial, 12.3 mg (0.0020 mmol) quantity of insulin (from bovine pancreas) was dissolved in 2 mL of deionized water. The resulting solution was cloudy in appearance, therefore the pH was lowered to 4, with 1 drop of 1N hydrochloric acid to dissolve the solid.

In a third vial, 88.7 mg (0.46 mmol) quantity of EDAC is dissolved in 1 mL of deionized water.

The insulin solution was added to the stirring dendrimer solution over 1–2 minutes and clouded up immediately. The pH was then adjusted from pH of 7.0 to 4.0 using the 1N hydrochloric acid. (Solution cleared near pH 4.2). With continued stirring, the EDAC solution was added in 200–300 µL increments every 10 to 15 minutes (over 1 hour). The pH of the reaction mixture was maintained between 3.90 and 4.2 with 1N hydrochloric acid. After the final EDAC addition, the reaction was allowed to stir overnight at room temperature (15–20 hours).

The reaction mixture was then placed into Centricon™ microconcentrator tubes (molecular weight cutoff: 3,000

Daltons) and ultrafiltered with deionized water (which formed a precipitate), but was then resuspended by adding 1 drop of 1N hydrochloric acid. This process was repeated 2 to 3 times and the dansylated dendrimer/insulin conjugate resolubilized. Approximately 1 mL of the dansylated dendrimer/insulin conjugate was recovered from the ultrafiltration process.

C. Preparation of Insulin/Dichlorotriazinyl Fluorescein (I)

To a 2 dram vial, 9.3 mg (0.002 mmole) quantity of insulin (from bovine pancreas) was dissolved in 2 mL of 0.1M phosphate buffer (pH=9.0). Dichlorotriazinyl fluorescein (Isomer I) hydrochloride [DTAF(I)] (4.1 mg, 0.008 mmol) was dissolved in 0.5 mL of methanol, in the dark, and two drops of triethylamine added.

The DTAF(I) solution was added to the stirring insulin solution dropwise over 2 minutes. The reaction mixture was protected from light and stirred at room temperature for 6 hours, then placed at 2°–8° C. overnight. (The solution remained clear and orange throughout the reaction).

The following morning, the reaction mixture was placed into two Centricon™ microconcentrator tubes (molecular weight cutoff: 3,000 Daltons), and was ultrafiltered to remove any unreacted DTAF(I). Ten, 2 mL additions of 0.1M phosphate buffer of pH 9.0 were made during the ultrafiltration in order to facilitate the purification. Approximately 2 mL of insulin-DTAF(I) were recovered from the purification.

D. Preparation of Insulin-DTAF(I)/Dendrimer Conjugate

To a 2 dram vial, 1 mL (7.05 mg, 0.0014 mmol) of G4 ($NH_3$) dendrimer was added, and pH adjusted to 4.5 using 1N hydrochloric acid. A 1 mL (10.1 mg, 0.0020 mmole) quantity of insulin-DTAF(I) (previously prepared) was added to the stirring dendrimer and pH readjusted to 4.0 using 1N hydrochloric acid.

In a second vial, 54.3 mg (0.28 mmol) quantity of EDAC was dissolved in 0.5 mL of deionized water.

The EDAC solution was added to the reaction mixture in 100 µL increments every 10–15 minutes (over 1 hour). The pH of the reaction mixture was maintained between 3.90 and 4.20 with 1N hydrochloric acid. After the final EDAC addition, the reaction was allowed to continue at room temperature for 6 hours, then placed at 2°–8° C. overnight.

The reaction mixture was then placed into Centricon™ microconcentrator tubes (molecular weight cutoff: 10,000 Daltons) and ultrafiltered with deionized water, while maintaining a pH between 4 to 5 with 1N hydrochloric acid.

This process was repeated 2–3 times and the insulin-DTAF(I)/dendrimer conjugate collected to yield a clear orange liquid.

III. Dendrimer/Avidin Conjugation Couplings

A. Preparation of Dendrimer-Avidin Conjugates

In a 2 dram vial, 120 µL of G7 (EDA) dendrimer (21.9% solids) was added to 0.8 mL of deionized water. The diluted dendrimer, 0.5 mL, was removed and added to 4.5 mL of deionized water for a 2.6 mg/mL solution.

In a second vial, 3.0 mg (0.045 mmol) quantity of EDAC is dissolved in 0.5 mL of deionized water.

The avidin solution was added to the stirring dendrimer solution over 1–2 minutes and remained clear. The pH was then adjusted to 4.0 using 1N hydrochloric acid. With continued stirring, the EDAC solution was added in 100 µL increments every 10–15 minutes (over 1 hour). The pH of the reaction mixture was maintained between 4.5 and 5.5 with 1N hydrochloric acid. After the final EDAC addition, the reaction was allowed to stir overnight at room temperature (15–20 hours).

The reaction mixture was then placed into Centricon™ microconcentrator tubes (molecular weight cutoff: 100,000 Daltons) and ultrafiltered with 10 mM phosphate buffer to remove any unbound dendrimer or avidin. Eight, 2 mL additions of 10 mM phosphate buffer of pH 7.1 were made during the ultrafiltration in order to facilitate the purification.

Example OO

Targeting dense star dendrimers with pyruvic acid-sodium salt

One-half g of EDC was mixed with 0.0065 g of sodium salt of pyruvic acid in 2 mL of $H_2O$. The solution pH was adjusted to 5.0 (as determined by pH paper), and the solution was stirred for five minutes. Subsequently, 62 µL (20 mg) of G6 ($NH_3$) dendrimer (32.45% in solids) was added to the reaction mixture and the solution was shaken for 21 hours. Purification to rid the solution of excess EDC was accomplished by an Amicon™ Microcon-10 concentrator. The dilution factor was 57×10$^6$. A small $^{13}$C-NMR resonance was observed for the methyl group of pyruvate conjugated to G6 dendrimer; a unique capillary electrophoresis peak was also observed for the conjugate.

The preparation of the conjugates of this invention uses the starting materials described above, or starting materials that are prepared in an analogous manner, or starting materials described in the art, or starting materials that are available.

Example 1

Incorporation of 2-(acetyloxy)benzoic acid (aspirin) into STARBURST™ dendrimers

A widely accepted method for ascertaining whether a "probe molecule" is included in the interior of a micelle is to compare its carbon-13-spin lattice relaxation times ($T_1$) in a non-micellized versus micellized medium. A substantial decrease in $T_1$ for the micellized medium is indicative of "probe molecule" inclusion in the micelle. Since STARBURST™ dendrimers are "covalently fixed" analogs of micelles, this $T_1$ relaxation time technique was used to ascertain the degree/extent to which various pharmaceutical type molecules were associated with STARBURST™ polyamidoamines. In the following examples, $T_1$ values for (acetyloxy)benzoic acid (I) (aspirin) were determined in solvent ($CDCl_3$) and then compared to $T_1$ values in $CDCl_3$ at various [I:dendrimer] molar ratios.

Inclusion of aspirin (I) into various STARBURST™ polyamidoamine dendrimers as a function of generation.

Various half generation (ester terminated, initiated from $NH_3$) STARBURST™ polyamidoamine dendrimers (G=0.5→5.5) were combined with 2-(acetyloxy)benzoic acid in $CDCl_3$ to give acid:tertiary amine ratios of =1.0. A plot of $T_1$ values for 2-(acetyloxy)benzoic acid versus generation of STARBURST™ dendrimer added (see FIG. 4 where ● represent C-4, □ represent C-6, and ○ represent C-5) shows that $T_1$ reaches a minimum over the generation range of 2.5→5.5 for carbons 4, 5 and 6 in 2-(acetyloxy)benzoic acid. This demonstrates interior association of 2-(acetyloxy)benzoic acid in the dendrimers (G=2.5→5.5) and further confirms that polyamidoamine dendrimers (Gen=2.5 or greater) can function as carrier molecules.

Example 2

Release of pseudoephedrine from STARBURST™ dendrimer-PAMAM

Pseudoephedrine (0.83 mg/mL) and STARBURST™ PAMAM dendrimer [1.0 mg/mL; G=6.5; terminal group (Z)=192 (methyl ester)] were dissolved in deionized distilled water and the pH of the donor phase was adjusted to 9.5, with sodium hydroxide solution, and stored at room temperature for about 12 hours. Solution of pseudoephedrine alone was treated in the same way (control). The drug dendrimer solution was stored at 40° C. for 8 hours after the first experiment and dynamic dialysis performed. Dialysis membrane used was a gpectraPor™ 7, MWCO 1,000, 28.6 mm in diameter in spectrum separation cells (half cell volume 5 and 10 mL, cell dimensions: 38 mm diameter for both the cells and the cell depth of 10 and 20 mm for 5 and 10 mL cells, respectively).

Samples were analyzed by an HPLC procedure developed for pseudoephedrine conditions for which are as follows:

Column: µBondapak™ C-18

Mobile phase: pH 3.2 phosphate buffer plus acetonitrile (80:20)

Flow rate: 0.3 mL/min

Detection: UV at 210 nm

Retention time: 13.3 min

The dialysis membrane was washed with deionized water and was kept soaking in the receptor phase for at least 12 hours prior to use. The dialysis membrane was placed in between the donor and the receptor compartment, and the donor compartment was stirred with a small magnetic spin bar. Known volumes of donor and receptor solutions were introduced into the respective compartments and transfer of pseudoephedrine to the receptor compartment was followed as a function of time. To maintain sink conditions the entire receptor phase was removed periodically (every 30 minutes) and replaced with fresh receptor phase. The amount of pseudoephedrine was assayed in the sampled receptor phase. Experiments were conducted at room temperature (22° C.). The receptor phase was plain deionized distilled water.

The results of dynamic analysis are shown in FIG. 5. In FIG. 5, the ● represents pseudoephedrine only (control), the

represents pseudoephedrine plus the dendrimer, and the

represents pseudoephedrine plus the dendrimer held at 40° C., for 8 hours prior to dialysis. It is apparent that in presence of G 6.5 dendrimer in the donor compartment the rate of dialysis of pseudoephedrine is reduced. Storing the donor solution at 40° C., appears to further reduce the rate of dialysis.

The experiment was repeated at lower concentrations (the ratio of number of drug molecules to the number of terminal groups was kept the same). G 6.5 dendrimer 120 µg/mL pseudoephedrine 100 µg/mL (122 µg/mL salt).

Dynamic dialysis of pseudoephedrine (alone) at this lower concentration was almost identical to that at higher concentration. FIG. 6 summarizes the results of this experiment where ● represents pseudoephedrine only (control), and ○ represents pseudoephedrine plus dendrimer.

Example 3

The procedure of Example 2 was repeated using the modifications given below.

Receptor phase: pH 7.4 phosphate buffer

Donor phase: pH 7.4 phosphate buffer plus drug and dendrimer in the following ratios:

1. G 6.5: Drug:: 1: 192
2. G 5.5: Drug:: 1: 96
3. G 4.5: Drug:: 1: 48
4. G 6.5H: Drug:: 1: 192
5. G 5.5H: Drug:: 1: 96
6. G 4.5H: Drug:: 1: 48

The above donor phase compositions plus pseudoephedrine alone were subjected to dynamic dialysis. The letter "H" after the dendrimer generation number stands for hydrolyzed dendrimer. Hydrolysis was accomplished by the procedure described in Examples M and N.

The results of these experiments are summarized in FIG. 7 where the donor and receptor compartment contained pH 7.4 phosphate buffer. For pseudoephedrine alone (P) the mean curve of three experiments is plotted (shown by the solid line), and one typical run from the other experiments are shown. In FIG. 7, the following symbols represent the dendrimer of the indicated generation.

TABLE III

| Symbol | Dendrimer Generation |
|---|---|
| ⊖ | 5.5 |
| ● | 6.5 |
| ◐ | 4.5 |
| ⊖ | 5.5 H |
| ○ | 6.5 H |
| ⊕ | 4.5 H |

Pseudoephedrine appears not to strongly associate with the ester terminated dendrimer at pH 7.4. Hydrolysis of the terminal functional groups into carboxylate form, has a dramatic effect on the dialysis rate (reduction). The generation number appears not to influence the dialysis rate.

Example 4

Interaction studies of salicylic acid with PAMAM STARBURST™ dendrimers

This example evaluated interaction characteristics of salicylic acid with PAMAM STARBURST™ dendrimers. These dendrimers consisted of an ammonia initiated core with repeating units derived from N-(2-aminoethyl) acrylamide. Both full (amine terminated functions) and half (ester terminal groups) generation polymers were included in the studies. The ratio of salicylic acid to STARBURST™ dendrimers utilized in the experiments resulted in approximately one salicylic acid molecule to one terminal amine functional group for full generation polymers. In the half-generation polymer study, the same ratio was employed with adjustments made for the higher molecular weight polymer.

The experiments were conducted at room temperature using an equilibrium static cell dialysis methodology. Spectrum static dialysis cells (half cell volume, 10 mL) separated by SpectraPor™ 6 membranes (molecular weight cutoff =1000) were utilized for all experiments. Transport of salicylic acid was monitored as a function of time by removing aliquots from appropriate cell compartments and assayed by HPLC analysis using a U.V. detector at 296 nm (Bondapak C-18 Columns eluting mobile phase of acetonitrile/0.1M phosphate buffer (pH=3.2) at a ratio of 20:80 (V/V), set at a flow rate of 30 mL/hour).

Ten mL of a solution containing 1 mg/mL salicylic acid and 2.5 mg/mL STARBURST™ polymer (Gen=4.0) adjusted to pH 6.65 and 5.0 with HCl solution were placed in the donor compartment of the dialysis cell and an equal volume of purified water adjusted to the same pH's placed in the receptor compartment. Transport of salicylic acid into the receptor compartment was monitored. The results are given in FIG. 8. In FIG. 8, the free acid is represented by ●, the acid plus generation 4.0 dendrimer, pH 6.65 is represented by O, and the acid plus generation 4.0 dendrimer, pH 5.00 is represented by □.

Due to the lower percent ionization of the amine groups on the polymer at pH 6, a greater extent of interaction with salicylic may be expected at pH 5, resulting in less compound transported at the lower pH. The results given in FIG. 8 indicate a much lower percentage of salicylic acid transported in the presence of polymer at both pH's studied compared to the salicylic acid control study. It is also observed that more salicylic acid is transported at pH 6.65 than at pH 5.0 as predicted. The data demonstrates an interaction of the STARBURST™ polymer with salicylic acid that can be controlled by pH. Sustained release characteristics are also implied by these data since the salicylic acid levels in the presence of polymer continue to rise past the approximate 12-hour equilibrium point observed in the control study.

To further investigate the interaction characteristics of salicylic acid with STARBURST™ polymers (Gen=4.0) an experiment was designed at pH 8.0. The design of the study differed from that previously described in that only the salicylic acid solution (1 mg/mL), adjusted to pH 8.0, was placed in the donor compartment and the polymer solution (2.5 mg/mL) placed in the receptor compartment. Loss of salicylic acid from the donor compartment was monitored as previously described. The results of the experiment are given in FIG. 9. In FIG. 9, the free acid is represented by -●-, and the acid plus generation 4.0 dendrimer at pH 8.0 is represented by ---△---.

As indicated in FIG. 9, the equilibrium characteristics of salicylic acid in the donor compartment with STARBURST™ polymers in the receptor compartment differs from the salicylic acid control study. Based on the ionization characteristics of the molecules at pH 8, approximately 6–7% interaction is expected. The observed extent of interaction is indicated to be on the order of 4–5%. The lower association observed may be due to experimental variability or to an ionization constant of less than one.

This experiment indicates an uptake or removal of free salicylic acid from the continuous phase of the system by the polymer. This type of action could result in suppression of reactivity of molecules suggesting a possible chelating or molecular association type of property associated with the polymers.

The interaction characteristics of salicylic acid at pH 6.6 with a half generation STARBURST™ polymer (Gen=4.5) having ester terminated functional groups were evaluated. Salicylic acid (1 mg/mL) was combined with STARBURST™ polymer (Gen=4.5) 3.6 mg/mL at pH 6.6. Ten mL of the solution was placed in the donor compartment and transport from the donor compartment was monitored as previously described. The results are given in FIG. 10. In FIG. 10, the free acid is represented by -●-, and the acid plus polymer is represented by ---o---.

Under these experimental conditions no charge interaction is predicted to occur since the tertiary amine groups are non-ionized at pH 6.6. As is indicated in FIG. 10, the loss of salicylic acid in the presence of polymer (Gen 4.5) is virtually identical during the first 10 hours of dialysis to that of the salicylic acid control study.

The following observations are made from the data presented in this example:

(1) Full generation PAMAM STARBURST™ polymers function as a carrier for salicylic acid.
(2) Full generation PAMAM STARBURST™ polymers have sustained release functionality for salicylic acid.
(3) Salicylic acid carrier properties of full generation PAMAM STARBURST™ polymers can be controlled by pH.

Example 5

Demonstration of multiple chelation of iron by a sodium propionate terminated sixth generation STARBURST™ polyamidoamine The sodium propionate terminated sixth generation polyamidoamine (initiated from ammonia), prepared as in Example M and N, (97.1 mg, 2.45 mol.) was dissolved in 1.5 mL of deionized water. Addition of 0.5 mL of 0.5N HCl reduced the pH to 6.3. Ferric chloride was added (0.5 mL of 0.1.2M solution, 0.051 mmol) producing a light brown gelatinous precipitate. On heating at 60° C. for 0.5 hours, the gelatinous precipitate became soluble, resulting in a homogeneous orange solution. The solution was filtered through Biogel P2 acrylamide gel (10 g, twice) isolating the orange band (free of halide contamination). Removal of the solvent in vacuo gave the product as an orange film (30 mg). Analysis was consistent with chelation of approximately 20 moles of ferric ions per mole of STARBURST™ dendrimer.

TABLE IV

| Found | Theoretical | | |
|---|---|---|---|
| | $Na_4Fe_{20}H_{128}SB$ | $Na_5Fe_{20}H_{127}SB$ | $Na_6Fe_{20}H_{126}SB$ |
| Na 0.39, 0.24 (0.31 0.1%) | 0.25 | 0.31 | 0.38 |
| Fe 3.14, 3.11 (3.12 0.02%) | 3.05 | 3.05 | 3.04 |
| C 47.11 | 49.87 | 49.84 | 49.81 |
| H 7.33 | 7.31 | 7.30 | 7.29 |
| N 14.81 | 14.49 | 14.48 | 14.47 |
| O — | 25.03 | 25.02 | 25.01 |
| MW | 36632.23 | 36654.21 | 36676.18 |

$SB = C_{1521}H_{2467}N_{379}O_{573}$

These results confirm chelation of 20±2 moles of ferric ions per mole of STARBURST™ dendrimer.

Example 6

Preparation of a product containing more than one rhodium atom per STARBURST™ polymer 2.5 Gen PAMAM (ester terminated, initiated from $NH_3$), prepared as in Example GG, (0.18 g, 0.087 mmole) and $RhCl_3 \cdot 3H_2O$ (0.09 g, 0.3 mmole) were mixed in dimethylformamide (DMF) (15 mL) and heated for 4 hours at 70° C. The solution turned crimson and most of the rhodium was taken up. The unreacted rhodium was removed by filtration and the solvent removed on the rotary evaporator. The oil formed was chloroform soluble. This was washed with water and dried ($MgSO_4$) before removal of solvent to yield a red oil (0.18 g). The NMR spectrum was recorded in $CDCl_3$ only minor differences were noted between the chelated and unchelated STARBURST™. Dilution of some of this $CDCl_3$ solution with ethanol followed by $NaBH_4$ addition resulted in rhodium precipitation. $RhCl_3 \cdot 3H_2O$ is insoluble in chloroform and in chloroform STARBURST™ solution thus confirming chelation.

Example 7

Preparation of a product containing Pd chelated to a STARBURST™ polymer 3.5 Generation PAMAM (ester terminated, initiated from NH$_3$), prepared as in Example GG, (1.1 g, 0.24 mmole) was dissolved with stirring into acetonitrile (50 mL). Palladium chloride (0.24 g, 1.4 mmole) was added and the solution was heated at 70°14 75° C. (water bath) overnight. The PdCl$_2$ was taken up into the STARBURST™. After removal of the solvent, the NMR in CDCl$_3$ confirmed that chelation had occurred. Dilution of the CDCl$_3$ solution with ethanol and addition of NaBH$_4$ resulted in precipitation of the palladium. The chelated product (1.23 g) was isolated as a brown oil.

Example 8

Demonstration of multiple chelation of yttrium by a methylene carboxylate terminated second generation STARBURST™ polyethyleneimine by trans chelation from yttrium acetate The STARBURST™ polyethyleneimine methylene carboxylate terminated material (0.46 g, 52.5 percent active, remainder sodium bromide, 0.18 mmol active STARBURST™ dendrimer), from Example FF, was dissolved in 4.5 mL of deuterium oxide. The resultant pH was 11.5–12. A solution of yttrium acetate was prepared by dissolving yttrium chloride (0.15 g, 0.5 mmol) and sodium acetate (0.41 g, 0.5 mmol) in 1.5 mL of deuterium oxide (2.9 moles of yttrium per mole of dendrimer). Aliquots of 0.5 mL of the yttrium acetate solution were added to the dendrimer solution and the $^{13}$C NMR spectra recorded at 75.5 MHz.

The $^{13}$C NMR spectrum of yttrium acetate shows two resonances, 184.7 ppm for the carboxyl carbon and 23.7 ppm for the methyl carbon, compared with 182.1 and 24.1 ppm for sodium acetate, and 177.7 and 20.7 ppm for acetic acid (Sadtler $^{13}$C NMR Standard Spectra). Monitoring the positions of these bands indicates degree of chelation with the STARBURST™ dendrimer. The most informative signal for the STARBURST™ dendrimer which is indicative of chelation is the α-CH$_2$ (of the methylene carboxylate group involved in chelation), which appears at 58.4 ppm in the unchelated dendrimer, and 63.8 ppm in the chelated dendrimer. Upon chelation with yttrium, the spin lattice relaxation times of the time α-CH$_2$ shortens as expected from 0.24±0.01 sec to 0.14±0.01 sec, indicative of chelation.

Following the addition of 0.5 mL of the yttrium acetate solution to the STARBURST™ dendrimer, all the yttrium appeared to be chelated by the dendrimer, confirmed by the signals for the acetate being that of sodium acetate. The same observation was noted for the addition of a second 0.5 mL aliquot of the yttrium acetate solution. Upon addition of the third aliquot of yttrium acetate, not all of the yttrium was observed to be taken up as the STARBURST$^T$ chelate, the acetate carboxyl resonance was observed to shift to 183.8 ppm indicating that some of the yttrium was associated with the acetate. The integrated area of the chelated —CH$_2$groups on the dendrimer increased, indicating that some of the third mole equivalent of yttrium added was indeed chelated with the dendrimer. These results indicate that the dendrimer can chelate from 2–3 yttrium ions per dendrimer molecule (Generation=2.0).

Example 9

Demonstration of multiple chelation of yttrium by a methylene carboxylate terminated second generation STARBURST™ polyamidoamine by trans-chelation from yttrium acetate The same experimental methods were used for this study as were used for Example 8. The STARBURST™ polyamidoamine methylene-carboxylate terminated material (0.40 g 62.5% active, remainder sodium bromide, 0.12 mmol) was dissolved in 4–5 mL of deuterium oxide. The resultant pH was 11.5–12, which was lowered to 9.4 with 6N HCl prior to the experiment. A solution of yttrium acetate was prepared by dissolving yttrium chloride (0.1125 g, 0.37 mmol) and sodium acetate (0.0915 g, 1.1 mmol) in 1.5 mL of deuterium oxide, thus every 0.5 mL of solution contains one mole equivalent of metal.

The first two mole equivalents of yttrium acetate added were fully chelated by the STARBURST™ polyamidoamine. On addition of a third mole equivalent of yttrium, precipitation of the product occurred and as such no NMR data could be obtained. The signals which gave the most information about chelation by the STARBURST™ dendrimer were those of the two carbons adjacent to the chelating nitrogen. The chemical shifts of these carbons in the unchelated dendrimer occurred at 59.1 ppm for the α-CH$_2$, and 53.7 ppm for the first methylene carbon of the backbone. Upon chelation these two resonances were observed to shift downfield to 60.8 and 55.1 ppm respectively. The trans chelation shows that two metal ions can be readily chelated per dendrimer molecule, however upon chelation of some unknown fraction of a third mole equivalent, the product precipitates out of solution.

Example 10

Demonstration of Multiple Chelation of $^{90}$Y by a methylenecarboxylate terminated second generation STARBURST™ polyethyleneimine Standard solution of yttrium chloride (3×10$^{-2}$M, spiked with non-carrier added $^{90}$Y) and methylenecarboxylate terminated second generation STARBURST™ polyethyleneimine of Example FF (6×10$^{-2}$M) were prepared. These were reacted together at various metal:STARBURST™ ratios in HEPES buffer. The complex yield was determined by ion exchange chromatography using Sephadex G50 ion exchange beads, eluting with 10% NaCl:NH$_4$OH, 4:1 at pH 10. Noncomplexed metal is removed on the column, complexed metal elutes. Yields were obtained by comparing the radioactivity eluted with that on the column, using a well counter.

TABLE V

| Chelation of 2.5 Gen. PEI Acetate with $^{90}$Y | | | | | |
|---|---|---|---|---|---|
| Vol. Y + 3 | Vol. PEI | Vol HEPES | M:L Theor. | % Complex | M:L Act. |
| 5 | 30 | 370 | 0.1 | 110 | 0.1 |
| 10 | 30 | 360 | 0.2 | 101 | 0.2 |
| 20 | 30 | 350 | 0.4 | 95 | 0.4 |
| 30 | 35 | 340 | 0.5 | 97 | 0.5 |
| 30 | 30 | 340 | 0.5 | 102 | 0.5 |
| 60 | 30 | 310 | 1.0 | 99 | 1.0 |
| 120 | 30 | 250 | 2.0 | 100 | 2.0 |
| 180 | 30 | 180 | 3.0 | 94 | 2.8 |
| 250 | 30 | 120 | 4.1 | 80 | 3.3 |
| 300 | 20 | 80 | 7.5 | 44 | 3.3 |
| 300 | 20 | 70 | 5.0 | 40 | 2.0 |
| 300 | 20 | 70 | 5.0 | 41 | 2.0 |

All volumes in Table V are in microliters

Within the accuracy of the experiments, these results indicate that the 2.5 Gen. STARBURST™ PEI acetate can chelate between 2 and 3 metals per dendrimer giving a soluble complex.

Example 11

Conjugation of 4-isothiocyanatophenyl methylenecarboxylate terminated third generation STARBURST™ polyethyleneimine with IgG monoclonal antibody The isothiocyanate, 10 mg (50 µmoles), from Example DD, was dissolved in 500 µL of 3 mM indium chloride which had been spiked with radioactive indium-111 chloride and the pH was adjusted to 9 with 660 µL of 1N NaOH. Aliquots of whole monoclonal antibody IgG CC-46 were then mixed with aliquots of the chelated STARBURST™. The mixtures were shaken then left for 18 hours. The mixtures were then analyzed by HPLC (column Dupont Zorbax Biosphere GF-250; eluent 0.25M sodium acetate, pH 6) and a UV detector at 254 nm and a radioactivity detector. Results are shown in Table VI.

TABLE VI

| | Starburst-IgG Conjugates | | | |
|---|---|---|---|---|
| | 1 | 2 | 3 | 4 |
| IgG solution (µL) | 20 | 20 | 20 | 20 |
| Chelated Starburst solution (µL) | 5 | 20 | 50 | 100 |
| % Radioactivity on IgG | 6 | 5 | 5 | 3 |
| % IgG conjugated | 2 | 7 | 17 | 22 |

Example 12

Conjugation of 4-isothiocyanatophenyl methylenecarboxylate terminated third generation STARBURST™ polyethyleneimine with IgG monoclonal antibody The isothiocyanate from Example DD, 4 mg (20 µmoles) was mixed with 200 µL of 3 mM indium chloride (60 µmoles). A 20 µL aliquot of the solution was then spiked with radioactive indium-111 chloride and the pH adjusted to 9 by the addition of 30 µL 1N NaOH and 10 µL of 0.1N HCl. The indium chelate was mixed with 150 µL of CC-49 whole antibody IgG, 10 mg/mL in 50 mM HEPES buffer at pH 9.5. After 18 hours at room temperature the antibody was recovered by preparative HPLC (column Dupont Zorbax Biosphere GF 250; eluent 0.25M sodium acetate, pH 6); and a UV detector at 254 nm and a radioactivity detector. The recovered antibody was concentrated on an Amicon membrane and exchanged into PBS buffer (phosphate buffered saline pH 7.4 which contains 0.12M NaCl, 2.7 mM KCl and 10.0 mM phosphate) at pH 7.4. The recovered antibody had specific activity of approximately 0.5 µCi/100 µg.

Example 13

In vivo localization of $^{111}$In labeled STARBURST™ antibody conjugate

The usefulness of the labeled STARBURST™ antibody conjugate prepared in Example 12 was demonstrated by measuring the uptake of the material in vivo by a human tumor xenograft in an athymic mouse. Female athymic mice were inoculated subcutaneously with the human colon carcinoma cell line, LS174T (approximately $4 \times 10^6$ cells/animal). Approximately two weeks after inoculation, each animal was injected via the tail vein. The mice were sacrificed after 17 and 48 hours (five animals at each time point), the tumor and selected tissues were excised and weighed, and radioactivity was measured in a gamma counter. After 17 hours 13.5 percent of the injected dose per gram of tissue had localized at the tumor. After 48 hours 21.6 percent of the injected dose per gram of tissue had localized at the tumor.

Example 14

Attachment of herbicidal molecules (2,4-D) to the surface of STARBURST™ dendrimers Third generation PAMAM (initiator core=NH$_3$) (2.0 g, 0.8 mmole) was dissolved in H$_2$O (10 mL) and combined with toluene (20 mL). The two-phase system was then stirred and cooled with an ice bath at which time the acid chloride of 2,4-D [2,4-dichlorophenoxy)-acetic acid] (2.4 g, 12 equiv) dissolved in toluene (10 mL) was added dropwise over 30 minutes. When the addition was nearly complete, NaOH (0.5 g, 12.5 mmole, 50% w/w solution) was added and the solution stirred for an additional two hours. The reaction mixture was then evaporated to dryness and the resulting solid residue repeatedly taken up in CHCl$_3$/MeOH (1:1 v/v) and filtered. The tan solid was not totally soluble in CHCl$_3$ and appeared to be insoluble in water; however, the addition of acetone facilitated dissolution. The tan solid was stirred in CHCl$_3$ for 24 hours and the solution filtered (a sticky tan solid was obtained). After drying over MgSO$_4$, the filtrate was concentrated to give a viscous orange oil which solidified on standing. The $^{13}$C NMR indicated partial amidation at the surface by 2,4-D and is consistent with the association of the 2,4-D to STARBURST™ polymer.

Example 15

Inclusion of 2,4-dichlorophenoxyacetic acid (2,4-D) into STARBURST™ dendrimers

A widely accepted method for ascertaining whether a "probe molecule" is included in the interior of a micelle is to compare its carbon-13-spin lattice relaxation times ($T_1$) in a non-micellized versus micellized medium. A substantial decrease in $T_1$ for the micellized medium is indicative of "probe molecule" inclusion in the micelle. Since STARBURST™ dendrimers are "covalently fixed" analogs of micelles, this $T_1$ relaxation time technique was used to ascertain the degree/extent to which various herbicide type molecules were associated with STARBURST™ polyamidoamines. In the following examples, $T_1$ values for 2,4-dichlorophenoxyacetic acid (I) (2,4-D) were determined in solvent (CDCl$_3$) and then compared to $T_1$ values in CDCl$_3$ at various [I:dendrimer] molar ratios.

Inclusion of 2,4-D into various STARBURST™ polyamidoamine dendrimers as a function of generation.

Various half generation (ester terminated, initiated off NH$_3$) STARBURST™ polyamidoamine dendrimers (Generation (Gen)=0.5, 1.5, 2.5, 3.5, 4.5 and 5.5) were combined with 2,4-dichlorophenoxyacetic acid (I) in CDCl$_3$ to give an acid:tertiary amine ratio of 1:3.5 and molar ratios of acid:dendrimer of 1:86 as shown in Table VII. The relaxation times ($T_1$) obtained for the various carbon atoms in 2,4-dichlorophenoxyacetic acid and a generation=3.5 STARBURST™ PAMAM dendrimers are shown in Table VIII, both for 1:1 acid/amine ratios and for saturated solutions of 2,4-D.

TABLE VII

| Gen | (A) Acid/Amine | (B) Acid/Amine | (C) Acid/Total Nitrogen | (D) Molar Ratio (Acid/Star-burst) |
|---|---|---|---|---|
| 0.5 | 1 | — | 1 | 1 |
| 1.5 | 1 | 1.33 | 0.57 | 6 |
| 2.5 | 1(3.5)* | 1.11(3.8)* | 0.53(1.8)* | 9(34)* |
| 3.5 | 1(3.0)* | 1.05(3.2)* | 0.51(1.6)* | 20(67)* |
| 4.5 | 1 | 1.02 | 0.51 | 42 |
| 5.5 | 1 | 1.01 | 0.50 | 86 |

*represents examples of 2,4-D inclusion into the interior of the dendrimer in amounts greater than stoichiometric.

TABLE VIII $T_1$'s for 2,4-D/G = 3.5 PAMAM STARBURST™
Inclusion complex; Concentration Effects

| Carbon | (A) 1:1 Acid/Amine | | (B) Saturated with 2,4-D | |
|---|---|---|---|---|
| | $T_1$ | $^{13}C**$ | $T_1$ | $^{13}C**$ |
| 1 | 3.19 ± .12 | (152.73) | 3.08 ± .09 | (152.30) |
| 3 | 0.34 ± .01 | (128.64) | 0.29 ± .01 | (129.62) |
| 5 | 0.38 ± .01 | (127.41) | 0.32 ± .01 | (127.34) |
| 2 | 3.28 ± .08 | (125.79) | 2.72 ± .68 | (125.99) |
| 4 | 4.58 ± .16 | (123.27) | 3.95 ± .07 | (123.16) |
| 6 | 0.31 ± .01 | (114.66) | 0.28 ± .01 | (114.48) |
| $CH_2$ | 0.16 ± .01 | (67.29) | 0.146 ± .003 | (66.79) |
| C=O | 1.24 ± .07 | (170.12) | — | — |

**represents $^{13}C$ chemical shifts referenced to chloroform at 76.9 ppm.

These data show that larger than stoichiometric amounts of 2,4-dichlorophenoxyacetic acid (i.e., [(I):Gen=3.5 dendrimer]=67) can be used without increasing the $T_1$ in any case in the saturated state (see Columns (A) and (B) in Table VIII). In fact, the relaxation times $T_1$ in Column (B) are decreased slightly, thus indicating that larger than stoichiometric amounts of 2,4-dichlorophenoxyacetic acid can be included into the interior of the dendrimer. For example, a molar ratio of

[(I):Gen=2.5 dendrimer]=34 whereas [(I):Gen=3.5 dendrimer]=67, (see Column D in Table VII).

FIG. 11 is a plot of $T_1$ values for carbons-3, 5 and 6 in 2,4-dichlorophenoxyacetic acid as a function of dendrimer generation (i.e., 0.5→5.5). The lower dashed line ( - - - ) is for carbons-3 and 6 and the upper solid line is for carbon 5. A minimum in $T_1$ is reached in all cases for generation 2.5→5.5, thus indicating incorporation in that dendrimer generation range is occurring. FIG. 11 also includes $T_1$ values for 2,4-D in the presence of triethylamine [N(Et)] (points B1 and B2) and N(Et)$_3$+N-methylacetamide (points A1 and A2). It can be seen that these values are much larger than for dendrimers G=1.5→5.5, thus further supporting molecular incorporation into the dendrimer molecule.

Example 16

Preparation of a product containing fluorescein with a STARBURST™ polymer

A sample of 5-carboxyfluorescein (0.996 g) and STARBURST™ polyethyleneimine (Gen=2.0; amine terminated, initiated off $NH_3$) (0.202 g) were mixed in 10 mL of methylene chloride and 5 mL of methanol and allowed to reflux for 10 minutes. Upon filtering, an insoluble red powder (0.37 g) was obtained (mostly unreacted 5-carboxy fluorescein). From the filtrate was isolated 0.4 g of a brilliant-red solid which exhibited a softening point of 98°–103° C. and foamed to a brilliant red melt at 175°–180° C.; NMR spectra ($D_2O$) of this product were consistent with dendrimer having fluorescein bound to the surface.

Example 17

In a procedure similar to that described in Example 16, STARBURST™ polyethyleneimine (Gen=2.0; amine terminated, initiated off $NH_3$) was reacted with fluorescein isothiocyanate to give a brilliant-red iridescent solid which was suitable for use as a fluorescent labelling reagent.

Example 18

Encapsulation of R(+)-Limonene in polyamidoamine STARBURST™ dendrimers

A 5–50 weight percent solids solution in methanol of STARBURST™-PAMAM dendrimer (M.W. about 175,000; generation=9.0) is added dropwise to R(+) limonene in methanol until saturated. The solution is stirred at room temperature (about 25° C.) for several hours and then devolatized on a Büchi rotovap at room temperature to give a solid product. Warming at temperatures greater than 80° C. gives solvent insoluble products which retain substantial amounts of R(+) limonene in an encapsulated form. These products are excellent prototypes for slow release of (R+)-limonene as a fragrance and deodorizer product.

Example 19

Encapsulation of heavy metal salts in polyamidoamine STARBURST™ dendrimers

A 5–50 weight percent solids solution in water of STARBURST™ PAMAM dendrimer (M.W. about 350,000; generation=10.0) is stirred as a saturated solution of lead acetate [Pb($C_2H_3O_2$)$_2$] is added dropwise. The solution is stirred at room temperature (about 25° C.) for several hours and then devolatilized on a Büchi rotovap to give solid products. Scanning transmission electronmicrograph of these products showed that these heavy metal Pb salts are encapsulated in the interior of the dendrimers. These films containing heavy metal salts are useful as shields for absorbing electromagnetic radiation.

Example 20

Encapsulation of fluorescein (water soluble) dye in polyamidoamine STARBURST™ dendrimers A 5–50 weight percent solids solution ($H_2O/CH_3OH$) of STARBURST™-PAMAM dendrimer (M.W. about 175,000; generation=9.0) is stirred as fluorescein, disodium salt (Acid Yellow 73, Cl. 45350; Uranine; available from Aldrich Chemical Co., Milwaukee, Wis.) is added until saturated. The solution is stirred at room temperature (about 25° C.) for several hours and then devolatilized at room temperature to give a colored solid product. These dye encapsulated dendrimers are excellent reference probes for calibrating ultrafiltration membranes.

Example 21

Preparation of dendrimers with terminal fluorescent groups
A. Reaction of Amine Terminated Dendrimer with N-Dansyl Aziridine A sample (1.5 g, 1.6×10$^{-3}$ mole) of STARBURST™ polyethyleneimine (PEI), G=3.0, terminal groups (Z)=12, M.W.=920) is dissolved in 20 mL of methanol. The solution is stirred and 0.884 g (3.84×10$^{-2}$ mole) of a solution of N-dansyl aziridine (ICN Biomedicals, Costa Mesa, Calif.) is added dropwise over a period of 20 minutes. The reaction mixture is allowed to stir at room temperature overnight. Removal of solvent under vacuum gives a solid product. NMR and infrared analysis indicate that the product possessed covalently bonded dansyl groups on the surface of the dendrimer.

B. Reaction of amine terminated dendrimers with Dansyl chloride

A solution of STARBURST™ polyamidoamine (1.0 g, 1.9×10$^{-4}$ mole) (initiated from ammonia, G=4.0, terminal groups (Z)=24, M.W.=5,147) in 30 mL of water is stirred in a 3-neck flask with 80 mL of toluene while a solution of dansyl chloride (1.23 g, 4.5×10$^{-3}$ mole) (5-dimethyl-amino-1-naphthalenesulfonyl chloride, from Aldrich Chemical Co., Milwaukee Wis.) in 40 mL of toluene is added dropwise while cooling with ice. Concurrently, a solution of 10 percent NaOH (13.3 mole, 10% excess) is added to the reaction mixture to give an oily ball. The crude product is washed with water, dissolved in methanol, and precipitated with diethyl ether to give a solid product. NMR and infrared analyses are consistent with covalently bonded dansyl groups on the dendrimer surface.

Example 22

Preparation of manganese PAMAM dense star polymer

Following the procedure set forth in Example 1 of U.S. Pat. No. 4,587,329, a third generation ester-terminated polyamidoamine dense star polymer is prepared. The ester moieties are hydrolyzed to sodium salt form by dissolving the dense star polymer in 0.1N NaOH. A 131-mg (0.496 mmol) portion of the resulting crude sodium salt of the dense star polymer is dissolved in water (1 mL, pH 11.4) and neutralized to a pH of 7.0 by adding 0.5M HCl. A 26-mg (2 equiv) portion of $MnCl_2 \cdot 4H_2O$ is added to the neutralized solution and the solution is heated at 55° C. for 2 days. The resultant light yellow solution is purified using a Bio-Gell P2 column (15.0 g, 150 mm length×25 mm diameter) eluting with water, and isolating the colored band. The product was confirmed to be chloride free (e.g. NaCl, $MgCl_2$) by silver nitrate test. The eluate was stripped to dryness to produce a clear gel which was dried under high vacuum to yield 45 mg of the desired dense star polymer complex which was determined to have the following elemental constituency, $[NaMn_2H_7][C_{69}H_{105}N_{19}O_{33}]$.

|  | Na | Mn | C | H | N |
|---|---|---|---|---|---|
| Calculated: | 1.23; | 5.88; | 44.35; | 5.66; | 14.24 |
| Found: | 1.42; | 4.80; | 43.33; | 7.91; | 14.72. |

Following a similar procedure using a seventh generation sodium carboxylate-terminated polyamidoamine dense star polymer, an additional manganese dense star polymer complex is prepared which is determined to have the following elemental constituency, $[Na_{30}H_{354}][Mn_{10}C_{3057}H_{4965}N_{763}O_{1149}]$.

|  | Mn | C | H | N |
|---|---|---|---|---|
| Calculated: | 0.759; | 50.72; | 7.41; | 14.76; |
| Found: | 0.72; | 46.34; | 7.91; | 14.72. |

The relaxivities for the foregoing complexes are measured in water and the results are reported in Table IX. For the purposes of comparison, the relaxivities of complexes of manganese with two known complexing agents are calculated from the corresponding relaxation times measured by nuclear magnetic resonance. The results are reported in Table IX.

TABLE IX

| COMPOUND | RELAXIVITY* | |
|---|---|---|
|  | $R_1$ | $R_2$ |
| $MnCl_2$ | 5.2 | >20 |
| MnEDTA | 2.9 | — |
| MnDTPA | 1.3 | — |
| $Mn_2$[PAMAM-A(2.5 G)] | 3.63 ± 0.02 | 16.35 ± 0.78 |

*$(mM \cdot sec)^{-1}$, 37° C., 90 MHz. Values per metal atom.

Example 23

Following the procedure of Example 22, dense star polymer complexes of iron are prepared. In one embodiment, the sodium salt of the acid form of a sixth generation polyamidoamine is prepared by dissolving the ester form of the polyamidoamine made in accordance with the excess reactant method of U.S. Pat. No. 4,587,329 in 1N NaOH. The sodium salt (97 mg, $2.4 \times 10^{-3}$ mmol) is then dissolved in 2 mL of water and the solution (pH of 11.3) is neutralized to a pH of 7 with 0.5M HCl. To this neutralized solution is added an aqueous solution of $FeCl_3$ (0.102M, pH 1.4, 0.5 mL, 0.051 mmol, 21.6 equiv). The resulting deep orange solution (pH 4.9) is heated at 55° C. for 23 hr. The solution is cooled to ambient temperature and filtered by gel filtration chromatography (Biogel P2 column, 175×25 mm). The orange eluate is stripped to dryness under vacuum at 50° C. to yield 45 mg of an orange solid having the following molecular formula: $[Na_5H_{127}]\{Fe_{20}[PAMAM-P(6.5G)]\}$ wherein PAMAM-P represents the dense star polyamidoamine in the propionate terminated form. This orange solid is determined to be a complex of iron and the polyamidoamine dense star polymer represented by the formula $Na_5H_{127}Fe_{20}(C_{1521}H_{2469}N_{379}O_{573})$.

|  | Na | Mn | C | H | N |
|---|---|---|---|---|---|
| Calculated: | 0.31; | 3.05; | 49.84; | 7.30; | 14.48 |
| Found: | 0.31; | 3.12; | 47.11; | 7.33; | 14.81. |

Following the above procedure, similar complexes of iron and acetate-terminated polyamidoamine dense star polymers or acetate-terminated polyethyleneimines dense star polymers having from 2 to 6 generations are prepared. The relaxation times for these complexes are measured using nuclear magnetic resonance and the corresponding relaxivities are calculated and reported in Table X.

TABLE X

| COMPOUND | RELAXIVITY* | |
|---|---|---|
|  | $R_1$ | $R_2$ |
| $FeCl_3$ | 8.4 ± 0.1 | — |
| FeEDTA | 1.7 | — |
| FeDTPA | 0.73 | 0.85 |
| FeEHPG | 0.95 | 1.1 |
| $Fe_2$[PEI-A(2.5 G)] | 0.40 ± 0.02 | 0.88 ± 0.03 |
| $Fe_2$[PAMAM-A(2.5 G)] | 0.77 ± 0.01 |  |
| $Fe_2$[PAMAM-P(2.5 G)] | 0.135 ± 0.004 | 0.42 ± 0.02 |
| $Fe_4$[PAMAM-P(4.5 G)] | 0.038 ± 0.006 | 1.01 ± 0.05 |
| $Fe_{20}$[PAMAM-P(6.5 G)] | 0.047 ± 0.007 | 0.50 ± 0.07 |
| $Fe_{50-60}$[PAMAM-P(7.5 G)] | about 0.3** | about 62** |
| {SPEI-[DTPA][Fe(DTPA)]$_2$} | 1.094 ± 0.050 | 1.70 ± 0.02 |

*$(mM \cdot sec)^{-1}$, 37° C., 90 MHz. Values per metal atom.
**Values per complex.

Example 24

Using the method of Example 22 complexes of gadolinium and the polyamidoamine and polyethyleneimine dense star polymers described in Example 23 are prepared and their relaxation times are measured and relaxivities calculated with the result being shown in Table XI. As an illustration of the preparation of the gadolinium complex, 0.40 g (0.16 mmol) of the sodium acetate form of a polyethyleneimine dense star polymer (second generation) prepared as in Example 6 of U.S. Pat. No. 4,587,329 and followed by reaction with an excess of bromoacetic acid at pH=9, 40° C., is dissolved in 5 mL of water. The pH of the resulting solution is lowered to 9.2 with 0.5N HCl and 3.2 mL of an aqueous solution of $GdCl_3$ (0.31 mmol) is added. The pH of the resulting solution is increased from 4.1 to 8.3 with 1N NaOH and the solution is allowed to stand for 24 hrs. The volatiles are then removed from the solution in vacuo and the residue twice chromatographed in chelex resin. The recovered light yellow solid was found to have an atomic ratio of Gd to N of 2:1.

Found (%): C, 14.5; H, 2.1; N, 3.6; Gd, 7.9; Br, 28.7.

Following the above procedure, similar complexes of gadolinium and acetate-terminated polyamidoamine dense star polymers or acetate-terminated polyethyleneimines dense star polymers having from 2 to 6 generations are prepared. The relaxation times for these complexes are measured using nuclear magnetic resonance and the corresponding relaxivities are calculated and reported in Table XI.

TABLE XI

| COMPOUND | RELAXIVITY* $R_1$ |
| --- | --- |
| Gd(NO$_3$)$_3$ | 8.6 ± 0.3 |
| GdCl$_3$ | 8.7 ± 0.1 |
| GdCl$_3$(0.15M saline) | 10.43 ± 0.36 |
| GdEDTA | 6.5 |
| GdDTPA | 3.9 |
| GdDOTA | about 4 |
| Gd(PAMAM-A) | 9.90 ± 0.43 |
| Gd$_2$(PAMAM-A) | 13.00 ± 0.33 |
| Gd(PEI-A) | 8.85 ± 0.19 |
| Gd$_2$(PEI-A) | 15.35 ± 0.17 |
| Gd$_2$(PEI-A) + 3PEI-A | 8.0 ± 0.19 |
| Gd(DTPMP) | 10.8 ± 0.4 |
| Gd$_2$(PEI-A) + 2EDTA | about 6 |

*(mM · sec)$^{-1}$, 37° C., 90 MHz. Values per metal atom.

Example 25

Preparation of polyamidoamine STARBURST™ conjugate with Bradykinin C Bradykinin Potentiator C, 4.7 mg (Sigma Chemical Company), was taken up in 90 μL of N-methylpyrrolidinone (NMP) containing 7.1 mg/mL N-hydroxybenzotriazole (HOBT) and mixed with 33 μL of a freshly prepared solution of dicyclohexylcarbodiimide (DCC) (28 mg/mL NMP). After four hours at room temperature, 60 μL of fifth generation (G5) PAMAM in NMP (13.4 mg/mL) was added to the Bradykinin mixture. After 72 hours at room temperature, 1.5 mL of 17 mM acetic acid was added. The mixture was centrifuged and the solution decanted from the solid and the solid then washed with 1.5 mL of dilute acetic acid. The solution and washings were combined and filtered through a 25 mm PTFE 0.45μ syringe filter. Unreacted peptide, HOBT and solvent were separated from the conjugate by ultrafiltration using two Centricon™-10 Microconcentrators. The conjugate was washed with 2 mL of 17 mM acetic acid, then 2 mL PBS buffer. The conjugate was recovered in 450 μL of retentate and diluted to 750 μL with fresh PBS buffer.

Four aliquots of the conjugate were hydrolyzed with concentrated HCl at 115° C. for 20 hours and analyzed for glutamic acid. The glutamic acid was quantified as the o-phthalaldehyde/2-mercaptoethanol derivative using reverse phase HPLC with a fluorescence detector (column: Whatman Partisil™ 5CCS/C8 (10 cm); Gilson Spectra™/ Glo detector; tyrosine as internal standard; eluent 50 mM sodium acetate and methanol; gradient: 12% to 30% methanol in 5 min., held for 1 min. at 30%, then increased to 80% methanol over 14 min. and held at 80% for 5 min.). The o-phthalaldehyde derivative was prepared by mixing 25 μL of the amino acid solution with 50 μL fluoraldehyde™ o-phthalaldehyde reagent solution (Pierce), mixing for one minute and then diluting with 0.05 mL of PBS buffer (phosphate buffered saline; 120 millimolar sodium chloride, 2.7 millimolar potassium chloride, 10 millimolar phosphate buffer salts, pH 7.4). For a 25 μL aliquot of the conjugate, 58 nmoles of glutamic acids were found. This corresponds to 1.74 μmoles Bradykinin C on the conjugate.

Example 26

Preparation of polyamidoamine STARBURST™ conjugate with BOCPheLeuPheLeuPhe

N-t-butoxycarbonyl-L-Phenylalanyl-D-Leucyl-L-Phenylalanyl-D-Leucyl-L-Phenylalanine (BOCPheLeuPheLeuPhe), 4.1 mg (Sigma Chemical Company), was taken up in 100 μL NMP which contained 7.1 mg/mL HOBT and mixed with 30 μL of a freshly prepared solution of DCC (36 mg/mL) in NMP. After 90 minutes at room temperature, 60 μL of a solution of 5G PAMAM in NMP (13.4 mg/mL) was added. After 72 hours at room temperature, the conjugate was isolated following the procedure in Example 24. The conjugate was recovered in 750 μL of retentate.

Four aliquots of the conjugate were hydrolyzed with concentrated HCl at 115° C. for 20 hours and analyzed for phenylalanine. The phenylalanine was quantified as the o-phthalaldehyde/2-mercaptoethanol derivative using reverse phase HPLC with a fluorescence detector (HPLC conditions as Example 24 except the eluent gradient was 12% to 80% methanol over 20 min. and then held at 80% for 5 min.). The o-phthalaldehyde derivative was prepared as given in Example 24. For a 25 μL aliquot of the conjugate, 26 nmoles phenylalanine were found. This corresponds to 0.26 μmoles BOCPheLeuPheLeuPhe on the conjugate.

Example 27

To a methanol solution of 1,4,7-tris-(carbomethoxymethyl)-1,4,7,10-tetraazacyclododecane (DO3A methyl ester) is added 1.0 equivalent of freshly prepared anhydrous sodium methoxide and the solution is allowed to stir for several hours. To this solution is added one equivalent of 10,11-epoxyundecanoic acid and the solution is brought to reflux overnight. The solvent is removed in vacuo to give a crude hydroxyethylated product, 1,4,7-tris-(carbomethoxymethyl)-10-[2'-hydroxy-10'-carboxy (decyl)]-1,4,7,10-tetraazacyclododecane. Two to five equivalents of this product are dissolved in dimethylformamide (DMF) and corresponding equivalents of dicyclohexylcarbodiimide (DCC) and N-hydroxysuccinimide are added with stirring overnight. To this solution is added one equivalent of generation 2 PAMAM and stirring is continued another 24 hours. The corresponding DO3A methyl ester conjugate is selectively hydrolyzed by treatment with aqueous sodium hydroxide in methanol. Treatment of the DO3A conjugate with excess Gadolinium(III) acetate [Gd(OAc)$_3$, buffered to pH=6] followed by incubation with excess diethylenetriaminepentaacetic acid (DTPA) and purification of the conjugate using preparative reverse phase HPLC gives a hydroxyethyl DO3A PAMAM STARBURST™ conjugate product which contains two to five equivalents of gadolinium which can not be removed by further challenges with excess DTPA.

Example 28

To an aqueous solution of generation 2 PAMAM, which is buffered to pH=9.0, is added two to five equivalents of 1-[1-carboxy-3(4'-isothiocyanatophenyl)propyl]-4,7,10-tris (carboxymethyl)-1,4,7,10-tetraazacyclododecane prepared by the method described in EP published application 0353450, published Feb. 7, 1990. The solution is stirred overnight at room temperature. Treatment of the solution with excess Gd(OAc)₃ at pH=6.0 results in the formation of a thiourea linked DOTA PAMAM STARBURST™ conjugate which contains two to five equivalents of inertly bound gadolinium which can not be removed with a DTPA challenge.

Example 29

Preparation of IgG/dendrimer-FITC I Conjugate
A: Preparation of PAMAM dendrimer conjugated to fluorescein isothiocyanate A 2.2 mL methanolic solution of G9 (EDA) PAMAM dendrimer was dried under vacuum on a rotary evaporator. Approximately 300 mg (7.4 µmol) of the dried dendrimer was quickly removed and dissolved in 1 mL of deionized water to form the stock dendrimer solution. A 60 mg/mL solution was prepared by mixing 200 µL of the stock dendrimer solution and adding it to 800 µL of deionized water. In order to achieve a final dendrimer concentration of 10 mg/mL (final dendrimer solution), 5 mL of 0.1M phosphate buffer (pH=9.0) was added to the 60 mg/mL solution. The final dendrimer solution, 3 mL, was transferred to a 2 dram vial (30 mg, 0.13 µmol).

Fluorescein isothiocyanate (FITC I, Molecular Probes), 5 mg, was dissolved in 1 mL of dimethyl sulfoxide in the dark. The fluorescein isothiocyanate solution (200 µL, 2.57 µmol) was added to the stirring dendrimer solution. The resulting reaction mixture was protected from light and stirred at room temperature for 15 to 20 hours. The solution remained clear and amber in appearance.

After stirring, the reaction mixture was placed into two Centricon™ microconcentrator tubes (molecular weight cut-off: 10,000 Daltons), and was ultrafiltered to remove any unreacted FITC I. During the ultrafiltration, ten, 2 mL additions of 0.1M phosphate buffer of pH 9.0 were made to facilitate the purification. The ultra filtrations were monitored for purity by thin-layer chromatography in order to insure the complete removal of any unreacted FITC I. The thin-layer chromatography was run using silica gel 60 plates (Merck) using an ethyl acetate (100%) solvent system. While the labelled dendrimer remained at the origin, the remaining FITC I eluted near an $R_f$=0.7. Approximately 2 mL of conjugated G9 PAMAM dendrimer-FITC I was recovered from the purification.

B: Preparation of PAMAM dendrimer conjugated to fluorescein isothiocyanate and IgG Rabbit immunoglobulin (IgG, Sigma Chemical Co.), 9.8 mg, was dissolved in 1 mL of 30 mM of sodium acetate and 150 mM of sodium chloride buffer (pH=5.5). To the IgG solution was added 1.5 mg of sodium periodate with gentle stirring until dissolved. The mixture was protected from light and gently stirred at room temperature for 15–18 hours. After stirring, the reaction mixture was placed into two Centricon™ microconcentrator tubes (molecular weight cut-off: 10,000 Daltons), and was ultrafiltered into 20 mM phosphate buffer of pH=6.0 (4×2 mL). Approximately 1–2 mL of the IgG dialdehyde solution was recovered from the purification.

An aliquot of the labelled dendrimer-FITC I solution from Step A (0.88 mL, 17.6 mg, 0.075 µmol) was added dropwise to the IgG dialdehyde solution. (This represents about 1.15:1 ratio of labelled dendrimer to antibody.) Upon the addition of the first drop of the labelled dendrimer solution, the reaction mixture precipitated. An additional 3 mL of 20 mM phosphate buffer (pH=6.0) was added, but it did not solubilize the solids.

The IgG/dendrimer-FITC I conjugate was protected from the light and allowed to stir at room temperature for 1 hour. After that hour, 1.7 mg of sodium cyanoborohydride was added and the reaction was stirred overnight (15–20 hours) at room temperature. The solution was a fluorescent orange with some precipitate. The reaction product, including the precipitate, was placed into two Centricon™ microconcentrator tubes (molecular weight cutoff: 100,000 Daltons), and was ultrafiltered. Six additional 2 mL volumes of the 20 mM phosphate buffer (pH=6.0) were added during the process to remove any unbound dendrimer-FITC I. The IgG/dendrimer-FITC I conjugate was recovered and transferred to an amber glass vial for storage at −10° C.

Example 30

Preparation of IgG/dendrimer-dansyl Conjugate
A: Preparation of G9 PAMAM dendrimer-dansyl Conjugate Using 200 µL of the stock dendrimer solution prepared in Example 29A and adding 800 µL of deionized water, the 60 mg/mL solution was prepared. To achieve the final dendrimer concentration of 10 mg/mL, 5 mL of 0.1M phosphate buffer (pH=9.0) was added to the 60 mg/mL solution.

Dansyl chloride (13.9 mg, 0.052 mmol, Aldrich Chemical Co.) was added to 5 mL of acetone and shaken for 5–10 minutes. (This solution was a deep yellow color and had traces of solid present.) The dansyl chloride solution was added to the dendrimer solution over a 30 second period and the reaction flask was placed in a water bath at 40° C. for 90 minutes. During the heating, the reaction mixture was shaken intermittently. The reaction mixture was slightly hazy in appearance and the color faded from a deep yellow to a faint yellow. After 90 minutes, the reaction flask was removed from the heat and allowed to cool to room temperature. The reaction mixture was then placed on a rotary evaporator, under vacuum at 30°–35° C. to remove the acetone. The reaction product was placed into two Centricon™ microconcentrator tubes (molecular weight cutoff: 100,000 Daltons), and was ultrafiltered to remove any unbound dansyl chloride. Ten, 2 mL additions of 0.1M phosphate buffer (pH=9.0) were made during the ultrafiltration.

The ultrafiltrations were monitored for purity by thin-layer chromatography in order to insure the complete removal of any unreacted dansyl chloride. The thin-layer chromatography was run using silica gel 60 plates (Merck) using an ethyl acetate (100%) solvent system (visualization by UV light). While the labelled dendrimer remained at the origin, the remaining dansyl chloride eluted near an $R_f$=0.3. Approximately 1–2 mL of conjugated G9 PAMAM dendrimer-dansyl was recovered from the purification.

B: Preparation of PAMAM dendrimer conjugated to dansyl and IgG

Rabbit immunoglobulin (IgG, Sigma Chemical Co.), 9.8 mg, was dissolved in 1 mL of 30 mM of sodium acetate and 150 mM of sodium chloride buffer (pH=5.5). To the IgG solution was added 1.5 mg of sodium periodate with gentle stirring until dissolved. The mixture was protected from light and gently stirred at room temperature for 15–18 hours. After stirring, the reaction mixture was placed into two Centricon™ microconcentrator tubes (molecular weight cut-off: 100,000 Daltons), and was ultrafiltered into 20 mM phosphate buffer of pH=6.0 (4×2 mL). Approximately 1.9 mL of the IgG dialdehyde solution was recovered from the purification.

An aliquot, 1.25 mL, of the labelled dendrimer-dansyl solution from Step A (14.1 mg/mL) was added dropwise to the IgG dialdehyde solution. (This represents about 1.15:1 ratio of labelled dendrimer to antibody.) Upon the addition of the first drop of the labelled dendrimer solution, the reaction mixture precipitated.

The IgG/dendrimer-dansyl conjugate was protected from the light and allowed to stir at room temperature for 1 hour. After that hour, 1.7 mg of sodium cyanoborohydride was added and the reaction was stirred overnight (15–20 hours) at room temperature. The reaction product, including the precipitate, was placed into two Centricon™ microconcentrator tubes (molecular weight cutoff: 100,000 Daltons), and was ultrafiltered. Six additional 2 mL volumes of the 20 mM phosphate buffer (pH=6.0) were added during the process to remove any unbound dendrimer-dansyl. The IgG/dendrimer-dansyl conjugate was recovered and transferred to an amber glass vial for storage at −10° C.

Example 31

Preparation of PAMAM dendrimer conjugated to HRP and IgG

A: Preparation of PAMAM dendrimer conjugated to IgG

Rabbit immunoglobulin (IgG, Sigma Chemical Co.), 9.6 mg, was dissolved in 1 mL of 30 mM of sodium acetate and 150 mM of sodium chloride buffer (pH=5.5). To the IgG solution was added 1.5 mg of sodium periodate with gentle stirring until dissolved. The mixture was protected from light and gently stirred at room temperature for 15–18 hours. After stirring, the reaction mixture was placed into two Centricon™ microconcentrator tubes (molecular weight cutoff: 100,000 Daltons), and was ultrafiltered into 20 mM phosphate buffer of pH=6.0 (4×2 mL). Approximately 1.5 mL of the IgG dialdehyde solution was recovered from the purification.

An aliquot, 100 μL, dendrimer stock solution from Step A of Example 29 was added to 100 μL of deionized water to yield 150 mg/mL solution. A final concentration of 15 mg/mL was attained by further dilution of 100 μL of the dendrimer solution with 900 μL of deionized water. The final dendrimer solution, 1 mL, was added dropwise to the IgG dialdehyde solution and the mixture stirred for 1 hour at room temperature. A precipitate was formed. After that hour, 1.7 mg of sodium cyanoborohydride was added and the reaction was stirred overnight (15–20 hours) at room temperature. The reaction product, including the precipitate, was placed into two Centricon™ microconcentrator tubes (molecular weight cutoff: 100,000 Daltons), and was ultrafiltered. Four additional 2 mL volumes of the 20 mM phosphate buffer (pH=6.0) were added during the process to remove any unbound dendrimer-IgG. The IgG/dendrimer conjugate was recovered and transferred to a 2 dram vial.

B: Preparation of PAMAM dendrimer/IgG-HRP Conjugate

Horse-radish peroxidase (HRP, 2.6 mg, Pierce) was dissolved in 0.5 mL of deionized water to form the HRP solution. Sodium periodate, 10.7 mg, was dissolved in 5 mL of 10 mM sodium phosphate (pH =7.0). Approximately 1.6 mL of the periodate solution was added to the HRP solution at room temperature. The enzyme reaction mixture was protected from light and gently stirred at room temperature for 30 minutes. The oxidized HRP product was placed into two Centricon™ microconcentrator tubes (molecular weight cutoff: 10,000 Daltons), and was ultrafiltered. Four additional 2 mL volumes of the 30 mM sodium acetate/150 mM sodium chloride buffer (pH=5.5) were added during the process.

The oxidized enzyme solution was added to the PAMAM dendrimer-IgG conjugate mixture with stirring. Although the precipitate remained in the reaction, the mixture was allowed to stir for 2 hours at room temperature. After the 2 hours, 2.1 mg of sodium borohydride was dissolved in 1 mL of deionized water and 100 μL of the borohydride solution added to the PAMAM dendrimer-IgG-HRP mixture. The reaction was stirred overnight (15–20 hours) at 2°–8° C.

The reaction product, including the precipitate, was placed into two Centricon™ microconcentrator tubes (molecular weight cutoff: 100,000 Daltons), and was ultrafiltered. Four additional 2 mL volumes of the 20 mM phosphate buffer (pH=6.0) were added during the process. The IgG/dendrimer/HRP conjugate was recovered and transferred to a 2 dram vial for storage at −10° C.

Example 32

Preparation of IgG/Dansylated PAMAM dendrimer/HRP Conjugate

A: Preparation of HRP Solution

Horse-radish peroxidase (HRP, 2.6 mg, Pierce) was dissolved in 0.5 mL of deionized water to form the HRP solution. Sodium periodate, 10.7 mg, was dissolved in 5 mL of 10 mM sodium phosphate (pH =7.0). Approximately 1.6 mL of the periodate solution was added to the HRP solution at room temperature. The enzyme reaction mixture was protected from light and gently stirred at room temperature for 30 minutes. The oxidized HRP product was placed into two Centricon™ microconcentrator tubes (molecular weight cutoff: 10,000 Daltons), and was ultrafiltered. Four additional 2 mL volumes of the 30 mM sodium acetate/150 mM sodium chloride buffer (pH =5.5) were added during the process. The oxidized enzyme solution was recovered and placed into a 2 dram glass vial.

B: Preparation of Dansyl G4 PAMAM Dendrimer Solution

A 5 mL methanolic solution of 12.7% (w/w) of G4 ($NH_3$) PAMAM dendrimer ($NH_3$ core) solution was prepared and dried under vacuum on a rotary evaporator. Approximately 40 mg (7.4 μmol) of the dried dendrimer was removed and dissolved in 5 mL of 0.1M phosphate buffer (pH =9.0).

A 10 mg (0.037 mmol) quantity of dansyl chloride was added to 5 mL of acetone and shaken for 5 to 10 minutes. The solution was a deep yellow and had traces of solid present. The dansyl chloride solution was added to the dendrimer solution over a 30 second period and the reaction flask was placed in a water bath at 40° C. for 90 minutes. During the heating, the reaction mixture was shaken intermittently. The color of the solution was a faint yellow. After the 90 minutes, the reaction flask was removed from the heat and allowed to cool to room temperature. The reaction mixture was slightly hazy in appearance.

The reaction solution was evaporated to remove the acetone using a rotary evaporator under vacuum at 30°–35° C. The solution was clarified by this process. The reaction mixture was then transferred into two centrifuge tubes and centrifuged at 5000 rpm for 30 minutes. The dendrimer solution was then placed into two Centricon™ microconcentrator tubes (molecular weight cutoff: 3,000 Daltons), and was ultrafiltered four times from a volume of 2 mL to remove any unbound dansyl chloride. Approximately 1–2 mL of the dansylated dendrimer product solution was recovered.

C: Preparation of IgG/Dansyl G4 PAMAM Dendrimer Solution

A 6.9 mg quantity of rabbit immunoglobulin (IgG) was dissolved in 1 mL of 50 mM phosphate buffer (pH=7.2). A 14.8 mg quantity of sodium periodate was added and the mixture was swirled until the solids were dissolved. The mixture was protected from light and stirred for an additional 30 minutes at room temperature. The solution was then placed into two Centricon™ microconcentrator tubes (molecular weight cutoff: 3,000 Daltons), and was ultrafiltered four times from a volume of 2 mL each time using 50 mM phosphate buffer (pH=7.2) to ensure the removal of any unreacted sodium periodate. Approximately 1 mL of the dialdehyde solution was recovered and transferred to a vial in preparation for coupling with the dansylated dendrimer.

An aliquot of the labelled dansyl dendrimer from Part B was removed from stock and diluted to a final dendrimer concentration of 3.0 mg/mL. A 100 µL volume of the diluted dansylated dendrimer was added to the IgG dialdehyde solution and dispersed. This represents about 1.2:1 ratio of the labelled dendrimer to IgG.

The IgG/dansylated dendrimer conjugate was protected from the light and allowed to stir at room temperature for 1 hour. After that time, 1.4 mg of sodium cyanoborohydride was added and the reaction stirred overnight (15–20 hours) at room temperature. The solution appeared clear. An electrophoresis sample, 200 µL, was removed and the rest of the solution was then placed into two Centricon™ microconcentrator tubes (molecular weight cutoff: 100,000 Daltons), and was ultrafiltered. Four additional 2 mL volumes of the 50 mM phosphate buffer (pH=7.2) were added during the process to remove any unbound dansyl dendrimer. The desired conjugate was recovered.

D: Preparation of G4 PAMAM dendrimer/dansyl/IgG-HRP Conjugate

To 650 µL (10.1 mg) of IgG/Dansyl G4 PAMAM dendrimer solution (prepared in Part C) was added 2.6 mg of the oxidized HRP. The IgG/dansyl dendrimer/HRP conjugate was protected from light and allowed to stir at room temperature for 2 hours. After 1 hour, 2.1 mg of sodium borohydride was dissolved in 1 mL of deionized water and 100 µL of the borohydride solution added to the PAMAM dendrimer-IgG-HRP mixture. The reaction was stirred overnight (15–20 hours) at 2° to 8° C. The mixture was a clear amber liquid.

The reaction product was placed into two Centricon™ microconcentrator tubes (molecular weight cutoff: 100,000 Daltons), and was ultrafiltered. Four additional 2 mL volumes of the 20 mM phosphate buffer (pH=6.0) were added during the process. The IgG/dansyl/dendrimer/HRP conjugate was recovered and transferred to a amber glass vial for storage at −10° C.

E: Characterization of G4 PAMAM dendrimer/dansyl/IgG-HRP Conjugate

Aliquots of the IgG/Dendrimer/HRP conjugates were evaluated for the presence of HRP enzyme using 3,3',5,5'-tetramethylbenzidine (TMB). HRP catalyzes the hydrogen peroxide oxidation of substrates, such as TMB, by transferring electrons from the TMB to the peroxide to yield a colored product. Therefore, the loss of one electron yields a blue color and the loss of two electrons produces a yellow color.

The following dendrimer/dansyl/IgG-HRP conjugates were prepared to confirm the presence of HRP enzyme:

(1) 0.1 mg/mL IgG/dansyl G4 PAMAM dendrimer
(2) 0.1 mg/mL IgG/dansyl G4 PAMAM dendrimer/HRP
(3) 0.1 mg/mL IgG/G9 PAMAM dendrimer/HRP
(4) Ultrafiltrate from IgG/G9 PAMAM dendrimer/HRP, containing unbound HRP The TMB substrate solution was prepared using TMB-dihydrochloride. Each of the above diluted samples, 200 µL, were added to 200 µL of TMB substrate solution. The two HRP conjugates (#2 & #3) immediately turned green, then yellow. The ultrafiltrate (#4) turned bright yellow. The IgG/dendrimer (#1) remained colorless. All four samples were incubated at room temperature for 30 minutes, then quenched with 200 µL of 1N sulfuric acid. The yellow color of the enzyme conjugates (#2 & #3) became more intense. The IgG/dendrimer (#1) was slightly green and showed fluorescence under UV light.

Aliquots of all the conjugates were analyzed by polyacrylamide gel electrophoresis. Sample concentrations of approximately 1 mg/mL were prepared for the electrophoresis, which corresponds to about 10 µg of electrophoresis sample. An Amicon Gradipore™ (Hylinx) 5–50% T gradient gel was used in combination with 0.05M sodium acetate buffer (0.025% in sodium azide) of pH=4.0. The gel was run at a constant voltage of 200 V for 2 hours. Conjugates containing precipitate were centrifuged prior to electrophoresis analysis. The supernatant was removed and used for the electrophoresis. The following samples were run:

(1) G9 PAMAM dendrimer
(2) Dansylated G9 PAMAM dendrimer
(3) G9 PAMAM dendrimer-FITC I
(4) IgG (control)
(5) IgG/Dansyl G9 PAMAM dendrimer
(6) IgG/G9 PAMAM dendrimer-FITC I
(7) IgG/G9 PAMAM dendrimer/HRP
(8) HRP (control)
(9) IgG/Dansyl G4 (NH$_3$) PAMAM dendrimer/HRP
(10) Open
(11) Repeat of #7
(12) Repeat of #9

Prior to staining, the gel was placed under UV light to identify any fluorescence. Only Samples #2, 3 and 6 showed fluorescence.

Visualization of the gel following TMB, but prior to staining showed Samples #7, 8, 9, 11, and 12 present and confirmed the presence of enzyme at the higher molecular weights on the gel.

The gel was subsequently stained with 0.025% Coomassie Blue Stain overnight in 5% acetic acid and 7% methanol. Sample #10 was the only unstained lane on the gel. Samples #4 and 8 were at the lower molecular weights. All other Samples showed higher molecular weights without any lower molecular weights present.

Example 33

Preparation of G6 PAMAM dendrimer/Dichlorotriazinyl Fluorescein

G6 (EDA) PAMAM dendrimer, 300 µL (21.5% solids) was added to 700 µL of deionized water and dispersed (64.5 mg, 2.24 µmol). The dendrimer was further diluted with 4 mL of deionized water to a concentration of 12.9 mg/mL.

Dichlorotriazinyl fluorescein hydrochloride DTAF I, (available from Sigma), 6.0 mg (11.3 µmol) was dissolved in 0.5 mL of methanol in the dark, and 2 drops of triethylamine added. The DTAF I solution was added to the stirring dendrimer solution dropwise over 30 seconds. The reaction mixture was protected from the light and stirred at room temperature for 15–20 hours. The solution remained clear and orange throughout the reaction. After stirring, the reaction mixture was placed into two Centricon™ microconcentrator tubes (molecular weight cutoff: 10,000 Daltons), and was ultrafiltered to remove any unreacted DTAF I. Fifteen, 2 mL volumes of 0.1M phosphate buffer (pH=9.0) were added during the process. Approximately 3 mL of conjugated G6 (EDA) PAMAM dendrimer/DTAF I were recovered.

Example 34

Preparation of G5.5 PAMAM dendrimer/Aminomethyl Fluorescein

G5.5 (NH$_3$) PAMAM dendrimer, 1 mL solution (4.2% solids, 42 mg, 1.7 μmol) was added to a 2 dram vial.

In a separate vial, 6.6 mg (1.7 μmol) of 4'-aminomethyl fluorescein (AMF) was dissolved in 0.5 mL of deionized water. The pH was adjusted to 9 by adding 2 drops of triethylamine.

In a third vial, 63.8 mg of 1-ethyl-3-(3-dimethylaminopropyl)carbodiimide (EDAC) was dissolved in 1 mL of deionized water.

The AMF solution was added to the stirring dendrimer solution over 1–2 minutes at room temperature. The pH of the dendrimer-AMF solution was adjusted to 4.5–5.5 using 1N hydrochloric acid. The solution remained clear. With continued stirring, to the mixture was added the EDAC solution, in 200–300 μL increments, at 15–20 minute intervals over 1 hour. The pH of the reaction mixture was maintained between 4.5–5.5 using 1N hydrochloric acid. The reaction mixture was protected from light and stirred at room temperature for 15–20 hours. The solution was clear and orange.

After stirring, the reaction mixture was placed into two Centricon™ microconcentrator tubes (molecular weight cutoff: 10,000 Daltons), and was ultrafiltered to remove any unreacted AMF. Fifteen, 2 mL volumes of 0.1M phosphate buffer (pH=9.0) were added during the process. Approximately 2 mL of conjugated G5.5 PAMAM dendrimer/AMF were recovered.

Example 35

Preparation of 3.0 Generation PAMAM/Isatoic Anhydride Conjugate

Generation 3.0 PAMAM, 2 g, was dissolved in methanol and cooled in an ice bath. To this solution was added 0.01 g of isatoic anhydride. The mixture was stirred for 2 hours, the bath allowed to warm to room temperature, and stirring continued for several days. The methanol was then removed by rotary evaporation and the product taken up in water. The solution was then dialyzed using a Spectrapor #1 membrane. The solution was then concentrated to 38 mL and its fluorescence spectrum run by using irradiation at 340 nm and detection at 420 nm. The fluorescence was still detectable after a 10,000 fold dilution, and the response was linear for dilutions of 100 and 1,000.

Example 36

Preparation of 4.0 Generation PAMAM dendrimer/DTPA/Gd Conjugate

A: Preparation of a 4.0 Generation PAMAM dendrimer, methyl ester terminated

A 3.5 generation PAMAM dendrimer, methyl ester terminated, was prepared by sequential reaction with methyl acrylate and ethylenediamine. Then to 1,000 g of predistilled ethylenediamine was added about 5 g of 3.0 generation PAMAM dendrimer, methyl ester terminated, as a 15 wt % solution in methanol. The solution was allowed to stand at room temperature for 48 hours. The methanol and most of the excess ethylenediamine were removed by rotary evaporation under vacuum at a temperature of less than 60° C. A total of about 7.5 g of product was recovered. To remove entrapped ethylenediamine, the product was dissolved in 100 mL of methanol and ultrafiltered two Centricon™ microconcentrator tubes (molecular weight cutoff: 2,000 Daltons). When most of the solution had passed through the membrane, several additional portions of methanol were added and the ultrafiltration process was repeated. The retentate was transferred to a round-bottomed flask and the filter cup was rinsed repeatedly with methanol and combined with the retentate. Volatile solvents were removed from the retentate solution by rotary evaporation under vacuum. About 6 g of 4.0 generation PAMAM (MW 5,147 Daltons, 24 terminal amino groups) was recovered.

B: Preparation of 4.0 Generation PAMAM dendrimer/DTPA Anhydride Conjugate

A solution of PAMAM (4 g, 7.6×10$^{-4}$ mol) in 300 mL of water was stirred in a three-neck flask. Over the next hour, 29 g (72×10$^{-3}$ mol) of the solid, N$^3$-(2,6-dioxomorpholinoethyl)-N$^6$-ethoxycarbonylmethyl-3,6-diazaoctane diacid (DTPA anhydride) was added by portions. During the addition the pH was maintained at 8.8–9.2 by the addition of 1N aqueous sodium hydroxide solution. When the addition was completed, the solution was stirred for an additional 30 minutes. The solution pH was adjusted to a pH of 7 by the addition of an ion exchange resin (H$^+$ form), and the resulting slurry was filtered by suction to remove the ion exchange resin. The filtrate was transferred to two Centricon™ microconcentrator tubes (molecular weight cutoff: 5,000 Daltons) and ultrafiltered. The filtrate was collected and freeze-dried. The yield was about 12 g of a colorless flaky power. The product was a polyamidoamide (24 terminal amino groups) having each terminus linked via an amide bond to one of the carboxyl groups of DTPA.

C: Preparation of 4.0 Generation PAMAM dendrimer/DTPA/Gd Conjugate

About 10 g of the chelating agent described above was dissolved in 600 mL of water and mixed with 2.8 g of Gd$_2$O$_3$. The slurry was stirred for about 90 minutes at 80° C. After cooling to room temperature, the solution pH was adjusted to 7 by the addition of an ion exchange resin. The resulting slurry was filtered by suction to remove the ion exchange resin. The filtrate was transferred to two Centricon™ microconcentrator tubes (molecular weight cutoff: 5,000 Daltons) and ultrafiltered. The filtrate was collected and freeze-dried. The yield was about 12 g of colorless, flaky lyophilizate, known to contain Gd by atomic absorption spectroscopic analysis.

Example 37

Preparation of a 3.0 Generation, Amino terminated Dendrimer/DTPA/Gd Conjugate

A: Preparation of a 3.0 Generation, Hydroxy terminated dendrimer

A 3.0 generation, hydroxy terminated dendrimer was prepared from pentaerythrityltetrabromide and 4-hydroxymethyl-2,6,7-trioxabicyclo[2.2.2]-octane as described by Tomalia et al. in U.S. Pat. No. 4,587,329, Example 11. Following the procedure of Step C of Example 11 of U.S. Pat. No. 4,587,329, the second generation hydroxy-terminated polyether dendrimer was converted to the corresponding perbromide. Then, following the procedures of Steps A and B of that Example, the brominated derivative of Step C was allowed to react first with a 4-hydroxymethyl-2,6,7-trioxabicyclo[2.2.2]-octane and then demasked with water to form the desired third generation dendrimer.

B: Preparation of a 3.0 Generation, Chloride terminated dendrimer

A 500 mL, three-neck flask equipped with a stirrer, condenser and addition funnel is charged with a 0.1 mole of the third generation dendrimer from Part A and 15 mole of freshly distilled thionyl chloride is added at a rate to maintain the temperature below 45° C. Upon completion of the addition, the solution is warmed to about 50° C. and maintained at this temperature for about 4 hours. The excess thionyl chloride is removed under vacuum. By this process the hydroxy groups are converted to chloride moieties.

C: Preparation of a 3.0 Generation, Amino terminated dendrimer

The chloride terminated dendrimer from Part B was transferred to a large polyolefin bottle and a large excess of ammonium hydroxide solution was added. The bottle was sealed and the contents were stored at about 55° C. for several days. The solution formed a residual oil which was redissolved in a small volume of water, the pH adjusted to 8 by addition of sodium bicarbonate, and the desired amine was extracted with chloroform. The chloroform extracts were dried over anhydrous magnesium sulfate, filtered and concentrated to a residual oil. By this process the chloride terminated dendrimer was converted to an amino terminated dendrimer.

D: preparation of a 3.0 Generation, Amino terminated dendrimer

Alternatively, the hydroxy terminated dendrimer from Part A was dissolved in dimethylformamide and allowed to react with an excess of methanesulfonyl chloride. The resulting tosylate ester was isolated by dilution of the dimethylformamide with water and extraction with chloroform. The chloroform extracts were washed with dilute sodium bicarbonate solution and with water, then dried over anhydrous magnesium sulfate. After filtration to remove any solids, the filtrate was concentrated to dryness. The residual oil, the desired polymethanesulfonate ester, was used without further purification, was transferred to a large polyolefin bottle and a large excess of ammonium hydroxide solution was added. The bottle was sealed and the contents were stored at about 55° C. for several days. The amino-terminated dendrimer was isolated as described above in Part C.

E: Preparation of a 3.0 Generation, Amino terminated dendrimer/DTPA Conjugate

A mixed anhydride of DTPA was prepared by reaction of diethylenetriaminepentaacetic acid (DTPA) and isobutyl chloroformate. The anhydride (1 mole) was dissolved in dimethylformamide, and the solution was added to a solution of amine-terminated dendrimer (from either Part C or D) in the same solvent. To the solution was added 2,6-lutidine as necessary to maintain a basic environment. By this means, covalent bonds were formed between the amino terminus of the dendrimer and the carboxyl group of DTPA.

F: Preparation of a 3.0 Generation, Amino terminated dendrimer/DTPA Conjugate

Alternatively, 1 mmole of an amine-terminated dendrimer (from either Part C or D) was dissolved in 300 mL of water. Within 2 hours, 150 mmol of the solid form of $N^3$-(2,6-dioxomorpholinoethyl)-$N^6$-ethoxycarbonylmethyl-3,6-diazaoctane.diacid was added by portions to the solution. The pH was maintained at about 9.0 by the addition of 1N sodium hydroxide. The solution was stirred for an additional 30 minutes, the pH adjusted to 7.0 with an ion exchange resin ($H^+$), and then filtered to remove the ion exchange resin. The solution was placed into two Centricon ™ microconcentrator tubes (molecular weight cutoff: 5,000 Daltons) and ultrafiltered. The filtrate was collected and freeze-dried. The DTPA-conjugated dendrimer was obtained as a colorless flaky powder.

G: Preparation of a 3.0 Generation, Amino terminated dendrimer/DTPA/Gd Conjugate About 10 g of the DTPA-conjugated dendrimer was dissolved in 600 mL of water for injection and mixed with about 3 g of $Gd_2O_3$. The slurry was stirred for about 90 minutes at 80° C. After cooling, the solution pH was adjusted to 7 by the addition of an ion exchange resin. The solution was filtered to remove the resin and then ultrafiltered as described above. The filtrate was collected and freeze-dried. The Gd/DTPA-conjugated dendrimer was obtained as a colorless, flaky lyophilizate containing Gd by atomic absorption spectroscopy analysis.

Example 38

Zero Valent Nickel In Dendrimers

To 10 g of 1% $NiCl_2$ (aqueous) was added 177 mg generation 0.5 diethylenetriamine (DETA) Core STARBURST™ dendrimer (Na-salt form). The solution turned pale blue. To this solution was added 0.5 mL of 28% aqueous ammonium hydroxide, causing the solution to turn a darker blue. Addition of 12 g of 2.78% aqueous sodium hypophosphite to the solution and then heating to boiling gave a precipitate of nickel metal with a supernatant blue solution. The supernatant was concentrated in vacuo to give the metallized dendrimer as a mixture with excess phosphites (0.6 g). Purification was carried out by ultrafiltration on a hollow fiber filtration unit (The Dow Chemical Company). (A control reaction, carried out the same as above except that no dendrimer was added, gave a colorless solution with complete precipitation of nickel metal after boiling.)

Example 39

Zero Valent Nickel In Dendrimers

To 10 g of 1% aqueous $NiCl_2$ was added 270 mg of generation 1.5 linear polyethyleneimine (PEI) core STARBURST™ dendrimer (sodium carboxylate form). The solution turned a darker green than the control mixture (no STARBURST™ added). After addition of 0.5 mL of concentrated ammonium hydroxide, the control was blue and the STARBURST™ containing solution was still green. Addition of 12 g of 2.78% aqueous sodium hypophosphite and heating to boiling caused, in the control, precipitation of black nickel metal and gave a colorless solution. The STARBURST™ containing solution gave a pale green suspension under the same conditions. The pale green suspension was centrifuged to remove a small amount of solids (50 mg) and concentrated in vacuo to give 500 mg of pale green powder. Ultrafiltration of an aqueous solution of this mixture of metallized dendrimer and phosphites using an Amicon™ YM2 membrane was continued until no more green color was seen in the filtrate. Concentration in vacuo of the green retentate solution gave approximately 100 mg of a dark green glass.

Example 40

Preparation of Epoxyoctane modified Generation 5.0 PAMAM Dendrimer

Generation 5.0 PAMAM dendrimer, 0.30 g (2.7 meq) was dissolved in 10 mL of methanol. Epoxyoctane, 0.5 g, (Aldrich, 3.9 mmol) was added to the solution. The solution was then heated at 40° C. in an oil bath for 3 days. The solvent was removed by distillation in vacuo, then the residue was devolatilized at room temperature under high vacuum to give 0.60 g (93% of theory) of the modified dendrimer as a colorless oil. The $^{13}C$ and $^1H$ NMR spectra indicated attachment at the surface by epoxyoctane and is consistent with the association of the epoxyoctane dendrimer.

When the above procedure was repeated using generation 2.0, 3.0, 4.0, 6.0 or 7.0 PAMAM dendrimer, the corresponding conjugate was formed.

Example 41

Preparation of Abscisic Acid modified Generation 4.5 PAMAM Dendrimer

An aqueous solution of a generation 4.5 PAMAM dendrimer was hydrolyzed by NaOH/MeOH (1 mM, 10 mL) and the pH adjusted to 11 by NaOH/HCl. To the solution was added a large excess of solid abscisic acid. The solution was stirred vigorously at room temperature. After 1, 2, 6 and 24 hours, 500 μL of the solution was removed into an Eppendorf tube (1.5 mL microcentrifuge tube) and any undissolved abscisic acid removed by centrifugation at 15,000 rpm for 1 minute. The abscisic acid concentration was calculated from the absorbance of the supernatant ($\lambda=260$ nm, $\epsilon=19400$).

When the procedure was repeated using different generations of PAMAM dendrimers, the higher the generation, the more abscisic acid was dissolved. The generation 5 and 6 dendrimers dissolved more of the acid than generation 4. At pH=7, only 0.004M of the abscisic acid dissolved in water and β-CD solution, while the dendrimer solutions dissolved 0.02–0.08M. The half-generations of dendrimers dissolved the same amounts of acid as the whole generations. Thus the abscisic acid is believed to be taken into the dendrimer interior.

When the above procedure was used with nifedipine ($\epsilon=8300$ in chloroform), the nifedipine took a long time to dissolve in water, but once dissolved, it was taken into the dendrimer very rapidly.

Examples Relating to Carrying Genetic Material and Gene Transfection

Examples 42 on relate to carrying and transfecting genetic material. Example 43 is directed to the preparation of dendrimers with particular target directors which are exemplary of those which would be useful in transfecting cells with genetic material. Examples 42 and 44–78 utilize one or more of the following techniques:

1. Transfection
2. Electrophoresis
3. Cytotoxicity determinations
4. Radiographic analysis
5. Cell photography

PROTOCOL FOR DENDRIMER-DEXTRAN TRANSFECTION

The protocol for transfection is basically as follows:
Day 1: Seed 6-well plates with approximately 200,000 cells per well (dependent on growth characteristics).
Day 2:
Step 1:
Prepare the following solutions:
  A. Dendrimer Dilution Buffer
    20 mM HEPES pH 7.9
    100 mM KCl
    0.2 mM EDTA
    0.5 mM DTT
    20% (v/v) glycerol
  B. 10×Binding Buffer
    10 mM EDTA
    40% (v/v) glycerol
    50 mM DTT
    100 mM TRIS HCl pH 7.5
    1000 mM NaCl Mix and filter sterilize.
  C. Solution 1 (used in some examples)
    25 mg DEAE-dextran (Pharmacia or Sigma Chemical)
    5.0 mL 1M TRIS pH 7.4
    95 mL serum-free DMEM
    Mix in 37° C. shaker for 30 minutes, filter sterilize (1 mL of Solution 1 is needed for each well)
  D. Solution 2 (used in some examples)
    10% DMSO in PBS pH 7.4
    Mix and filter sterilize (2 mL of Solution 2 are needed for each well)
Step 2
  Prepare DNA/dendrimer complexes:
    (20 μL of complex will be needed for each well)
    Place an appropriate volume of 10×Binding Buffer and H₂O in a sterile Eppendorf™ tube.
    Add diluted dendrimer followed by DNA.
    (Conc. stocks of dendrimers should be suspended in water, free of methanol, if possible. Dilute dendrimers in Dilution Buffer to a concentration approximately 10×the final concentration before adding to Binding Buffer.
    Although the complex appears to form immediately upon mixing, the mixture should stand for 3 to 15 minutes to allow complex formation.

DNA/DENDRIMER COMPLEXING EXAMPLE:
RSV-luc DNA and G10 (EDA) Dendrimer

The 7.2 kb RSV-luc plasmid DNA has $1.71 \times 10^{15}$ (−) charges per μg. G10 (EDA) dendrimer has $2.64 \times 10^{15}$ (+) charges per μg. Therefore, a charge ratio of 1:10 requires a ratio of 1 μg DNA to 6.5 μg dendrimer. Stock G10 (EDA) is at a conc. of 236.4 μg/μL. A dilution of 364 in dilution buffer yields 0.65 μg/μL. To make 20 μL of complexes (enough to transfect 1 μg of DNA into one well of cells in a 6-well plate), combine 2 μL of 10× Binding Buffer, 7 μL of sterile H₂O, 10 μL of diluted dendrimer, and 1 μL of DNA (at 1 μg/μL). If more than one well is to be transfected or larger amounts of DNA are to be used, simply prepare a larger volume of complexes using the same proportions of Binding Buffer, dendrimer, and DNA.
Step 3
  Wash cells 2× with 2 mL serum-free media.
Step 4
  Add 1 mL of Solution 1 to each well.
Step 5
  Add 20 μL of DNA/dendrimer complexes to each well. Mix by gently shaking the plate.
Step 6
  Incubate for 3 hours at 37° C.
Step 7
  Wash 1× with 2 mL serum-free DMEM.
Step 8
  Shock cells with Solution 2, 2 mL per well, for 2 minutes.
Step 9
  Wash cells 2× with 2 mL serum-free DMEM.
Step 10
  Replace media with DMEM with 5% Serum. Incubate overnight at 37° C.
Day 3
  Prepare the following solutions:
  Solution 4 Cell Culture Lysis 1× Reagent
    25 mM TRIS-phosphate pH 7.8
    2 mL DTT
    2 mM 1,2-diaminocyclohexane-N,N,N',N'-tetraacetic acid 10% glycerol
1% Triton X-100
Solution 5 Luciferase Assay Reagent
2 mM TRIS glycine
1.07 mM (MgCO$_3$)Mg(OH)$_2$.5H$_2$O
2.67 mM MgSO$_4$
0.1 mM EDTA
33.3 mM DTT
270 µM Coenzyme A
40 µM Luciferin™
530 µM ATP; adjust to final pH of 7.8

Step 1
Rinse cells 2× with 2 mL of 1× PBS pH 7.4 (Mg++, Ca++ free)

Step 2
Add 200 µL of Solution 4 to each well and let sit for 15 min. at 27° C.

Step 3
Scrape cells and collect in Eppendorf™ tubes.

Step 4
Determine protein concentration of each cell lysate.

Step 5
Aliquot no more than 20 µL of each cell lysate into Eppendorf™ tubes.

Step 6
Add 80 µL Solution 5 and immediately measure chemiluminescence.

Several different types of genetic material were used in the examples. Unless otherwise indicated, the DNA used was a bacterial expression plasmid (RSV-luc) which contains the gene for luciferase enzyme that is expressed by a promoter from the Respiratory Syncitial Virus (RSV). The concentration of genetic material with respect to dendrimer was determined either based on charge ratio of DNA:dendrimer desired or molar ratio, as indicated in a particular example. In the transfection examples, sufficient DNA:dendrimer complex was used so that one microgram (µg) of DNA was added per test well (approximately 200,000 cells), unless otherwise indicated.

In most of the examples, dense star PAMAM dendrimers are used. The generation and hence diameter of the dendrimers vary, as do the cores, and in some cases also the surface functionalities.

Several different cell lines were successfully transfected. Unless otherwise indicated in the example, RAT2 cells are being transfected.

Where DEAE-dextran is used in the examples, the concentration is 0.5 µM, unless otherwise indicated. Also, unless otherwise indicated, the quantity of DNA in DNA::dendrimer complex used is 1.0 µg per test well.

ELECTROPHORESIS

The agarose gels used in electrophoresis are placed in electric field with the cathode at the top of the gel (as viewed in the Figures) and the anode at the bottom of the gel (as viewed in the Figures). The gels are stained with ethidium bromide, which binds to the DNA and fluoresces, thus indicating the extent to which the DNA has migrated in the gel. In some examples, lanes were started both at the top of the gel plate and in the middle thereof, with migration being towards the bottom of the figure in each case. Complexing and charge neutralization of the DNA is presumed to occur when migration towards the anode is retarded.

To the extent not described above, the experimental techniques used in the examples are known to those of ordinary skill in the art and available in the literature, making further description unnecessary.

Example 42

Preparation of dendrimer conjugates with genetic material, and experiments (FIGS. 17–19)

In this series of experiments, various dendritic polymers were complexed with DNA and transfected under various conditions. The DNA complexed to the dendrimer was dual column cesium gradient purified RSV-luc plasmid. Transfection of the DNA expression plasmid results in the successful transcription and translation of the luciferase gene. This produces luciferase protein, an enzyme which catalyzes the break-down of LUCIFERIN™, resulting in the generation of measurable light. Quantitation of the amount of light produced is a measure of the degree of success of transfection of this gene.

The dendrimers tested were as follows:

A. A G8 (NH$_3$) dense star dendrimer having a molecular weight (MW) of approximately 87,342 and a diameter of approximately 76 Å.

B. A G6 (NH$_3$) dense star dendrimer having a MW of approximately 21,591 and a diameter of approximately 53 Å.

C. A G5 (NH$_3$) dense star dendrimer having a MW of approximately 10,633 and a diameter of approximately 40 Å.

D. A G7 (NH$_3$) dense star dendrimer having a MW of approximately 43,508 and a diameter of approximately 67 Å.

E. A G3 (NH$_3$) dense star dendrimer having a MW of approximately 2,414 and a diameter of approximately 22 Å.

F. A G4 (NH$_3$) dense star dendrimer having a MW of approximately 5,154 and a diameter of approximately 31 Å.

G. A G2 (NH$_3$) dense star dendrimer having a MW of approximately 1,044 and a diameter of approximately 15.8 Å.

H. A G1 (NH$_3$) dense star dendrimer having a MW of approximately 359 and a diameter of approximately 10.4 Å.

I. A G1 (EDA) dense star dendrimer having a MW of approximately 517 and a diameter of approximately 14 Å.

J. A G2 (EDA) dense star dendrimer having a MW of approximately 1,430 and a diameter of approximately 19 Å.

K. A G3 (EDA) dense star dendrimer having a MW of approximately 3,256 and a diameter of approximately 26 Å.

L. A G4 (EDA) dense star dendrimer having a MW of approximately 6,909 and a diameter of approximately 36 Å.

M. A G5 (EDA) dense star dendrimer having a MW of approximately 14,215 and a diameter of approximately 44 Å.

N. A G6 (EDA) dense star dendrimer having a MW of approximately 28,826 and a diameter of approximately 57 Å.

O. A G7 (EDA) dense star dendrimer having a MW of approximately 58,048 and a diameter of approximately 72 Å.

P. A blend of dense star dendrimers in the following percentages:
1. G6 (NH$_3$) 58.8%
2. G5 (NH$_3$) 30.5%
3. G2 (EDA) 1.86%
4. G2 (NH$_3$) 1.10%
5. G1 (EDA) 3.37%

6. G1 (NH$_3$) 4.41%

Q. A blend of dense star dendrimers in the following percentages:
1. G6 (NH$_3$) 60.0%
2. G5 (NH$_3$) 31.1%
3. G2 (EDA) 1.90%
4. G2 (NH$_3$) 1.12%
5. G1 (EDA) 1.30%
6. G1 (NH$_3$) 4.50%

R. A G6 (NH$_3$) partially degraded dense star dendrimer.

S. A G7 (NH$_3$) partially degraded dense star dendrimer.

Essential data on these dendrimers is set forth in Table XII below:

TABLE XII

| Dendrimer | MW | Surface NH$_2$ Groups | Minimum Dendrimer Quantity$^a$ | |
|---|---|---|---|---|
| | | | 0.5 µg$^c$ DNA | 1 µg$^c$ DNA |
| A | 87,342 | 384 | 0.1 µg | ND |
| B | 21,591 | 96 | 0.1 µg | ND |
| C | 10,633 | 48 | 0.1 µg | ND |
| D | 43,508 | 192 | 0.1 µg | ND |
| E | 2,414 | 12 | * | 0.5 µg |
| F | 5,154 | 24 | * | 0.1 µg |
| G | 1,044 | 6 | * | * |
| H | 359 | 3 | * | * |
| I | 517 | 4 | * | * |
| J | 1,430 | 8 | 0.5 µg | ND |
| K | 3,256 | 16 | 0.1 µg | ND |
| L | 6,909 | 32 | 0.1 µg | ND |
| M | 14,215 | 64 | 0.1 µg | ND |
| N | 28,826 | 128 | 0.1 µg | ND |
| O | 58,048 | 256 | 0.1 µg | ND |
| P | 25,951 | 96 | * | 0.1 µg |
| Q | 25,951 | 96 | * | 0.1 µg |
| R | b | b | 0.001 mg | ND |
| S | b | b | 0.001 µg | ND |

* = no binding observed
$^a$ = a minimum amount of dendrimer required to totally complex DNA (totally retard any gel migration of the DNA toward the anode)
$^b$ = mixtures, varied size; see previous pages in the Example for definition
$^c$ = minimum amount of dendrimer required to totally complex DNA
ND = Not determined Table XII shows that all of the dendrimers, other than NH$_3$ core of generation less than G4 (G, H, I), can bind and complex/charge neutralize DNA.

In order to determine whether dendrimers complexed with DNA would be useful for transfection, experiments were carried out under a variety of conditions.

FIG. 17 shows the results of the transfection of samples into RAT2 cells, with the light units measured per microgram of cellular protein for each of the different conditions, annotated by numbers 1–18, as indicated in Table XIII below:

TABLE XIII

| Sample No. | Dendrimer or Control | Charge Ratio DNA:Dendrimer | Condition |
|---|---|---|---|
| 1 | D | 1:0.7 | a |
| 2 | S | 1:0.7 | a |
| 3 | Q | 1:0.8 | a |
| 4 | D | 1:3.3 | a |
| 5 | S | 1:3.3 | a |
| 6* | RAT2 untransfected | NA | a |
| 7 | D | 1:0.7 | b |
| 8 | S | 1:0.7 | b |
| 9 | Q | 1:0.8 | b |
| 10 | D | 1:3.3 | b |
| 11 | S | 1:3.3 | b |
| 12* | Dex alone | NA | b |
| 13 | D | 1:0.7 | c |
| 14 | S | 1:0.7 | c |
| 15 | Q | 1:0.8 | c |
| 16 | D | 1:3.3 | c |
| 17 | S | 1:3.3 | c |
| 18* | RSV + hsDNA-Dex | NA | c |

* = controls
NA = not applicable
a = DNA and dendrimer complexed in Binding Buffer, and transfected in DMEM.
b = DNA and dendrimer complexed in HBS, and transfected in DMEM.
c = DNA and dendrimer complexed in Binding Buffer, and transfected in DEAE-dextran.

Samples 6, 12, and 18 are the controls. Sample 6 is untransfected RAT2 cells. Sample 12 is similar to Sample 6 but has DEAE-dextran added. In Sample 18, transfection is attempted using the vector and herring sperm DNA in the presence of DEAE-dextran. Data in Table XIII shows that dendrimers of generation lower than G8 do not mediate transfection unless the DNA:dendrimer complexes are placed in DEAE-dextran.

In order to confirm these results using a wider range of DNA:dendrimer charge ratios, the studies illustrated by FIG. 18 were performed. Test parameters are shown in Table XIV below:

TABLE XIV

| Sample No. | Dendrimer or Control | Charge Ratio DNA:Dendrimer | Condition |
|---|---|---|---|
| 1 | D | 1:14.6 | c |
| 2 | D | 1:3.3 | c |
| 3 | D | 1:1.2 | c |
| 4 | D | 1:0.6 | c |
| 5 | D | 1:0.3 | c |
| 6 | D | 1:0.15 | c |
| 7 | S | 1:14.6 | c |
| 8 | S | 1:3.3 | c |
| 9 | S | 1:1.2 | c |
| 10 | S | 1:0.6 | c |
| 11 | S | 1:0.3 | c |
| 12 | S | 1:0.15 | c |
| 13 | D | 1:14.6 | b |
| 14 | D | 1:3.3 | b |
| 15 | D | 1:0.6 | b |
| 16 | S | 1:14.6 | b |
| 17 | S | 1:3.3 | b |
| 18 | S | 1:0.6 | b |
| 19 | D | 1:0.03 | c |
| 20 | S | 1:0.03 | c |
| 21 | RSV Dex* | NA | NA |
| 22 | RSV + hsDNA Dex* | NA | NA |
| 23 | Dex alone* | NA | NA |
| 24 | HBS alone* | NA | NA |

* = controls
NA = not applicable
b = DNA and dendrimer complexed in HBS, and transfected in DMEM.
c = DNA and dendrimer complexed in Binding Buffer, and transfected in DEAE-dextran.

Controls 21–24 comprise the vector in DEAE-dextran, the vector and herring sperm DNA in DEAE-dextran, DEAE-dextran and HBS, respectively.

The results demonstrate that the DNA-dendrimer complexes are surprisingly more efficient in transfection of cells in the presence of DEAE-dextran. They also suggest that for pure dendrimers having amino (positive charge) surface functionality, only complexes with excess dendrimer positive charges are capable of efficient transfection (see lane 4, FIG. 18).

Transfection capability for a broad spectrum of different dendrimers is demonstrated (A–S) in FIG. 19. A bar graph of relative light units per microgram of protein, from cells transfected with DNA complexed with different dendrimers (A–S) in the presence of DEAE-dextran is presented. Three different charge ratios of DNA to dendrimer were utilized: 1:2, 1:10 and 1:20 in duplicate. Thus, there are six bars for each dendrimer A–S in FIG. 19, the first two showing transfection at a DNA:dendrimer charge ratio of 1:2, the second pair at 1:10 and the third pair 1:20. The control (RSVa) comprises transfection of plasmid DNA done in the presence of DEAE-dextran. It can be seen that for various ratios of DNA:dendrimer, successful transfection, transcription and translation, varies according to the certain type of dendrimer used.

Example 43

Electronmicroscopy of DNA:dendrimer complexes in the presence and absence of DEAE-dextran. (FIG. 60, Panels 3, 4 and 5)

The addition of DEAE-dextran or other agents to the DNA:dendrimer complex after it has been formed has been shown to be effective in enhancing transfection in a unique manner. In order to further understand the role of these agents in altering non-specific transfection, electronmicrographs were made of DNA:dendrimer complexes with and without the addition of DEAE-dextran. In this example, DNA was complexed with dendrimers as indicated below in FIG. 60.

Panel 3—DNA:dendrimer G11 (EDA) dendrimer in a charge ratio of 1:10

Panel 4—DNA:dendrimer G11 (EDA) dendrimer in 0.5 µM of DEAE-dextran

Panel 5—DNA complexed with polydispersed mixture of dendrimers (compound B) in a charge ratio of 1:10

In FIG. 60, panels 3, 4 and 5 represent electronmicrographs of DNA:dendrimer complexes. The DNA was complexed with G11 (EDA) dendrimer at a DNA:dendrimer charge ratio of 1:10 in 1 mM TRIS, pH 7.8. In this condition electronmicroscopy revealed that DNA:dendrimer complexes form large irregular aggregates not observed with a dendrimer alone (FIG. 60, Panel 3). The addition of DEAE-dextran to a final concentration of 0.5 µM reduced the size of the DNA:dendrimer complexes dramatically (FIG. 60, Panel 4). Smaller size complexes (and complete absence of e.g., large aggregates) were also seen when DNA was complexed with polydispersed mixtures of dendrimers described as compound B) at a charge ratio of 1:10. That result provides a rationale for why these agents may enhance transfection. While not wishing to be bound by theory, it is likely that the smaller complex size that is achieved with these agents is more likely to gain access to the cells and achieve transfection.

Example 44

Comparison of the DNA binding and transfection capability of dendrimers with and without surface substitutions at different DNA:dendrimer charge ratios (FIGS. 12 and 13)

In order to determine the effect of reducing the surface charge of the dendrimer on transfection efficiency, the following experiment was conducted. DNA-dendrimer complexes were prepared in the charge ratios indicated, for the various dendrimers listed in Table XV below. As before, the "G" number indicates the generation of the dendrimer; and the "$NH_3$" or "EDA" designation indicates the dendrimer core. The substituted dendrimers are represented as samples 26–31 in FIG. 12 and lane 26–31 in FIG. 13. Substituted dendrimers had positive surface charge amines modified by reaction with acrylic acid. Therefore, in these substituted dendrimers, the numbers of surface amino groups are decreased. Thus a 25% substituted G6 ($NH_3$) dendrimer theoretically has had 25% of its surface amino groups reacted with carboxyl groups of acrylic acid. In a 100% substituted G6 dendrimer, each surface amino group has been reacted with a carboxyl group. Therefore, the functional positive charge on these dendrimers that is available for interaction with negatively charged DNA is reduced. Items 1 and 32 in Table XV below are the "plasmid controls," or in other words DNA alone.

TABLE XV

| Lane No. | Generation & Core | DNA:dendrimer Charge Ratio |
|---|---|---|
| 1 | Plasmid alone | Control |
| 2 | G5 ($NH_3$) | 1:1 |
| 3 | G5 ($NH_3$) | 1:5 |
| 4 | G5 ($NH_3$) | 1:10 |
| 5 | G5 (EDA) | 1:1 |
| 6 | G5 (EDA) | 1:5 |
| 7 | G5 (EDA) | 1:10 |
| 8 | G6 ($NH_3$) | 1:1 |
| 9 | G6 ($NH_3$) | 1:5 |
| 10 | G6 ($NH_3$) | 1:10 |
| 11 | G6 (EDA) | 1:1 |
| 12 | G6 (EDA) | 1:5 |
| 13 | G6 (EDA) | 1:10 |
| 14 | G7 ($NH_3$) | 1:1 |
| 15 | G7 ($NH_3$) | 1:5 |
| 16 | G7 ($NH_3$) | 1:10 |
| 17 | G7 (EDA) | 1:1 |
| 18 | G7 (EDA) | 1:5 |
| 19 | G7 (EDA) | 1:10 |
| 20 | G4 ($NH_3$) | 1:1 |
| 21 | G4 ($NH_3$) | 1:5 |
| 22 | G4 ($NH_3$) | 1:10 |
| 23 | G4 (EDA) | 1:1 |
| 24 | G4 (EDA) | 1:5 |
| 25 | G4 (EDA) | 1:10 |
| 26 | G6 ($NH_3$)[a] | 1:1 |
| 27 | G6 ($NH_3$)[a] | 1:5 |
| 28 | G6 ($NH_3$)[a] | 1:10 |
| 29 | G6 ($NH_3$)[b] | N.A. |
| 30 | G6 ($NH_3$)[b] | N.A. |
| 31 | G6 ($NH_3$)[b] | N.A. |
| 32 | Plasmid alone | Control |

[a] = 25% substituted
[b] = 100% substituted
N.A. = Not applicable; 100% substituted dendrimers were mixed in the same amounts as the 25% substituted dendrimers Samples of the DNA:dendrimer complexes in solution were added to cells for transfection in accordance with the protocol for dendrimer transfection described above, in the presence of DEAE-dextran at a concentration of 0.5 µM. As can be seen in FIG. 12, it is also noted that the G6 dendrimers are more efficient (compare columns 8–19 with columns 2–7 and columns 20–25). Where the surface of the dendrimer has been 25% substituted with negative functionality, it is necessary that the charge ratio of DNA to dendrimer be lowered.

Dendritic complexes and control Samples 1–32, as listed in Table XV were placed in agarose gels for electrophoresis (See FIG. 13). Lanes 1 and 32 indicate the extent to which the DNA alone migrated through the gel (FIG. 13). Lanes 2–28 show no migration, indicating that the DNA has complexed with the dendrimer and hence migration through the gel is retarded. However, migration was seen for lanes 29–31, where the dendritic polymers have reduced positive charge functionality. Some residual positive charge activity is apparent even in the 100% substituted dendrimers because retardation is seen at lower DNA:dendrimer ratios (lanes 30–31). The results from FIGS. 12 & 13 indicate that positive surface charge density in the dendrimer was important in DNA binding, complexing and transfection.

Example 45

Increase in DNA transfection efficiency as a function of dendrimer generation as compared to a DEAE-dextran control (FIG. 14)

In this example, complexes of DNA and dendrimer were prepared using G2 through G8 ($NH_3$) dendrimers and G3 through G11 (EDA) dendrimers. Their ability to transfect DNA into RAT2 cells, in the presence of DEAE-dextran, was compared to the degree of transfection achieved using only DNA and DEAE-dextran. The percent increase in transfection for each of the dendrimers as compared to the DNA/DEAE-dextran control is indicated in FIG. 14. This figure documents that transfection efficiency increased exponentially as the generation of dendrimer increased, from generation five through ten. This suggests that increasing surface area and charge of the dendrimers increases efficiency of transfection.

Example 46

Determination of effect of sequential addition of G9 and G5 dendrimers on transfection efficiency in RAT2 cells in the absence of DEAE-dextran (FIGS. 15 and 16)

In this example, either:

1. DNA was first complexed with a G9 dendrimer, and a solution which contained a G5 dendrimer was added; or
2. DNA was first complexed with a G5 dendrimer, and then a solution which contained a G9 dendrimer was added.

The results obtained when EDA core dendrimers were used are indicated in FIG. 15, while the results for ammonia core dendrimers are indicated in FIG. 16. In both FIGS. 15 and 16, the concentration of the second dendrimer added to the complex is indicated on the abscissa of the bar graph. In the first column, the "zero" concentration is a control where no second dendrimer was used.

In both cases the initial dendrimers of G9 and G5 generations were added to achieve 0.5 µM and 20.0 µM concentration, respectively. In each case, the G5 dendrimer has an approximate diameter of about 40 Å, while the G9 dendrimer has a diameter of approximately 88 Å. In both cases, spherical dense star dendrimers are used. When the G9 dendrimer was added to the G5 DNA:dendrimer complex, substantially superior transfection results are typically achieved, as compared to adding a G5 dendrimer to a previously complexed G9 dendrimer. This indicates that DNA:dendrimer complex formation may involve two steps; namely, complexing and contracting DNA, followed by "covering" the complex with a positive charge for adherence to cells. The latter of these two steps appears to prefer a larger diameter dendrimer with greater surface charge density.

Example 47

Comparison of the complexing properties and transfection ability of several ($NH_3$) dendrimers with DNA fragments (FIGS. 20 and 21)

In this example, relatively small fragments of DNA were complexed with different dendrimers. In the data shown in FIG. 20, a 15 nucleotide synthetic single stranded DNA was complexed with G2 through G7 ($NH_3$) dendrimers at the DNA:dendrimer charge ratios indicated in Table XVI below.

TABLE XVI

| Lanes | DNA:Dendrimer Charge Ratio | Dendrimer |
|---|---|---|
| 1 | 6:1 | G6 ($NH_3$) |
| 2 | 1:1 | G6 ($NH_3$) |
| 3 | 1:1.5 | G6 ($NH_3$) |
| 4 | 6:1 | G7 ($NH_3$) |
| 5 | 1:1 | G7 ($NH_3$) |
| 6 | 1:1.5 | G7 ($NH_3$) |
| 7 | 6:1 | G3 ($NH_3$) |
| 8 | 1:1 | G3 ($NH_3$) |
| 9 | 1:1.5 | G3 ($NH_3$) |
| 10 | 6:1 | G4 ($NH_3$) |
| 11 | 1:1 | G4 ($NH_3$) |
| 12 | 1:1.5 | G4 ($NH_3$) |
| 13 | 5:1 | G2 ($NH_3$) |
| 14 | 1:1 | G2 ($NH_3$) |
| 15 | 1:2 | G2 ($NH_3$) |
| 16 | — | * |

* DNA Size Marker

FIG. 20 shows an agarose gel electrophoresis of the various complexes. As can be seen in columns 1, 4, 7 and 10, there was substantial migration of the oligonucleotide. This indicated that stable complexes did not form at a DNA:dendrimer charge ratio of 6:1. However, the lack of oligonucleotide migration in columns 2, 3, 5, 6, 8, 9, 11, and 12 indicated that the synthetic oligonucleotide DNA forms stable complexes with G3–G7 ($NH_3$) dendrimers at charge ratios of 1:1 and 1.5. Columns 13–15 indicate that the oligonucleotide did not form stable complexes at any charge ratio with G2 ($NH_3$) dendrimers.

The successful transfer of a radiolabeled 23 base pair (bp) double stranded oligonucleotide complexed with a G8 ($NH_3$) dendrimer (at a charge ratio of 1:10) is indicated in FIG. 21. Since the oligomer was not a functional reporter gene, successful transfer was measured by the uptake of the radiolabeled DNA. The radioactive counts within the cells after transfer is charted on the ordinate in FIG. 21, against the time following initiation of transfer on the abscissa.

The finding that the DNA-dendrimer uptake into the cell was energy dependent was indicated by the data showing that the addition of sodium azide to the complex lowered the degree of transfer substantially, almost to the level achieved for the oligonucleotide alone. This indicated that dendrimers can facilitate the uptake by cells of low molecular weight nucleic acids.

Example 48

Transfection of circular (supercoiled) and linearized RSV-luc in RAT2 cells using G8 ($NH_3$) dendrimers and G11 (EDA) dendrimers, with and without DEAE-dextran (FIG. 22)

In this example, the RSV-luc gene was complexed with G8 ($NH_3$) and G11 (EDA) dendrimers, either in its circular (supercoiled) form or in linear form. Linearization was achieved using a single site specific restriction endonuclease. In FIG. 22 on the horizontal axis, the bars numbered 1, 3, 5 and 7 represent plasmid in linear form, whereas the bars numbered 2, 4, 6 and 8 represent plasmid in circular form of the DNA. FIG. 22 illustrates the fact that transfection of both the linear and the circular form of the DNA was achieved using either a G8 ($NH_3$) or a G11 (EDA) dendrimer, and that transfection is enhanced in all cases when DEAE-dextran is employed.

Example 49

Unique DNA binding properties of dendrimers (FIG. 23)

In this example, the preferred DNA:dendrimer charge ratios and binding conditions for effective formation of stable DNA-dendrimer complexes were determined. DNA-dendrimer complexes were formed in charge ratios of about 40:1 to 1:50 (FIG. 23 and Table XVII below):

TABLE XVII

| Lane | DNA:Dendrimer Charge Ratio |
|---|---|
| 1 | a |
| 2 | b |
| 3 | 40:1 |
| 4 | 20:1 |
| 5 | 10:1 |
| 6 | 2:1 |
| 7 | 1:1 |
| 8 | 1:5 |
| 9 | 1:10 |
| 10 | 1:20 |
| 11 | 1:25 |
| 12 | 1:50 | a = DNA Size Marker
b = Control - DNA without dendrimer

Electrophoresis was performed on these complexes in the gels shown in FIGS. 23 (a–d). Lane 1 in each of the electrophoretic gels is the DNA size marker and lane 2 is the DNA control, i.e., without dendrimer. In gels A and B in FIG. 23, a G8 (NH$_3$) dendrimer was used to complex the DNA. In gels C and D of FIG. 23, a G8 (EDA) dendrimer was used. In the upper panels (23a and c), the complexes were formed in the presence of dithiotreitol (DTT), which eliminates (by reduction of disulfide bonds) any protein impurities, and exposed to EDTA, which would complex any cations present which might precipitate the DNA. These two steps remove contaminants that might falsely indicate DNA:dendrimer complexes. The results further indicate that complex formation does not require reducing conditions or presence of metal ions.

The results for panels A and C are comparable to the results obtained in panels B and D. DNA complexed with dendrimers at charge ratios of 20:1 or greater did not form stable complexes (see lanes 2–5 in plates A–D of FIG. 23). Retardation of the DNA:dendrimer complexes, begins at a DNA:dendrimer charge ratio of 2:1 and continues through a charge ratio of 1:50 (see lanes 6–12 in each of panels a–d of FIG. 23). This indicates that the DNA continues to be complexed to the dendrimer even at low DNA:dendrimer charge ratios.

Example 50

DNA binding properties of dendrimers were primarily a function of charge ratio (FIG. 24)

In this example, 0.2 μg of plasmid DNA (2.9 kb) was complexed with G8 (NH$_3$) and G11 (EDA) dendrimers in the molar ratios indicated in Table XVIII below, with lane 1 being an uncomplexed DNA size marker:

TABLE XVIII

| Lane | DNA:Dendrimer Molar Ratio |
|---|---|
| 1 | a |
| 2 | 1:0.32[b] |
| 3 | 1:3.2[b] |
| 4 | 1:16[b] |
| 5 | 1:32[b] |
| 6 | 1:64[b] |
| 7 | 1:128[b] |
| 8 | 1:0.32[c] |
| 9 | 1:3.2[c] |
| 10 | 1:16[c] |
| 11 | 1:32[c] |
| 12 | 1:64[c] |
| 13 | 1:128[c] |

[a] = DNA Size Marker
[b] = DNA:G8 NH$_3$
[c] = DNA:G11 EDA

Electrophoresis was performed on these complexes in agarose gel with the results indicated in FIG. 24. It can be seen that at molar ratios of 1:0.32, 1:3.2, and 1:16 (see lanes 2–4 in FIG. 24), the DNA did not complex with G8 (NH$_3$) dendrimer. In contrast, it was only at molar ratios of 1:0.32 and 3.2 (lanes 8 and 9) that DNA did not complex with G11 (EDA) dendrimer. This indicates that the larger G11 (EDA) dendrimer, which has substantially greater surface charge density than the G8 (NH$_3$) dendrimer, is able to complex at lower DNA:dendrimer molar ratios, indicating that the more important parameter of DNA complexing by dendrimer appears to be charge ratio.

The stable complexes, which are shown in lanes 5–7 and 11–13 in FIG. 24, are all at charge ratios smaller than 5:1 DNA:dendrimer.

Example 51

DNA-dendrimer complex stability in a broad range of pH (FIG. 25)

In this example, DNA complexed with G8 (NH$_3$) and G8 (EDA) dendrimers in DNA:dendrimer charge ratios of 10:1 and 1:5 were prepared in a buffer containing 100 mM sodium chloride and 10 mM TRIS at varying pH's as indicated in Table XIX below.

TABLE XIX

| Lane | pH | DNA: Dendrimer* Charge Ratio (Core) |
|---|---|---|
| 1 | 7.4 | 10:1 (NH$_3$) |
| 2 | 7.4 | 1:5 (NH$_3$) |
| 3 | 7.4 | 10:1 (EDA) |
| 4 | 7.4 | 1:5 (EDA) |
| 5 | 7.4 | DNA alone |
| 6 | 5.2 | 10:1 (NH$_3$) |
| 7 | 7.0 | 10:1 (NH$_3$) |
| 8 | 9.8 | 10:1 (NH$_3$) |
| 9 | 5.2 | 1:5 (NH$_3$) |
| 10 | 7.0 | 1:5 (NH$_3$) |
| 11 | 9.8 | 1:5 (NH$_3$) |
| 12 | 5.2 | 10:1 (EDA) |
| 13 | 7.0 | 10:1 (EDA) |
| 14 | 9.8 | 10:1 (EDA) |
| 15 | 5.2 | 1:5 (EDA) |
| 16 | 7.0 | 1:5 (EDA) |
| 17 | 9.8 | 1:5 (EDA) |

TABLE XIX-continued

| Lane | pH | DNA: Dendrimer* Charge Ratio (Core) |
|---|---|---|
| 18 | 5.2 | DNA alone |
| 19 | 7.0 | DNA alone |
| 20 | 9.8 | DNA alone |

*G8

Electrophoresis was performed on the resulting complexes in an agarose gel and the results are indicated in FIG. 25.

Lanes 1–5 represent complexing performed in standard condition (pH 7.4). As expected, DNA did not complex with dendrimer at a charge ratio of 10:1 (lanes 1, 3, 6–8, and 12–14) and as with the control DNA, which was subjected to electrophoresis without dendrimer (lanes 5 and 18–20), migrated in the gel. The partial complexing of DNA at the 10:1 charge ratio (documented by the smearing observed in lanes 1, 3, 6–8 and 12–14) was also not affected by alteration of pH. On the other hand, the DNA complex formed at a 1:5 charge ratio showed stability at pH's ranging from 5.2 to 9.8, and did not migrate in the gel (lanes 9–11 and 15–17). Lanes 9 and 15 show formation of the complex at pH 5.2, while lane 17 shows disassociation of the complex at pH 9.8. Thus, complexes formed with G8 ($NH_3$) dendrimers were stable at pH 9.8 while those made with G8 (EDA) dendrimers were not. This suggests that the charge characteristics are different for those two dendrimers, and may affect their DNA binding under certain conditions.

Example 52
DNA-dendrimer binding in increasing sodium chloride concentrations (FIGS. 26a and b)

In Example 52, DNA was complexed in charge ratios of 5:1 and 1:5, with both G8 ($NH_3$) and G8 (EDA) dendrimers, at increasing concentrations of sodium chloride as indicated in Table XX below:

TABLE XX

| Lane | NaCl Conc. |
|---|---|
| 1 | * |
| 2ª & 10ᵇ | 0 |
| 3ª & 11ᵇ | 50 μM |
| 4ª & 12ᵇ | 100 μM |
| 5ª & 13ᵇ | 200 μM |
| 6ª & 14ᵇ | 500 μM |
| 7ª & 15ᵇ | 750 μM |
| 8ª & 16ᵇ | 1.0 μM |
| 9ª & 17ᵇ | 1.5 μM |

*DNA Size Marker
a = charge ratio 5:1
b = charge ratio 1:5

Figure 26B:
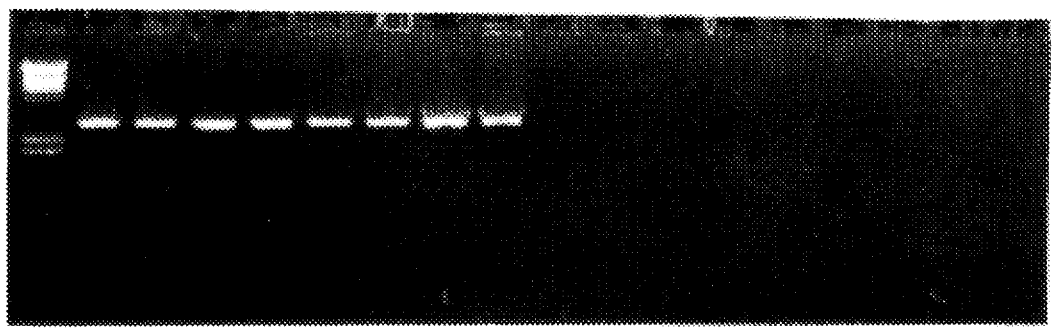

Electrophoresis was performed on these complexes with the results indicated in FIGS. 26a and 26b; 26a comprising the G8 ($NH_3$) dendrimer-DNA complexes and FIG. 26b comprising the G8 (EDA) dendrimer-DNA complexes. Complete DNA:dendrimer complexes did not form at a charge ratio of 5:1 in any of the employed conditions, and as a result the DNA migrated in the gel (lanes 2–9 in FIGS. 26a and 26b). On the other hand, complete DNA:dendrimer complexes formed and were stable at a charge ratio of 1:5, in sodium chloride concentration ranging from zero (lanes 2 and 10) to 1.5 molar (lanes 9 and 17). Thus, DNA:dendrimer complex formation occurs independent of the ionic strength of the buffer.

Example 53
Stability of DNA complexed to dendrimer in the presence of restriction endonucleases (FIG. 27).

In these examples, 0.2 μg of plasmid pRSV-lac DNA were complexed with G8 ($NH_3$) or G11 (EDA) dendrimers in a charge ratio of 1:10 and incubated with HindIII or EcoR1 restriction endonuclease enzymes for 1 hour at 37° C. Samples were then treated with SDS to separate DNA from the dendrimer, and electrophoresis performed in an agarose gel (FIG. 27, lanes as indicated in Table XXI below):

TABLE XXI

| Lane | Plasmid Complex |
|---|---|
| 1 | DNA Size Marker |
| 2 | Non-digested plasmid DNA |
| 3 | Plasmid DNA digested with Hind III |
| 4 | Plasmid DNA complexed with G8 $NH_3$ digested with Hind III |
| 5 | Plasmid DNA complexed with G11 EDA digested with Hind III |
| 6 | Plasmid DNA digested with EcoR1 |
| 7 | Plasmid DNA complexed with G8 $NH_3$ digested with EcoR1 |
| 8 | Plasmid DNA complexed with G11 EDA digested with EcoR1 |

Non-complexed plasmid DNA digested with either Hind III or EcoR1 migrated in fragments consistent with the number of restriction sites in the plasmid (compare lanes 3 and 6 to digested DNA in lane 2, FIG. 27). In contrast, complexed DNA remained primarily undigested (lanes 4, 5, 7, and 8) indicating that dendrimer complexing protects DNA from endonuclease digestion.

Example 54
Stability of DNA-dendrimer complexes in the presence of cellular nucleases (FIG. 28)

Example 54 is similar to Example 53, except that cellular nucleases obtained from the cytoplasm of U937 cells were used to nonspecifically digest the DNA. Plasmid DNA (2.9 kb), was complexed to G8 (EDA) dendrimer in charge ratios that either completely (1:5) or incompletely (5:1) complexed the DNA. The DNA:dendrimer complexes were then incubated with the cell extract for four hours at 37° C. SDS was then added to separate the DNA from the dendrimer and the samples were subjected to electrophoresis in an agarose gel (FIG. 28) with lanes identified as indicated in Table XXII below:

Table XXII

| Lane | Samples |
|---|---|
| 1 | DNA Size Marker |
| 2 | Plasmid Control; no cell extract, no dendrimer |
| 3 | Plasmid Digest Control; 5 μg of cell extract, no dendrimer, no SDS |
| 4 | Plasmid DNA:G8 (EDA) (1:5); no cell extract |
| 5 | Plasmid DNA:G8 (EDA) (1:5); 5 μg of cell extract |
| 6 | Plasmid DNA:G8 (EDA) (5:1); |

115

Table XXII-continued

| Lane | Samples |
|------|---------|
|      | no cell extract |
| 7    | Plasmid DNA:G8 (EDA) (5:1); 5 μg of cell extract |

Migration of the intact plasmid is indicated in lane 2, while the migration of the plasmid that has been digested by the cellular nucleases is shown in lane 3A comparison of lane 3 to lane 2 indicates that exposure of the DNA to cellular nucleases digests it into small fragments of diverse size (as is indicated by the smear seen in lane 3).

In lane 4, a 1:5 charge ratio DNA:dendrimer complex that was not exposed to cellular extract or exposed to SDS was then subjected to electrophoresis. No migration is shown, as would be expected for a stable DNA:dendrimer complex.

In lane 5, the same 1:5 complex was exposed to cellular extract (5 μg), then disassociated with SDS and then subjected to electrophoresis. The plasmid remains primarily intact, as can be seen by comparison of lane 5 to lanes 3 and 4. This indicates that little or no digestion of the DNA has occurred while it was complexed to dendrimer.

In lane 6, a 5:1 DNA:dendrimer complex not exposed to the cellular extract was subjected to electrophoresis. As expected, the complex is not stable and the DNA migrates in the gel. In lane 7, the same complex was exposed to 5 μg of cellular extract, then treated with SDS to release the DNA from the dendrimer and subjected to electrophoresis. Since the complex is not stable, the DNA was almost completely digested, and the differential migration of various digested fragments can be seen in lane 7 of FIG. 28. This indicates that complete complexing of DNA to dendrimer protects DNA from nuclease digestion.

Example 55

Transfection of DNA complexed with G8 ($NH_3$) dendrimers, with or without DEAE-dextran, as compared to transfection using LIPOFECTIN™ (FIG. 29)

In this Example, DNA was complexed with G8 ($NH_3$) dendrimers at various DNA:dendrimer charge ratios (1:100 to 1:1). It was then transfected in different quantities of DNA (1, 5, and 10 μg) in the presence or absence of DEAE-dextran. The aforementioned quantities of DNA were also transfected with 20 μg of LIPOFECTIN™.

The results of these transfections, as indicated by the production of luminescence (in light units per μg of protein), are presented in FIG. 29. Very little transfection was obtained for the controls, i.e., DNA in the presence of DEAE-dextran or DNA alone. Substantial transfection is achieved with DNA:dendrimer complexes made with 10 μg, 5 μg, and 1 μg of DNA per well at charge ratios ranging from 1:100 to 1:1 (DNA:dendrimer) in the presence of DEAE-dextran. Substantial transfection was also achieved with DNA:dendrimer complexes even in the absence of DEAE-dextran when larger amounts of DNA were complexed at lower charge ratios. In the absence of DEAE-dextran, transfection with DNA:dendrimer complexes only occurs with higher generation dendrimers (>G7).

In the cases where transfection is significant, the results compare favorably to those obtained using a lipid-based transfection agent, LIPOFECTIN™.

Example 56

Transfection of DNA complexed with various dendrimers, in the presence or absence of DEAE-dextran (FIGS. 30 and 31)

116

In this example, the transfection results for DNA complexed with G9 (EDA), G9 ($NH_3$) (FIG. 30), G8 ($NH_3$) and G11 (EDA) (FIG. 31) dendrimers at various DNA:dendrimer charge ratios are charted. Transfection of DNA in the presence of DEAE-dextran was substantially enhanced where the charge ratio varies from about 1:5 (0.2) to about 1:100 (0.01) DNA:dendrimer (FIGS. 30 and 31). Even at charge ratios as high as about (4.0) and as low as about 1:10,000 (0.0001), some transfection was observed. Transfection in the absence of DEAE-dextran, was only significant where the charge ratio of DNA:dendrimer was less than 1:5, and tends to increase as one proceeds to charge ratios as low as 1:1,000, and even as low as 1:10,000 for G9 ($NH_3$) (FIG. 30). This suggests that lower genetic material dendrimer charge ratios can possibly substitute for the enhancing effect of DEAE-dextran.

Example 57

Transfection of DNA complexed with G7 ($NH_3$) dendrimer in DEAE-dextran versus HBS (FIG. 32)

In this example, DNA-dendrimer complexes at the charge ratios indicated on the abscissa in FIG. 32 were transfected into RAT2 cells either in the presence of DEAE-dextran or in the presence of HBS. The transfection results as measured by luminescence in relative light units per μg of cellular protein are indicated in FIG. 32. As can be seen, DEAE-dextran substantially enhanced transfection for complexes where the charge ratio ranges from about 1:15 to about 1:1, specifically as high as 1:0.6. Substantially no transfection was achieved in HBS, thus confirming that transfection with dendrimers of generation 7 and lower requires the addition of DEAE-dextran.

Example 58

Effect of dendrimer generation and DNA/dendrimer charge ratio on transfection efficiency (FIG. 33)

In this example, DNA complexed with G4–G8 ($NH_3$) dense star dendrimers in charge ratios of 1:1, 1:5, and 1:10 (DNA:dendrimer) were transfected into RAT2 cells in the presence of DEAE-dextran. The percent increase in transfection over a DEAE-dextran DNA control mixture is indicated for each of the resulting complexes in FIG. 33. Highly significant improvement over control was seen for G6, G7, and G8 dendrimers at all charge ratios, these dendrimers having a diameter greater than about 50 Å, while little improvement is seen for G4 and G5 dendrimers. Further, when the charge ratio was 1:5 or 1:10, the transfection was substantially enhanced relative to the complexes where the charge ratio is 1:1. Thus, increasing dendrimer generation and charge ratio synergistically improved transfection efficiency.

Example 59

Effect of DEAE-dextran on transfection over widely varying DNA:dendrimer charge ratios (FIG. 34)

In this example, DNA was complexed with G8 ($NH_3$) dendrimers in charge ratios varying from 1:1 to 1:3805. The transfection results, with and without DEAE-dextran present are indicated in FIG. 34 as the degree of luminescence in relative light units per μg of protein achieved. For 1:1 and 1:100 minimal transfection was achieved either with or without DEAE-dextran. However, for charge ratios of 1:5 and 1:10, transfection was again synergistically enhanced by the use of DEAE-dextran. Thus, DEAE-dextran can only enhance transfection of DNA:dendrimer complexes formed at appropriate charge ratios.

Example 60

Effect of varying DEAE-dextran concentration on transfection efficiency (FIG. 35)

In this Example, DNA:G11 (EDA) dendrimer complexes, formed at charge ratios of 1:1–1:100 (DNA:dendrimer), were used to transfect RAT2 cells in the presence of varying concentrations of DEAE-dextran (0 to 2 μM). The transfection results, measured as luminescence in relative light units per μg of cellular protein, are indicated in FIG. 35. Some transfection was seen in all conditions, and in concentrations from 0.125 to 2 μM, DEAE-dextran tended to enhance transfection. Enhancement was most pronounced however at a DEAE-dextran concentration from about 0.25 to about 1 μM, and where the DNA:dendrimer charge ratio was 1:5 or 1:10. This indicates that both the charge ratio and the DEAE-dextran concentration must be optimized to obtain synergistic transfection improvements.

Example 61

Transfection of DNA using dendrimers versus LIPOFECTIN™ compared (FIG. 36)

In this Example, 5 μg DNA was complexed with G8 (NH$_3$) dendrimers at a charge ratio of 1:5 and used to transfect five different cell lines. Transfection of the five cell types indicated in FIG. 36 was compared to transfection mediated by LIPOFECTIN™. In addition, transfection of the DNA:dendrimer complex enhanced by DEAE-dextran was compared to transfection using the complex alone. In FIG. 36 the transfecting agents are identified with the following numbers: 1 is LIPOFECTIN™ at two different concentrations (20 μg and 2 μg); 2 is dendrimer and DEAE-dextran; 3 is dendrimer alone; 4 is DEAE-dextran alone as control; and 5 is plasmid control.

As seen in FIG. 36, transfection using the DNA:dendrimer complex in the presence of DEAE-dextran were far superior to that achieved by LIPOFECTIN™ at either 2 or 20 μg per test well, in all the cells except the human HMEC-1 cells. Transfection of DNA:dendrimer complexes in the presence of DEAE-dextran was also better than that obtained using DNA-dendrimer alone. In some cells, e.g., rat:Clone9, mouse:NIH3T3 and mouse:10-1, transfection using DNA:dendrimer complexes alone is superior to that achieved using LIPOFECTIN™ at either 2 or 20 μg. This indicates that DNA:dendrimer complexes can be used to transfect a wide variety of cells; however, it suggests that the efficiency of transfection may vary between different cell types.

Example 62

Transfection of additional cell lines that are difficult to transfect with currently available transfection agents (FIG. 37)

Transfection of additional cell lines that have proven to be particularly difficult to transfect with other techniques was attempted with DNA:dendrimer complexes. DNA was complexed with G8 (NH$_3$) dendrimer at a 1:5 DNA:dendrimer charge ratio, and the extent to which the DNA:dendrimer complexes transfected the cell lines NRK52E and YB2 was compared to transfection of the same cells with the commercially available transfection agent LIPOFECTIN™ at 20 μg or 2 μg. In FIG. 37, the agents are numbered as in FIG. 36.

The transfection results are indicated by luminescence in relative light units per μg of protein in FIG. 37. The best results in either cell were achieved using the DNA-dendrimer complex in conjunction with DEAE-dextran. While LIPOFECTIN™ showed efficient transfection in NRK52E cell line, it did not work with the YB2 cell lines, where the performance of the DNA:dendrimer complex in DEAE-dextran was far superior. Again, it should be noted that overall transfection efficiency varied between the different cell lines.

Example 63

Comparison of DNA transfection using dendrimers, as compared to two different lipid agents: LIPOFECTIN™ and LIPOFECTAMINE™ (FIG. 38)

In this Example, RAT2 cell lines were transfected with the RSV-luc DNA complexed with either G8 (NH$_3$) dendrimer or G11 (EDA) dendrimer. Charge ratios of 1:1, 1:5, and 1:10 (DNA:dendrimer) were examined. In some cases, DEAE-dextran was used to enhance transfection. The transfection results are compared to transfection using 2, 10, and 20 μL of LIPOFECTIN™ or 2, 12.5, and 25 μL of LIPOFECTAMINE™.

The results, shown in FIG. 38, demonstrate the exceptional degree to which DNA is transfected when complexed with dendrimers at 1:5 or 1:10 DNA:dendrimer charge ratios in the presence of DEAE-dextran. LIPOFECTAMINE™ did achieve transfection, but was effective in a very limited range of concentrations. LIPOFECTIN™ showed minimal activity in this cell line.

Example 64

Effect of permeablizing cell membranes with DMSO on the efficiency of transfection as compared to DEAE-dextran (FIG. 39)

To test the premise that DEAE-dextran was acting merely as a perturbation or permeablizing agent, the transfection of RAT2 cells with DNA complexed with a G9 (NH$_3$) dendrimer was compared in the presence and absence of DMSO treatment of the cells. The results, shown in FIG. 39, indicate a 3-fold enhancement of transfection using DEAE-dextran, as compared transfection without dextran. Indeed, DMSO had no effect on transfection in the absence of DEAE-dextran. Hence, DEAE-dextran enhancement does not merely result from cell perturbation or permeablization.

Interestingly, the combination of DMSO and DEAE-dextran appears to further synergize the transfection of DNA complexed with dendrimer, particularly at the 1:5 and 1:10 DNA:dendrimer charge ratios. This suggests that these two agents work by different mechanisms.

Example 65

The use of conjugated dendrimers for transfecting cells (FIGS. 40 and 41)

The conjugation of a target director (galactose trisaccharide) to dendrimers did not interfere with the formation of a stable DNA:dendrimer complex (FIG. 41) and could be employed to enhance transfection efficiency (FIG. 40). In this example, G11 (EDA) dendrimer was conjugated with galactose trisaccharide. DNA was then complexed with the targeted dendrimer, and the complex was used to transfect RAT2, HepG2, NIH3T3, and AL cells. Non-conjugated dendrimers were also complexed with DNA and used as controls. The results, shown in FIG. 40, demonstrate that the attachment of a target director enhances the transfection of HepG2 and AL cells that express the receptor for galactose trisaccharide.

The DNA:dendrimer complexes were also subjected to electrophoresis. In FIG. 41, 1 μg of DNA was complexed to G11 (EDA) dendrimer with or without a target director as follows in Table XXIII:

TABLE XXIII

| Lane No. | Concentration in μM of dendrimer |
|---|---|
| 1 | DNA only |
| 2 | 0.1[a] |
| 3 | 0.05[a] |
| 4 | 0.025[a] |
| 5 | 0.1[b] |
| 6 | 0.05[b] |
| 7 | 0.025[b] |

[a] = not conjugated
[b] = conjugated

At very low concentrations of dendrimer, high DNA:dendrimer charge ratio, stable complexes were not formed (as would be expected) with either the untargeted, i.e., unconjugated, dendrimer or with the galactose trisaccharide conjugated dendrimer (see lanes 3, 4, 6, and 7). However, stable complexes were formed with either the unconjugated or conjugated dendrimers at appropriate charge ratios (see lanes 2 and 5 of FIG. 41). This indicates the potential utility of conjugated dendrimers in targeted transfection.

Example 66

Effect of serum on non-targeted transfection. (FIG. 42)

The necessity for target directors in vivo was illustrated in this example, where transfection is attempted using DNA:dendrimer G8 ($NH_3$) complexes in varying concentrations of serum. The results, shown in FIG. 42, indicate that increasing concentrations of serum inhibits the transfection of RAT2 cells with DNA:dendrimer complexes even in the presence of DEAE-dextran. Thus, another method such as a target director must be used to mediate adhesion of DNA:dendrimer complexes to cells in vivo.

Example 67

Effect of potential target directors and other dendrimer surface modification on transfection efficiency (FIG. 43)

In this example, G5 and G6 ($NH_3$) dendrimers were conjugated with 20 biotins per dendrimer, 100 pyruvates per dendrimer or 64 pyruvates per dendrimer, or alternatively, were modified at their surface by reaction of 25% of their surface functional amino groups with acrylic acid. The dendrimers were then used to complex the RSV-luc plasmid DNA and transfect RAT2 cells. The extent of transfection is indicated by the relative light units per μg of protein. All attempted transfection was performed in the presence of DEAE-dextran. The charge ratios on substituted dendrimers were determined as if no substitution of negative functionality had been made. Transfection results, shown in FIG. 43, indicate that these surface modifications do not adversely affect transfection as compared to transfection using an unmodified G6 ($NH_3$) dendrimer.

Example 68

Persistence of LUCIFERASE™ Activity After Dendrimer-Mediated Transfection (FIG. 44)

In this Example, the time course of LUCIFERASE™ activity was determined in RAT2 cells transfected using DNA:dendrimer complexes with and without DEAE-dextran. Activity was measured at 21 hours, 45 hours, 69 hours and 141 hours. The results are shown in FIG. 44.

Either with or without DEAE-dextran, the extent of transfection was substantially greater, particularly at 21 and 45 hours, for DNA complexed with dendrimer than for DNA transfected alone (plasmid control). The charge ratio of each complex was 1:10. The results were particularly striking for DNA:dendrimer transfection in the presence of DEAE-dextran at 21 and 45 hours. This suggests that genes are expressed for longer periods of time when transfected with dendrimers.

Example 69

Cytotoxicity (FIGS. 45 and 46)

In this Example, tests were conducted to determine the cytotoxicity of DNA:dendrimer complexes, with and without DEAE-dextran, on a number of different cell types: RAT2 cells (FIG. 45), Clone9 cells, NIH3T3 cells, 10-1 cells and COS7 cells (FIG. 46). In FIG. 45 the various numbers on the bar graph indicate: 1 is media control; 2 is media control with DNA; 3 is dendrimer; 4 is dendrimer with DNA; 5 is DEAE-dextran control; 6 is DEAE-dextran control with DNA; 7 is dendrimer with DEAE-dextran; and 8 is dendrimer with DNA with DEAE-dextran. Normal cell viability in culture is 90 to 95%. DNA dendrimer complexes alone had little or no impact on cell viability with the exception of the Clone9 cell line, where the degree of attrition approximately doubled with DNA-dendrimer complexes. The addition of DEAE-dextran increased the cytotoxicity somewhat, but not sufficiently to deter from the exceptional utility of this combination in vitro.

Example 70

Uptake And Cellular Localization Of Radiolabeled DNA Transfected With Dendrimer (FIG. 47)

In this Example, radiolabeled DNA (2.9 kb) was transferred into RAT2 and U937 cells using G8 ($NH_3$) dendrimer. Overall transfer into the cell is recorded in FIG. 47a–f, along with localization results obtained by fractionating the cells into membrane, nuclear and cytoplasmic associated fractions. The amount of radiolabeled DNA in the nucleus and membrane fractions were thus separately determined.

In 47a–c, U937 cells were transfected using DNA only (47a), DNA plus dendrimer (47b) and DNA plus dendrimer plus sodium azide (47c). The same series of transfections was done for RAT2 cells in 47d, e and f, respectively.

The results indicate not only substantial cellular uptake when DNA and dendrimer are used, but also substantial nuclear uptake (FIGS. 47b and e). The energy dependence of DNA modulated transfection was indicated by the addition of sodium azide (FIGS. 47c and f), which reduced the degree of DNA uptake to approximately that observed when DNA was incubated alone with the cells (FIGS. 47a and d).

Example 71

Photomicrographs Of Transfected Cells (FIGS. 48a, 48b, 49, 50a and 50b)

In this Example, photomicrographs were taken of D5 mouse melanoma and RAT2 rat fibroblast cells transfected with RSV-β-gal plasmid DNA, using G11 (EDA) dense star dendrimers and G8 ($NH_3$) dense star dendrimers, respectively. Cells which were successfully transfected show up as dark (blue) cells in FIGS. 48–50.

In FIG. 48a, transfection of D5 cells was performed using DNA-dendrimer complexes containing 1 μg of genetic material per well. FIG. 48b shows that a greater proportion of cells are transfected when the quantity of DNA in the complex is increased to 5 μg per well. FIG. 49 is an enlarged view of several transfected cells where 3 μg of genetic material were used per well.

Figure 50B:
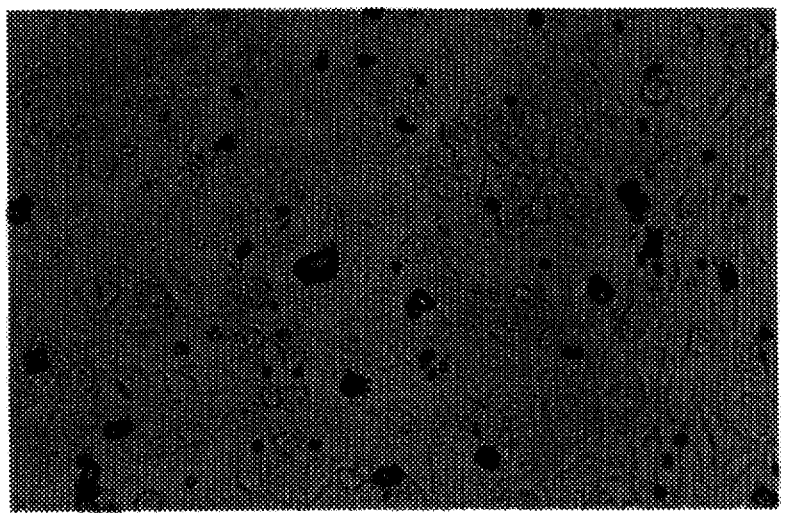

FIG. 50a is a photomicrograph of RAT2 rat fibroblast cells transfected with 3 μg per well of the genetic material. FIG. 50b is a control showing nontransfected cells. These studies show that the vast majority of cells in culture (50–95%) were transfected when DNA:dendrimer complexes are used.

Example 72

Comparison of different methods of obtaining stably transfected D5, RAT2, MSU 1.2 cell lines (FIGS. 52, 53, 54, 55 and 59)

In this Example, transfection of D5, RAT2, MSU 1.2 cell lines was attempted using 5 or 10 μg per culture well of a plasmid containing genes resistance for G418 antibiotic (neomycin) resistance and β-galactosidase or mygromycin B resistance. In FIG. 52 the following transfection techniques are compared using D5 cell line and the indicated quantities of RSV-β-gal plasmid DNA per well:

1. 10 μg in the presence of 0.125M of calcium phosphate;
2. 10 μg in the presence of 0.5 μM of DEAE-dextran;
3. 5 μg complexed with 0.5 μM of G8 (NH$_3$) dendrimer at a DNA:dendrimer charge ratio of 1:13; and
4. 10 μg complexed with 0.5 μM of G8 (NH$_3$) dendrimer at a DNA:dendrimer charge ratio of 1:7.

In FIG. 53 the following transfection techniques are compared, using RAT2 cell line and the indicated quantities of plasmid DNA per well:

1. 10 μg in the presence of 0.125M calcium phosphate;
2. 10 μg in the presence of 0.5 μM DEAE-dextran;
3. 5 μg complexed with 0.2 μM G8 (NH$_3$) dendrimer at a DNA:dendrimer charge ratio of 1:6;
4. 10 μg complexed with 0.2 μM G8 (NH$_3$) dendrimer at a DNA:dendrimer charge ratio of 1:3;
5. 5 μg complexed with 0.5 μM G8 (NH$_3$) dendrimer at a DNA:dendrimer charge ratio of 1:13; and
6. 10 μg complexed with 0.5 μM G8 (NH$_3$) dendrimer at a DNA:dendrimer charge ratio of 1:7.

DEAE-dextran, 0.5 μM, was included in the transfection medium after genetic material was complexed with dendrimer.

The cells were placed in media containing either G418 antibiotic or hygromycin B. These cells have a 24 hour doubling cycle (i.e., replicating every 24 hours). At four weeks, the cultures were assessed for the number of clones expressing G418 resistance and β-galactosidase and/or hygromycin resistance.

In FIG. 54 the following transfection techniques are compared using MSU 1.2 cell line and the indicated quantities of EBV-A-hygromycin plasmid DNA per well:

1. 5 μg in the presence of 0.5 μM DEAE-dextran
2. 5 μg in the presence of 0.125 μM calcium phosphate
3. 5 μg complexed with G11 (EDA) dendrimer at a DNA:dendrimer charge ratio of 1:2
4. 5 μg complexed with G11 (EDA) dendrimer at a DNA:dendrimer charge ratio of 1:5
5. 5 μg complexed with G11 (EDA) dendrimer at a DNA:dendrimer charge ratio of 1:10
6. 5 μg complexed with G11 (EDA) dendrimer at a DNA:dendrimer charge ratio of 1:20
7. 5 μg complexed with 10 μg of LIPOFECTAMINE™

This indicates that DNA dendrimer transfection is more efficient than LIPOFECTAMINE™ in producing stably transfected cell lines.

FIG. 59 illustrates the transfections presented in FIG. 52. The following transfection techniques were compared using D5 cell line and the indicated quantities of RSV-β-gal plasmid DNA per well:

1. 10 μg in the presence of 0.125M calcium phosphate
2. 10 μg in the presence of 0.5 μM DEAE-dextran
3. 5 μg complexed with 0.5 μM of G8 (NH$_3$) dendrimer at a DNA:dendrimer charge ratio of 1:13
4. 10 μg complexed with 0.5 μM of G8 (NH$_3$) dendrimer at a DNA:dendrimer charge ratio of 1:7
5. 5 μg complexed with 0.2 μM of G8 (NH$_3$) dendrimer at a DNA:dendrimer charge ratio of 1:6

Note the increased number of clones produced by dendrimer transfection.

FIG. 55 illustrates transfection of D5 cell line using ICAM expression plasmid and G11 (EDA) dendrimer at a DNA:dendrimer charge ratio of 1:10. Clones expressing ICAM gene were first selected for neomycin resistance. Neomycin resistant clones were further analyzed by Fluorescence Activated Cell Sorting (FACS) using anti-ICAM antibody conjugated with fluorescein. The following cell lines and clones are compared:

1. D5 cell line, negative (not stained) for anti-ICAM antibody
2. IC-21 cell line, positively stained with anti-ICAM antibody
3. Clone #23 after transfection with 15 μg of DNA with G11 (EDA) dendrimer, at a DNA:dendrimer charge ratio of 1:10
4. Clone #27 obtained as described above.
5. Clone #31 obtained as described above.
6. Clone #9 obtained as described above.

Profiles of positively stained cells dotted were superimposed over the profile of the ICAM negative control D5 cell line (FIG. 55A) used for transfection. These results show that DNA:dendrimer transfection was able to produce permanent cell lines that express high levels of ICAM from transfected gene.

As can be seen in FIGS. 52, 53, 54, 55 and 59, the number of clones which continue to express both G418 resistance and the β-galactosidase gene, hygromycin resistance and gene for ICAM at four weeks is remarkable where transfection was achieved in accordance with the present invention, i.e., by complexing the genetic material with dendritic polymers, as compared to attempting transfection only in the presence of calcium phosphate or DEAE-dextran, or LIPOFECTAMINE™. This indicates that transfection of cells with DNA:dendrimer is much more efficient than other available techniques in producing stably transfected cell lines.

Example 73

Comparison of transfection of COS1 and RAT2 cells using different dendrimers and dendrimer combinations at different charge ratios and under three different conditions (FIGS. 61A and 61B)

In this example, 1 μg of RSV-luc per test well was complexed with the indicated dendrimers or controls and at the indicated charge ratios set forth in Table XXVI below:

TABLE XXVI

| Sample Number | Transfection Agent | Genetic Material:Dendrimer Charge Ratio |
|---|---|---|
| 1 | An aggergate of G8 (NH$_3$) and G8.5 (NH$_3$) dendrimers at a G8:G8.5 charge ratio of 50 (Sample 13 from Example 74 below) | 1:10 |
| 2 | Same as Sample 1 above. | 1:20 |
| 3 | Same as Sample 1 above. | 1:50 |
| 4 | An aggergate of G6 (NH$_3$) and G6.5 (NH$_3$) dendrimers at a G6:G6.5 charge ratio of 100 (Sample 8 from Example 74 below). | 1:10 |
| 5 | Same as Sample 4 above. | 1:20 |
| 6 | Same as Sample 4 above. | 1:50 |
| 7 | Sample Q from Example 42, a polydisperse dendrimer blend. | 1:10 |
| 8 | Same as Sample 7 above. | 1:50 |
| 9 | G10 (NH$_3$) | 1:20 |
| 10 | G10 (NH$_3$) | 1:50 |
| 11 | LIPOFECTAMINE™ | Not applicable: used per manufacturer's recommendations. |

The foregoing combinations were used to transfect both COS1 (FIG. 61A) and RAT2 (FIG. 61B) cells under three different conditions. In all three conditions, DMEM was the essential medium used. In the examples shown by the speckled bars in FIGS. 61A and 61B, the genetic material-:dendrimer complexes were used alone. In the examples shown by the diagonally hatched bars, transfection was conducted in the presence of 0.5 µM DEAE-dextran. In the examples illustrated by the solid bars, transfection was conducted in the presence of 25 µg/mL of chloroquine.

The results from this experiment indicate that the effectiveness of chloroquine is a function of the cell being transfected (FIG. 61B); and that in at least some cells, the use of chloroquine yields strikingly superior transfection efficiencies (FIG. 61A).

Example 74

Preparation of pH controlled dendrimer aggregates and use of these aggregates in transfection studies Dendrimer aggregates were prepared from solutions of dendrimers with terminal amino groups and dendrimers with sodium carboxylate groups. The ratio of the different dendrimers used in this example is shown in Table XXIV, below.

TABLE XXIV

| Sample | Gn.5 NH$_3$ | Gn NH$_3$ | Charge Ratio Gn/Gn.5 |
|---|---|---|---|
| 1 | G6.5 | G6 | 0.5 |
| 2 | G6.5 | G6 | 1 |
| 3 | G6.5 | G6 | 2.5 |
| 4 | G6.5 | G6 | 5 |
| 5 | G6.5 | G6 | 10 |
| 6 | G6.5 | G6 | 25 |
| 7 | G6.5 | G6 | 50 |
| 8 | G6.5 | G6 | 100 |
| 9 | G6.5 | G6 | 200 |
| 10 | G6.5 | G8 | 25 |
| 11 | G6.5 | G8 | 50 |
| 12 | G6.5 | G8 | 100 |
| 13 | G8.5 | G8 | 50 |
| 14 | G8.5 | G8 | 100 |
| 15 | * | G6 | * |
| 16 | * | G8 | * |

* means not applicable

The "0.5" generation number (e.g., G8.5 and G6.5) indicate that these are half generation dendrimers (in this instance, half generation PAMAM dendrimers). At the half generation tier, these dendrimers are carboxylate terminated, whereas at the full generation tier they are amino terminated.

A typical dendrimer aggregates formulation is discussed below. Stock solutions were prepared of the G8.5 (NH$_3$) dendrimer (2.34 wt. %) and G8 (NH$_3$) dendrimer (2.28 wt. %) in a TRIS buffer (pH 7.4). In order to prepare the dendrimer aggregates at a 50:1 charge ratio, 8.8 mg of the G8.5 (NH$_3$) dendrimer solution was mixed with 15.4 mg of the G8 (NH$_3$) dendrimer solution. The resulting solution was then diluted to a total solution weight of 2.0689 g with TRIS buffer. The total solution concentration was 0.74 wt. %. FIG. 56 shows the luciferase activity in RAT2 cells after transfection with the dendrimer aggregates. The aggregates formed between G6.5 (NH$_3$) and G8 (NH$_3$) dendrimers, as well as those prepared from G8.5 (NH$_3$) and G8 (NH$_3$) dendrimers, show a greatly enhanced transfection efficiency when compared to the parent full generation dendrimers themselves, if the appropriate ratio of the amino-terminated to sodium carboxylate-terminated dendrimers is used in the aggregate formulation.

Example 75

Preparation of Lysine-modified dendrimers and transfection studies using the modified dendrimer vectors. (FIG. 57)

A solution of G7 (NH$_3$) (0.50 g, 11 µmoles) in anhydrous dimethylformamide was vigorously stirred while the p-nitrophenyl ester of N,N'-di-t-butoxycarbonyl-L-lysine was rapidly added. After about five minutes, the pH of the mixture was adjusted to about 8.5 with triethylamine. The mixture was stirred for 24 hours, then slowly added to water while vigorously stirring. Triethylamine (0.6 ml) and saturated NaCl (35 ml) were then added to the aqueous mixture which was then stirred for two days. The supernatant was decanted off, and the recovered crude product was dried under vacuum at 40° C. for 12 hours. The dried, crude product was vigorously stirred in diethyl ether and then filtered while rinsing the product with additional diethyl ether. NMR analysis of the dried solid product (0.96 g, 78% yield) was consistent with attachment of N,N'-di-t-butoxycarbonyl-L-lysine groups to the surface of the dendrimer.

The t-butoxycarbonyl protecting groups were then removed from the lysine residues by dissolving the product (0.35 g, 3.3 µmole) in anhydrous methylene chloride and then slowly adding trifluoroacetic acid (3 ml) to the mixture. The gases that evolve were swept out of the flask with a stream of nitrogen. After three hours, the mixture was concentrated under a stream of nitrogen (40° C.) and then the sample was dried under vacuum. The crude product was purified by dialysis (10,000 molecular weight cutoff membrane) for 24 hours against 1 liter of water. After removal of particulate solids by filtration and concentrating under vacuum, a colorless solid was collected (0.26 g, 69% yield). Analysis of the product by $^1$H and $^{13}$C nuclear magnetic resonance spectroscopy, size exclusion chromatography, capillary electrophoresis, and polyacrylamide gel electrophoresis, all indicated the correct structure.

FIG. 57 shows the relative light units per µg of protein produced for transfection into RAT2 cells using the lysine-modified G7 (NH$_3$) dendrimer in comparison to the unmodified G7 (NH$_3$) through G10 (NH$_3$) dendrimers (all at a DNA:dendrimer charge ratio of 1:10 and in the presence of DEAE-dextran). The lysine-modified dendrimer shows surprisingly high transfection efficiency in comparison to the unmodified dendrimer of the same generation, and in fact, the transfection efficiency is equivalent to that of an unmodified G10 (NH$_3$) dendrimer.

Example 76

Transfection efficiency in COS1 and RAT2 cell lines using polydispersed mixtures of dendrimers, (FIG. 58)

In this example, DNA was complexed with G11 (EDA) dendrimer, a mixture of G11, G3, G2, and G1 (EDA) dendrimers, and a polydispersed mixture of dendrimers as indicate in Table XXV below.

TABLE XXV

| Sample | Dendrimer or Control | DNA: dendrimer charge ratio |
|---|---|---|
| 1 | G11 (EDA) | 1:10 |
| 1 | G11 (EDA) | 1:20 |
| 1 | G11 (EDA) | 1:100 |
| 2 | Mixture 1 (EDA)$^a$ | 1:10 |
| 2 | Mixture 1 (EDA)$^a$ | 1:20 |
| 2 | Mixture 1 (EDA)$^a$ | 1:100 |
| 3 | Mixture 2 (EDA)$^b$ | 1:10 |
| 3 | Mixture 2 (EDA)$^b$ | 1:20 |
| 3 | Mixture 2 (EDA)$^b$ | 1:100 |
| 4 | Q$^c$ | 1:10 |
| 4 | Q$^c$ | 1:20 |
| 4 | Q$^c$ | 1:100 |
| 5 | LIPOFECTAMINE ™ | 6 µL |
| 5 | LIPOFECTAMINE ™ | 10 µL |

$^a$ = mixture of G1 (EDA), G2 (EDA) and G3 (EDA) dendrimers
$^b$ = mixture of 90% of G11 (EDA) and 10% of Mixture 1
$^c$ = mixture of dendrimers as described in Example 42, a polydisperse dendrimer blend The results obtained from transfections using these complexes are indicated in FIG. 58. In COS1 cells, the transfection efficiency achieved with the polydispersed mixture was much higher than that achieved with G11 (EDA), the mix of G11, G1, G2 and G3 (EDA), or LIPOFECTAMINE™. This difference is especially great at DNA:dendrimer charge ratios of 1:10 and 1:20. However, a comparison between results in COS1 and RAT2 lines indicates differences in the transfection efficiencies in the two cells using the same type of dendrimer preparations. For example, the polydispersed mix (dendrimer Q from Example 42) appears to be less effective for transfection of RAT2 than for COS1 cells. This property can possibly be useful in gene transfer.

Example 77

(FIG. 60, Panels 1 and 2)

To determine whether DNA:dendrimer complexes can be employed to transfect cells in vivo, D5 melanoma cells were seeded subcutaneously into syngenetic mice. Tumors approximately 0.5 cm in diameter developed and were directly injected with RSV-β-gal DNA, either alone or complexed to G11 (EDA) dendrimer, and dendrimer alone as a control. Twenty-four hours later, the animals were sacrificed and the tumors were fixed in formalin, sectioned and stained with X-gal to detect the expression of B-galactosidase enzyme. As can be seen in FIG. 60, Panel 1, significant numbers of cells showed evidence of transfection (X-gal staining) in the tumor injected with the DNA:dendrimer complex as compared to background staining (dendrimer injected tumor, Panel 2). No evidence of toxicity or tissue damage was noted in either tumor. Staining of tumors injected with DNA alone showed no evidence of expression, indicating that transfection in vivo was enhanced by the use of DNA:dendrimer complexes.

Example 78

Comparison of LUCIFERASE™ activity in RAT2 cells after transfection with lysine-based, Unsymmetrically-branched Dendrimers and G8 (NH$_3$) and G11 (EDA) Dense Star Dendrimers (FIG. 62)

In this Example, lysine-based, unsymmetrically branched dendrimers were compared to dense star dendrimers for transfection ability. The lysine-based dendrimers were prepared generally in accordance with instructions in U.S. Pat. Nos. 4,289,872, 4,360,646, and 4,410,688. Transfection was attempted with and without DEAE-dextran present. The charge ratio of DNA:dendrimer was, in all instances, 1:5. Sufficient DNA:dendrimer complex was used to yield 1 µg of DNA per test well. The dendrimers used in columns 1–16 are as follows:

1. a G1 TREN core lysine-based, unsymmetrically branched dendrimer;
2. a G2 TREN core lysine-based, unsymmetrically branched dendrimer;
3. a G3 TREN core lysine-based, unsymmetrically branched dendrimer;
4. a G4 TREN core lysine-based, unsymmetrically branched dendrimer;
5. a G5 TREN core lysine-based, unsymmetrically branched dendrimer;
6. a G1 BHA core lysine-based, unsymmetrically branched dendrimer trifluoroacetate salt;
7. a G2 BHA core lysine-based, unsymmetrically branched dendrimer trifluoroacetate salt;
8. a G3 BHA core lysine-based, unsymmetrically branched dendrimer trifluoroacetate salt;
9. a G4 BHA core lysine-based, unsymmetrically branched dendrimer trifluoroacetate salt;
10. a G5 BHA core lysine-based, unsymmetrically branched dendrimer trifluoroacetate salt;
11. a G6 BHA core lysine-based, unsymmetrically branched dendrimer trifluoroacetate salt;
12. a G7 BHA core lysine-based, unsymmetrically branched dendrimer trifluoroacetate salt;
13. a G8 BHA core lysine-based, unsymmetrically branched dendrimer trifluoroacetate salt;
14. a G8 BHA core lysine-based, unsymmetrically branched dendrimer free amine, that is without trifluoroacetate salt;

15. a G8 (NH$_3$) dense star dendrimer; and
16. a G11 (EDA) dense star dendrimer.

As can be seen from FIG. 62 the lysine-based, unsymmetrically branched dendrimers begin to show significant transfection at G4 and G5, at least with the TREN core. The trifluoroacetate salts of the unsymmetrically branched dendrimers seem to inhibit transfection somewhat for the BHA core dendrimers. The G8 BHA core dendrimer in the absence of trifluoroacetate salt appears to show good transfection.

As with dense star dendrimers, the lysine-based, unsymmetrically branched dendrimers all show superior transfection at the 1:5 DNA:dendrimer charge ratio in the presence of DEAE-dextran.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A dense star polymer conjugate which comprises at least one dense star polymer associated with at least one unit of at least one bioactive agent, selected from the group consisting of a therapeutic agent, a diagnostic agent, and a therapeutic/diagnostic agent.

2. The conjugate of claim 1 wherein the dense star polymer is a dendrimer.

3. The conjugate of claim 2 wherein the dendrimer is radially symmetrical in configuration.

4. The conjugate of claim 2 wherein the dendrimer is generally spherical, ellipsoidal, or rod-shaped in configuration.

5. The conjugate of claim 1 wherein said dense star polymer comprises at least one solvent soluble, radially symmetrical dense star polymer wherein the dense star polymer has at least one core branch emanating from a core, said branch having at least one terminal group provided that
   (1) the ratio of terminal groups to the core branches is two or greater,
   (2) the density of terminal groups per unit volume in the polymer is at least 1.5 times that of an extended conventional star polymer having similar core and monomeric moieties and a comparable molecular weight and number of core branches, each of said branches of the extended conventional star polymer bearing only one terminal group, and
   (3) molecular volume that is no more than about 80% of the molecular volume of said extended conventional star polymer as determined by dimensional studies using scaled Corey-Pauling molecular models, and has regular dendritic branching.

6. The conjugate of claim 1 wherein the bioactive agent is a biological response modifier.

7. The conjugate of claim 6 wherein two or more biological response modifiers are present.

8. The conjugate of claim 6 wherein said biological response modifier is selected from the group consisting of an interleukin, and interferon.

9. The conjugate of claim 6 wherein said biological response modifier is genetic material.

10. The conjugate of claim 9 wherein said dense star polymer comprises predominately amino functional surface groups.

11. The conjugate of claim 9 wherein said genetic material extends between and serves to connect a plurality of dense star polymer particles together.

12. The conjugate of claim 9 wherein said dense star polymer has one cross-sectional dimension of at least about 50 Å, wherein said dimension is the narrowest dimension of said dense star polymer.

13. The conjugate of claim 9 wherein the dense star polymer is a dendrimer and the charge ratio of genetic material to dendrimer is from about 10:1 to about 1:10,000.

14. The conjugate of claim 13 wherein the charge ratio of genetic material to dendrimer is from about 3:1 to about 1:1,000.

15. The conjugate of claim 13 wherein the charge ratio of genetic material to dendrimer is from about 1:1 to about 1:100.

16. The conjugate of claim 13 wherein the charge ratio of genetic material to dendrimer is from about 1:1 to about 1:15.

17. A dense star polymer conjugate of the formula:

$$(T)_e{}^*(P)_x{}^*(M)_y \qquad (II)$$

wherein:
   each P represents a dense star polymer;
   x represents an integer of 1 or greater;
   each M represents at least one unit of a bioactive agent, selected from the group consisting of a therapeutic agent, a diagnostic agent, and a therapeutic/diagnostic agent, said bioactive agent can be the same bioactive agent or a different bioactive agent;
   y represents an integer of 1 or greater;
   each T represents one or more target directors;
   e represents an integer of 1 or greater; and
   * indicates that the bioactive agent is associated with the dense star polymer;
with the proviso that the bioactive agent maintains its effectiveness.

18. A dense star polymer conjugate of the formula

$$[(T)_e{-}(C')_f]_g{}^*(P)_x{}^*[(C'')_h{-}(M)_y]_k \qquad (III)$$

wherein:
   each C' represents the same or different connecting group;
   each C'' represents the same or different connecting group;
   g and k each individually represent an integer of 1 or greater;
   e represents an integer of 1 or greater;
   f and h each individually represent an integer of 0 or greater;
   - indicates a covalent bond in instances where a connecting group is present;
   each P represents a dense star polymer;
   x represents an integer of 1 or greater;
   T represents a target director;
   each M represents at least one unit of a carried bioactive agent, selected from the group consisting of a therapeutic agent, a diagnostic agent, and a therapeutic/diagnostic agent;
   y represents an integer of 1 or greater; and
   * indicates that the carried bioactive agent is associated with the polymer;
with the proviso that the carried bioactive agent maintains its effectiveness.

19. The conjugate of claim 17 or 18 wherein the dense star polymer, P, is a dendrimer.

20. The conjugate of claim 19 wherein the dendrimer is polyamidoamine or a polyalkyleneimine.

21. The conjugate of claim 17 or 18 wherein the target director, T, is a polyclonal or monoclonal antibody or fragment thereof.

22. The conjugate of claim 17 or 18 wherein M is selected from the group consisting of a drug, pesticide, radionuclide, chelator, chelated metal, toxin, antibody, antibody fragment, antigen, signal generator, signal reflector, signal absorber and fragrance.

23. The conjugate of claim 22 wherein the signal absorber is a contrast agent.

24. The conjugate of claim 23 wherein the contrast agent is a chelated metal ion selected from Gd, Mn and Fe.

25. The conjugate of claim 22 wherein the signal generator is a fluorescing entity or radionuclide.

26. The conjugate of claim 22 wherein the signal reflector is a metal ion selected from Fe, Rh, Pd and Y.

27. The conjugate of claim 17 wherein at least one of the carried materials is an electron beam opacifier.

28. The conjugate of claim 17 or 18 wherein M is an aromatic ultraviolet absorber.

29. The conjugate of claim 18 wherein said bioactive agent is a biological response modifier.

30. The conjugate of claim 29 wherein said biological response modifier is selected from the group consisting of an interleukin, interferon, tumor necrosis factor, and granulocyte colony stimulating factor.

31. The conjugate of claim 30 wherein said biological response modifier is genetic material.

32. The conjugate of claim 17, 18, 19 or 20 for use as a reagent in positron emission tomography, computer aided tomography, or magnetic resonance imaging.

33. The conjugate of claim 17, 18, 19 or 20 for use as a diagnostic agent.

34. A composition comprising a dendritic polymer complexed with at least one unit of biological response modifier, selected from the group consisting of an interleukin, interferon, tumor necrosis factor, and granulocyte colony stimulating factor.

35. A composition comprising a dendritic polymer complexed with at least one unit of biological response modifier, wherein said biological response modifier is genetic material.

36. The composition of claim 35 wherein said dendritic polymer comprises a dendritic polymer having positive surface functionality over a substantial portion of the polymer surface.

37. The composition of claim 36 wherein said positive surface functionality is created by amino groups at the dendritic polymer surface.

38. The composition of claim 36 wherein said dendritic polymer comprises a dendrimer having positive surface functionality over at least 75% of its dendrimer surface.

39. The composition of claim 36 wherein said genetic material and said dendritic polymer are complexed in a charge ratio from about 10:1 to about 1:10,000.

40. The composition of claim 36 wherein said genetic material and said dendritic polymer are complexed in a charge ratio from about 3:1 to about 1:10,000.

41. The composition of claim 36 wherein said genetic material and said dendritic polymer are complexed in a charge ratio from about 1:1 to about 1:1,000.

42. The composition of claim 36 wherein said genetic material and said dendritic polymer are complexed in a charge ratio from about 1:1 to about 1:15.

43. The composition of claim 36 wherein said genetic material and said dendritic polymer are complexed in a charge ratio from about 1:10 to about 1:10,000.

44. A composition of claim 36 which comprises a complex of dendritic polymer with genetic material, in solution with either DEAE-dextran or glycerol.

45. The composition of claim 44 wherein said genetic material and said dendritic polymer are complexed in a charge ratio from about 1:1 to about 1:15.

46. The composition of claim 44 wherein said genetic material and said dendritic polymer are complexed in a charge ratio from about 1:5 to about 1:10.

47. The composition of claim 45 wherein the complex is in solution with DEAE-dextran at a concentration from about 0.125 to about 2 μM.

48. The composition of claim 47 wherein the concentration of DEAE-dextran in said composition is from about 0.25 to about 1 μM.

49. The composition of claim 44 wherein said complex is in solution with glycerol at a concentration from about 2.0 to about 10.0% by volume.

50. The composition of claim 49 wherein said complex is in solution with glycerol at a concentration from about 2.0 to about 5.0% by weight.

51. The composition of claim 44, 47 or 50 wherein said composition further comprises DMSO.

52. The composition of claim 44 or 45 wherein said composition further comprises chloroquine.

53. The composition of claim 36 wherein a target director is associated with said dendritic polymer.

54. The composition of claim 53 wherein said genetic material and said dendritic polymer are complexed in a charge ratio from about 10:1 to about 1:10,000.

55. The composition of claim 53 wherein said genetic material and said dendritic polymer are complexed in a charge ratio from about 1:1 to about 1:15.

56. The composition of claim 53 wherein said genetic material and said dendritic polymer are complexed in a charge ratio from about 3:1 to about 1:10.

57. The composition of claim 53 or 55 which comprises a complex of dendritic polymer with genetic material, in solution with either DEAE-dextran or glycerol.

58. The composition of claim 53 or 55 wherein the target director is a polyclonal or monoclonal antibody or fragment thereof.

59. The composition of claim 53 or 55 wherein said target director is galactose trisaccharide, biotin, pyruvic acid, insulin or avidin.

60. The composition of claim 36, 39, 44, 45, 53 or 55 wherein said dendritic polymer comprises particles whose dimensions are from about 20 Å at their narrowest dimensions to about 1,000 Å at their largest dimensions.

61. The composition of claim 60 wherein the dendritic polymer is a dense star polymer.

62. The composition of claim 61 wherein the dense star polymer is a dendrimer.

63. The composition of claim 61 wherein said dense star polymer comprises dense star dendrimer which is generally spherical, ellipsoidal, or rod-shaped in configuration.

64. The composition of claim 61 wherein said dendritic polymer comprises aggregates of dendrimers having positive surface functionality and dendrimers having negative surface functionality at a positive:negative charge ratio from about 25:1 to about 100:1.

65. The composition of claim 61 wherein said dendritic polymer comprises a dense star polymer having amino acids over a substantial portion of its surface, and substantially only on its surface.

66. The composition of claim 65 wherein said amino acid is lysine or arginine.

67. The composition of claim 61 wherein the dense star polymer comprises a collection of bridged dense star dendrimers.

68. The composition of claim 67 wherein said genetic material extends between and serves to connect a plurality of dense star polymer particles.

69. The composition of claim 61 wherein said dendritic polymer is comprised of a dispersion of different sized dendrimer particles, ranging from particles having a diameter as small as about 20 Å at their smallest dimension to particles having a diameter of about 110 Å, there being other particles of intermediate diameters in said dispersion.

70. A composition of claim 36, 39, 44, 45, 53, 55 or 57 wherein a genetic material is complexed with a first dendritic polymer which has been placed in a solution containing a second dendritic polymer, said second dendritic polymer being larger than said first dendritic polymer.

71. The composition of claim 70 wherein said dendritic polymer is a dense star polymer.

72. The composition of claim 70 or 71 wherein said first dendritic polymer has a diameter at its narrowest dimension from about 22 to about 50 Å, and said second dendritic polymer has at its narrowest dimension a diameter from about 50 to about 1,000 Å.

73. The composition of claim 70, 71 or 72 wherein one or both of said first and second dendritic polymers are comprised of spherically shaped dendrimers.

74. The composition of claim 70 wherein both of said first and second dendritic polymers are comprised of spherically shaped dendrimers.

75. The composition of claim 36, 39, 44, 45, 53 or 55 wherein said dendritic polymer comprises an unsymmetrically branched dendritic polymer.

76. The composition of claim 75 wherein the monomeric building block of said unsymmetrically branched dendritic polymer is an amino acid.

77. The composition of claim 76 wherein the said amino acid is lysine.

78. The composition of claim 36, 39, 44, 45, 53 or 55 wherein said dendritic polymer comprises aggregates of dendrimers having positive surface functionality and dendrimers having negative surface functionality at a positive:negative charge ratio from about 25:1 to about 100:1.

79. The composition of claim 36, 39, 44, 45, 53 or 55 wherein said dendritic polymer comprises a dense star polymer having amino acids over a substantial portion of its surface, and substantially only on its surface.

80. The composition of claim 79 wherein said amino acid is lysine or arginine.

81. The composition of claim 36, 39, 44, 45, 53 or 55 wherein said dendritic polymer is comprised of a dispersion of different sized dendrimer particles, ranging from particles having a diameter as small as about 20 Å at their smallest dimension to particles having a diameter of about 110 Å, there being other particles of intermediate diameters in said dispersion.

82. The composition of claim 36, 39, 53 or 55 wherein said composition further includes chloroquine.

83. A formulation which comprises a conjugate of claim 1 having at least one pharmaceutically acceptable diluent or carrier present.

84. A formulation which comprises a conjugate of claim 17 having at least one pharmaceutically acceptable diluent or carrier present.

85. A formulation which comprises a conjugate of claim 18 having at least one pharmaceutically acceptable diluent or carrier present.

86. A formulation which comprises a conjugate of claim 34 having at least one pharmaceutically acceptable diluent or carrier present.

87. A formulation which comprises a conjugate of claim 53 having at least one pharmaceutically acceptable diluent or carrier present.

88. A process for preparing a conjugate of dendritic polymer and biological response modifier, selected from the group consisting of an interleukin, interferon, tumor necrosis factor, and granulocyte colony stimulating factor, comprising reacting the dendritic polymer with the biological response modifier in a suitable solvent at a temperature which facilitates the association of the biological response modifier and the dendritic polymer.

89. A process for preparing a conjugate of dendritic polymer and biological response modifier, wherein said biological response modifier comprises genetic material and said dendritic polymer has a predominantly cationic surface character, comprising reacting the dendritic polymer with the biological response modifier in a suitable solvent at a temperature which facilitates the association of the biological response modifier and the dendritic polymer, said process comprising electrostatically attaching said genetic material to said dendritic polymer to create said conjugate.

90. A process for preparing a complex of dendritic polymer and genetic material comprising:

reacting said dendritic polymer with said genetic material in a suitable solvent at a temperature which facilitates the complexing of said genetic material with said dendritic polymer, said process comprising placing said complex in a solution with DEAE-dextran or glycerol.

91. The process of claim 90 which includes attaching a target director to said dendritic polymer before complexing it with genetic material.

92. The process of claim 90 wherein said dendritic polymer has a predominantly cationic surface, said process comprising electrostatically attaching genetic material to said dendritic polymer to create said complex.

93. A process for forming a dendritic polymer-genetic material complex comprising:

complexing genetic material with a first dendritic polymer by reacting the polymer with the genetic material in a suitable solvent at a temperature which facilitates association of the genetic material with the polymer; and placing said complex in a solution containing a second dendritic polymer, said second dendritic polymer being larger than said first dendritic polymer.

94. The process of claim 93 which includes attaching a target director to said dendritic polymer before complexing it with genetic material.

95. The process of claim 93 wherein said dendritic polymer has a predominately cationic surface, said process comprising electrostatically attaching said genetic material to said dendritic polymer.

96. A process for forming a genetic material:dendritic polymer complex comprising:

mixing, in water, sufficient genetic material to yield a final concentration from about 1 to about 10 μg per mL, with sufficient dendritic polymer, having positive surface functionality, to yield a genetic material:dendritic polymer charge ratio from about 3:1 to about 1:10,000;

said mixing being done at a pH from about 5 to about 10 and at a temperature from about 20° to about 40° C.

97. The process of claim 96 wherein said charge ratio is from about 1:1 to about 1:1,000.

98. The process of claim 96 which includes adding sufficient DEAE-dextran to said complex after it is formed, to yield a DEAE-dextran concentration from about 0.125 to about 2 μM.

99. The process of claim 98 wherein said charge ratio is from about 1:1 to about 1:15.

100. The process of claim 99 wherein said charge ratio is from about 1:5 to about 1:10.

101. The process of claim 98 wherein sufficient DEAE-dextran is added to yield a DEAE-dextran concentration from about 0.25 to about 1 μM.

102. The process of claim 98 wherein said dendritic polymer has a diameter from about 50 Å at its narrowest diameter, to a maximum diameter of about 1,000 Å.

103. The process of claim 96 wherein said dendritic polymer is comprised of a dispersion of different sized dendrimer particles, ranging from particles having a diameter as small as about 20 Å at their smallest dimension to particles having a diameter of about 110 Å, there being other particles of intermediate diameters in said dispersion.

104. The process of claim 96 wherein said dendritic polymer comprises aggregates of dendrimers having positive surface functionality and dendrimers having negative surface functionality at a positive:negative charge ratio from about 25:1 to about 100:1, said aggregates having diameters of no more than about 1,000 Å.

105. The process of claim 96 wherein said dendritic polymer comprises a dense star polymer having amino acids over a substantial portion of its surface, and substantially only on its surface.

106. The process of claim 105 wherein said amino acid is lysine or arginine.

107. The process of claim 96 wherein said dendritic polymer comprises relatively small dendrimer particles having a diameter of 22 to 50 Å at their smallest dimension;
said process further including adding dendritic polymers whose particles have diameters from about 50 to about 110 Å at their smallest dimension, after said complex has formed.

108. The process of claim 96 wherein said dendritic polymer particles include target director moieties attached thereto.

109. The process of claim 96 which includes adding sufficient glycerol to said complex after it is formed, to yield a glycerol concentration from about 2 to about 10 percent by weight.

110. The process of claim 109 wherein said glycerol concentration is from about 2 to about 5 percent by weight.

111. The process of claim 109 wherein said charge ratio is from about 1:1 to about 1:15.

112. The process of claim 109 wherein said dendritic polymer has a diameter from about 50 Å at its narrowest diameter, to a maximum diameter of about 1,000 Å.

113. A process for forming a concentrated genetic material:dendritic polymer complex which can be diluted for use comprising:
mixing, in water, sufficient genetic material to yield a concentration from about 1 to about 10 μg per 20 μL, with sufficient dendritic polymer, having positive surface functionality, to yield a genetic material:dendritic polymer charge ratio from about 4:1 to about 1:10,000; said mixing being done at a pH from about 5 to about 10 and at a temperature from about 20° to about 40° C.

114. The process of claim 113 wherein said charge ratio is from about 1:1 to about 1:1,000.

115. The process of claim 113 wherein said charge ratio is from about 1:1 to about 1:15.

116. The process of claim 113 wherein said charge ratio is from about 1:5 to about 1:10.

117. The process of claim 113 wherein said dendritic polymer has a diameter from about 50 Å at its narrowest diameter, to a maximum diameter of about 1,000 Å.

118. The process of claim 113 wherein said dendritic polymer is comprised of a dispersion of different sized dendrimer particles, ranging from particles having a diameter as small as about 20 Å at their smallest dimension to particles having a diameter of about 110 Å, there being other particles of intermediate diameters in said dispersion.

119. The process of claim 113 wherein said dendritic polymer comprises aggregates of dendrimers having positive surface functionality and dendrimers having negative surface functionality at a positive:negative charge ratio from about 25:1 to about 100:1, said aggregates having diameters of no more than about 1,000 Å.

120. The process of claim 113 wherein said dendritic polymer comprises a dense star polymer having amino acids over a substantial portion of its surface, and substantially only on its surface.

121. The process of claim 120 wherein said amino acid is lysine or arginine.

122. The process of claim 113 wherein said dendritic polymer particles include target director moieties attached thereto.

123. The process of claim 123 wherein said dendritic polymer comprises relatively small dendrimer particles having a diameter of about 22 to about 50 Å at their smallest dimension;
said process further including adding dendritic polymers whose particles have diameters from about 50 to about 110 Å at their smallest dimension, after said complex is formed.

124. A method of effecting cell transfection and bioavailability of genetic material comprising providing a complex of a dendritic polymer and genetic material, and making said complex available to cells to be transfected.

125. A method for transporting genetic material through a cellular membrane and into a cellular nucleus comprising:
complexing said genetic material with dendritic polymer; followed by making said complex available to cells to be transfected.

126. A method for protecting genetic material from digestion during transit to and transfection into a cell comprising:
complexing said genetic material with dendritic polymer prior to exposing the said genetic material to digestive enzymes.

127. A method for stabilizing and compacting genetic material comprising: complexing said genetic material with dendritic polymer.

128. A method of effecting cell transfection and bioavailability of genetic material comprising providing a complex of a dendritic polymer and genetic material, in solution with DEAE-dextran or glycerol, and making said complex available to cells to be transfected.

129. The method of claim 128 which includes attaching a target director to said dendritic polymer.

130. A method for effecting cell transfection and bioavailability of genetic material comprising:
forming a complex of a first dendritic polymer and genetic material, followed by placing said complex in a solution containing a second dendritic polymer, wherein said second dendritic polymer is larger than said first dendritic polymer; and
making the resulting complex and second dendritic polymer available to cells to be transfected.

131. The method of claim 130 wherein at least one of said first and second dendritic polymers has attached a target director.

132. A dense star polymer conjugate which comprises at least one dense star polymer associated with at least one unit of at least one bioactive agent, selected from the group consisting of therapeutic agents, diagnostic agents, and therapeutic/diagnostic agents.

133. A dense star polymer conjugate of the formula:

$$(T)_e *(P)_x *(M)_y \qquad (II)$$

wherein:

each P represents a dense star polymer;

x represents an integer of 1 or greater;

each M represents at least one unit of a bioactive agent, said bioactive agent can be the same bioactive agent or a different bioactive agent, said bioactive agent, selected from the group consisting of therapeutic agents, diagnostic agents, and therapeutic/diagnostic agents;

y represents an integer of 1 or greater;

each T represents one or more target directors;

e represents an integer of 1 or greater; and

* indicates that target director and bioactive agent are associated with the dense star polymer;

with the proviso that the bioactive agent maintains its effectiveness.

134. A dense star polymer conjugate of the formula:

$$[(T)_e-(C')_f]_g *(P)_x *[(C'')_h-(M)_y]_k \qquad (III)$$

wherein:

each C' represents the same or different connecting group;

each C" represents the same or different connecting group;

g and k each individually represent an integer of 1 or greater;

e represents an integer of 1 or greater;

f and h each individually represent an integer of 0 or greater;

- indicates a covalent bond in instances where a connecting group is present;

each P represents a dense star polymer;

x represents an integer of 1 or greater;

each T represents one or more target directors;

each M represents at least one unit of a carried bioactive agent, selected from the group consisting of therapeutic agents, diagnostic agents, and therapeutic/diagnostic agents;

y represents an integer of 1 or greater; and

* indicates that target director and carried bioactive agent are associated with the dense star polymer;

with the proviso that the carried bioactive agent maintains its effectiveness.

135. A dense star polymer conjugate of the formula:

$$(T)_e *(P)_x *(M)_y \qquad (II)$$

wherein:

each P represents a dense star polymer;

x represents an integer of 1 or greater;

each M represents at least one unit of a earned material, said carried material can be the same carried material or a different carried material, said carrier material selected from the group consisting of fragrance moieties, scavenging agents, pheromones, pesticides, agricultural materials, and pollutants;

y represents an integer of 1 or greater;

each T represents one or more target directors;

e represents an integer of 1 or greater; and

* indicates that target director and carried material are associated with the dense star polymer;

with the proviso that the carrier material maintains its effectiveness.

136. A dense star polymer conjugate of the formula:

$$[(T)_e-(C')_f]_g *(P)_x *[(C'')_h-(M)_y]_k \qquad (III)$$

wherein:

each C' represents the same or different connecting group;

each C" represents the same or different connecting group;

g and k each individually represent an integer of 1 or greater;

e represents an integer of 1 or greater;

f and h each individually represent an integer of 0 or greater;

- indicates a covalent bond in instances where a connecting group is present;

each P represents a dense star polymer;

x represents an integer of 1 or greater;

each T represents one or more target directors;

each M represents at least one unit of a carried material, selected from the group consisting of fragrance moieties, scavenging agents, pheromones, pesticides, agricultural materials, and pollutants;

y represents an integer of 1 or greater; and

* indicates that target director and carried material are associated with the dense star polymer;

with the proviso that the carried material maintains its effectiveness.

* * * * *